US007833784B2

(12) United States Patent
Barbas, III et al.

(10) Patent No.: US 7,833,784 B2
(45) Date of Patent: Nov. 16, 2010

(54) ZINC FINGER BINDING DOMAINS FOR TNN

(75) Inventors: Carlos F. Barbas, III, La Jolla, CA (US); Birgit Dreier, Regensdorf (CH)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/564,141

(22) Filed: Nov. 28, 2006

(65) Prior Publication Data

US 2007/0213269 A1   Sep. 13, 2007

Related U.S. Application Data

(60) Provisional application No. 60/740,525, filed on Nov. 28, 2005.

(51) Int. Cl.
*C12N 5/00* (2006.01)
*C12N 15/00* (2006.01)
*C07H 21/02* (2006.01)

(52) U.S. Cl. ............... 435/325; 435/252.3; 435/320.1; 536/23.1

(58) Field of Classification Search ............... 536/23.1; 435/320.1, 325, 252.3; 530/350
See application file for complete search history.

(56) References Cited

U.S. PATENT DOCUMENTS

| 5,096,815 | A | 3/1992 | Ladner et al. |
| 5,223,409 | A | 6/1993 | Ladner et al. |
| 5,789,538 | A | 8/1998 | Rebar et al. |
| 6,140,081 | A | 10/2000 | Barbas, III |
| 6,610,512 | B1 | 8/2003 | Barbas, III |
| 2002/0081614 | A1 | 6/2002 | Case et al. |
| 2002/0165356 | A1 | 11/2002 | Barbas et al. |
| 2004/0224385 | A1 | 11/2004 | Barbas et al. |
| 2007/0213269 | A1 | 9/2007 | Barbas et al. |

FOREIGN PATENT DOCUMENTS

| WO | WO 91/07509 | 5/1991 |
| WO | WO 95/19431 | 7/1995 |
| WO | WO 96/06166 | 2/1996 |
| WO | WO 00/23464 | 4/2000 |
| WO | WO03066828 A2 | 8/2003 |
| WO | WO-2007/062422 | 5/2007 |
| WO | WO-2007062422 A2 | 5/2007 |

OTHER PUBLICATIONS

Nierman et al. 2001; Complete Genome Sequence of *Caulobacter crescentus*.PNAS 98:4136-4141.*
Birren et al. Aug. 2005; Accession No. Q1EA36.*
Loftus et al. Oct. 2005; Accession No. Q16SE6.*
Theologis et al. 2000; Sequence and analysis of chromosome 1 of the plant *Arabidopsis thaliana*. Nature 408: 816-820; Accession No. Q9LPV1.*

Goodner et al. 2001. Genome Sequence of the Plant Pathogen and Biotechnology Agent *Agrobacterium tumefaciens* C58. Science 294:2323-2328.*
N.P. Pavletich & C.O. Pabo, "Zinc Finger-DNA Recognition: Crystal Structure of a Zif268-DNA Complex at 2.1 Å," Science 252: 809-817 (1991).
M. Elrod-Erickson et al., "Zif268 Protein-DNA Complex Refined at 1.6 Å: A Model System for Understanding Zinc Finger-DNA Interactions," Structure 4: 1171-1180 (1996).
M. Isalan et al., "Synergy Between Adjacent Zinc Fingers in Sequence-Specific DNA Recognition," Proc. Natl. Acad. Sci. USA 94: 5617-5621 (1997).
Y.Choo & A. Klug, "Selection of DNA Binding Sites for Zinc Fingers Using Rationally Randomized DNA . . . ," Proc. Natl. Acad. Sci. USA 91: 11168-11172 (1994).
E.J. Rebar & C.O. Pabo, "Zinc Finger Phage: Affinity Selection of Fingers with New DNA-Binding Specificities," Science 263: 671-673 (1994).
A.C. Jamieson et al., "In Vitro Selection of Zinc Fingers with Altered DNA-Binding Specificities," Biochemistry 33: 5689-5695 (1994).
H. Wu et al., "Building Zinc Fingers by Selection: Toward a Therapeutic Application," Proc. Natl. Acad. Sci. USA 92: 344-348 (1995).
A.C. Jamieson et al., "A Zinc Finger Directory for High-Affinity DNA Recognition," Proc. Natl. Acad. Sci. USA 93: 12834-12839 (1996).
H.A. Greisman & C.O. Pabo, "A General Strategy for Selecting High-Affinity Zinc Finger Proteins for Diverse DNA Target Sites," Science 275: 657-661 (1997).
D.J. Segal et al., "Toward Controlling Gene Expression at Will: Selection and Design of Zinc Finger Domains Recognizing . . . ," Proc. Natl. Acad. Sci. USA 96: 2758-2763 (1999).
J.M. Spotts et al. "Time-Lapse Imaging of a Dynamic Phosphorylation Protein-Protein Interaction in Mammalian Cells," Proc. Natl. Acad. Sci. USA 99: 15142-15147 (2002).
B. Dreier et al., "Insights Into the Molecular Recognition of the 5'-GNN-3' Family of DNA Sequences by Zinc Finger Domains," J. Mol. Biol. 303: 489-502 (2000).
C.F. Barbas III et al., "Assembly of Combinatorial Antibody Libraries on Phage Surfaces: The Gene III Site," Proc. Natl. Acad. Sci. USA 88: 7978-7982 (1991).
C. Rader & C.F. Barbas III, "Phage Display of Combinatorial Antibody Libraries," Curr. Opin. Biotechnology 8: 503-508 (1997).
S. Chandrasegaran & J. Smith, "Chimeric Restriction Enzymes: What Is Next?,"Biol. Chem. 380:841-848 (1999).
D.N. Sgouras et al., "Ti ERF: An ETS Domain Protein With Strong Transcriptional Repressor Activity, Can Suppress ets-Associated . . . ," EMBO J. 14: 4781-4793 (1995).

(Continued)

*Primary Examiner*—Karen Cochrane Carlson
(74) *Attorney, Agent, or Firm*—Schwegman, Lundberg & Woessner, P.A.

(57) ABSTRACT

Polypeptides that contain zinc finger-nucleotide binding regions that bind to nucleotide sequences of the formula TNN are provided. Compositions containing a plurality of polypeptides, isolated heptapeptides possessing specific binding activity, polynucleotides that encode such polypeptides and methods of regulating gene expression with such polypeptides, compositions and polynucleotides are also provided.

44 Claims, 14 Drawing Sheets

OTHER PUBLICATIONS

J.F. Margolin et al., "Kruppel-Associated Boxes are Potent Transcriptional Repression Domains," Proc. Natl. Acad. Sci. USA 91: 4509-4513 (1994).

G. Pengue & L. Lania, "Krüppel-Associated Box-Mediated Repression of RNA Polymerase II Promoters Is Influenced by . . . ," Proc. Natl. Acad. Sci. USA 93: 1015-1020 (1996).

J.R. Friedman et al., "KAP-1, a Novel Corepressor for the Highly Conserved KRAB Repression Domain," Genes & Dev. 10: 2067-2078 (1996).

D.E. Ayer et al., "Mad Proteins Contain a Dominant Transcription Repression Domain," Mol. Cell. Biol. 16: 5772-5781 (1996).

T. Heinzel et al., "N-CoR, mSin3, and Histone Deacetylases Are Components of a Complex Mediating Transcriptional Repression," Nature 387:43-46 (1997).

I. Sadowski et al., "GAL4-VP16 is an Unusually Potent Transcriptional Activator," Nature 335: 563-564 (1988).

K. Seipel et al., "Different Activation Domains Stimulate Transcription from Remote ('Enhancer') and Proximal ('Promoter') Positions," EMBO J. 11: 4961-4968 (1992).

L.G. Hudson et al., "Structure and Inducible Regulation of the Human c-erb B2/neu Promoter," J. Biol. Chem. 265: 4389-4393 (1990).

P. Blancafort et al., "Designing Transcription Factor Architectures for Drug Discovery," Mol. Pharmacol. 66: 1361-1371 (2004).

R.R. Beerli & C.F. Barbas III, "Engineering Polydactyl Zinc-Finger Transcription Factors," Nat. Biotechnol. 20: 135-141 (2002).

D. Jantz et al., "The Design of Functional DNA-Binding Proteins Based on Zinc Finger Domains," Chem. Rev. 104: 789-799 (2004).

L. Zhang et al., "Synthetic Zinc Finger Transcription Factor Action at an Endogenous Chromosomal Site. Activation of the Human . . . ," J. Biol. Chem. 275: 33850-33860 (2000).

P.-Q. Liu et al., "Regulation of an Endogenous Locus Using a Panel of Designed Zinc Finger Proteins Targeted to Accessible . . . ," J. Biol. Chem. 276: 11323-11334 (2001).

P. Blancafort et al., "Scanning the Human Genome With Combinatorial Transcription Factor Libraries," Nat. Biotechnol. 21: 269-274 (2003).

F.D. Urnov et al., "Highly Efficient Endogenous Human Gene Correction Using Designed Zinc-Finger Nucleases," Nature 435: 646-651 (2005).

M. Bibikova et al., "Enhancing Gene Targeting With Designed Zinc Finger Nucleases," Science 300: 764 (2003).

J. Miller et al., "Repetitive Zinc-Binding Domains in the Protein Transcription Factor IIIA from *Xenopus* Oocytes," EMBO J. 4: 1609-1614 (1985).

M.S. Lee et al., "Three-Dimensional Solution Structure of a Single Zinc Finger DNA-Binding Domain," Science 245: 635-637 (1989).

B. Dreier et al., "Development of Zinc Finger Domains for Recognition of the 5'-Ann-3' Family of DNA Sequences . . . ," J. Biol. Chem. 276: 29466-29478 (2001).

X. Guan et al., "Heritable Endogenous Gene Regulation in Plants With Designed Polydactyl Zinc Finger Transcription Factors," Proc. Natl. Acad. Sci. USA 99: 13296-13301 (2002).

S. Tan et al., "Zinc-Finger Protein-Targeted Gene Regulation: Genomewide Single-Gene Specificity," Proc. Natl. Acad. Sci. USA 100: 11997-12002 (2003).

R.R. Beerli et al., "Chemically Regulated Zinc Finger Transcription Factors," J. Biol. Chem. 275: 32617-32627 (2000).

N.P. Pavletich & C.O. Pabo, et al., "Crystal Structure of a Five-Finger GLI-DNA Complex: New Perspectives on Zinc Fingers," Science 261: 1701-1707 (1993).

L. Fairall et al., "The Crystal Structure of a Two Zinc-Finger Peptide Reveals an Extension to the Rules for Zinc-Finger/DNA Recognition," Nature 366: 483-487 (1993).

H.B. Houbaviy et al., "Cocrystal Structure of YY1 Bound to the Adeno-Associated Virus P5 Initiator," Proc. Natl. Acad. Sci. USA 93: 13577-13582 (1996).

D.S. Wuttke et al., "Solution Structure of the First Three Zinc Fingers of TFIIIA Bound to the Cognate DNA Sequence . . . ," J. Mol. Biol. 273: 183-206 (1997).

R.T. Nolte et al., "Differing Roles for Zinc Fingers in DNA Recognition: Structure of a Six-Finger . . . ," Proc. Natl. Acad. Sci. USA 95: 2938-2943 (1998).

J.J. Havranek et al., "A Simple Physical Model for the Prediction and Design of Protein-DNA Interactions," J. Mol. Biol. 344: 59-70 (2004).

S.A. Wolfe et al., "Analysis of Zinc Fingers Optimized via Phage Display: Evaluating the Utility of a Recognition Code," J. Mol. Biol. 285: 1917-1934 (1999).

C.O. Pabo & L. Nekludova, "Geometric Analysis and Comparison of Protein-DNA Interfaces: Why Is There No Simple Code for Recognition," J. Mol. Biol. 301: 597-624 (2000).

V.A. Narayan et al., "Structures of Zinc Finger Domains From Transcription Factor Spl," J. Biol. Chem. 272: 7801-7809 (1997).

M. Gossen & H. Bujard, "Tight Control of Gene Expression in Mammalian Cells by Tetracycline-Responsive Promoters," Proc. Natl. Acad. Sci. USA 89: 5547 (1992).

X. Liu et al., "Transforming Growth Factor Beta-Induced Phosphorylation of Smad3 . . . ," Proc. Natl. Acad. Sci. USA 94: 10669-10674 (1997).

D. Graus-Porta et al., "Single-Chain Antibody-Mediated Intracellular Retention of ErbB-2 Impairs Neu Differentiation Factor . . . ," Mol. Cell. Biol. 15: 1182-1191 (1995).

N.E. Hynes & D.F. Stern, "The Biology of erbB-2/neu/HER-2 and Its Role in Cancer," Biochim. Biophys. Acta 1198: 165-184 (1994).

N. Altiok et al., "ErbB3 and ErbB2/neu Mediate the Effect of Heregulin on Acetylcholine Receptor Gene Expression in Muscle . . . ," EMBO J. 14: 4258-4266 (1995).

S. Ishii et al., "Characterization of the Promoter Region of the Human c-erbB-2 Protooncogene," Proc. Natl. Acad. Sci. USA 84: 4374-4378 (1987).

R.R. Beerli et al., "Toward Controlling Gene Expression at Will: Specific Regulation of the erbB-2/HER-2 Promoter . . . ," Proc. Natl. Acad. Sci. USA 95: 14628-14633 (1998).

Q. Liu et al., "Design of Polydactyl Zinc-Finger Proteins for Unique Addressing within Complex Genomes," Proc. Natl. Acad. Sci. USA 94: 5525-5530 (1997).

C.A. Kim & J.M. Berg, "A 2.2 Å Resolution Crystal Structure of a Designed Zinc Finger Protein Bound to DNA," Nature Struct. Biol. 3: 940-945 (1996).

J.-S. Kim et al., "Design of TATA Box-Binding Protein/Zinc Finger Fusions for Targeted Regulation of Gene Expression," Proc. Natl. Acad. Sci. USA 94: 3616-3620 (1997).

J.S. Kim & C.O. Pabo, "Transcriptional Repression by Zinc Finger Peptides," J. Biol. Chem. 272: 29795-29800 (1997).

M. Elrod-Erickson et al., "High-Resolution Structures of Variant Zif268-DNA Complexes: Implications for Understanding Zinc Finger-DNA . . . ," Structure 6: 451-464 (1998).

Y. Choo & A. Klug, "Toward a Code for the Interactions of Zinc Fingers with DNA: Selection of Randomized Fingers . . . ," Proc. Natl. Acad. Sci. USA 91: 11163-11167 (1994).

T.E. Abbink et al.,"Forced Selection of a Human Immunodeficiency Virus Type 1 Variant That Uses a Non-Self tRNA Primer . . . ," J. Virol. 78:10706-10714 (2004).

J.S. Barnor et al., "Intracellular Expression of Antisense RNA Transcripts Complementary to the Human Immunodeficiency . . . ," Biochem. Biophys. Res. Commun. 320:544-550 (2004).

R.R. Beerli et al., "Positive and Negative Regulation of Endogenous Genes by Designed Transcription Factors," Proc. Natl. Acad. Sci. USA 97:1495-1500 (2000).

D.O. Boden et al., "Human Immunodeficiency Virus Type 1 Escape from RNA Interference," J. Virol. 77:11531-11535 (2003).

K.E. Boyd et al., "c-Myc Target Gene Specificity Is Determined by a Post-DNA Binding Mechanism," Proc. Natl. Acad. Sci. USA 95:13887-13892 (1998).

G.A. Coburn & B. R. Cullen, "Potent and Specific Inhibition of Human Immunodeficiency Virus Type 1 Replication by RNA Interference," J. Virol. 76:9225-9231 (2002).

A.T. Das & B. Berkhout, "Efficient Extension of a Misaligned tRNA-Primer During Replication of the HIV-1 Retrovirus," Nucleic Acids Res. 23: 1319-1326 (1995).

A.T. Das et al., "Human Immunodeficiency Virus Type 1 Escapes From RNA Interference-Mediated Inhibition," J. Virol. 78:2601-2605 (2004).

A.T. Das et al., "Reduced Replication of Human Immunodeficiency Virus Type 1 Mutants That Use Reverse Transcription Primers . . . ," J. Virol. 69:3090-3097 (1995).

A.T. Das et al., "Sequence Variation of the Human Immunodeficiency Virus Primer-Binding Site Suggests the Use of an Alternative . . . ," J. Gen. Virol. 78: 837-840 (1997).

A.T. Das et al., "Alternative tRNA Priming of Human Immunodeficiency Virus Type 1 Reverse Transcription Explains Sequence . . . ," J. Virol. 79:3179-3181 (2005).

M.P. Be Baar et al., "Subtype-Specific Sequence Variation of the HIV Type 1 Long Terminal Repeat And Primer-Binding Site," AIDS Res. Hum. Retrovir. 16:499-504 (2000).

C.A. Derdeyn et al., "Sensitivity of Human Immunodeficiency Virus Type 1 to The Fusion Inhibitor T-20 Is Modulated by . . . ," J. Virol. 74:8358-8367 (2000).

B. Dreier et al., "Development of Zinc Finger Domains for Recognition of the 5'-CNN-3' Family DNA Sequences And Their Use . . . ," J. Biol. Chem. 280:35588-35597 (2005).

Y. Feng et al., "Inhibition of CCR5-Dependent HIV-1 Infection by Hairpin Ribozyme Gene Therapy Against CC-Chemokine Receptor," J. Virol. 276:271-278 (2000).

A.D. Frankel & C. O. Pabo, "Cellular Uptake of the Tat Protein From Human Immunodeficiency Virus," Cell 55:1189-1193 (1988).

J.C. Gea-Banacloche et al., "Immune Reconstitution in HIV Infection," AIDS 13:525-538 (1999).

T. Graslund et al., "Exploring Strategies for the Design of Artificial Transcription Factors: Targeting Sites Proximal to . . . ," J. Biol. Chem. 280:3707-3714 (2005).

W. Han et al., "Inhibition of Human Immunodeficiency Virus Type 1 Replication by siRNA Targeted to the Highly Conserved Primer Binding Site," Virology 330:221-232 (2004).

W.V. Hu et al., "Inhibition of Retroviral Pathogenesis by RNA Interference," Curr. Biol. 12: 1301-1311 (2002).

J.M. Jacque et al., "Modulation of HIV-1 Replication by RNA Interference," Nature 418:435-438 (2002).

R.E. Jeeninga et al., "Functional Differences Between the Long Terminal Repeat Transcriptional Promoters of Human . . . ," J. Virol. 74:3740-3751 (2000).

Y. Jouvenot et al., "Targeted Regulation of Imprinted Genes by Synthetic Zinc-Finger Transcription Factors," Gene Ther. 10:513-522 (2003).

W. Keulen et al., "Initial Appearance of the 184Ile Variant in Lamivudine-Treated Patients Is Caused by the Mutational Bias of Human . . . ," J. Virol. 71:3346-3350 (1997).

Y.S. Kim et al., "Artificial Zinc Finger Fusions Targeting Sp1-Binding Sites and the Trans-Activator-Responsive . . . ," J. Biol. Chem. 280:21545-21552 (2005).

L. Kleiman, "tRNA(Lys3): The Primer tRNA for Reverse Transcription in HIV-1," IUBMB Life 53:107-114 (2002).

H.S. Kwon et al., "Suppression of Vascular Endothelial Growth Factor Expression at the Transcriptional and Post-Transcriptional Levels," Nucleic Acids Res. 33:e74 (2005).

X. Li et al., "Effects of Alterations of Primer-Binding Site Sequences on Human Immunodeficiency Virus Type 1 Replication," J. Virol. 68:6198-6206 (1994).

L. Magnenat et al., "In Vivo Selection of Combinatorial Libraries and Designed Affinity Maturation of Polydactyl Zinc Finger . . . ," J. Mol. Biol. 341:635-649 (2004).

J. Mak & L. Kleiman, "Primer tRNAs for Reverse Transcription," J. Virol. 71:8087-8095 (1997).

A. Marcello et al., "Nuclear Organization and the Control of HIV-1 Transcription," Gene 326:1-11 (2004).

I.L. Marquet et al., "tRNAs as Primer of Reverse Transcriptases," Biochimie 77:113-124 (1995).

K.L.Moore-Rigdon et al., "Preferences for the Selection of Unique tRNA Primers Revealed From Analysis of HIV-1 Replication . . . ," Retrovirology 2:21 (2005).

P.O. Moosmann et al., "Silencing of RNA Polymerases II and III-Dependent Transcription by the KRAB Protein Domain of KOX1, a Kruppel-Type . . . ," Biol. Chem. 378:669-677 (1997).

T. Nagashunmugam et al., "Mutation in the Primer Binding Site of the Type 1 Human Immunodeficiency Virus Genome Affects . . . ," Proc. Natl. Acad. Sci. USA 89:4114-4118 (2000).

L.A. Pereira et al., "A Compilation of Cellular Transcription Factor Interactions With the HIV-1 LTR Promoter," Nucleic Acids Res. 28:663-668 (2000).

E.J. Platt et al., "Effects of CCR5 and CD4 Cell Surface Concentrations on Infections by Macrophagetropic Isolates of Human . . . ," J. Virol. 72:2855-2864 (1998).

L. Reynolds et al., "Repression of the HIV-1 5 LTR Promoter and Inhibition of HIV-1 Replication . . . ," Proc. Natl. Acad. Sci. USA 100:1615-1620 (2003).

H. Rhim et al., "Deletions in the tRNA Lys Primer Binding Site of Human Immunodeficiency Virus Type 1 . . . ," J. Virol. 65:4555-4564 (1991).

L.K. Schrager & M. P. D'Souza, "Cellular and Anatomical Reservoirs of HIV-1 in Patients Receiving Potent Antiretroviral Combination Therapy," JAMA 280:67-71 (1998).

D.J. Segal et al., "Attenuation of HIV-1 Replication in Primary Human Cells With a Designed Zinc Finger Transcription Factor," J. Biol. Chem. 279: 14509-14519 (2004).

B. Senatore et al., "A variety of RNA Polymerases II and III-Dependent Promoter Classes Is Repressed by Factors Containing . . . , " Gene 234:381-394 (1999).

J. Sodroski et al., "Role of the HTLV-III/LAV Envelope in Syncytium formation and Cytopathicity," Nature 322:470-474 (1986).

J.T. Stege et al., "Controlling Gene Expression in Plants Using Synthetic Zinc Finger Transcription Factors," Plant J. 32:1077-1086 (2002).

E. Verdin et al., "Chromatin Disruption in the Promoter of Human Immunodeficiency Virus Type 1 During Transcriptional Activation," EMBO J. 12:3249-3259 (1993).

J.K. Wakefield et al., "Construction of a Type 1 Human Immunodeficiency Virus That Maintains a Primer Binding Site Complementary . . . ," J. Virol. 70:966-975 (1996).

J.K. Wakefield & C. D. Morrow, "Mutations Within the Primer Binding Site of the Human Immunodeficiency Virus Type 1 Define Sequence . . . ," Virology 220:290-298 (1996).

J.K. Wakefield et al., "Minimal Sequence Requirements of a Functional Human Immunodeficiency Virus Type 1 Primer Binding Site," J. Virol. 68:1605-1614 (1994).

J.K. Wakefield et al., "Human Immunodeficiency Virus Type 1 Can Use Different tRNAs as Primers for Reverse Transcription But SelectivelY . . . ," J. Virol. 69:6021-6029 (1995).

S. Waninger, "Identification of Cellular Cofactors for Human Immunodeficiency Virus Replication via a Ribozyme-Based Genomics Approach," J. Virol. 78:12829-12837 (2004).

X. Wei et al., "Emergence of Resistant Human Immunodeficiency Virus Type 1 in Patients Receiving Fusion Inhibitor . . . ," Antimicrob. Agents Chemother. 46:1896-1905 (2002).

International Application Serial No. PCT/US2006/061289: Search Report mailed Aug. 5, 2008, P220.

International Application Serial No. PCT/US2006/061289: Written Opinion mailed Aug. 5, 2008, P237.

06846383.5, "European Application No. 06846383.5, Search report Mailed on Mar. 10, 2009", 14.

Segal, D J, et al., ""Evaluation of a modular strategy for the construction of novel polydactyl zinc finger DNA-binding proteins"", Biochemistry . ,Biochemistry . , vo 1. 42, No. 7, XP002516792 US American Chemical Society. Easton, PA. p. 2139, right-hand column, line 30 line 40 , (Jan. 28, 2003), 2137-2148.

"European Application Serial No. 06846383.5, Office Action mailed Jul. 7, 2009", 2 pgs.

* cited by examiner (a) TAA-1a-2 QASNLIS (SEQ ID NO. 1)

(b) TAC-2c-2 SRGNLKS (SEQ ID NO. 2)

(c) TAC-2d-2 ARGNLKS (SEQ ID NO. 7)

(d) TAG-3c-2 RLDNLQT (SEQ ID NO. 3)

(e) TAG-3d-2 RSDNLTT (SEQ ID NO. 8)

(f) TAT-4c-8 ARGNLRT (SEQ ID NO. 4)

(g) TAT-4d-2 VRGNLKS (SEQ ID NO. 9)

(h) TTG-6c-2 RKDALRG (SEQ ID NO. 5)

(a) TAG: RLD-N-LQT (SEQ ID NO. 3)

(b) TAT: ARG-N-LRT (SEQ ID NO. 4)

(c) TAT: SRG-N-LKS (SEQ ID NO. 2)

(d) TAA: QAS-N-LIS (SEQ ID NO. 1)

(e) TAG: RED-N-LHT (SEQ ID NO. 6)

(f) TAT: ARG-N-LKS (SEQ ID NO. 7)

A

B

C

ZINC FINGER BINDING DOMAINS FOR TNN

CROSS-REFERENCES

This application claims priority from Provisional Application Ser. No. 60/740,525, by Carlos F. Barbas III and Birgit Dreier, entitled "Zinc Finger Binding Domains for TNN," and filed on Nov. 28, 2005, which is incorporated herein in its entirety by this reference.

GOVERNMENT INTERESTS

This invention was made with U.S. Government support under Contract No. GM53910 and No. CA 86258 by the National Institutes of Health. The U.S. Government has certain rights in the invention.

TECHNICAL FIELD OF THE INVENTION

The field of this invention is zinc finger protein binding to target nucleotides. More particularly, the present invention pertains to amino acid residue sequences within the α-helical domain of zinc fingers that specifically bind to target nucleotides of the formula 5'-(TNN)-3'.

BACKGROUND OF THE INVENTION

The construction of artificial transcription factors has been of great interest in the past years. Gene expression can be specifically regulated by polydactyl zinc finger proteins fused to regulatory domains. Zinc finger domains of the $Cys_2$-$His_2$ family have been most promising for the construction of artificial transcription factors due to their modular structure. Each domain consists of approximately 30 amino acids and folds into an α-helical structure stabilized by hydrophobic interactions and chelation of a zinc ion by the conserved $Cys_2$-$His_2$ residues. To date, the best characterized protein of this family of zinc finger proteins is the mouse transcription factor Zif 268 [Pavletich et al., (1991) Science 252(5007), 809-817; Elrod-Erickson et al., (1996) Structure 4(10), 1171-1180]. The analysis of the Zif 268/DNA complex suggested that DNA binding is predominantly achieved by the interaction of amino acid residues of the α-helix in position −1, 3, and 6 with the 3', middle, and 5' nucleotide of a 3 bp DNA subsite, respectively. Positions 1, 2 and 5 have been shown to make direct or water-mediated contacts with the phosphate backbone of the DNA. Leucine is usually found in position 4 and packs into the hydrophobic core of the domain. Position 2 of the α-helix has been shown to interact with other helix residues and, in addition, can make contact to a nucleotide outside the 3 bp subsite [Pavletich et al., (1991) Science 252(5007), 809-817; Elrod-Erickson et al., (1996) Structure 4(10), 1171-1180; Isalan, M. et al., (1997) Proc Natl Acad Sci USA 94(11), 5617-5621].

The selection of modular zinc finger domains recognizing each of the 5'-(GNN)-3' DNA subsites with high specificity and affinity and their refinement by site-directed mutagenesis has been demonstrated (U.S. Pat. No. 6,140,081, the disclosure of which is incorporated herein by reference). These modular domains can be assembled into zinc finger proteins recognizing extended 18 bp DNA sequences which are unique within the human genome or any other genome. In addition, these proteins function as transcription factors and are capable of altering gene expression when fused to regulatory domains and can even be made hormone-dependent by fusion to ligand-binding domains of nuclear hormone receptors. To allow the rapid construction of zinc finger-based transcription factors binding to any DNA sequence it is important to extend the existing set of modular zinc finger domains to recognize each of the 64 possible DNA triplets which are assigned meaning in the genetic code. This aim can be achieved by phage display selection and/or rational design. Due to the limited structural data on zinc finger/DNA interaction, rational design of zinc proteins is very time-consuming and may not be possible in many instances. In addition, most naturally occurring zinc finger proteins consist of domains recognizing the 5'-(GNN)-3' type of DNA sequences. The most promising approach to identify novel zinc finger domains binding to DNA target sequences of the type 5'-(NNN)-3' is selection via phage display. The limiting step for this approach is the construction of libraries that allow the specification of a 5' adenine, cytosine or thymine in the subsite recognized by each module. Phage display selections have been based on Zif268 in which different fingers of this protein were randomized [Choo et al., (1994) Proc. Natl. Acad. Sci. U.S.A. 91(23), 11168-72; Rebar et al., (1994) Science (Washington, D.C., 1883-) 263(5147), 671-3; Jamieson et al., (1994) Biochemistry 33, 5689-5695; Wu et al., (1995) PNAS 92, 344-348; Jamieson et al., (1996) Proc Natl Acad Sci USA 93, 12834-12839; Greisman et al., (1997) Science 275(5300), 657-661]. A set of 16 domains recognizing the 5'-(GNN)-3' type of DNA sequences has previously been reported from a library where finger 2 of C7, a derivative of Zif268 [Wu et al., (1995) PNAS 92, 344-348 Wu, 1995], was randomized [Segal et al., (1999) Proc Natl Acad Sci USA 96(6), 2758-2763]. In such a strategy, selection is limited to domains recognizing 5'-(GNN)-3' or 5'-(TNN)-3' due to the $Asp^2$ of finger 3 making contact with the complementary base of a 5' guanine or thymine in the finger-2 subsite [Pavletich et al., (1991) Science 252(5007), 809-817; Elrod-Erickson et al., (1996) Structure 4(10), 1171-1180].

Despite the possible selection of zinc finger domains recognizing sequences of the form 5'-(TNN)-3' by the strategy described above, in practice very few such sequences have been selected and identified. Therefore, there is a need to discover zinc finger domains recognizing sequences of the form 5'-(TNN)-3' so that a broader "vocabulary" of zinc finger domains is available for the construction of multifinger zinc finger proteins. The availability of zinc finger domains recognizing sequences of the form 5'-(TNN)-3' would lead to the ability to prepare artificial transcription factors and proteins having other nucleic acid sequence recognizing functions that recognize a far greater variety of nucleic acid sequences. The ability to specifically recognize sequences of the form 5'-(TNN)-3' is particularly important because the major stop codons, TGA, TAG, and TAA, are of this form and regulatory sequences are frequently located in close proximity to chain termination regions. Additionally, the stop codons are frequently found in tandem in naturally occurring DNA and it would be desirable to target these regions. The scarcity of zinc finger domains recognizing sequences of the form 5'-(TNN)-3' has made this very difficult.

The present approach is based on the modularity of zinc finger domains that allows the rapid construction of zinc finger proteins by the scientific community and demonstrates that the concerns regarding limitation imposed by cross-subsite interactions only occurs in a limited number of cases. The present disclosure introduces a new strategy for selection of zinc finger domains specifically recognizing the 5'-(TNN)-3' type of DNA sequences. Specific DNA-binding properties of these domains were evaluated by a multi-target ELISA against all sixteen 5'-(CNN)-3' triplets. These domains can be readily incorporated into polydactyl proteins containing various numbers of 5'-(TNN)-3' domains, each specifically recognizing extended 18 bp sequences. Furthermore, these domains can specifically alter gene expression when fused to regulatory domains. These results underline the feasibility of constructing polydactyl proteins from predefined building blocks. In addition, the domains characterized here greatly increase the number of DNA sequences that can be targeted with artificial transcription factors.

BRIEF SUMMARY OF THE INVENTION

In one aspect, the present invention provides an isolated and purified zinc finger nucleotide binding polypeptide that contains a nucleotide binding region of from 5 to 10 amino acid residues, which region binds preferentially to a target nucleotide of the formula TNN, where N is A, C, G or T. Preferably, the target nucleotide has the formula TAN, TCN, TGN, TTN, TNA, TNC, TNG or TNT. More preferably, the target nucleotide has the formula TAA, TAC, TAG, TAT, TCA, TCC, TCG, TCT, TGA, TGC, TGG, TGT, TTA, TTC, TTG or TTT. In one embodiment, a polypeptide of the invention contains a binding region that has an amino acid sequence with the same nucleotide binding characteristics as any of SEQ ID NO: 1 through SEQ ID NO: 411. Such a polypeptide competes for binding to a nucleotide target with any of SEQ ID NO: 1 through SEQ ID NO: 411. That is, a preferred polypeptide contains a binding region that will displace, in a competitive manner, the binding of any of SEQ ID NO: 1 through SEQ ID NO: 411. Means for determining competitive binding are well known in the art. Preferably, the binding region has the amino acid sequence of any of SEQ ID NO: 1 through SEQ ID NO: 411. More preferably, the binding region has the amino acid sequence of any of SEQ ID NO: 1 through SEQ ID NO: 46. Still more preferably, the binding region has the amino acid sequence of any of SEQ ID NO: 1 through SEQ ID NO: 6. Alternatively, the binding region can have an amino acid sequence selected from the group consisting of: (1) the binding region of the amino acid sequence of any of SEQ ID NO: 1 through SEQ ID NO: 411, any of SEQ ID NO: 1 through SEQ ID NO: 46, or any of SEQ ID NO: 1 through SEQ ID NO: 6; and (2) a binding region differing from the amino acid sequence of any of SEQ ID NO: 1 through SEQ ID NO. 411, any of SEQ ID NO: 1 through SEQ ID NO: 46, or any of SEQ ID NO: 1 through SEQ ID NO: 6 by no more than two conservative amino acid substitutions, wherein the dissociation constant is no greater than 125% of that of the polypeptide before the substitutions are made, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. In still another alternative, the nucleotide binding region comprises a 7-amino acid zinc finger domain in which the seven amino acids of the domain are numbered from –1 to 6, and wherein the domain is selected from the group consisting of: (1) a zinc finger nucleotide binding domain specifically binding the nucleotide sequence 5'-(TAA)-3', wherein the amino acid residue of the domain numbered –1 is selected from the group consisting of Q, N, and S; (2) a zinc finger nucleotide binding domain specifically binding the nucleotide sequence 5'-(TCA)-3', wherein the amino acid residue of the domain numbered –1 is S; (3) a zinc finger nucleotide binding domain specifically binding the nucleotide sequence 5'-(TNG)-3', wherein N is any of A, C, G, or T, wherein the amino acid residue of the domain numbered –1 is selected from the group consisting of R, N, Q, H, S, T, and I; (4) a zinc finger nucleotide binding domain specifically binding the nucleotide sequence 5'-(TNG)-3', wherein N is any of A, C, G, or T, wherein the amino acid residue numbered 2 of the domain is D; (5) a zinc finger nucleotide binding domain specifically binding the nucleotide sequence 5'-(TNT)-3', wherein N is any of A, C, G, or T, wherein the amino acid residue of the domain numbered –1 is selected from the group consisting of R, N, Q, H, S, T, A, and C; (6) a zinc finger nucleotide binding domain specifically binding the nucleotide sequence 5'-(TNC)-3', wherein N is any of A, C, G, or T, wherein the amino acid residue of the domain numbered –1 is selected from the group consisting of Q, N, S, G, H, and D; (7) a zinc finger nucleotide binding domain specifically binding the nucleotide sequence 5'-(TAN)-3', wherein N is any of A, C, G, or T, wherein the amino acid residue of the domain numbered 3 is selected from the group consisting of H, N, G, V, P, I, and K; (8) a zinc finger nucleotide binding domain specifically binding the nucleotide sequence 5'-(TCN)-3', wherein N is any of A, C, G, or T, wherein the amino acid residue of the domain numbered 3 is selected from the group consisting of T, D, H, K, R, and N; (9) a zinc finger nucleotide binding domain specifically binding the nucleotide sequence 5'-(TCC)-3', wherein the amino acid residue of the domain numbered 3 is selected from the group consisting of N, H, S, D, T, Q, and G; (10) a zinc finger nucleotide binding domain specifically binding the nucleotide sequence 5'-(TCG)-3', wherein the amino acid residue of the domain numbered 3 is selected from the group consisting of T, H, S, D, N, Q, and G; (11) a zinc finger nucleotide binding domain specifically binding the nucleotide sequence 5'-(TGN)-3', wherein N is any of A, C, G, or T, wherein the amino acid residue of the domain numbered 3 is H; (12) a zinc finger nucleotide binding domain specifically binding a nucleotide sequence selected from the group consisting of 5'-(TGG)-3' and 5'-(TGT)-3', wherein the amino acid residue of the domain numbered 3 is selected from the group consisting of S, D, T, N, Q, G, and H; (13) a zinc finger nucleotide binding domain specifically binding the nucleotide sequence 5'-(TGC)-3', wherein the amino acid residue of the domain numbered 3 is selected from the group consisting of W, T, and H; (14) a zinc finger nucleotide binding domain specifically binding the nucleotide sequence 5'-(TGN)-3', wherein N is any of A, C, G, or T, wherein the amino acid residue of the domain numbered 3 is H; (15) a zinc finger nucleotide binding domain specifically binding a nucleotide sequence selected from the group consisting of 5'-(TTA)-3' and 5'-(TTG)-3', wherein the amino acid residue of the domain numbered 3 is selected from the group consisting of S and A; (16) a zinc finger nucleotide binding domain specifically binding a nucleotide sequence selected from the group consisting of 5'-(TTC)-3' and 5'-(TTT)-3', wherein the amino acid residue of the domain numbered 3 is H; (17) a zinc finger nucleotide binding domain specifically binding the nucleotide sequence 5'-(TNA)-3', wherein N is any of A, C, G, or T, wherein the amino acid residue of the domain numbered –1 is R; (18) a zinc finger nucleotide binding domain specifically binding the nucleotide sequence 5'-(TNT)-3', wherein N is any of A, C, G, or T, wherein the amino acid residue of the domain numbered –1 is selected from the group consisting of S, T, and H; and (19) a zinc finger nucleotide binding domain specifically binding the nucleotide sequence 5'-(TNN)-3', wherein N is any of A, C, G, or T, wherein the amino acid residue of the domain numbered 4 is selected from the group consisting of L, V, I, and C.

In another aspect, the present invention provides a polypeptide composition that contains a plurality of and, preferably from about 2 to about 18 of zinc finger nucleotide binding domains as disclosed herein. The domains are typically operatively linked such as linked via a flexible peptide linker of from 5 to 15 amino acid residues. Operatively linked preferably occurs via a flexible peptide linker such as that shown in SEQ ID NO: 412. Such a composition typically binds to a nucleotide sequence that contains a sequence of the formula 5'-(TNN)$_n$-3', where N is A, C, G or T and n is 2 to 12. Preferably, the polypeptide composition contains from about 2 to about 6 zinc finger nucleotide binding domains and binds to a nucleotide sequence that contains a sequence of the formula 5'-(TNN)$_n$-3', where n is 2 to 6 Binding occurs with a $K_D$ of from 1 μM to 10 μM. Preferably binding occurs with a $K_D$ of from 10 μM to 1 μM, from 10 pM to 100 nM, from 100 pM to 10 nM and, more preferably with a $K_D$ of from 1 nM to 10 nM. In preferred embodiments, both a polypeptide and a polypeptide composition of this invention are operatively linked to one or more transcription regulating factors such as a repressor of transcription or an activator of transcription.

In yet another aspect, the invention further provides an isolated heptapeptide having an α-helical structure and that binds preferentially to a target nucleotide of the formula TNN, where N is A, C, G or T. Preferred target nucleotides are as described above. The preferred heptapeptides are the same as those of the binding regions of the polypeptides described above.

Additionally, the invention further provides bispecific zinc fingers, the bispecific zinc fingers comprising two halves, each half comprising six zinc finger nucleotide binding domains, where at least one of the halves includes at least one domain binding a target nucleotide sequence of the form 5'-(TNN)-3', such that the two halves of the bispecific zinc fingers can operate independently.

Additionally, the invention further provides a sequence-specific nuclease comprising the nuclease catalytic domain of FokI, the sequence-specific nuclease cleaving at a site including therein at least one target nucleotide sequence of the form 5'-(TNN)-3'. The invention further provides methods for sequence-specific cleavage of nucleic acid sequences using such sequence-specific nucleases.

The present invention further provides polynucleotides that encode a polypeptide or a composition of this invention, expression vectors that contain such polynucleotides and host cells transformed with the polynucleotide or expression vector.

The present invention further provides a process of regulating expression of a nucleotide sequence that contains the target nucleotide sequence 5'-(TNN)-3'. The target nucleotide sequence can be located anywhere within a longer 5'-(NNN)-3' sequence. The process includes the step of exposing the nucleotide sequence to an effective amount of a zinc finger nucleotide binding polypeptide or composition as set forth herein. In one embodiment, a process regulates expression of a nucleotide sequence that contains the sequence 5'-(TNN)$_n$-3', where n is 2 to 12. The process includes the step of exposing the nucleotide sequence to an effective amount of a composition of this invention. The sequence 5'-(TNN)$_n$-3' can be located in the transcribed region of the nucleotide sequence, in a promoter region of the nucleotide sequence, or within an expressed sequence tag. The composition is preferably operatively linked to one or more transcription regulating factors such as a repressor of transcription or an activator of transcription. In one embodiment, the nucleotide sequence is a gene such as a eukaryotic gene, a prokaryotic gene or a viral gene. The eukaryotic gene can be a mammalian gene such as a human gene, or, alternatively, a plant gene. The prokaryotic gene can be a bacterial gene. One specific method according to the present invention is a method of inhibiting the replication of HIV-1 virus comprising the step of administering to an individual infected with HIV-1 virus a sufficient quantity of an artificial transcription factor according to the present invention capable of binding to the tRNA primer-binding site such that replication of HIV-1 is inhibited. Alternatively, another specific method according to the present invention is a method for inhibiting the replication of HIV-1 virus comprising the step of administering to an individual infected with HIV-1 virus a sufficient quantity of a polynucleotide encoding an artificial transcription factor according to the present invention such that replication of HIV-1 is inhibited.

In yet another embodiment, the invention provides a pharmaceutical composition comprising:

(1) a therapeutically effective amount of a polypeptide, polypeptide composition, such as an artificial transcription factor, or isolated heptapeptide according to the present invention as described above; and (2) a pharmaceutically acceptable carrier.

In yet another embodiment, the invention provides a pharmaceutical composition comprising:

(1) a therapeutically effective amount of a nucleotide sequence that encodes a polypeptide, polypeptide composition, such as an artificial transcription factor, or isolated heptapeptide according to the present invention as described above; and (2) a pharmaceutically acceptable carrier.

BRIEF DESCRIPTION OF THE DRAWINGS

The following invention will become better understood with reference to the specification, appended claims, and accompanying drawings, where:

DETAILED DESCRIPTION OF THE INVENTION

Definitions

Figure 1:
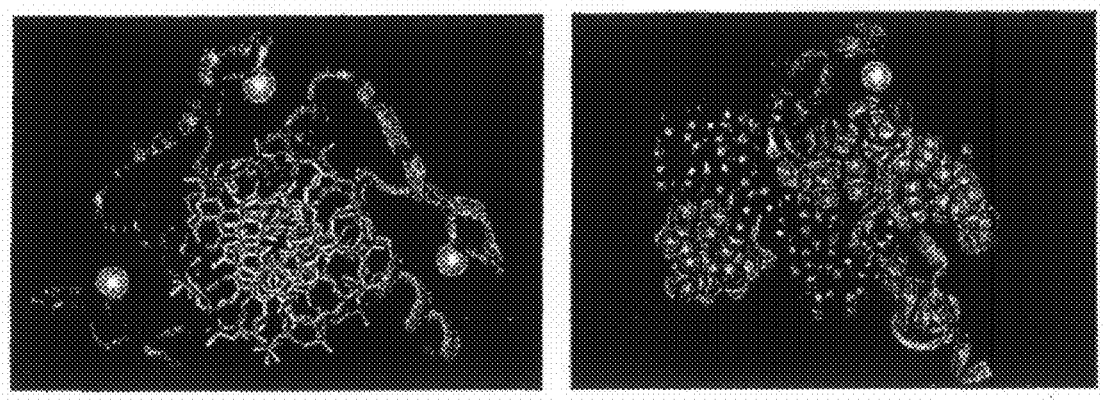
FIG. 1 is a model of the zinc finger-DNA complex of murine transcription factor Zif268.

Unless defined otherwise, all technical and scientific terms used herein have the same meaning as is commonly understood by one of skill in the art to which this invention belongs.

As used herein, the term "nucleic acid," "nucleic acid sequence," "polynucleotide," or similar terms, refers to a deoxyribonucleotide or ribonucleotide oligonucleotide or polynucleotide, including single- or double-stranded forms, and coding or non-coding (e.g., "antisense") forms The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically, such as zinc finger proteins. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031, 092; 6,001,982; 5,684,148; see also, WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug (Dev 6:153-156).

As used herein, the term "transcription regulating domain or factor" refers to the portion of the fusion polypeptide provided herein that functions to regulate gene transcription. Exemplary and preferred transcription repressor domains are ERD, KRAB, SID, Deacetylase, and derivatives, multimers and combinations thereof such as KRAB-ERD, SID-ERD, (KRAB)$_2$, (KRAB)$_3$, KRAB-A, (KRAB-A)$_2$, (SID)$_2$, (KRAB-A)-SID and SID-(KRAB-A). As used herein, the term "nucleotide binding domain or region" refers to the portion of a polypeptide or composition provided herein that provides specific nucleic acid binding capability. The nucleotide binding region functions to target a subject polypeptide to specific genes. As used herein, the term "operatively linked" means that elements of a polypeptide, for example, are linked such that each performs or functions as intended. For example, a repressor is attached to the binding domain in such a manner that, when bound to a target nucleotide via that binding domain, the repressor acts to inhibit or prevent transcription. Linkage between and among elements may be direct or indirect, such as via a linker. The elements are not necessarily adjacent. Hence a repressor domain can be linked to a nucleotide binding domain using any linking procedure well known in the art. It may be necessary to include a linker moiety between the two domains. Such a linker moiety is typically a short sequence of amino acid residues that provides spacing between the domains. So long as the linker does not interfere with any of the functions of the binding or repressor domains, any sequence can be used.

As used herein, the term "modulating" envisions the inhibition or suppression of expression from a promoter containing a zinc finger-nucleotide binding motif when it is overactivated, or augmentation or enhancement of expression from such a promoter when it is underactivated.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4th Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or Ile), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

As used herein, the term "expression vector" refers to a plasmid, virus, phagemid, or other vehicle known in the art that has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in a cell. The expression vector typically contains an origin of replication, a promoter, as well as specific genes that permit phenotypic selection of transformed cells.

As used herein, the term "host cells" refers to cells in which a vector can be propagated and its DNA expressed. The term also includes any progeny of the subject host cell. It is understood that all progeny may not be identical to the parental cell since there may be mutations that occur during replication. Such progeny are included when the term "host cell" is used. Methods of stable transfer where the foreign DNA is continuously maintained in the host are known in the art.

As used herein, genetic therapy involves the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor inhibitor thereof or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof. Genetic therapy may also involve delivery of an inhibitor or repressor or other modulator of gene expression.

As used herein, heterologous DNA is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease. Typically, DNA encoding a desired gene product is cloned into a plasmid vector and introduced by routine methods, such as calcium-phosphate mediated DNA uptake (see, (1981) Somat. Cell. Mol. Genet. 7:603-616) or microinjection, into producer cells, such as packaging cells. After amplification in producer cells, the vectors that contain the heterologous DNA are introduced into selected target cells.

As used herein, an expression or delivery vector refers to any plasmid or virus into which a foreign or heterologous DNA may be inserted for expression in a suitable host cell—i.e., the protein or polypeptide encoded by the DNA is synthesized in the host cell's system. Vectors capable of directing the expression of DNA segments (genes) encoding one or more proteins are referred to herein as "expression vectors". Also included are vectors that allow cloning of cDNA (complementary DNA) from mRNAs produced using reverse transcriptase.

As used herein, a gene refers to a nucleic acid molecule whose nucleotide sequence encodes an RNA or polypeptide. A gene can be either RNA or DNA. Genes may include regions preceding and following the coding region (leader and trailer) as well as intervening sequences (introns) between individual coding segments (exons).

As used herein, the term "isolated" with reference to a nucleic acid molecule or polypeptide or other biomolecule means that the nucleic acid or polypeptide has been separated from the genetic environment from which the polypeptide or nucleic acid were obtained. It may also mean that the biomolecule has been altered from the natural state. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compound can be substantially purified by the one-step method described in Smith et al. (1988) Gene 67:3140. The terms isolated and purified are sometimes used interchangeably.

Thus, by "isolated" is meant that the nucleic acid is free of the coding sequences of those genes that, in a naturally-occurring genome immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

"Isolated" or "purified" as those terms are used to refer to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. Particularly for proteins, the procedures may include for example, but are not limited to, ammonium sulfate fractionation, gel filtration, ion exchange change chromatography, affinity chromatography, density gradient centrifugation, electrofocusing, chromatofocusing, and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

As used herein, "modulate" refers to the suppression, enhancement or induction of a function. For example, zinc finger-nucleic acid binding domains and variants thereof may modulate a promoter sequence by binding to a motif within the promoter, thereby enhancing or suppressing transcription of a gene operatively linked to the promoter cellular nucleotide sequence. Alternatively, modulation may include inhibition of transcription of a gene where the zinc finger-nucleotide binding polypeptide variant binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript.

As used herein, the term "inhibit" refers to the suppression of the level of activation of transcription of a structural gene operably linked to a promoter. For example, for the methods herein the gene includes a zinc finger-nucleotide binding motif.

As used herein, the term "transcriptional regulatory region" refers to a region that drives gene expression in the target cell. Transcriptional regulatory regions suitable for use herein include but are not limited to the human cytomegalovirus (CMV) immediate-early enhancer/promoter, the SV40 early enhancer/promoter, the JC polyoma virus promoter, the albumin promoter, PGK and the α-actin promoter coupled to the CMV enhancer. Other transcriptional regulatory regions are also known in the art.

As used herein, a promoter region of a gene includes the regulatory element or elements that typically Ile 5' to a structural gene; multiple regulatory elements can be present, separated by intervening nucleotide sequences. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or, for example, an onco-promoter. An onco-promoter is generally a virus-derived promoter. Viral promoters to which zinc finger DNA binding polypeptides may be targeted include, but are not limited to, retroviral long terminal repeats (LTRs), and Lentivirus promoters, such as promoters from human T-cell lymphotrophic virus (HTLV) 1 and 2 and human immunodeficiency virus (HIV) 1 or 2. An example of a zinc finger binding polypeptide that includes a TNN-specific zinc finger DNA binding domain that represses transcription from the HIV-1 LTR is provided in Example 12, below.

As used herein, the term "effective amount" includes that amount that results in the deactivation of a previously activated promoter or that amount that results in the inactivation of a promoter containing a zinc finger-nucleotide binding motif, or that amount that blocks transcription of a structural gene or translation of RNA. The amount of zinc finger derived-nucleotide binding polypeptide required is that amount necessary to either displace a native zinc finger-nucleotide binding protein in an existing protein/promoter complex, or that amount necessary to compete with the native zinc finger-nucleotide binding protein to form a complex with the promoter itself. Similarly, the amount required to block a structural gene or RNA is that amount which binds to and blocks RNA polymerase from reading through on the gene or that amount which inhibits translation, respectively. Preferably, the method is performed intracellularly. By functionally inactivating a promoter or structural gene, transcription or translation is suppressed. Delivery of an effective amount of the inhibitory protein for binding to or "contacting" the cellular nucleotide sequence containing the zinc finger-nucleotide binding protein motif, can be accomplished by one of the mechanisms described herein, such as by retroviral vectors or liposomes, or other methods well known in the art.

As used herein, the term "truncated" refers to a zinc finger-nucleotide binding polypeptide derivative that contains less than the full number of zinc fingers found in the native zinc finger binding protein or that has been deleted of non-desired sequences. For example, truncation of the zinc finger-nucleotide binding protein TFIIIA, which naturally contains nine zinc fingers, might result in a polypeptide with only zinc fingers one through three. The term "expansion" refers to a zinc finger polypeptide to which additional zinc finger modules have been added. For example, TFIIIA can be expanded to 12 fingers by adding 3 zinc finger domains. In addition, a truncated zinc finger-nucleotide binding polypeptide may include zinc finger modules from more than one wild type polypeptide, thus resulting in a "hybrid" zinc finger-nucleotide binding polypeptide.

As used herein, the term "mutagenized" refers to a zinc finger derived-nucleotide binding polypeptide that has been obtained by performing any of the known methods for accomplishing random or site-directed mutagenesis of the DNA encoding the protein. For instance, in TFIIIA, mutagenesis can be performed to replace nonconserved residues in one or more of the repeats of the consensus sequence. Truncated or expanded zinc finger-nucleotide binding proteins can also be mutagenized.

As used herein, a polypeptide "variant" or "derivative" refers to a polypeptide that is a mutagenized form of a polypeptide or one produced through recombination but that still retains a desired activity, such as the ability to bind to a ligand or a nucleic acid molecule or to modulate transcription.

As used herein, a zinc finger-nucleotide binding polypeptide "variant" or "derivative" refers to a polypeptide that is a mutagenized form of a zinc finger protein or one produced through recombination. A variant may be a hybrid that contains zinc finger domain(s) from one protein linked to zinc finger domain(s) of a second protein, for example. The domains may be wild type or mutagenized. A "variant" or "derivative" can include a truncated form of a wild type zinc finger protein, which contains fewer than the original number of fingers in the wild type protein. Examples of zinc finger-nucleotide binding polypeptides from which a derivative or variant may be produced include TFIIIA and zif268. Similar terms are used to refer to "variant" or "derivative" nuclear hormone receptors and "variant" or "derivative" transcription effector domains.

As used herein a "zinc finger-nucleotide binding target or motif" refers to any two or three-dimensional feature of a nucleotide segment to which a zinc finger-nucleotide binding derivative polypeptide binds with specificity. Included within this definition are nucleotide sequences, generally of five nucleotides or less, as well as the three dimensional aspects of the DNA double helix, such as, but are not limited to, the major and minor grooves and the face of the helix. The motif is typically any sequence of suitable length to which the zinc finger polypeptide can bind. For example, a three finger polypeptide binds to a motif typically having about 9 to about 14 base pairs. Preferably, the recognition sequence is at least about 16 base pairs to ensure specificity within the genome. Therefore, zinc finger-nucleotide binding polypeptides of any specificity are provided. The zinc finger binding motif can be any sequence designed empirically or to which the zinc finger protein binds. The motif may be found in any DNA or RNA sequence, including regulatory sequences, exons, introns, or any non-coding sequence.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier. Vectors include, but are not necessarily limited to, expression vectors.

As used herein with regard to nucleic acid molecules, including DNA fragments, the phrase "operatively linked" means the sequences or segments have been covalently joined, preferably by conventional phosphodiester bonds, into one strand of DNA, whether in single or double-stranded form such that operatively linked portions function as intended. The choice of vector to which transcription unit or a cassette provided herein is operatively linked depends directly, as is well known in the art, on the functional properties desired, e.g., vector replication and protein expression, and the host cell to be transformed, these being limitations inherent in the art of constructing recombinant DNA molecules.

As used herein, administration of a therapeutic composition can be effected by any means, and includes, but is not limited to, oral, subcutaneous, intravenous, intramuscular, intrasternal, infusion techniques, intraperitoneal administration and parenteral administration.

I. The Invention

The present invention provides zinc finger-nucleotide binding polypeptides, compositions containing one or more such polypeptides, polynucleotides that encode such polypeptides and compositions, expression vectors containing such polynucleotides, cells transformed with such polynucleotides or expression vectors and the use of the polypeptides, compositions, polynucleotides and expression vectors for modulating nucleotide structure and/or function.

II. Polypeptides

The present invention provides an isolated and purified zinc finger nucleotide binding polypeptide. The polypeptide contains a nucleotide binding region of from 5 to 10 amino acid residues and, preferably about 7 amino acid residues. Typically, the nucleotide binding region is a sequence of seven amino acids, referred to herein as a "domain," that is predominantly α-helical in its conformation. The structure of this domain is described below in further detail. However, the nucleotide binding region can be flanked by up to five amino acids on each side and the term "domain," as used herein, includes these additional amino acids. The nucleotide binding region binds preferentially to a target nucleotide of the formula TNN, where N is A, C, G or T. Preferably, the target nucleotide has the formula TAN, TCN, TGN, TTN, TNA, TNC, TNG or TNT. More preferably, the target nucleotide has the formula TAA, TAC, TAG, TAT, TCA, TCC, TCG, TCT, TGA, TGC, TGG, TGT, TTA, TTC, TTG or TTT.

A polypeptide of this invention is a non-naturally occurring variant. As used herein, the term "non-naturally occurring" means, for example, one or more of the following: (a) a polypeptide comprised of a non-naturally occurring amino acid sequence; (b) a polypeptide having a non-naturally occurring secondary structure not associated with the polypeptide as it occurs in nature; (c) a polypeptide which includes one or more amino acids not normally associated with the species of organism in which that polypeptide occurs in nature; (d) a polypeptide which includes a stereoisomer of one or more of the amino acids comprising the polypeptide, which stereoisomer is not associated with the polypeptide as it occurs in nature; (e) a polypeptide which includes one or more chemical moieties other than one of the natural amino acids; or (f) an isolated portion of a naturally occurring amino acid sequence (e.g., a truncated sequence). A polypeptide of this invention exists in an isolated form and purified to be substantially free of contaminating substances. The polypeptide can be isolated and purified from natural sources; alternatively, the polypeptide can be made de novo using techniques well known in the art such as genetic engineering or solid-phase peptide synthesis. A zinc finger-nucleotide binding polypeptide refers to a polypeptide that is, preferably, a mutagenized form of a zinc finger protein or one produced through recombination. A polypeptide may be a hybrid which contains zinc finger domain(s) from one protein linked to zinc finger domain(s) of a second protein, for example. The domains may be wild type or mutagenized. A polypeptide can include a truncated form of a wild type zinc finger protein.

Examples of zinc finger proteins from which a polypeptide can be produced include SP1C, TFIIIA and Zif268, as well as C7 (a derivative of Zif268) and other zinc finger proteins known in the art. These zinc finger proteins from which other zinc finger proteins are derived are referred to herein as "backbones" or "scaffolds".

A zinc finger-nucleotide binding polypeptide of this invention comprises a unique heptamer (contiguous sequence of 7 amino acid residues) within the α-helical domain of the polypeptide, which heptameric sequence determines binding specificity to a target nucleotide. That heptameric sequence can be located anywhere within the α-helical domain but it is preferred that the heptamer extend from position −1 to position 6 as the residues are conventionally numbered in the art. A polypeptide of this invention can include any β-sheet and framework sequences known in the art to function as part of a zinc finger protein. A large number of zinc finger-nucleotide binding polypeptides were made and tested for binding specificity against target nucleotides containing a TNN triplet.

The zinc finger-nucleotide binding polypeptide derivative can be derived or produced from a wild type zinc finger protein by truncation or expansion, or as a variant of the wild type-derived polypeptide by a process of site directed mutagenesis, or by a combination of the procedures. In addition, a truncated zinc finger-nucleotide binding polypeptide may include zinc finger modules from more than one wild type polypeptide, thus resulting in a "hybrid" zinc finger-nucleotide binding polypeptide.

The term "mutagenized" refers to a zinc finger derived-nucleotide binding polypeptide that has been obtained by performing any of the known methods for accomplishing random or site-directed mutagenesis of the DNA encoding the protein. For instance, in TFIIIA, mutagenesis can be performed to replace nonconserved residues in one or more of the repeats of the consensus sequence. Truncated zinc finger-nucleotide binding proteins can also be mutagenized. Examples of known zinc finger-nucleotide binding polypeptides that can be truncated, expanded, and/or mutagenized according to the present invention in order to inhibit the function of a nucleotide sequence containing a zinc finger-nucleotide binding motif includes TFIIIA and Zif268. Those of skill in the art know other zinc finger-nucleotide binding proteins.

Typically, the binding region has seven amino acid residues and has an α-helical structure.

In addition, the polypeptides of the present invention can be incorporated within longer polypeptides. Some examples of this are described below, when the polypeptides are used to create artificial transcription factors. In general, though, the polypeptides can be incorporated into longer fusion proteins and retain their specific DNA binding activity. These fusion proteins can include various additional domains as are known in the art, such as purification tags, enzyme domains, or other domains, without significantly altering the specific DNA-binding activity of the zinc finger polypeptides. In one example, the polypeptides can be incorporated into two halves of a split enzyme like a β-lactamase to allow the sequences to be sensed in cells or in vivo. Binding of two halves of such a split enzyme then allows for assembly of the split enzyme (J. M. Spotts et al. "Time-Lapse Imaging of a Dynamic Phosphorylation Protein-Protein Interaction in Mammalian Cells," *Proc. Natl. Acad. Sci.* USA 99: 15142-15147 (2002)). In another example, multiple zinc finger domains according to the present invention can be tandemly linked to form polypeptides that have specific binding affinity for longer DNA sequences. This is described further below. Specifically, the polypeptide can be operatively linked to at least one other zinc finger nucleotide binding polypeptide binding preferentially to a target nucleotide of the formula ANN, CNN, or GNN, where N is A, C, G, or T. Alternatively, the polypeptide can be operatively linked to one or more transcription regulating factors.

A polypeptide of this invention can be made using a variety of standard techniques well known in the art. As disclosed in detail hereinafter in the Examples, phage display libraries of zinc finger proteins were created and selected under conditions that favored enrichment of sequence specific proteins. Zinc finger domains recognizing a number of sequences required refinement by site-directed mutagenesis that was guided by both phage selection data and structural information.

Previously we reported the characterization of 16 zinc finger domains specifically recognizing each of the 5'-(GNN)-3' type of DNA sequences, that were isolated by phage display selections based on C7, a variant of the mouse transcription factor Zif268 and refined by site-directed mutagenesis [Segal et al., (1999) Proc Natl Acad Sci USA 96(6), 2758-2763; Dreier et al., (2000) J. Mol. Biol. 303, 489-502; and U.S. Pat. No. 6,140,081, the disclosure of which is incorporated herein by reference]. In general, the specific DNA recognition of zinc finger domains of the $Cys_2$-$His_2$ type is mediated by the amino acid residues -1, 3, and 6 of each α-helix, although not in every case are all three residues contacting a DNA base. One dominant cross-subsite interaction has been observed from position 2 of the recognition helix. $Asp^2$ has been shown to stabilize the binding of zinc finger domains by directly contacting the complementary adenine or cytosine of the 5'-thymine or guanine, respectively, of the following 3 bp subsite. These non-modular interactions have been described as target site overlap. In addition, other interactions of amino acids with nucleotides outside the 3 bp subsites creating extended binding sites have been reported [Pavletich et al., (1991) Science 252(5007), 809-817; Elrod-Erickson et al., (1996) Structure 4(10), 1171-1180; Isalan et al., (1997) Proc Natl Acad Sci USA 94(11), 5617-5621].

Some of the generalizations of sequences of zinc finger domains binding particular DNA triplets obtained from results on a large number of zinc finger domains are shown in Table 1, below. In general, the -1-amino acid of a zinc finger domain is primarily responsible for the specification of the 3'-nucleotide of a triplet site, the 3-amino acid of a zinc finger domain is primarily responsible for the specification of the middle nucleotide of a triplet site, and the 6-amino acid of a zinc finger domain is primarily responsible for the specification of the 5'-nucleotide of a triplet site. These generalizations are used below to construct additional zinc fingers based on the zinc fingers that are described in Example 1.

TABLE 1

Protein/DNA-Interactions of Zinc finger domains (D. J. Segal, B. Dreier, R. R. Beerli, C. F. Barbas III, Proc. Natl. Acad. Sci. USA 1999, 96, 2758-2763.)

| | Position within the triplet | | |
|---|---|---|---|
| Nucleotide | 5' | Middle | 3' |
| Adenine | Nd | Asn | Gln |
| Cytosine | Nd | Thr, Asp, Glu | Asp, Glu |
| Guanine | Arg | His, Lys | Arg |
| Thymine | Nd | Ser, Ala | Thr, Ser |

Selection of the previously reported phage display library for zinc finger domains binding to 5' nucleotides other than guanine or thymine met with no success, due to the cross-subsite interaction from aspartate in position 2 of the finger-3 recognition helix RSD-E-LKR (SEQ ID NO: 413) to extend the availability of zinc finger domains for the construction of artificial transcription factors, domains specifically recognizing the 5'-(ANN)-3' type of DNA sequences were selected (U.S. patent application Ser. No. 09/791,106, filed Feb. 21, 2001, the disclosure of which is incorporated herein by reference). Other groups have described a sequential selection method which led to the characterization of domains recognizing four 5'-(ANN)-3' subsites, 5'-(AAA)-3', 5'-(AAG)-3', 5'-(ACA)-3', and 5'-(ATA)-3' [Greisman et al., (1997) Science 275(5300), 657-661; Wolfe et al., (1999) J Mol Biol 285(5), 1917-1934]. The present disclosure uses an approach to select zinc finger domains recognizing TNN sites by eliminating the target site overlap.

Based on the 3-finger protein C7.GAT, a library was previously constructed in the phage display vector pComb3H [Barbas et al., (1991) Proc. Natl. Acad. Sci. USA 88, 7978-7982; Rader et al., (1997) Curr. Opin. Biotechnol. 8(4), 503-508]. Randomization involved positions -1, 1, 2, 3, 5, and 6 of the α-helix of finger 2 using a VNS codon doping strategy (V=adenine, cytosine or guanine, N=adenine, cytosine, guanine or thymine, S=cytosine or guanine). This allowed 24 possibilities for each randomized amino acid position, whereas the aromatic amino acids Trp, Phe, and Tyr, as well as stop codons, were excluded in this strategy. Because Leu is predominately found in position 4 of the recognition helices of zinc finger domains of the type $Cys_2$-$His_2$ this position was not randomized. After transformation of the library into ER2537 cells (New England Biolabs) the library contained $1.5 \times 10^9$ members. This exceeded the necessary library size by 60-fold and was sufficient to contain all amino acid combinations.

Previously, with respect to zinc finger domains binding sequences of the form 5'-(CNN)-3', six rounds of selection of zinc finger-displaying phage were performed binding to each of the sixteen 5'-GAT-CNN-GCG-3' (SEQ ID NO. 369) biotinylated hairpin target oligonucleotides, respectively, in the presence of non-biotinylated competitor DNA. Stringency of the selection was increased in each round by decreasing the amount of biotinylated target oligonucleotide and increasing amounts of the competitor oligonucleotide mixtures. In the sixth round the target concentration was usually 18 nM, 5'-(ANN)-3', 5'-(GNN)-3', and 5'-(TNN)-3' competitor mixtures were in 5-fold excess for each oligonucleotide pool, respectively, and the specific 5'-(CNN)-3' mixture (excluding the target sequence) in 10-fold excess. Phage binding to the biotinylated target oligonucleotide was recovered by capture to streptavidin-coated magnetic beads. Clones were usually analyzed after the sixth round of selection. A similar selection process can be used for the selection of zinc finger domains binding specifically to sequences of the form 5'-(TNN)-3'. This process is described below in Example 1.

These results provide a number of guidelines for the determination of sequences within the present invention to one of ordinary skill in the art Some of these guidelines are also useful for selection of zinc finger domains specifically binding sequences of the form 5'-(TNN)-3'. These guidelines include the following: (1) It is preferred that Gln, Asn, or Ser be at position -1 when the subsite is 5'-TAA-3' (2) It is preferred that Ser be at position -1 when the subsite is 5'-TCA-3'. (3) It is generally preferred to have Arg, Asn, Gln, His, Ser, Thr or Ile at position -1 when the target subsite has a 3'-guanine, with Arg particularly preferred. (4) It is generally preferred to have Asp at position 2 for binding to 5'-TNG-3' subsites. (5) For binding to the subsite 5'-TNT-3', Arg, Asn, Gln, His, Ser, Thr, Ala, and Cys are generally preferred at position −1. (6) For subsites containing a 3'-cytosine, Gln, Asn, Ser, Gly, His, or Asp are typically preferred in position −1. (7) For the recognition of 5'-TAN-3' (i.e., a middle adenine), His, Asn, Gly, Val, Pro, Ile, and Lys are typically preferred in position 3; Asn is strongly preferred. (8) Thr or Asp are particularly preferred in position 3 of the helix that recognized 5'-TCN-3' subsites (i.e., a middle cytosine), but His, Lys, Arg, and Asn can also be accommodated. (9) For the target site 5'-TCC-3', position 3 is preferably Asn or His. (10) For the target site 5'-TCG-3', position 3 is preferably either Thr or His. (11) For the target site 5'-TGN-3', His is preferred at position 3. (12) For target sites 5'-TG(G/T)-3', Ser, Asp, Thr, Asn, Gln and Gly are preferred at position 3; His is also possible. (13) For the target site 5'-TGC-3' Trp and Thr are typically preferred at position 3; His is also possible. (14) In general, a middle guanine in 5'-TGN-3' can be recognized by His at position 3. (15) For the target site 5'-TTN-3', position 3 is preferably either Ser or Ala, except for 5'-TTC-3' and 5'-TTT-3' where His is preferred. (16) Positions 1, 2, and 5 can vary widely. (17) For recognition of a 3' adenine, Gln is typically preferred at position −1. (18) For recognition of a 3' guanine, Arg is typically preferred at position −1. (19) For recognition of a 3' thymine, Ser, Thr, or His is typically preferred at position −1. These are only guidelines, and the secondary or tertiary structure of a protein or polypeptide incorporating a zinc finger domain according to the present invention can lead to different amino acids being preferred for recognition of particular subsites or particular nucleotides at a defined position of such subsites. Additionally, the conformation of a particular zinc finger moiety within a protein having a plurality of zinc finger moieties can affect the binding.

Other amino acid residues are also subject to mutation or substitution. For example, leucine is often located in position 4 of the seven-amino acid domain and packs into the hydrophobic core of the protein. Accordingly, the leucine in position 4 can be replaced with other relatively small hydrophobic residues, such as valine and isoleucine, without disturbing the three-dimensional structure or function of the protein. Alternatively, the leucine in position 4 can also be replaced with other hydrophobic residues such as phenylalanine or tryptophan.

Other amino acid substitutions are possible. For example, substitution can occur among His, Lys, Arg, Asn, Asp and Thr for position 3 of the helix when the triplet site has a C in the middle position. When G is in the middle position of the triplet, His is a possibility for position 3 of the helix and can replace another amino acid there. When the last two bases of the triplet are CO or CC, Ser, Asp, Thr, Asn, Gln and Gly are alternatives at position 3 and can replace another amino acid there. When the last two bases of the triplet are GC, Trp and Thr are alternatives at position 3 and can replace another amino acid there. When the middle base of the triplet is T, alternatives for position 3 of the helix include Ser, Ala, and possibly His; these amino acid residues can replace another amino acid in position 3 of the helix. Cys is also an alternative for position 4, particularly when Leu was present there.

The following table (Table 2) describes a potentially useful range of amino acid substitutions assuming that the 5'-base is T.

TABLE 2

| Middle Base | 3' Base | Zinc Finger Amino Acid Position | Amino Acid Alternatives |
|---|---|---|---|
| A | A | −1 | Q, N, S |
| C | A | −1 | S |
| N | G | −1 | R, N, Q, H, S, T, I |
| N | G | 2 | D |
| N | T | −1 | R, N, Q, H, S, T, A, C |
| N | C | −1 | Q, N, S, G, H, D |
| A | N | 3 | H, N, G, V, P, I, K |
| C | N | 3 | T, D, H, K, R, N |
| C | C | 3 | N, H, S, D, T, Q, G |
| C | G | 3 | T, H, S, D, N, Q, G |
| G | N | 3 | H |
| G | G/T | 3 | S, D, T, N, Q, G, H |
| G | C | 3 | W, T, H |
| G | N | 3 | H |
| T | A/G | 3 | S, A |
| T | C/T | 3 | H |
| N | A | −1 | R |
| N | T | −1 | S, T, H |
| N | N | 4 | L, V, I, C |

In Table 2, particularly preferred amino acids are underlined "N" is any of the four possible naturally-occurring nucleotides (A, C, G, or T).

Additionally, Example 12 provides an additional zinc finger domain, RGG-W-LQA (SEQ ID NO: 46) that binds the triplet 5'-TCT-3'. This zinc finger domain is within a six-finger DNA binding sequence of an artificial transcription factor that targets the highly-conserved primer-binding site of HIV-1 and that binds the overall DNA sequence of 5'-AAATCTCTAGCAGTGGCG-3' (SEQ ID NO: 425) (Example 12, Table 13).

Accordingly, preferred zinc finger domains included in polypeptides according to the present invention and binding sequences of the form 5'-(TNN)-3' include the following:

```
(1)    QAS-N-LIS    (SEQ ID NO: 1)    (binding to 5'-TAA-3')

(2)    SRG-N-LKS    (SEQ ID NO: 2)    (binding to 5'-TAC-3')

(3)    RLD-N-LQT    (SEQ ID NO: 3)    (binding to 5'-TAG-3')

(4)    ARG-N-LRT    (SEQ ID NO: 4)    (binding to 5'-TAT-3')

(5)    RKD-A-LRG    (SEQ ID NO: 5)    (binding to 5'-TTG-3')

(6)    RED-N-LHT    (SEQ ID NO: 6)    (binding to 5'-TAG-3')

(7)    ARG-N-LKS    (SEQ ID NO: 7)    (binding to 5'-TAC-3')

(8)    RSD-N-LTT    (SEQ ID NO: 8)    (binding to 5'-TAC-3')

(9)    VRG-N-LKS    (SEQ ID NO: 9)    (binding to 5'-TAT-3')
```

-continued

```
(10)  VRG-N-LRT   (SEQ ID NO: 10)  (binding to 5'-TAT-3')
(11)  RLR-A-LDR   (SEQ ID NO: 11)  (binding to 5'-TCG-3')
(12)  DMG-A-LEA   (SEQ ID NO: 12)  (binding to 5'-TCG-3')
(13)  EKD-A-LRG   (SEQ ID NO: 13)  (binding to 5'-TTG-3')
(14)  RSD-H-LTT   (SEQ ID NO: 14)  (binding to 5'-TCA-3')
(15)  AQQ-L-LMW   (SEQ ID NO: 15)  (binding to 5'-TCA-3')
(16)  RSD-E-RKR   (SEQ ID NO: 16)  (binding to 5'-TCG-3')
(17)  DYQ-S-LRQ   (SEQ ID NO: 17)  (binding to 5'-TCG-3')
(18)  CFS-R-LVR   (SEQ ID NO: 18)  (binding to 5'-TCC-3')
(19)  GDG-G-LWE   (SEQ ID NO: 19)  (binding to 5'-TCG-3')
(20)  LQR-P-LRG   (SEQ ID NO: 20)  (binding to 5'-TCG-3')
(21)  QGL-A-CAA   (SEQ ID NO: 21)  (binding to 5'-TCG-3')
(22)  WVG-W-LGS   (SEQ ID NO: 22)  (binding to 5'-TCT-3')
(23)  RLR-D-IQF   (SEQ ID NO: 23)  (binding to 5'-TCT-3')
(24)  GRS-Q-LSC   (SEQ ID NO: 24)  (binding to 5'-TGT-3')
(25)  GWQ-R-LLT   (SEQ ID NO: 25)  (binding to 5'-TGA-3')
(26)  SGR-P-LAS   (SEQ ID NO: 26)  (binding to 5'-TGA-3')
(27)  APR-L-LGP   (SEQ ID NO: 27)  (binding to 5'-TGA-3')
(28)  APK-A-LGW   (SEQ ID NO: 28)  (binding to 5'-TGG-3')
(29)  SVH-E-LQG   (SEQ ID NO: 29)  (binding to 5'-TGG-3')
(30)  AQA-A-LSW   (SEQ ID NO: 30)  (binding to 5'-TGC-3')
(31)  GAN-A-LRR   (SEQ ID NO: 31)  (binding to 5'-TCA-3')
(32)  QSL-L-LGA   (SEQ ID NO: 32)  (binding to 5'-TCA-3')
(33)  HRG-T-LGG   (SEQ ID NO: 33)  (binding to 5'-TCA-3')
(34)  QVG-L-LAR   (SEQ ID NO: 34)  (binding to 5'-TCC-3')
(35)  GAR-G-LRG   (SEQ ID NO: 35)  (binding to 5'-TGG-3')
(36)  DKH-M-LDT   (SEQ ID NO: 36)  (binding to 5'-TCC-3')
(37)  DLG-G-LRQ   (SEQ ID NO: 37)  (binding to 5'-TCC-3')
(38)  QCY-R-LER   (SEQ ID NO: 38)  (binding to 5'-TGG-3')
(39)  AEA-E-LQR   (SEQ ID NO: 39)  (binding to 5'-TCT-3')
(40)  QGG-V-LAA   (SEQ ID NO: 40)  (binding to 5'-TGT-3')
(41)  QGR-C-LVT   (SEQ ID NO: 41)  (binding to 5'-TGA-3')
(42)  HPE-A-LDN   (SEQ ID NO: 42)  (binding to 5'-TGA-3')
(43)  GRG-A-LQA   (SEQ ID NO: 43)  (binding to 5'-TGG-3')
(44)  LAS-R-LQQ   (SEQ ID NO: 44)  (binding to 5'-TGC-3')
(45)  RED-N-LIS   (SEQ ID NO: 45)  (binding to 5'-TAG-3')
(46)  RGG-W-LQA   (SEQ ID NO: 46)  (binding to 5'-TGT-3')
```

Of these, SEQ ID NO: 1, SEQ ID NO: 2, SEQ ID NO: 3, SEQ ID NO: 4, SEQ ID NO: 5, and SEQ ID NO: 6 are particularly preferred.

The following amino acid sequences of zinc finger domains are derived from those of SEQ ID NO: 1 through SEQ ID NO: 46 by the rules of general applicability for substitution of amino acids set forth above in Table 1. These include SEQ ID NO: 359 through SEQ ID NO: 411, which are derived from RGG-W-LQA (SEQ ID NO: 46) from Example 12. Accordingly, these sequences are within the scope of the invention and polypeptides incorporating these sequences and binding the specified nucleotide triplet sequences are also within the scope of the invention. The triplets bound by each of these sequences are in brackets. These sequences are:

| | | | |
|---|---|---|---|
| (47) | DAS-N-LIS | (SEQ ID NO: 47) | [TAC] |
| (48) | EAS-N-LIS | (SEQ ID NO: 48) | [TAC] |
| (49) | RAS-N-LIS | (SEQ ID NO: 49) | [TAG] |
| (50) | TAS-N-LIS | (SEQ ID NO: 50) | [TAT] |
| (51) | SAS-N-LIS | (SEQ ID NO: 51) | [TAT] |
| (52) | QAS-T-LIS | (SEQ ID NO: 52) | [TCA] |
| (53) | QAS-D-LIS | (SEQ ID NO: 53) | [TCA] |
| (54) | QAS-E-LIS | (SEQ ID NO: 54) | [TCA] |
| (55) | QAS-H-LIS | (SEQ ID NO: 55) | [TGA] |
| (56) | QAS-K-LIS | (SEQ ID NO: 56) | [TGA] |
| (57) | QAS-S-LIS | (SEQ ID NO: 57) | [TTA] |
| (58) | QAS-A-LIS | (SEQ ID NO: 58) | [TTA] |
| (59) | DAS-T-L1S | (SEQ ID NO: 59) | [TCC] |
| (60) | DAS-D-LIS | (SEQ ID NO: 60) | [TCC] |
| (61) | DAS-E-LIS | (SEQ ID NO: 61) | [TCC] |
| (62) | DAS-H-LIS | (SEQ ID NO: 62) | [TGC] |
| (63) | DAS-K-LIS | (SEQ ID NO: 63) | [TGC] |
| (64) | DAS-S-LIS | (SEQ ID NO: 64) | [TTC] |
| (65) | DAS-A-LIS | (SEQ ID NO: 65) | [TTC] |
| (66) | EAS-T-LIS | (SEQ ID NO: 66) | [TCC] |
| (67) | EAS-D-LIS | (SEQ ID NO: 67) | [TCC] |
| (68) | EAS-E-LIS | (SEQ ID NO: 68) | [TCC] |
| (69) | EAS-H-LIS | (SEQ ID NO: 69) | [TGC] |
| (70) | EAS-K-LIS | (SEQ ID NO: 70) | [TGC] |
| (71) | EAS-S-LIS | (SEQ ID NO: 71) | [TTC] |
| (72) | EAS-A-LIS | (SEQ ID NO: 72) | [TTC] |
| (73) | RAS-T-LIS | (SEQ ID NO: 73) | [TCG] |
| (74) | RAS-D-LIS | (SEQ ID NO: 74) | [TCG] |
| (75) | RAS-E-LIS | (SEQ ID NO: 75) | [TCG] |
| (76) | RAS-H-LIS | (SEQ ID NO: 76) | [TGG] |
| (77) | RAS-K-LIS | (SEQ ID NO: 77) | [TGG] |
| (78) | RAS-S-LIS | (SEQ ID NO: 78) | [TTG] |
| (79) | RAS-A-LIS | (SEQ ID NO: 79) | [TTG] |
| (80) | TAS-T-LIS | (SEQ ID NO: 80) | [TCT] |
| (81) | TAS-D-LIS | (SEQ ID NO: 81) | [TCT] |
| (82) | TAS-E-LIS | (SEQ ID NO: 82) | [TCT] |
| (83) | TAS-H-LIS | (SEQ ID NO: 83) | [TGT] |
| (84) | TAS-K-LIS | (SEQ ID NO: 84) | [TGT] |
| (85) | TAS-S-LIS | (SEQ ID NO: 85) | [TTT] |
| (86) | TAS-A-LIS | (SEQ ID NO: 86) | [TTT] |
| (87) | SAS-T-LIS | (SEQ ID NO: 87) | [TCT] |
| (88) | SAS-D-LIS | (SEQ ID NO: 88) | [TCT] |
| (89) | SAS-E-LIS | (SEQ ID NO: 89) | [TCT] |
| (90) | SAS-H-LIS | (SEQ ID NO: 90) | [TGT] |
| (91) | SAS-K-LIS | (SEQ ID NO: 91) | [TGT] |
| (92) | SAS-S-LIS | (SEQ ID NO: 92) | [TTT] |
| (93) | SAS-A-LIS | (SEQ ID NO: 93) | [TTT] |
| (94) | QLD-N-LQT | (SEQ ID NO: 94) | [TAA] |
| (95) | DLD-N-LQT | (SEQ ID NO: 95) | [TAC] |
| (96) | ELD-N-LQT | (SEQ ID NO: 96) | [TAC] |
| (97) | TLD-N-LQT | (SEQ ID NO: 97) | [TAT] |
| (98) | SLD-N-LQT | (SEQ ID NO: 99) | [TAT] |
| (99) | RLD-T-LQT | (SEQ ID NO: 99) | [TCG] |
| (100) | RLD-D-LQT | (SEQ ID NO: 100) | [TCG] |
| (101) | RLD-E-LQT | (SEQ ID NO: 101) | [TCG] |
| (102) | RLD-H-LQT | (SEQ ID NO: 102) | [TGG] |
| (103) | RLD-K-LQT | (SEQ ID NO: 103) | [TGG] |
| (104) | RLD-S-LQT | (SEQ ID NO: 104) | [TTG] |
| (105) | RLD-A-LQT | (SEQ ID NO: 105) | [TTG] |
| (106) | QLD-T-LQT | (SEQ ID NO: 106) | [TCA] |
| (107) | QLD-D-LQT | (SEQ ID NO: 107) | [TCA] |
| (108) | QLD-E-LQT | (SEQ ID NO: 108) | [TCA] |
| (109) | QLD-H-LQT | (SEQ ID NO: 109) | [TGA] |
| (110) | QLD-K-LQT | (SEQ ID NO: 110) | [TGA] |
| (111) | QLD-S-LQT | (SEQ ID NO: 111) | [TTA] |
| (112) | QLD-A-LQT | (SEQ ID NO: 112) | [TTA] |
| (113) | DLD-T-LQT | (SEQ ID NO: 113) | [TCG] |
| (114) | DLD-D-LQT | (SEQ ID NO: 114) | [TCC] |
| (115) | DLD-E-LQT | (SEQ ID NO: 115) | [TCC] |
| (116) | DLD-H-LQT | (SEQ ID NO: 116) | [TGC] |
| (117) | DLD-K-LQT | (SEQ ID NO: 117) | [TGC] |
| (118) | DLD-S-LQT | (SEQ ID NO: 118) | [TTC] |
| (119) | DLD-A-LQT | (SEQ ID NO: 119) | [TTC] |
| (120) | ELD-T-LQT | (SEQ ID NO: 120) | [TCC] |
| (121) | ELD-D-LQT | (SEQ ID NO: 121) | [TCC] |
| (122) | ELD-E-LQT | (SEQ ID NO: 122) | [TCC] |
| (123) | ELD-H-LQT | (SEQ ID NO: 123) | [TGC] |
| (124) | ELD-K-LQT | (SEQ ID NO: 124) | [TGC] |

-continued

| | | | |
|---|---|---|---|
| (125) | ELD-S-LQT | (SEQ ID NO: 125) | [TTC] |
| (126) | ELD-A-LQT | (SEQ ID NO: 126) | [TTC] |
| (127) | TLD-T-LQT | (SEQ ID NO: 127) | [TCT] |
| (128) | TLD-D-LQT | (SEQ ID NO: 128) | [TCT] |
| (129) | TLD-E-LQT | (SEQ ID NO: 129) | [TCT] |
| (130) | TLD-H-LQT | (SEQ ID NO: 130) | [TGT] |
| (131) | TLD-K-LQT | (SEQ ID NO: 131) | [TGT] |
| (132) | TLD-S-LQT | (SEQ ID NO: 132) | [TTT] |
| (133) | TLD-A-LQT | (SEQ ID NO: 133) | [TTT] |
| (134) | SLD-T-LQT | (SEQ ID NO: 134) | [TCT] |
| (135) | SLD-D-LQT | (SEQ ID NO: 135) | [TCT] |
| (136) | SLD-E-LQT | (SEQ ID NO: 136) | [TCT] |
| (137) | SLD-H-LQT | (SEQ ID NO: 137) | [TGT] |
| (138) | SLD-K-LQT | (SEQ ID NO: 138) | [TGT] |
| (139) | SLD-S-LQT | (SEQ ID NO: 139) | [TTT] |
| (140) | SLD-A-LQT | (SEQ ID NO: 140) | [TTT] |
| (141) | ARG-T-LRT | (SEQ ID NO: 141) | [TCT] |
| (142) | ARG-D-LRT | (SEQ ID NO: 142) | [TCT] |
| (143) | ARG-E-LRT | (SEQ ID NO: 143) | [TCT] |
| (144) | ARG-H-LRT | (SEQ ID NO: 144) | [TGT] |
| (145) | ARG-K-LRT | (SEQ ID NO: 145) | [TGT] |
| (146) | ARG-S-LRT | (SEQ ID NO: 146) | [TTT] |
| (147) | ARG-A-LRT | (SEQ ID NO: 147) | [TTT] |
| (148) | SRG-T-LRT | (SEQ ID NO: 148) | [TCC] |
| (149) | SRG-D-LRT | (SEQ ID NO: 149) | [TCC] |
| (150) | SRG-E-LRT | (SEQ ID NO: 150) | [TCC] |
| (151) | SRG-H-LRT | (SEQ ID NO: 151) | [TGC] |
| (152) | SRG-K-LRT | (SEQ ID NO: 152) | [TGC] |
| (153) | SRG-S-LRT | (SEQ ID NO: 153) | [TTC] |
| (154) | SRG-A-LRT | (SEQ ID NO: 154) | [TTC] |
| (155) | QKD-A-LRG | (SEQ ID NO: 155) | [TTA] |
| (156) | DKD-A-LRG | (SEQ ID NO: 156) | [TTC] |
| (157) | EKD-A-LRG | (SEQ ID NO: 157) | [TTC] |
| (158) | TKD-A-LRG | (SEQ ID NO: 158) | [TTT] |
| (159) | SKD-A-LRG | (SEQ ID NO: 159) | [TTT] |
| (160) | RKD-N-LRG | (SEQ ID NO: 160) | [TAG] |
| (161) | RKD-T-LRG | (SEQ ID NO: 161) | [TCG] |
| (162) | RKD-D-LRG | (SEQ ID NO: 162) | [TCG] |
| (163) | RKD-E-LRG | (SEQ ID NO: 163) | [TCG] |
| (164) | RKD-H-LRG | (SEQ ID NO: 164) | [TGG] |
| (165) | RKD-K-LRG | (SEQ ID NO: 165) | [TGG] |
| (166) | RKD-S-LRG | (SEQ ID NO: 166) | [TTG] |
| (167) | QKD-N-LRG | (SEQ ID NO: 167) | [TAA] |
| (168) | QKD-T-LRG | (SEQ ID NO: 168) | [TCA] |
| (169) | QKD-D-LRG | (SEQ ID NO: 169) | [TCA] |
| (170) | QKD-E-LRG | (SEQ ID NO: 170) | [TCA] |
| (171) | QKD-H-LRG | (SEQ ID NO: 171) | [TGA] |
| (172) | QKD-K-LRG | (SEQ ID NO: 172) | [TGA] |
| (173) | QKD-S-LRG | (SEQ ID NO: 173) | [TTA] |
| (174) | DKD-N-LRG | (SEQ ID NO: 174) | [TAC] |
| (175) | DKD-T-LRG | (SEQ ID NO: 175) | [TCC] |
| (176) | DKD-D-LRG | (SEQ ID NO: 176) | [TCC] |
| (177) | DKD-E-LRG | (SEQ ID NO: 177) | [TCC] |
| (178) | DKD-H-LRG | (SEQ ID NO: 178) | [TGC] |
| (179) | DKD-K-LRG | (SEQ ID NO: 179) | [TGC] |
| (180) | DKD-S-LRG | (SEQ ID NO: 180) | [TTC] |
| (181) | EKD-N-LRG | (SEQ ID NO: 181) | [TAC] |
| (182) | EKD-T-LRG | (SEQ ID NO: 182) | [TCC] |
| (183) | EKD-D-LRG | (SEQ ID NO: 183) | [TCC] |
| (184) | EKD-E-LRG | (SEQ ID NO: 184) | [TCC] |
| (185) | EKD-H-LRG | (SEQ ID NO: 185) | [TGC] |
| (186) | EKD-K-LRG | (SEQ ID NO: 186) | [TGC] |
| (187) | EKD-S-LRG | (SEQ ID NO: 187) | [TTC] |
| (188) | TKD-N-LRG | (SEQ ID NO: 188) | [TAT] |
| (189) | TKD-T-LRG | (SEQ ID NO: 189) | [TCT] |
| (190) | TKD-D-LRG | (SEQ ID NO: 190) | [TCT] |
| (191) | TKD-E-LRG | (SEQ ID NO: 191) | [TCT] |
| (192) | TKD-H-LRG | (SEQ ID NO: 192) | [TGT] |
| (193) | TKD-K-LRG | (SEQ ID NO: 193) | [TGT] |
| (194) | TKD-S-LRG | (SEQ ID NO: 194) | [TTT] |
| (195) | SKD-N-LRG | (SEQ ID NO: 195) | [TAT] |
| (196) | SKD-T-LRG | (SEQ ID NO: 196) | [TCT] |
| (197) | SKD-D-LRG | (SEQ ID NO: 197) | [TCT] |
| (198) | SKD-E-LRG | (SEQ ID NO: 198) | [TCT] |
| (199) | SKD-H-LRG | (SEQ ID NO: 199) | [TGT] |
| (200) | SKD-K-LRG | (SEQ ID NO: 200) | [TGT] |
| (201) | SKD-S-LRG | (SEQ ID NO: 201) | [TTT] |
| (202) | VRG-T-LRT | (SEQ ID NO: 202) | [TCT] |
| (203) | VRG-D-LRT | (SEQ ID NO: 203) | [TCT] |
| (204) | VRG-E-LRT | (SEQ ID NO: 204) | [TCT] |

-continued

| (205) | VRG-H-LRT | (SEQ ID NO: 205) | [TGT] |
| (206) | VRG-K-LRT | (SEQ ID NO: 206) | [TGT] |
| (207) | VRG-S-LRT | (SEQ ID NO: 207) | [TTT] |
| (208) | VRG-T-LRT | (SEQ ID NO: 208) | [TTT] |
| (209) | QLR-A-LDR | (SEQ ID NO: 209) | [TCA] |
| (210) | DLR-A-LDR | (SEQ ID NO: 210) | [TCC] |
| (211) | ELR-A-LDR | (SEQ ID NO: 211) | [TCC] |
| (212) | TLR-A-LDR | (SEQ ID NO: 212) | [TCT] |
| (213) | SLR-A-LDR | (SEQ ID NO: 213) | [TCT] |
| (214) | RSD-N-RKR | (SEQ ID NO: 214) | [TAC] |
| (215) | RSD-T-RKR | (SEQ ID NO: 215) | [TCC] |
| (216) | RSD-D-RKR | (SEQ ID NO: 216) | [TCC] |
| (217) | RSD-H-RKR | (SEQ ID NO: 217) | [TGC] |
| (218) | RSD-K-RKR | (SEQ ID NO: 218) | [TGC] |
| (219) | RSD-S-RKR | (SEQ ID NO: 219) | [TTC] |
| (220) | RSD-A-RKR | (SEQ ID NO: 220) | [TTC] |
| (221) | QYQ-S-LRQ | (SEQ ID NO: 221) | [TCA] |
| (222) | EYQ-S-LRQ | (SEQ ID NO: 222) | [TCC] |
| (223) | RYQ-S-LRQ | (SEQ ID NO: 223) | [TCG] |
| (224) | TYQ-S-LRQ | (SEQ ID NO: 224) | [TCT] |
| (225) | SYQ-S-LRQ | (SEQ ID NO: 225) | [TCT] |
| (226) | RLR-N-IQF | (SEQ ID NO: 226) | [TAG] |
| (227) | RLR-T-IQF | (SEQ ID NO: 227) | [TCG] |
| (228) | RLR-E-IQF | (SEQ ID NO: 228) | [TCG] |
| (229) | RLR-H-IQF | (SEQ ID NO: 229) | [TGG] |
| (230) | RLR-K-IQF | (SEQ ID NO: 230) | [TGG] |
| (231) | RLR-S-IQF | (SEQ ID NO: 231) | [TTG] |
| (232) | RLR-A-IQF | (SEQ ID NO: 232) | [TTG] |
| (233) | DSL-L-LGA | (SEQ ID NO: 233) | [TCC] |
| (234) | ESL-L-LGA | (SEQ ID NO: 234) | [TCC] |
| (235) | RSL-L-LGA | (SEQ ID NO: 235) | [TCG] |
| (236) | TSL-L-LGA | (SEQ ID NO: 236) | [TCT] |
| (237) | SSL-L-LGA | (SEQ ID NO: 237) | [TCT] |
| (238) | HRG-N-LGG | (SEQ ID NO: 238) | [TAA] |
| (239) | HRG-D-LGG | (SEQ ID NO: 239) | [TCA] |
| (240) | HRG-E-LGG | (SEQ ID NO: 240) | [TCA] |
| (241) | HRG-H-LGG | (SEQ ID NO: 241) | [TGA] |
| (242) | HRG-K-LGG | (SEQ ID NO: 242) | [TGA] |
| (243) | HRG-S-LGG | (SEQ ID NO: 243) | [TTA] |
| (244) | HRG-A-LGG | (SEQ ID NO: 244) | [TTA] |
| (245) | QKH-M-LDT | (SEQ ID NO: 245) | [TCA] |
| (246) | EKH-M-LDT | (SEQ ID NO: 246) | [TCC] |
| (247) | RKH-M-LDT | (SEQ ID NO: 247) | [TCG] |
| (248) | TKH-M-LDT | (SEQ ID NO: 248) | [TCT] |
| (249) | SKH-M-LDT | (SEQ ID NO: 249) | [TCT] |
| (250) | QLG-G-LRQ | (SEQ ID NO: 249) | [TCA] |
| (251) | ELG-G-LRQ | (SEQ ID NO: 251) | [TCC] |
| (252) | RLG-G-LRQ | (SEQ ID NO: 252) | [TCG] |
| (253) | TLG-G-LRQ | (SEQ ID NO: 253) | [TCT] |
| (254) | SLG-G-LRQ | (SEQ ID NO: 254) | [TCT] |
| (255) | AEA-N-LQR | (SEQ ID NO: 255) | [TAT] |
| (256) | AEA-T-LQR | (SEQ ID NO: 256) | [TCT] |
| (257) | AEA-D-LQR | (SEQ ID NO: 257) | [TCT] |
| (258) | AEA-H-LQR | (SEQ ID NO: 258) | [TGT] |
| (259) | AEA-K-LQR | (SEQ ID NO: 259) | [TGT] |
| (260) | AEA-S-LQR | (SEQ ID NO: 260) | [TTT] |
| (261) | AEA-A-LQR | (SEQ ID NO: 261) | [TTT] |
| (262) | DGR-C-LVT | (SEQ ID NO: 262) | [TGC] |
| (263) | EGR-C-LVT | (SEQ ID NO: 263) | [TGC] |
| (264) | RGR-C-LVT | (SEQ ID NO: 264) | [TGG] |
| (265) | TGR-G-LVT | (SEQ ID NO: 265) | [TGT] |
| (266) | SGR-G-LVT | (SEQ ID NO: 266) | [TGT] |
| (267) | QED-N-LHT | (SEQ ID NO: 267) | [TAA] |
| (268) | DED-N-LHT | (SEQ ID NO: 268) | [TAC] |
| (269) | EED-N-LHT | (SEQ ID NO: 269) | [TAT] |
| (270) | SED-N-LHT | (SEQ ID NO: 270) | [TAT] |
| (271) | RED-T-LHT | (SEQ ID NO: 271) | [TCG] |
| (272) | RED-D-LHT | (SEQ ID NO: 272) | [TCG] |
| (273) | RED-E-LHT | (SEQ ID NO: 273) | [TCG] |
| (274) | RED-H-LHT | (SEQ ID NO: 274) | [TGG] |
| (275) | RED-K-LHT | (SEQ ID NO: 275) | [TGG] |
| (276) | RED-S-LHT | (SEQ ID NO: 276) | [TTG] |
| (277) | RED-A-LHT | (SEQ ID NO: 277) | [TTG] |
| (278) | QED-T-LHT | (SEQ ID NO: 278) | [TCA] |
| (279) | QED-D-LHT | (SEQ ID NO: 279) | [TCA] |
| (280) | QED-E-LHT | (SEQ ID NO: 280) | [TCA] |
| (281) | QED-H-LHT | (SEQ ID NO: 281) | [TGA] |
| (282) | QED-K-LHT | (SEQ ID NO: 282) | [TGA] |
| (283) | QED-S-LHT | (SEQ ID NO: 283) | [TTA] |
| (284) | QED-A-LHT | (SEQ ID NO: 284) | [TTA] |

-continued

| | | | |
|---|---|---|---|
| (285) | DED-T-LHT | (SEQ ID NO: 285) | [TCC] |
| (286) | DED-D-LHT | (SEQ ID NO: 286) | [TCC] |
| (287) | DED-E-LHT | (SEQ ID NO: 287) | [TCC] |
| (288) | DED-H-LHT | (SEQ ID NO: 288) | [TGC] |
| (289) | DED-K-LHT | (SEQ ID NO: 289) | [TGC] |
| (290) | DED-S-LHT | (SEQ ID NO: 290) | [TTC] |
| (291) | DED-A-LHT | (SEQ ID NO: 291) | [TTC] |
| (292) | EED-T-LHT | (SEQ ID NO: 292) | [TCC] |
| (293) | EED-D-LHT | (SEQ ID NO: 293) | [TCC] |
| (294) | EED-E-LHT | (SEQ ID NO: 294) | [TCC] |
| (295) | EED-H-LHT | (SEQ ID NO: 295) | [TGC] |
| (296) | EED-K-LHT | (SEQ ID NO: 296) | [TGC] |
| (297) | EED-S-LHT | (SEQ ID NO: 297) | [TTC] |
| (298) | EED-A-LHT | (SEQ ID NO: 298) | [TTC] |
| (299) | TED-T-LHT | (SEQ ID NO: 299) | [TCT] |
| (300) | TED-D-LHT | (SEQ ID NO: 300) | [TCT] |
| (301) | TED-E-LHT | (SEQ ID NO: 301) | [TCT] |
| (302) | TED-H-LHT | (SEQ ID NO: 302) | [TGT] |
| (303) | TED-K-LHT | (SEQ ID NO: 303) | [TGT] |
| (304) | TED-S-LHT | (SEQ ID NO: 304) | [TTT] |
| (305) | TED-A-LHT | (SEQ ID NO: 305) | [TTT] |
| (306) | SED-T-LHT | (SEQ ID NO: 306) | [TCT] |
| (307) | SED-D-LHT | (SEQ ID NO: 307) | [TCT] |
| (308) | SED-E-LHT | (SEQ ID NO: 308) | [TCT] |
| (309) | SED-H-LHT | (SEQ ID NO: 309) | [TGT] |
| (310) | SED-K-LHT | (SEQ ID NO: 310) | [TGT] |
| (311) | SED-S-LHT | (SEQ ID NO: 311) | [TTT] |
| (312) | SED-A-LHT | (SEQ ID NO: 312) | [TTT] |
| (313) | QED-N-LIS | (SEQ ID NO: 313) | [TAA] |
| (314) | DED-N-LIS | (SEQ ID NO: 314) | [TAC] |
| (315) | EED-N-LIS | (SEQ ID NO: 315) | [TAT] |
| (316) | SED-N-LIS | (SEQ ID NO: 316) | [TAT] |
| (317) | RED-T-LIS | (SEQ ID NO: 317) | [TCG] |
| (318) | RED-D-LIS | (SEQ ID NO: 318) | [TCG] |
| (319) | RED-E-LIS | (SEQ ID NO: 319) | [TCG] |
| (320) | RED-H-LIS | (SEQ ID NO: 320) | [TGG] |
| (321) | RED-K-LIS | (SEQ ID NO: 321) | [TGG] |
| (322) | RED-S-LIS | (SEQ ID NO: 322) | [TTG] |
| (323) | RED-A-LIS | (SEQ ID NO: 323) | [TTG] |
| (324) | QED-T-LIS | (SEQ ID NO: 324) | [TCA] |
| (325) | QED-D-LIS | (SEQ ID NO: 325) | [TCA] |
| (326) | QED-E-LIS | (SEQ ID NO: 326) | [TCA] |
| (327) | QED-H-LIS | (SEQ ID NO: 327) | [TGA] |
| (328) | QED-K-LIS | (SEQ ID NO: 328) | [TGA] |
| (329) | QED-S-LIS | (SEQ ID NO: 329) | [TTA] |
| (330) | QED-A-LIS | (SEQ ID NO: 330) | [TTA] |
| (331) | DED-T-LIS | (SEQ ID NO: 331) | [TCC] |
| (332) | DED-D-LIS | (SEQ ID NO: 332) | [TCC] |
| (333) | DED-E-LIS | (SEQ ID NO: 333) | [TCC] |
| (334) | DED-H-LIS | (SEQ ID NO: 334) | [TGC] |
| (335) | DED-K-LIS | (SEQ ID NO: 335) | [TGC] |
| (336) | DED-S-LIS | (SEQ ID NO: 336) | [TTC] |
| (337) | DED-A-LIS | (SEQ ID NO: 337) | [TTC] |
| (338) | EED-T-LIS | (SEQ ID NO: 338) | [TCC] |
| (339) | EED-D-LIS | (SEQ ID NO: 339) | [TCC] |
| (340) | EED-E-LIS | (SEQ ID NO: 340) | [TCC] |
| (341) | EED-H-LIS | (SEQ ID NO: 341) | [TGC] |
| (342) | EED-K-LIS | (SEQ ID NO: 342) | [TGC] |
| (343) | EED-S-LIS | (SEQ ID NO: 343) | [TTC] |
| (344) | EED-A-LIS | (SEQ ID NO: 344) | [TTC] |
| (345) | TED-T-LIS | (SEQ ID NO: 345) | [TCT] |
| (346) | TED-D-LIS | (SEQ ID NO: 346) | [TCT] |
| (347) | TED-E-LIS | (SEQ ID NO: 347) | [TCT] |
| (348) | TED-H-LIS | (SEQ ID NO: 348) | [TGT] |
| (349) | TED-K-LIS | (SEQ ID NO: 349) | [TGT] |
| (350) | TED-S-LIS | (SEQ ID NO: 350) | [TTT] |
| (351) | TED-A-LIS | (SEQ ID NO: 351) | [TTT] |
| (352) | SED-T-LIS | (SEQ ID NO: 352) | [TCT] |
| (353) | SED-D-LIS | (SEQ ID NO: 353) | [TCT] |
| (354) | SED-E-LIS | (SEQ ID NO: 354) | [TCT] |
| (355) | SED-H-LIS | (SEQ ID NO: 355) | [TGT] |
| (356) | SED-K-LIS | (SEQ ID NO: 356) | [TGT] |
| (357) | SED-S-LIS | (SEQ ID NO: 357) | [TTT] |
| (358) | SED-A-LIS | (SEQ ID NO: 358) | [TTT] |
| (359) | TGG-W-LQA | (SEQ ID NO: 359) | [TCT] |
| (360) | SGG-W-LQA | (SEQ ID NO: 360) | [TCT] |
| (361) | DGG-W-LQA | (SEQ ID NO: 361) | [TCC] |
| (362) | EGG-W-LQA | (SEQ ID NO: 362) | [TCC] |
| (363) | QGG-W-LQA | (SEQ ID NO: 363) | [TCA] |
| (364) | RGG-T-LQA | (SEQ ID NO: 364) | [TCT] |

-continued

| | | | |
|---|---|---|---|
| (365) | RGG-D-LQA | (SEQ ID NO: 365) | [TCT] |
| (366) | RGG-E-LQA | (SEQ ID NO: 366) | [TCT] |
| (367) | RGG-N-LQA | (SEQ ID NO: 367) | [TAT] |
| (368) | RGG-H-LQA | (SEQ ID NO: 368) | [TGT] |
| (369) | RGG-K-LQA | (SEQ ID NO: 369) | [TGT] |
| (370) | RGG-S-LQA | (SEQ ID NO: 370) | [TTT] |
| (371) | RGG-A-LQA | (SEQ ID NO: 371) | [TTT] |
| (372) | TGG-T-LQA | (SEQ ID NO: 372) | [TCT] |
| (373) | TGG-D-LQA | (SEQ ID NO: 373) | [TCT] |
| (374) | TGG-E-LQA | (SEQ ID NO: 374) | [TCT] |
| (375) | TGG-N-LQA | (SEQ ID NO: 375) | [TAT] |
| (376) | TGG-H-LQA | (SEQ ID NO: 376) | [TGT] |
| (377) | TGG-K-LQA | (SEQ ID NO: 377) | [TGT] |
| (378) | TGG-S-LQA | (SEQ ID NO: 378) | [TTT] |
| (379) | TGG-A-LQA | (SEQ ID NO: 379) | [TTT] |
| (380) | SGG-T-LQA | (SEQ ID NO: 380) | [TCT] |
| (381) | SGG-D-LQA | (SEQ ID NO: 381) | [TCT] |
| (382) | SGG-E-LQA | (SEQ ID NO: 382) | [TCT] |
| (383) | SGG-N-LQA | (SEQ ID NO: 383) | [TAT] |
| (384) | SGG-H-LQA | (SEQ ID NO: 384) | [TGT] |
| (385) | SGG-K-LQA | (SEQ ID NO: 385) | [TGT] |
| (386) | SGG-S-LQA | (SEQ ID NO: 386) | [TTT] |
| (387) | SGG-A-LQA | (SEQ ID NO: 387) | [TTT] |
| (388) | DGG-T-LQA | (SEQ ID NO: 388) | [TCC] |
| (389) | DGG-D-LQA | (SEQ ID NO: 389) | [TCC] |
| (390) | DGG-E-LQA | (SEQ ID NO: 390) | [TCC] |
| (391) | DGG-N-LQA | (SEQ ID NO: 391) | [TAC] |
| (392) | DGG-H-LQA | (SEQ ID NO: 392) | [TGC] |
| (393) | DGG-K-LQA | (SEQ ID NO: 393) | [TGC] |
| (394) | DGG-S-LQA | (SEQ ID NO: 394) | [TTC] |
| (395) | DGG-A-LQA | (SEQ ID NO: 395) | [TTC] |
| (396) | EGG-T-LQA | (SEQ ID NO: 396) | [TCC] |
| (397) | EGG-D-LQA | (SEQ ID NO: 397) | [TCC] |
| (398) | EGG-E-LQA | (SEQ ID NO: 398) | [TCC] |
| (399) | EGG-N-LQA | (SEQ ID NO: 399) | [TAC] |
| (400) | EGG-H-LQA | (SEQ ID NO: 400) | [TGC] |
| (401) | EGG-K-LQA | (SEQ ID NO: 401) | [TGC] |
| (402) | EGG-S-LQA | (SEQ ID NO: 402) | [TTC] |
| (403) | EGG-A-LQA | (SEQ ID NO: 403) | [TTC] |
| (404) | QGG-T-LQA | (SEQ ID NO: 404) | [TCA] |
| (405) | QGG-D-LQA | (SEQ ID NO: 405) | [TCA] |
| (406) | QGG-E-LQA | (SEQ ID NO: 406) | [TCA] |
| (407) | QGG-N-LQA | (SEQ ID NO: 407) | [TAA] |
| (408) | QGG-H-LQA | (SEQ ID NO: 408) | [TGA] |
| (409) | QGG-K-LQA | (SEQ ID NO: 409) | [TGA] |
| (410) | QGG-S-LQA | (SEQ ID NO: 410) | [TTA] |
| (411) | QGG-A-LQA | (SEQ ID NO: 411) | [TTA] |

In one embodiment, a polypeptide of the invention contains a binding region that has an amino acid sequence with the same nucleotide binding characteristics as any of SEQ ID NO: 1 through SEQ ID NO: 411. A detailed description of how those binding characteristics were determined can be found hereinafter in the Examples. Such a polypeptide competes for binding to a nucleotide target with any of SEQ ID NO: 1 through SEQ ID NO: 411. That is, a preferred polypeptide contains a binding region that will displace, in a competitive manner, the binding of any of SEQ ID NO: 1 through SEQ ID NO: 411. Means for determining competitive binding are well known in the art. More preferably, the polypeptide contains a binding region that has an amino acid sequence with the same nucleotide binding characteristics as any of SEQ ID NO: 1 through SEQ ID NO: 46, competes for binding to a nucleotide target with any of SEQ ID NO: 1 through SEQ ID NO: 46, or contains a binding region that will displace, in a competitive manner, the binding of any of SEQ ID NO: 1 through SEQ ID NO: 46. Still more preferably, the polypeptide contains a binding region that has an amino acid sequence with the same nucleotide binding characteristics as any of SEQ ID NO: 1 through SEQ ID NO: 6, competes for binding to a nucleotide target with any of SEQ ID NO: 1 through SEQ ID NO: 6, or contains a binding region that will displace, in a competitive manner, the binding of any of SEQ ID NO: 1 through SEQ ID NO: 6. Preferably, the binding region has the amino acid sequence of any of SEQ ID NO: 1 through SEQ ID NO: 411. More preferably, the binding region has the amino acid sequence of any of SEQ ID NO: 1 through SEQ ID NO: 46. Still more preferably, the binding region has the amino acid sequence of any of SEQ ID NO: 1 through SEQ ID NO: 6.

Also within the scope of the present invention are polypeptides that differ from the polypeptides disclosed above, such as polypeptides including therein any of SEQ ID NO: 1 through SEQ ID NO: 411, any of SEQ ID NO: 1 through SEQ ID NO: 46, or any of SEQ ID NO: 1 through SEQ ID NO: 6 by no more than two conservative amino acid substitutions and that have a binding affinity for the desired subsite or target region of at least 80% as great as the polypeptide before the substitutions are made. In terms of dissociation constants, this is equivalent to a dissociation constant no greater than 125% of that of the polypeptide before the substitutions are made. In this context, the term "conservative amino acid substitution" is defined as one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. Preferably, the polypeptide differs from the polypeptides described above by no more than one conservative amino acid substitution.

Additionally, proteins or polypeptides incorporating zinc fingers can be molecularly modeled, as detailed below in Example 11. One suitable computer program for molecular modeling is Insight II. Molecular modeling can be used to generate other zinc finger moieties based on variations of zinc finger moieties described herein and that are within the scope of the invention. When modeling establishes that such variations have a hydrogen-bonding pattern that is substantially similar to that of a zinc finger moiety within the scope of the invention and that has been used as the basis for modeling, such variations are also within the scope of the invention. As used herein, the term "substantially similar" with respect to hydrogen bonding pattern means that the same number of hydrogen bonds are present, that the bond angle of each hydrogen bond varies by no more than about 10 degrees, and that the bond length of each hydrogen bond varies by no more than about 0.2 Å.

Typically, binding between the polypeptide and the DNA of appropriate sequence occurs with a $K_D$ of from 1 µM to 10 µM. Preferably binding occurs with a $K_D$ of from 10 µM to 1 µM, from 10 pM to 100 nM, from 100 pM to 10 nM and, more preferably with a $K_D$ of from 1 nM to 10 nM. These binding parameters also characterize binding of other polypeptides incorporating these polypeptides, such as the polypeptide compositions described below herein.

Accordingly, other zinc finger nucleotide binding domains can be included in polypeptides according to the present invention. All of these domains include a 7-amino acid zinc finger domain wherein the seven amino acids of the domain are numbered from −1 to 6. These domains include: (1) a zinc finger nucleotide binding domain specifically binding the nucleotide sequence 5'-(TAA)-3', wherein the amino acid residue of the domain numbered −1 is selected from the group consisting of Q, N, and S; (2) a zinc finger nucleotide binding domain specifically binding the nucleotide sequence 5'-(TCA)-3', wherein the amino acid residue of the domain numbered −1 is S; (3) a zinc finger nucleotide binding domain specifically binding the nucleotide sequence 5'-(TNG)-3', wherein N is any of A, C, G, or T, wherein the amino acid residue of the domain numbered −1 is selected from the group consisting of R, N, Q, H, S, T, and I; (4) a zinc finger nucleotide binding domain specifically binding the nucleotide sequence 5'-(TNG)-3', wherein N is any of A, C, G, or T, wherein the amino acid residue numbered 2 of the domain is D; (5) a zinc finger nucleotide binding domain specifically binding the nucleotide sequence 5'-(TNT)-3', wherein N is any of A, C, G, or T, wherein the amino acid residue of the domain numbered −1 is selected from the group consisting of R, N, Q, H, S, T, A, and C; (6) a zinc finger nucleotide binding domain specifically binding the nucleotide sequence 5'-(TNC)-3', wherein N is any of A, C, G, or T, wherein the amino acid residue of the domain numbered −1 is selected from the group consisting of Q, N, S, G, H, and D; (7) a zinc finger nucleotide binding domain specifically binding the nucleotide sequence 5'-(TAN)-3', wherein N is any of A, C, G, or T, wherein the amino acid residue of the domain numbered 3 is selected from the group consisting of H, N, G, V, P, I, and K; (8) a zinc finger nucleotide binding domain specifically binding the nucleotide sequence 5'-(TCN)-3', wherein N is any of A, C, G, or T, wherein the amino acid residue of the domain numbered 3 is selected from the group consisting of T, D, H, K, R, and N; (9) a zinc finger nucleotide binding domain specifically binding the nucleotide sequence 5'-(TCC)-3', wherein the amino acid residue of the domain numbered 3 is selected from the group consisting of N, H, S, D, T, Q, and G; (10) a zinc finger nucleotide binding domain specifically binding the nucleotide sequence 5'-(TCG)-3', wherein the amino acid residue of the domain numbered 3 is selected from the group consisting of T, H, S, D, N, Q, and G; (11) a zinc finger nucleotide binding domain specifically binding the nucleotide sequence 5'-(TGN)-3', wherein N is any of A, C, G, or T, wherein the amino acid residue of the domain numbered 3 is H; (12) a zinc finger nucleotide binding domain specifically binding a nucleotide sequence selected from the group consisting of 5'-(TGG)-3' and 5'-(TGT)-3', wherein the amino acid residue of the domain numbered 3 is selected from the group consisting of S, D, T, N, O, G, and H; (13) a zinc finger nucleotide binding domain specifically binding the nucleotide sequence 5'-(TGC)-3', wherein the amino acid residue of the domain numbered 3 is selected from the group consisting of W, T, and H; (14) a zinc finger nucleotide binding domain specifically binding the nucleotide sequence 5'-(TGN)-3', wherein N is any of A, C, G, or T, wherein the amino acid residue of the domain numbered 3 is H; (15) a zinc finger nucleotide binding domain specifically binding a nucleotide sequence selected from the group consisting of 5'-(TTA)-3' and 5'-(TTG)-3', wherein the amino acid residue of the domain numbered 3 is selected from the group consisting of S and A; (16) a zinc finger nucleotide binding domain specifically binding a nucleotide sequence selected from the group consisting of 5'-(TTC)-3' and 5'-(TTT)-3', wherein the amino acid residue of the domain numbered 3 is H; (17) a zinc finger nucleotide binding domain specifically binding the nucleotide sequence 5'-(TNA)-3', wherein N is any of A, C, G, or T, wherein the amino acid residue of the domain numbered −1 is R; (18) a zinc finger nucleotide binding domain specifically binding the nucleotide sequence 5'-(TNT)-3', wherein N is any of A, C, G, or T, wherein the amino acid residue of the domain numbered −1 is selected from the group consisting of S, T, and H; and (19) a zinc finger nucleotide binding domain specifically binding the nucleotide sequence 5'-(TNN)-3', wherein N is any of A, C, G, or T, wherein the amino acid residue of the domain numbered 4 is selected from the group consisting of L, V, I, and C.

Still other zinc finger nucleotide binding domains that can be incorporated in polypeptides according to the present invention can be derived from the domains described above, namely SEQ ID NO: 1 through SEQ ID NO: 411, by site-derived mutagenesis and screening. Site-directed mutagenesis techniques, also known as site-specific mutagenesis techniques are well known in the art and need not be described in detail here. Such techniques are described, for example, in J. Sambrook & D. W. Russell, "Molecular Cloning: A Laboratory Manual" ($3^{rd}$ ed., Cold Spring Harbor Laboratory Press, Cold Spring Harbor, N.Y., 2001), v. 2, ch. 13, pp. 13.1-13.56.

III. Polypeptide Compositions

In another aspect, the present invention provides a polypeptide composition that comprises a plurality of zinc finger-nucleotide binding domains operatively linked in such a manner to specifically bind a nucleotide target motif defined as 5'-(TNN)$_n$-3', where n is an integer greater than 1. The target motif can be located within any longer nucleotide sequence (e.g., from 3 to 13 or more TNN, GNN, ANN or NNN sequences). Preferably, n is an integer from 2 to 18, more preferably from 2 to 12, and still more preferably from 2 to 6. The individual polypeptides are preferably linked with oligopeptide linkers. Such linkers preferably resemble a linker found in naturally occurring zinc finger proteins. A preferred linker for use in the present invention is the amino acid residue sequence TGEKP (SEQ ID NO: 412). Modifications of this linker can also be used. For example, the glutamic acid (E) at position 3 of the linker can be replaced with aspartic acid (D). The threonine (T) at position 1 can be replaced with serine (S). The glycine (G) at position 2 can be replaced with alanine (A). The lysine (K) at position 4 can be replaced with arginine (R). Another preferred linker for use in the present invention is the amino acid residue sequence TGGGGSGGGGTGEKP (SEQ ID NO: 414). This longer linker can be used when it is desired to have the two halves of a longer plurality of zinc finger binding polypeptides operate in a substantially independent manner. Modifications of this longer linker can also be used. For example, the polyglycine runs of four glycine (G) residues each can be of greater or lesser length (i.e., 3 or 5 glycine residues each). The serine residue (S) between the polyglycine runs can be replaced with threonine (T). The TGEKP (SEQ ID NO: 412) moiety that comprises part of the linker TGGGGSGGGGTGEKP (SEQ ID NO: 414) can be modified as described above for the TGEKP (SEQ ID NO: 412) linker alone. Other linkers such as glycine or serine repeats are well known in the art to link peptides (e.g., single chain antibody domains) and can be used in a composition of this invention. The use of a linker is not required for all purposes and can optionally be omitted.

Other linkers are known in the art and can alternatively be used. These include the linkers LRQKDGGGSERP (SEQ ID NO: 416), LRQKDGERP (SEQ ID NO: 417), GGRGRGR-GRQ (SEQ ID NO: 418), QNKKGGSGDGKKKQHI (SEQ ID NO: 419), TGGERP (SEQ ID NO: 420), ATGEKP (SEQ ID NO: 421), and GGGSGGGGEGP (SEQ ID NO: 422), as well as derivatives of those linkers in which amino acid substitutions are made as described above for TGEKP (SEQ ID NO: 412) and TGGGGSGGGGTGEKP (SEQ ID NO: 414). For example, in these linkers, the serine (S) residue between the diglycine or polyglycine runs in QNKKGGS-GDGKKKQHI (SEQ ID NO: 419) or GGGSGGGGEGP (SEQ ID NO: 422) can be replaced with threonine (T). In GGGSGGGGEGP (SEQ ID NO: 422), the glutamic acid (E) at position 9 can be replaced with aspartic acid (D). Polypeptide compositions including these linkers and derivatives of these linkers are included in polypeptide compositions of the present invention.

In these polypeptide compositions, each of the zinc finger domains is of the sequence SEQ ID NO: 1 to SEQ ID NO: 411 Typically, each of the zinc finger domains is of the sequence SEQ ID NO: 1 to SEQ ID NO: 46. Preferably, each of the zinc finger domains is of the sequence SEQ ID NO: 1 to SEQ ID NO: 6.

Alternatively, in these polypeptide compositions, each of these zinc finger domains contains a binding region that has an amino acid sequence with the same nucleotide binding characteristics as any of SEQ ID NO: 1 through SEQ ID NO: 411, that competes for binding to a nucleotide target with any of SEQ ID NO: 1 through SEQ ID NO: 411, or that will displace, in a competitive manner, the binding of any of SEQ ID NO: 1 through SEQ ID NO: 411. In this alternative, preferably, each of these zinc finger domains contains a binding region that has an amino acid sequence with the same nucleotide binding characteristics as any of SEQ ID NO: 1 through SEQ ID NO: 46, that competes for binding to a nucleotide target with any of SEQ ID NO: 1 through SEQ ID NO: 46, or that will displace, in a competitive manner, the binding of any of SEQ ID NO: 1 through SEQ ID NO: 46. More preferably, each of these zinc finger domains contains a binding region that has an amino acid sequence with the same nucleotide binding characteristics as any of SEQ ID NO: 1 through SEQ ID NO: 6, that competes for binding to a nucleotide target with any of SEQ ID NO: 1 through SEQ ID NO: 6, or that will displace, in a competitive manner, the binding of any of SEQ ID NO: 1 through SEQ ID NO: 6.

In another alternative, each of these zinc finger domains contains a binding region that differs from the binding region disclosed above, such as binding regions including therein any of SEQ ID NO: 1 through SEQ ID NO: 411, any of SEQ ID NO: 1 through SEQ ID NO: 46, or any of SEQ ID NO: 1 through SEQ ID NO: 6 by no more than two conservative amino acid substitutions and that have a binding affinity for the desired subsite or target region of at least 80% as great as the binding region before the substitutions are made. In assessing the binding affinity for the desired subsite or target region in these multi-binding region polypeptides, the binding affinity is determined in the absence of interference from other binding regions.

In yet another alternative, in polypeptide compositions according to the present invention as described above, each of the zinc finger domains is a domain such as the following: (1) a zinc finger nucleotide binding domain specifically binding the nucleotide sequence 5'-(TAA)-3', wherein the amino acid residue of the domain numbered −1 is selected from the group consisting of Q, N, and S; (2) a zinc finger nucleotide binding domain specifically binding the nucleotide sequence 5'-(TCA)-3', wherein the amino acid residue of the domain numbered −1 is S; (3) a zinc finger nucleotide binding domain specifically binding the nucleotide sequence 5'-(TNG)-3', wherein N is any of A, C, G, or T, wherein the amino acid residue of the domain numbered −1 is selected from the group consisting of R, N, Q, H, S, T, and I; (4) a zinc finger nucleotide binding domain specifically binding the nucleotide sequence 5'-(TNG)-3', wherein N is any of A, C, G, or T, wherein the amino acid residue numbered 2 of the domain is D; (5) a zinc finger nucleotide binding domain specifically binding the nucleotide sequence 5'-(TNT)-3', wherein N is any of A, C, G, or T, wherein the amino acid residue of the domain numbered −1 is selected from the group consisting of R, N, Q, H, S, T, A, and C; (6) a zinc finger nucleotide binding domain specifically binding the nucleotide sequence 5'-(TNC)-3', wherein N is any of A, C, GS, or T, wherein the amino acid residue of the domain numbered −1 is selected from the group consisting of Q, N, S, G, H, and D; (7) a zinc finger nucleotide binding domain specifically binding the nucleotide sequence 5'-(TAN)-3', wherein N is any of A, C, G, or T, wherein the amino acid residue of the domain numbered 3 is selected from the group consisting of H, N, G, V, P, I, and K; (8) a zinc finger nucleotide binding domain specifically binding the nucleotide sequence 5'-(TCN)-3', wherein N is any of A, C, G, or T, wherein the amino acid residue of the domain numbered 3 is selected from the group consisting of T, D, H, K, R, and N; (9) a zinc finger nucleotide binding domain specifically binding the nucleotide sequence 5'-(TCC)-3', wherein the amino acid residue of the domain numbered 3 is selected from the group consisting of N, H, S, D, T, Q, and G; (10) a zinc finger nucleotide binding domain specifically binding the nucleotide sequence 5'-(TCG)-3', wherein the amino acid residue of the domain numbered 3 is selected from the group consisting of T, H, S, D, N, Q, and G; (11) a zinc finger nucleotide binding domain specifically binding the nucleotide sequence 5'-(TGN)-3', wherein N is any of A, C, G, or T, wherein the amino acid residue of the domain numbered 3 is H; (12) a zinc finger nucleotide binding domain specifically binding a nucleotide sequence selected from the group consisting of 5'-(TGG)-3' and 5'-(TGT)-3', wherein the amino acid residue of the domain numbered 3 is selected from the group consisting of S, D, T, N, Q, G, and H; (13) a zinc finger nucleotide binding domain specifically binding the nucleotide sequence 5'-(TGC)-3', wherein the amino acid residue of the domain numbered 3 is selected from the group consisting of W, T, and H; (14) a zinc finger nucleotide binding domain specifically binding the nucleotide sequence 5'-(TGN)-3', wherein N is any of A, C, G, or T, wherein the amino acid residue of the domain numbered 3 is H; (15) a zinc finger nucleotide binding domain specifically binding a nucleotide sequence selected from the group consisting of 5'-(TTA)-3' and 5'-(TTG)-3', wherein the amino acid residue of the domain numbered 3 is selected from the group consisting of S and A; (16) a zinc finger nucleotide binding domain specifically binding a nucleotide sequence selected from the group consisting of 5'-(TTC)-3' and 5'-(TTT)-3', wherein the amino acid residue of the domain numbered 3 is H; (17) a zinc finger nucleotide binding domain specifically binding the nucleotide sequence 5'-(TNA)-3', wherein N is any of A, C, G, or T, wherein the amino acid residue of the domain numbered −1 is R; (18) a zinc finger nucleotide binding domain specifically binding the nucleotide sequence 5'-(TNT)-3', wherein N is any of A, C, G, or T, wherein the amino acid residue of the domain numbered −1 is selected from the group consisting of S, T, and H; and (19) a zinc finger nucleotide binding domain specifically binding the nucleotide sequence 5'-(TNN)-3', wherein N is any of A, C, G, or T, wherein the amino acid residue of the domain numbered 4 is selected from the group consisting of L, V, I, and C.

In still other alternatives, any of the zinc finger nucleotide binding domains described above can be included in a polypeptide composition according to the present invention.

Other alternatives for the binding regions of these polypeptides, including binding regions generated by molecular modeling as described above, are within the scope of the invention.

In still another alternative, the polypeptide composition can comprise a bispecific zinc finger protein comprising two halves, each half comprising six zinc finger nucleotide binding domains, where at least one of the halves includes at least one domain binding a target nucleotide sequence of the form 5'-(TNN)-3', such that the two halves of the bispecific zinc fingers can operate independently. The two halves can be linked by a linker such as the amino acid residue sequence TGGGGSGGGGTGEKP (SEQ ID NO: 414) or another linker as described above. Typically, the linker in this form of bispecific zinc finger protein will include from about 12 to about 18 amino acid residues.

In another alternative, the polypeptide compositions can include, in addition to the binding regions that specifically bind nucleotide subsites or target regions with the sequence 5'-(TNN)-3', one or more polypeptides that include binding regions that specifically bind nucleotide subsites or target regions with the sequence 5'-(ANN)-3', 5'-(CNN)-3', or 5'-(GNN)-3'. Binding regions that specifically bind nucleotide subsites with the sequence 5'-(ANN)-3' are disclosed, for example, in U.S. Patent Application Publication No. 2002/0165356 by Barbas et al., incorporated herein by this reference. Binding regions that specifically bind nucleotide subsites with the sequence 5'-(CNN)-3' are disclosed, for example, in U.S. Patent Application Publication No. 2004/0224385 by Barbas et al., incorporated herein by this reference. Binding regions that specifically bind nucleotide subsites with the sequence 5'-(GNN)-3' are disclosed, for example, in U.S. Pat. No. 6,610,512 to Barbas and in U.S. Pat. No. 6,140,081 to Barbas, both incorporated herein by this reference. Other binding regions that bind nucleotide sequences of the appropriate specificity are known in the art.

If the polypeptide includes binding regions that specifically bind nucleotide subsites of the structure 5'-(ANN)-3', 5'-(TNN)-3', or 5'-(TNN)-3', they can be in any order within the polypeptide, as long as the polypeptide has at least one binding region that binds a nucleotide subsite of the structure 5'-(TNN)-3'. For example, but not by way of limitation, the polypeptide can include a block of binding regions, all of which bind nucleotide subsites of the structure 5'-(TNN)-3', or have binding regions binding nucleotide subsites of the structure 5'-(TNN)-3' interspersed with binding regions binding nucleotide subsites of the structure 5'-(ANN)-3', 5'-(CNN)-3', or 5'-(TNN)-3'. The polypeptide can include 1, 2, 3, 4, 5, 6, 7, 8, 9, 10, 11, 12, 13, 14, 15, 16, 17, 18, or more binding regions each binding a subsite of the structure 5'-(ANN)-3', 5'-(CNN)-3', 5'-(GNN)-3', or 5'-(TNN)-3', again as long as the polypeptide has at least one binding region that binds a nucleotide subsite of the structure 5'-(TNN)-3'. In one alternative, all of the binding regions within the polypeptide bind nucleotide subsites of the structure 5'-(TNN)-3'. Therefore, the present invention includes a polypeptide composition as described above operatively linked to at least one other zinc finger nucleotide binding polypeptide binding preferentially to a target nucleotide of the formula ANN, CNN, or GNN, where N is A, C, G or T. Alternatively, as described below, a polypeptide composition of the present invention can be operatively linked to one or more transcription factors.

A polypeptide composition of this invention can be operatively linked to one or more functional polypeptides. Such functional polypeptides can be the complete sequence of proteins with a defined function, or can be derived from single or multiple domains that occur within a protein with a defined function. Such functional polypeptides are well known in the art and can be a transcription regulating factor such as a repressor or activation domain or a polypeptide having other functions. Exemplary and preferred functional polypeptides that can be incorporated are nucleases, lactamases, integrases, methylases, nuclear localization domains, and restriction enzymes such as endo- or exonucleases, as well as other domains with enzymatic activity such as hydrolytic activity (See, e.g. Chandrasegaran and Smith, Biol. Chem., 380:841-848, 1999). Typically, the operative linkage occurs by creating a single polypeptide joining the zinc finger domains with the other functional polypeptide or polypeptides to form a fusion protein; the linkage can occur directly or through one or more linkers as described above. Among the other polypeptides that can be joined to a polypeptide composition according to the present invention, for example, are the nuclease catalytic domain of FokI to generate a construct that can direct site-specific cleavage at a chosen genomic target.

An exemplary repression domain polypeptide is the ERF repressor domain (ERD) (Sgouras, D. N., Athanasiou, M. A., Beal, G. J., Jr., Fisher, R. J., Blair, D. G. & Mavrothalassitis, G. J. (1995) EMBO J. 14, 4781-4793), defined by amino acids 473 to 530 of the ets2 repressor factor (ERF). This domain mediates the antagonistic effect of ERF on the activity of transcription factors of the ets family. A synthetic repressor is constructed by fusion of this domain to the N- or C-terminus of the zinc finger protein. A second repressor protein is prepared using the Krüppel-associated box (KRAB) domain (Margolin, J. F., Friedman, J. R., Meyer, W., K.-H., Vissing, H., Thiesen, H.-J. & Rauscher III, F. J. (1994) Proc. Natl. Acad. Sci. USA 91, 4509-4513). This repressor domain is commonly found at the N-terminus of zinc finger proteins and presumably exerts its repressive activity on TATA-dependent transcription in a distance- and orientation-independent manner (Pengue, G. & Lania, L. (1996) Proc. Natl. Acad. Sci. USA 93, 1015-1020), by interacting with the RING finger protein KAP-1 (Friedman, J. R., Fredericks, W. J., Jensen, D. E., Speicher, D. W., Huang, X.-P., Neilson, E. G. & Rauscher III, F. J. (1996) Genes & Dev. 10, 2067-2078). We utilized the KRAB domain found between amino acids 1 and 97 of the zinc finger protein KOX1 (Margolin, J. F., Friedman, J. R., Meyer, W., K.-H., Vissing, H., Thiesen, H.-J. & Rauscher III, F. J. (1994) Proc. Natl. Acad. Sci. USA 91, 4509-4513). In this case an N-terminal fusion with a zinc-finger polypeptide is constructed. Finally, to explore the utility of histone deacetylation for repression, amino acids 1 to 36 of the Mad mSIN3 interaction domain (SID)) are fused to the N-terminus of the zinc finger protein (Ayer, D. E., Laherty, C. D., Lawrence, Q. A., Armstrong, A. P. & Eisenman, R. N. (1996) Mol. Cell. Biol. 16, 5772-5781). This small domain is found at the N-terminus of the transcription factor Mad and is responsible for mediating its transcriptional repression by interacting with mSIN3, which in turn interacts the co-repressor N-COR and with the histone deacetylase mRPD1 (Heinzel, T., Lavinsky, R. M., Mullen, T.-M., Soderstrom, M., Laherty, C. D., Torchia, J., Yang, W.-M., Brard, G., & Ngo, S. D. (1997) Nature 387, 43-46). To examine gene-specific activation, transcriptional activators are generated by fusing the zinc finger polypeptide to amino acids 413 to 489 of the herpes simplex virus VP16 protein (Sadowski, I., Ma, J., Triezenberg, S. & Ptashne, M. (1988) Nature 335, 563-564), or to an artificial tetrameric repeat of VP16's minimal activation domain (Seipel, K., Georgiev, O. & Schaffner, W. (1992) EMBO J. 11, 4961-4968), termed VP64.

A polypeptide of this invention as setforth above can be operatively linked to one or more transcription modulating or regulating factors. Modulating factors such as transcription activators or transcription suppressors or repressors are well known in the art. Means for operatively linking polypeptides to such factors are also well known in the art. Exemplary and preferred such factors and their use to modulate gene expression are discussed in detail hereinafter.

In order to test the concept of using zinc finger proteins as gene-specific transcriptional regulators, six-finger proteins are fused to a number of effector domains. Transcriptional repressors are generated by attaching either of three human-derived repressor domains to the zinc finger protein. The first repressor protein is prepared using the ERF repressor domain (ERD) (Sgouras, D. N., Athanasiou, M. A., Beal, G. J., Jr., Fisher, R. J., Blair, D. G. & Mavrothalassitis, G. J. (1995) EMBO J. 14, 4781-4793), defined by amino acids 473 to 530 of the ets2 repressor factor (ERF). This domain mediates the antagonistic effect of ERF on the activity of transcription factors of the ets family. A synthetic repressor is constructed by fusion of this domain to the C-terminus of the zinc finger protein. The second repressor protein is prepared using the Krüppel-associated box (KRAB) domain (Margolin, J. F., Friedman, J. R., Meyer, W., K.-H., Vissing, H., Thiesen, H.-J. & Rauscher III F. J. (1994) Proc. Natl. Acad. Sci. USA 91, 4509-4513). This repressor domain is commonly found at the N-terminus of zinc finger proteins and presumably exerts its repressive activity on TATA-dependent transcription in a distance- and orientation-independent manner (Pengue, G. & Lania, L. (1996) Proc. Natl. Acad. Sci. USA 93, 1015-1020), by interacting with the RING finger protein KAP-1 (Friedman, J. R., Fredericks, W. J., Jensen, D. E., Speicher, D. W., Huang, X.-P., Neilson, E. G. & Rauscher III, F. J. (1996) Genes & Dev. 10, 2067-2078). We utilize the KRAB domain found between amino acids 1 and 97 of the zinc finger protein KOX1 (Margolin, J. F., Friedman, J. R., Meyer, W., K.-H., Vissing, H., Thiesen, H.-J. & Rauscher III, F. J. (1994) Proc. Natl. Acad. Sci. USA 91, 4509-4513). In this case an N-terminal fusion with the six-finger protein is constructed. Finally, to explore the utility of histone deacetylation for repression, amino acids 1 to 36 of the Mad mSIN3 interaction domain (SID) are fused to the N-terminus of a zinc finger protein (Ayer, D. E., Laherty, C. D., Lawrence, Q. A., Armstrong, A. P. & Eisenman, R. N. (1996) Mol. Cell. Biol. 16, 5772-5781). This small domain is found at the N-terminus of the transcription factor Mad and is responsible for mediating its transcriptional repression by interacting with mSIN3, which in turn interacts the co-repressor N-CoR and with the histone deacetylase mRPD1 (Heinzel, T., Lavinsky, R. M., Mullen, T.-M., Soderstrom, M., Laherty, C. D., Torchia, J., Yang, W.-M., Brard, G., & Ngo, S. D. (1997) Nature 387, 43-46). Another alternative is direct fusion with a histone deacetylase such as HDAC1.

To examine gene-specific activation, transcriptional activators are generated by fusing the zinc finger protein to amino acids 413 to 489 of the herpes simplex virus VP16 protein (Sadowski, I., Ma, J., Triezenberg, S. & Ptashne, M. (1988) Nature 335, 563-564), or to an artificial tetrameric repeat of VP16's minimal activation domain, DALDDFDLDML (SEQ ID NO: 415) (Seipel, K., Georgiev, O. & Schaffner, W. (1992) EMBO J. 11, 4961-4968), termed VP64.

Reporter constructs containing fragments of the erbB-2 promoter coupled to a luciferase reporter gene are generated to test the specific activities of our designed transcriptional regulators. The target reporter plasmid contains nucleotides −758 to −1 with respect to the ATG initiation codon. Promoter fragments display similar activities when transfected transiently into HeLa cells, in agreement with previous observations (Hudson, L. G., Ertl, A. P. & Gill, G. N. (1990) J. Biol. Chem. 265, 4389-4393). To test the effect of zinc finger-repressor domain fusion constructs on erbB-2 promoter activity, HeLa cells are transiently co-transfected with zinc finger expression vectors and the luciferase reporter constructs. Significant repression is observed with each construct. The utility of gene-specific polydactyl proteins to mediate activation of transcription is investigated using the same two reporter constructs.

The data herein show that zinc finger proteins capable of binding novel 9- and 18-bp DNA target sites, as well as DNA target sites of other lengths, can be rapidly prepared using pre-defined domains recognizing 5'-(TNN)-3' sites, or, in addition, domains recognizing 5'-(TNN)-3', 5'-(TNN)-3', or 5'-(TNN)-3' sites. This information is sufficient for the preparation of 166 or 17 million novel six-finger proteins each capable of binding 18 bp of DNA sequence. This rapid methodology for the construction of novel zinc finger proteins has advantages over the sequential generation and selection of zinc finger domains proposed by others (Greisman, H. A. & Pabo, C. O. (1997) Science 275, 657-661) and takes advantage of structural information that suggests that the potential for the target overlap problem as defined above might be avoided in proteins targeting 5'-(TNN)-3' sites. Using the complex and well studied erbB-2 promoter and live human cells, the data demonstrate that these proteins, when provided with the appropriate effector domain, can be used to provoke or activate expression and to produce graded levels of repression down to the level of the background in these experiments.

Additional examples of an artificial transcription factor that includes a TNN-specific zinc finger DNA binding domain are provided in Example 12. These examples include: (1) an artificial transcription factor designated PBS1 that includes six zinc finger DNA-binding domains as follows: F1 RSD-D-LVR (SEQ ID NO: 453); F2 RSD-V-LVR (SEQ ID NO: 452); F3 QSG-D-LRR (SEQ ID NO: 451); F4 QRH-S-TLE (SEQ ID NO: 450); F5 RGG-W-LOA (SEQ ID NO: 46); and F6 QRA-N-LRA (SEQ ID NO: 449), and which binds the DNA sequence AAATCTCTAGCAGTGGCG (SEQ ID NO: 433), divided into two half-sites, in which RGG-W-LOA (SEQ ID NO: 46) binds the triplet 5'-TCT-3'; (2) an artificial transcription factor designated PBS1a that includes six zinc finger DNA-binding domains as follows: F1 RSD-D-LVR (SEQ ID NO: 453); F2 RSD-V-LVR (SEQ ID NO: 452); F3 QSG-D-LRR (SEQ ID NO: 451); F4 QRA-N-LRA (SEQ ID NO: 449); F5 RSD-H-LTT (SEQ ID NO: 14); and F6 RSD-V-LVR (SEQ ID NO: 452), and which binds the DNA sequence GTCTGGAAAATCTCTAGCAGTGGCG (SEQ ID NO: 434), divided into two half-sites with an unbound intervening sequence of ATCTCTA, in which RSD-H-LTT (SEQ ID NO: 14) binds the triplet 5'-TGG-3'; and (3) an artificial transcription factor designated PBS3 that includes six zinc finger DNA binding domains as follows: F1 DPG-N-LVR (SEQ ID NO: 460); F2 RSD-H-LTN (SEQ ID NO: 459); F3 DSG-N-LRV (SEQ ID NO: 458); F4 RND-T-LTE (SEQ ID NO: 457); F5 HTG-H-LLE (SEQ ID NO: 454)I and F6 RSD-H-LTT (SEQ ID NO: 14), and which binds the DNA sequence TGGCGCCCGAACAGGGAC (SEQ ID NO: 436), divided into two half-sites, in which RSD-H-LTT (SEQ ID NO: 14) binds the triplet 5'-TGG-3' (in this six-finger artificial transcription factor. These factors are shown in Table 13 in Example 1. Other artificial transcription factors based on these factors and substituting other TNN-specific zinc finger DNA-binding domains are also included within the scope of the present invention. For example, in PBS1, other TCT-binding zinc finger DNA-binding domains such as WVG-W-LGS (SEQ ID NO: 22), RLR-D-IQF (SEQ ID NO: 23), GRS-Q-LSC (SEQ ID NO: 24), AEA-E-LQR (SEQ ID NO: 39), QGG-V-LAA (SEQ ID NO: 40), TAS-T-LIS (SEQ ID NO: 80), TAS-D-LIS (SEQ ID NO: 81), TAS-E-LIS (SEQ ID NO: 82), SAS-T-LIS (SEQ ID NO: 87), SAS-D-LIS (SEQ ID NO: 88), SAS-E-LIS (SEQ ID NO: 89), SLD-T-LQT (SEQ ID NO: 134), SLD-D-LQT (SEQ ID NO: 135), SLD-E-LQT (SEQ ID NO: 136), ARG-T-LRT (SEQ ID NO: 141), ARG-D-LRT (SEQ ID NO: 142), ARG-E-LRT (SEQ ID NO: 143), TKD-T-LRG (SEQ ID NO: 189) TKD-D-LRG (SEQ ID NO: 190), TKD-E-LRG (SEQ ID NO: 191), SKD-T-LRG (SEQ ID NO: 196), SKD-D-LRG (SEQ ID NO: 197), SKD-E-LRG (SEQ ID NO: 198), VRG-T-LRT (SEQ ID NO: 202), VRG-D-LRT (SEQ ID NO: 203), VRG-E-LRT (SEQ ID NO: 204), TLR-A-LDR (SEQ ID NO: 212), SLR-A-LDR (SEQ ID NO: 213), TYQ-S-LRQ (SEQ ID NO: 224), SYQ-S-LRQ (SEQ ID NO: 225), TSL-L-LGA (SEQ ID NO: 236), SSL-L-LGA (SEQ ID NO: 237), TKH-M-LDT (SEQ ID NO: 248), SKH-M-LDT (SEQ ID NO: 249), TLG-G-LRQ (SEQ ID NO: 253), SLG-G-LRQ (SEQ ID NO: 254), AEA-T-LQR (SEQ ID NO: 256), AEA-D-LQR (SEQ ID NO: 257), TED-T-LHT (SEQ ID NO: 299), TED-D-LHT (SEQ ID NO: 300), TED-E-LHT (SEQ ID NO: 301), SED-T-LHT (SEQ ID NO: 306), SED-D-LHT (SEQ ID NO: 307), SED-E-LHT (SEQ ID NO: 308), TED-T-LIS (SEQ ID NO: 345), TED-D-LIS (SEQ ID NO: 346), TED-E-LIS (SEQ ID NO: 347), SED-T-LIS (SEQ ID NO: 352), SED-D-LIS (SEQ ID NO: 353), SED-E-LIS (SEQ ID NO: 354), TGG-W-LQA (SEQ ID NO.: 359), SGG-W-LQA (SEQ ID NO: 360), RGG-T-LQA (SEQ ID NO: 364), RGG-D-LQA (SEQ ID NO: 365), RGG-E-LQA (SEQ ID NO: 366), TGG-T-LQA (SEQ ID NO: 372), TGG-D-LQA (SEQ ID NO: 373), TGG-E-LQA (SEQ ID NO: 374), SGG-T-LQA (SEQ ID NO: 380), SGG-D-LQA (SEQ ID NO: 381), SGG-E-LQA (SEQ ID NO: 382), and modifications of these zinc finger DNA binding domains whose sequences follow the rules described above, such as in Table 2, can be substituted for RGG-W-LOA (SEQ ID NO: 46). In PBS1a and PBS3, other TGG-binding zinc finger DNA binding domains such as RAS-H-LIS (SEQ ID NO: 76), RAS-K-LIS (SEQ ID NO: 77), RLD-H-LQT (SEQ ID NO: 102), RLD-K-LQT (SEQ ID NO: 103), RKD-H-LRG (SEQ ID NO: 164), RKD-K-LRG (SEQ ID NO: 165), RLR-H-IQF (SEQ ID NO: 229), RLR-K-IQF (SEQ ID NO: 230), RGR-C-LVT (SEQ ID NO: 264), RED-H-LHT (SEQ ID NO: 274), RED-K-LHT (SEQ ID NO: 275), RED-H-LIS (SEQ ID NO: 320), and RED-K-LIS (SEQ ID NO: 321), and modifications of these zinc finger DNA-binding domains whose sequences follows the rules above, such as in Table 2, can be substituted for RSD-H-LTT (SEQ ID NO: 14). Additionally, the specificity of binding of these zinc-finger DNA binding domains can be altered by incorporation into a longer polypeptide or fusion protein, such as an artificial transcription factor. For example, the zinc finger DNA-binding domain RSD-H-LTT (SEQ ID NO: 14) binds TGG in PBS1a and PBS3; however, it has affinity for TCA and TCT (Table 9). Therefore, the specificity of binding of these zinc finger DNA binding domains is preferably determined in the context of the entire artificial transcription factor or at least the entire set of zinc finger DNA binding domains that are operatively linked to form a multiple-finger moiety. Typically, an artificial transcription factor according to the present invention binds at least a portion of the HIV-1 tRNA primer-binding site. Typically, the artificial transcription factor has six zinc finger DNA-binding domains and has one zinc finger DNA binding domain that binds preferentially to a target nucleotide of the formula TNN, where N is A, C, G or T. Typically, the artificial transcription factor is assembled in an Sp1C zinc finger scaffold. Typically, the artificial transcription factor includes at least one KRAB repression domain. However, the artificial transcription factor can include other repression domains or activation domains.

IV. Isolated Heptapeptides

Another aspect of the present invention is an isolated heptapeptide having an α-helical structure and that binds preferentially to a target nucleotide of the formula TNN, where N is A, C, G or T. Preferred target nucleotides are as described above. The heptapeptides can be of sequences SEQ ID NO: 1 through SEQ ID NO: 411.

Preferably, the heptapeptide has the amino acid sequence of any of SEQ ID NO: 1 through SEQ ID NO: 46. More preferably, the heptapeptide has the amino acid sequence of any of SEQ ID NO: 1 through SEQ ID NO: 6.

In another alternatives a heptapeptide according to the present invention has an amino acid sequence with the same nucleotide binding characteristics as any of SEQ ID NO: 1 through SEQ ID NO: 411. Such a heptapeptide competes for binding to a nucleotide target with any of SEQ ID NO: 1 through SEQ ID NO: 411. That is, the heptapeptide will displace, in a competitive manner, the binding of any of SEQ ID NO: 1 through SEQ ID NO. 411. More preferably, the heptapeptide has an amino acid sequence with the same nucleotide binding characteristics as any of SEQ ID NO: 1 through SEQ ID NO: 46, competes for binding to a nucleotide target with any of SEQ ID NO: 1 through SEQ ID NO: 46, or will displace, in a competitive manner, the binding of any of SEQ ID NO: 1 through SEQ ID NO: 46. Still more preferably, the heptapeptide has an amino acid sequence with the same nucleotide binding characteristics as any of SEQ ID NO: 1 through SEQ ID NO: 6, competes for binding to a nucleotide target with any of SEQ ID NO: 1 through SEQ ID NO: 6, or contains a binding region that will displace, in a competitive manner, the binding of any of SEQ ID NO: 1 through SEQ ID NO: 6.

In yet another alternative, the heptapeptide has an amino acid sequence selected from the group consisting of:

(1) the amino acid sequence of any of SEQ ID NO: 1 through SEQ ID NO: 411; and (2) an amino acid sequence differing from the amino acid sequence of any of SEQ ID NO: 1 through SEQ ID NO: 411 by no more than two conservative amino acid substitutions, wherein the dissociation constant is no greater than 125% of that of the polypeptide before the substitutions are made, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu.

In this alternative, preferably, the heptapeptide has an amino acid sequence selected from the group consisting of:

(1) the amino acid sequence of any of SEQ ID NO: 1 through SEQ ID NO: 46; and (2) an amino acid sequence differing from the amino acid sequence of any of SEQ ID NO: 1 through SEQ ID NO: 46 by no more than two conservative amino acid substitutions, wherein the dissociation constant is no greater than 125% of that of the polypeptide before the substitutions are made, and wherein a conservative amino acid substitution is one of the following substitutions. Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu.

More preferably, in this alternative, the heptapeptide has an amino acid sequence selected from the group consisting of:

(1) the amino acid sequence of any of SEQ ID NO: 1 through SEQ ID NO: 6; and (2) an amino acid sequence differing from the amino acid sequence of any of SEQ ID NO: 1 through SEQ ID NO: 6 by no more than two conservative amino acid substitutions, wherein the dissociation constant is no greater than 125% of that of the polypeptide before the substitutions are made, and wherein a conservative amino acid substitution is one of the following substitutions: Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu.

In these alternatives, preferably the heptapeptide differs from the amino acid sequence of SEQ ID NO: 1 through SEQ ID NO: 411, SEQ ID NO: 1 through SEQ ID NO: 46, or SEQ ID NO: 1 through SEQ ID NO: 6 by no more than one conservative amino acid substitution.

In still another alternative, the heptapeptide is one of the following (wherein the residues of the heptapeptide are numbered from −1 to 6 as described above): (1) an isolated heptapeptide specifically binding the nucleotide sequence 5'-(TAA)-3', wherein the amino acid residue of the domain numbered −1 is selected from the group consisting of Q, N, and S; (2) an isolated heptapeptide specifically binding the nucleotide sequence 5'-(TCA)-3', wherein the amino acid residue of the domain numbered −1 is S; (3) an isolated heptapeptide specifically binding the nucleotide sequence 5'-(TNG)-3', wherein N is any of A, C, G, or T, wherein the amino acid residue of the domain numbered −1 is selected from the group consisting of R, N, Q, H, S, T, and I; (4) an isolated heptapeptide specifically binding the nucleotide sequence 5'-(TNG)-3', wherein N is any of A, C, G, or T, wherein the amino acid residue numbered 2 of the domain is D; (5) an isolated heptapeptide specifically binding the nucleotide sequence 5'-(TNT)-3', wherein N is any of A, C, G, or T, wherein the amino acid residue of the domain numbered −1 is selected from the group consisting of R, N, Q, H, S, T, A, and C; (6) an isolated heptapeptide specifically binding the nucleotide sequence 5'-(TNC)-3', wherein N is any of A, C, G, or T, wherein the amino acid residue of the domain numbered −1 is selected from the group consisting of Q, N, S, G, H, and D; (7) an isolated heptapeptide specifically binding the nucleotide sequence 5'-(TAN)-3', wherein N is any of A, C, G, or T, wherein the amino acid residue of the domain numbered 3 is selected from the group consisting of H, N, G, V, P, I, and K; (8) an isolated heptapeptide specifically binding the nucleotide sequence 5'-(TCN)-3', wherein N is any of A, C, G, or T, wherein the amino acid residue of the domain numbered 3 is selected from the group consisting of T, D, H, K, R, and N; (9) an isolated heptapeptide specifically binding the nucleotide sequence 5'-(TCC)-3', wherein the amino acid residue of the domain numbered 3 is selected from the group consisting of N, H, S, D, T, Q, and G; (10) an isolated heptapeptide specifically binding the nucleotide sequence 5'-(TCG)-3', wherein the amino acid residue of the domain numbered 3 is selected from the group consisting of T, H, S, D, N, Q, and G; (11) an isolated heptapeptide specifically binding the nucleotide sequence 5'-(TGN)-3', wherein N is any of A, C, G, or T, wherein the amino acid residue of the domain numbered 3 is H; (12) an isolated heptapeptide specifically binding a nucleotide sequence selected from the group consisting of 5'-(TGG)-3' and 5'-(TGT)-3', wherein the amino acid residue of the domain numbered 3 is selected from the group consisting of S, D, T, N, Q, G, and H; (13) an isolated heptapeptide specifically binding the nucleotide sequence 5'-(TGC)-3', wherein the amino acid residue of the domain numbered 3 is selected from the group consisting of W, T, and H; (14) an isolated heptapeptide specifically binding the nucleotide sequence 5'-(TGN)-3', wherein N is any of A, C, G, or T, wherein the amino acid residue of the domain numbered 3 is H; (15) an isolated heptapeptide specifically binding a nucleotide sequence selected from the group consisting of 5'-(TTA)-3' and 5'-(TTG)-3', wherein the amino acid residue of the domain numbered 3 is selected from the group consisting of S and A; (16) an isolated heptapeptide specifically binding a nucleotide sequence selected from the group consisting of 5'-(TTC)-3' and 5'-(TTT)-3', wherein the amino acid residue of the domain numbered 3 is H; (17) an isolated heptapeptide specifically binding the nucleotide sequence 5'-(TNA)-3', wherein N is any of A, C, G, or T, wherein the amino acid residue of the domain numbered −1 is R; (18) an isolated heptapeptide specifically binding the nucleotide sequence 5'-(TNT)-3', wherein N is any of A, C, G, or T, wherein the amino acid residue of the domain numbered −1 is selected from the group consisting of S, T, and H; and (19) an isolated heptapeptide specifically binding the nucleotide sequence 5'-(TNN)-3', wherein N is any of A, C, G, or T, wherein the amino acid residue of the domain numbered 4 is selected from the group consisting of L, V, I, and C.

V. Polynucleotides, Expression Vectors, and Transformed Cells

The invention includes a nucleotide sequence encoding a zinc finger-nucleotide binding peptide or polypeptide, including polypeptides, polypeptide compositions, and isolated heptapeptides as described above. DNA sequences encoding the zinc finger-nucleotide binding polypeptides of the invention, including native, truncated, and extended polypeptides, can be obtained by several methods. For example, the DNA can be isolated using hybridization procedures that are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences of the invention can be obtained by methods known in the art (See, for example, Current Protocols in Molecular Biology, Ausubel, et al., Eds., 1989).

The development of specific DNA sequences encoding zinc finger-nucleotide binding polypeptides of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least common. This is especially true when it is desirable to obtain the microbial expression of mammalian polypeptides due to the presence of introns. For obtaining zinc finger derived-DNA binding polypeptides, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be clones. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucleic Acid Research 11:2325, 1983).

With respect to nucleotide sequences that are within the scope of the invention, all nucleotide sequences encoding the polypeptides that are embodiments of the invention as described are included in nucleotide sequences that are within the scope of the invention. This further includes all nucleotide sequences that encode polypeptides according to the invention that incorporate conservative amino acid substitutions as defined above. This further includes nucleotide sequences that encode larger proteins incorporating the zinc finger domains, including fusion proteins, and proteins that incorporate transcription modulators operatively linked to zinc finger domains.

Nucleic acid sequences of the present invention further include nucleic acid sequences that are at least 95% identical to the sequences above, with the proviso that the nucleic acid sequences retain the activity of the sequences before substitutions of bases are made, including any activity of proteins that are encoded by the nucleotide sequences and any activity of the nucleotide sequences that is expressed at the nucleic acid level, such as the binding sites for proteins affecting transcription. Preferably, the nucleic acid sequences are at least 97.5% identical. More preferably, they are at least 99% identical. For these purposes, "identity" is defined according to the Needleman-Wunsch algorithm (S. B. Needleman & C. D. Wunsch, "A General Method Applicable to the Search for Similarities in the Amino Acid Sequence of Two Proteins," *J. Mol. Biol.* 48: 443-453 (1970)).

Nucleotide sequences encompassed by the present invention can also be incorporated into a vector, including, but not limited to, an expression vector, and used to transfect or transform suitable host cells, as is well known in the art. The vectors incorporating the nucleotide sequences that are encompassed by the present invention are also within the scope of the invention. Host cells that are transformed or transfected with the vector or with polynucleotides or nucleotide sequences of the present invention are also within the scope of the invention. The host cells can be prokaryotic or eukaryotic; if eukaryotic, the host cells can be mammalian cells, insect cells, or yeast cells. If prokaryotic, the host cells are typically bacterial cells.

Transformation of a host cell with recombinant DNA may be carried out by conventional techniques as are well known to those skilled in the art. Where the host is prokaryotic, such as *Escherichia coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used.

A variety of host-expression vector systems may be utilized to express the zinc finger derived-nucleotide binding coding sequence. These include but are not limited to microorganisms such as bacteria transformed with recombinant bacteriophage DNA, plasmid DNA or cosmid DNA expression vectors containing a zinc finger derived-nucleotide binding polypeptide coding sequence; yeast transformed with recombinant yeast expression vectors containing the zinc finger-nucleotide binding coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a zinc finger derived-DNA binding coding sequence; insect cell systems infected with recombinant virus expression vectors (e.g., baculovirus) containing a zinc finger-nucleotide binding coding sequence; or animal cell systems infected with recombinant virus expression vectors (e.g., retroviruses, adenovirus, vaccinia virus) containing a zinc finger derived-nucleotide binding coding sequence, or transformed animal cell systems engineered for stable expression. In such cases where glycosylation may be important, expression systems that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., Methods in Enzymology, 153:516-544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted zinc finger-nucleotide binding polypeptide coding sequence.

In bacterial systems a number of expression vectors may be advantageously selected depending upon the use intended for the zinc finger derived nucleotide-binding polypeptide expressed. For example, when large quantities are to be produced, vectors which direct the expression of high levels of fusion protein products that are readily purified may be desirable. Those which are engineered to contain a cleavage site to aid in recovering the protein are preferred. Such vectors include but are not limited to the *Escherichia coli* expression vector pUR278 (Ruther, et al., EMBO J., 2:1791, 1983), in which the zinc finger-nucleotide binding protein coding sequence may be ligated into the vector in frame with the lac Z coding region so that a hybrid zinc finger-lac Z protein is produced; pIN vectors (Inouye & Inouye, Nucleic Acids Res. 13:3101-3109, 1985; Van Heeke & Schuster, J. Biol. Chem. 264:5503-5509, 1989); and the like.

In yeast, a number of vectors containing constitutive or inducible promoters may be used. For a review, see Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

In cases where plant expression vectors are used, the expression of a zinc finger-nucleotide binding polypeptide coding sequence may be driven by any of a number of promoters. For example, viral promoters such as the 35S RNA and 19S RNA promoters of CaMV (Brisson, et al., Nature, 310:511-514, 1984), or the coat protein promoter to TMV (Takamatsu, et al., EMBO J., 6:307-311, 1987) may be used; alternatively, plant promoters such as the small subunit of RUBISCO (Coruzzi, et al., EMBO J. 3:1671-1680, 1984; Broglie, et al., Science 224:838-843, 1984); or heat shock promoters, e.g., soybean hsp17.5-E or hsp17.3-B (Gurley, et al., Mol. Cell. Biol., 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421-463, 1988; and Grierson & Corey, Plant Molecular Biology, 2d Ed., Blackie, London, Ch. 7-9, 1988.

An alternative expression system that can be used to express a protein of the invention is an insect system. In one such system, *Autographa californica* nuclear polyhedrosis virus (AcNPV) is used as a vector to express foreign genes. The virus grows in *Spodoptera frugiperda* cells. The zinc finger-nucleotide binding polypeptide coding sequence may be cloned into non-essential regions (in *Spodoptera frugiperda,* for example, the polyhedrin gene) of the virus and placed under control of an AcNPV promoter (for example the polyhedrin promoter). Successful insertion of the zinc finger-nucleotide binding polypeptide coding sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. (E.g., see Smith, et al., J. Biol. 46:584, 1983; Smith, U.S. Pat. No. 4,215,051).

Eukaryotic systems, and preferably mammalian expression systems, allow for proper post-translational modifications of expressed mammalian proteins to occur. Therefore, eukaryotic cells, such as mammalian cells that possess the cellular machinery for proper processing of the primary transcript, glycosylation, phosphorylation, and, advantageously secretion of the gene product, are the preferred host cells for the expression of a zinc finger derived-nucleotide binding polypeptide. Such host cell lines may include but are not limited to CHO, VERO, BHK, HeLa, COS, MDCK, 293, and WI38.

Mammalian cell systems that utilize recombinant viruses or viral elements to direct expression may be engineered. For example, when using adenovirus expression vectors, the coding sequence of a zinc finger derived polypeptide may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the zinc finger polypeptide in infected hosts (e.g., see Logan & Shenk, Proc. Natl. Acad. Sci. USA 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA, 79:4927-4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the zinc finger-nucleotide binding protein gene in host cells (Cone & Mulligan, Proc. Natl. Acad. Sci. USA 81:6349-6353, 1984). High level expression may also be achieved using inducible promoters, including, but not limited to, the metallothionein IIA promoter and heat shock promoters.

For long-term, high-yield production of recombinant proteins, stable expression is preferred. Rather than using expression vectors which contain viral origins of replication, host cells can be transformed with a cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in enriched media, and then are switched to a selective medium. A number of selection systems may be used, including but not limited to the herpes simplex virus thymidine kinase (Wigler, et al., Cell 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes, which can be employed in tk$^-$, hgprt$^-$ or aprt$^-$ cells respectively. Also, antimetabolite resistance-conferring genes can be used as the basis of selection; for example, the genes for dhfr, which confer resistance to methotrexate (Wigler, et al., Natl. Acad. Sci. USA, 77:3567, 1980; O'Hare, et al., Proc. Natl. Acad. Sci. USA, 78:1527, 1981); gpt, which confers resistance to mycophenolic acid (Mulligan & Berg, Proc. Natl. Acad. Sci. USA, 78:2072, 1981; neo, which confers resistance to the aminoglycoside G418 (Colberre-Garapin, et al., J. Mol. Biol., 150:1, 1981); and hygro, which confers resistance to hygromycin (Santerre, et al., Gene, 30:147, 1984). Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:804, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with the zinc finger-nucleotide binding protein of the invention. Antibody which consists essentially of pooled monoclonal antibodies with different epitopic specificities, as well as distinct monoclonal antibody preparations, is provided. Monoclonal antibodies are made from antigen containing fragments of the protein by methods well known in the art (Kohler, et al., Nature, 256: 495, 1975; Current Protocols in Molecular Biology, Ausubel, et al., ed., 1989).

VI. Pharmaceutical Compositions

In another aspect, the present invention provides a pharmaceutical composition comprising:

(1) a therapeutically effective amount of a polypeptide, polypeptide composition, or isolated heptapeptide according to the present invention as described above; and (2) a pharmaceutically acceptable carrier.

Alternatively, the present invention also provides:

(1) a therapeutically effective amount of a nucleotide sequence that encodes a polypeptide, polypeptide composition, or isolated heptapeptide according to the present invention as described above; and (2) a pharmaceutically acceptable carrier.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. The active ingredient can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient. Still other ingredients that are conventional in the pharmaceutical art, such as chelating agents, preservatives, antibacterial agents, antioxidants, coloring agents, flavoring agents, and others, can be employed depending on the characteristics of the composition and the intended route of administration for the composition.

The pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylaminoethanol, histidine, procaine and the like. Physiologically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

In particular, a pharmaceutical composition according to the present invention can comprise: (1) a therapeutically effective amount of an artificial transcription factor that binds at least a portion of the HIV-1 tRNA primer-binding site or of a polynucleotide that encodes such an artificial transcription factor; and (2) a pharmaceutically acceptable carrier.

VII. Uses

In one embodiment, a method of the invention includes a process for modulating (inhibiting or suppressing) expression of a nucleotide sequence that contains a TNN target sequence. The method includes the step of contacting the nucleotide with an effective amount of a zinc finger-nucleotide binding polypeptide of this invention that binds to the motif. In the case where the nucleotide sequence is a promoter, the method includes inhibiting the transcriptional transactivation of a promoter containing a zinc finger-DNA binding motif. The term "inhibiting" refers to the suppression of the level of activation of transcription of a structural gene operably linked to a promoter, containing a zinc finger-nucleotide binding motif, for example. In addition, the zinc finger-nucleotide binding polypeptide can bind a target within a structural gene or within an RNA sequence.

The term "effective amount" includes that amount which results in the deactivation of a previously activated promoter or that amount which results in the inactivation of a promoter containing a target nucleotide, or that amount which blocks transcription of a structural gene or translation of RNA. The amount of zinc finger derived-nucleotide binding polypeptide required is that amount necessary to either displace a native zinc finger-nucleotide binding protein in an existing protein/promoter complex, or that amount necessary to compete with the native zinc finger-nucleotide binding protein to form a complex with the promoter itself. Similarly, the amount required to block a structural gene or RNA is that amount which binds to and blocks RNA polymerase from reading through on the gene or that amount which inhibits translation, respectively. Preferably, the method is performed intracellularly. By functionally inactivating a promoter or structural gene, transcription or translation is suppressed. Delivery of an effective amount of the inhibitory protein for binding to or "contacting" the cellular nucleotide sequence containing the target sequence can be accomplished by one of the mechanisms described herein, such as by retroviral vectors or liposomes, or other methods well known in the art. The term "modulating" refers to the suppression, enhancement or induction of a function. For example, the zinc finger-nucleotide binding polypeptide of the invention can modulate a promoter sequence by binding to a target sequence within the promoter, thereby enhancing or suppressing transcription of a gene operatively linked to the promoter nucleotide sequence. Alternatively, modulation may include inhibition of transcription of a gene where the zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript.

The promoter region of a gene includes the regulatory elements that typically lie 5' to a structural gene; multiple regulatory elements can be present, separated by intervening nucleotide sequences. If a gene is to be activated, proteins known as transcription factors attach to the promoter region of the gene This assembly resembles an "on switch" by enabling an enzyme to transcribe a second genetic segment from DNA to RNA. In most cases the resulting RNA molecule serves as a template for synthesis of a specific protein; sometimes RNA itself is the final product.

The promoter region may be a normal cellular promoter or, for example, an onco-promoter. An onco-promoter is generally a virus-derived promoter. For example, the long terminal repeat (LTR) of retroviruses is a promoter region that may be a target for a zinc finger binding polypeptide variant of the invention. Promoters from members of the Lentivirus group, which include such pathogens as human T-cell lymphotrophic virus (HTLV) 1 and 2, or human immunodeficiency virus (HIV) 1 or 2, are examples of viral promoter regions which may be targeted for transcriptional modulation by a zinc finger binding polypeptide of the invention A target TNN nucleotide sequence can be located in a transcribed region of a gene or in an expressed sequence tag. As described above, the target TNN sequence can also be located adjacent to the transcription termination site of a gene. A gene containing a target sequence can be a plant gene, an animal gene or a viral gene. The gene can be a eukaryotic gene or prokaryotic gene such as a bacterial gene. The animal gene can be a mammalian gene including a human gene. In a preferred embodiment, a method of modulating nucleotide expression is accomplished by transforming a cell that contains a target nucleotide sequence with a polynucleotide that encodes a polypeptide or composition of this invention. Preferably, the encoding polynucleotide is contained in an expression vector suitable for use in a target cell. Suitable expression vectors are well known in the art.

The TNN target can exist in any combination with other target triplet sequences. That is, a particular TNN target can exist as part of an extended TNN sequence (e.g., $[TNN]_{2-12}$) or as part of any other extended sequence such as $(GNN)_{1-12}$, $(ANN)_{1-12}$, $(CNN)_{1-12}$ or $(NNN)_{1-12}$.

In particular, the present invention also includes a method of inhibiting the replication of HIV-1 virus comprising the step of administering to an individual infected with HIV-1 virus a sufficient quantity of the artificial transcription factor of the present invention, as described above, capable of binding to the tRNA primer-binding site such that replication of HIV-1 is inhibited. As used herein, the term "inhibited" does not require complete inhibition or blockage of the replication of HIV-1, but includes any degree of inhibition of the replication of HIV-1 such that at least one clinically beneficial result occurs. The term "clinically beneficial result" includes, but is not limited to, increased numbers of circulating CD4-positive T-lymphocytes, reduced viral load, increased resistance to opportunistic infections, and increased energy and sense of well-being. Similarly, the present invention also includes a method for inhibiting the replication of HIV-1 virus comprising the step of administering to an individual infected with HIV-1 virus a sufficient quantity of a polynucleotide encoding an artificial transcription factor of the present invention such that replication of HIV-1 is inhibited.

The Examples that follow illustrate preferred embodiments of the present invention and are not limiting of the specification and claims in any way.

EXAMPLE 1

Selection and Characterization of Zinc Finger Domains with Unique Binding Specificity for 5'-(TNN)-3' DNA Sequences Introduction $Cys_2$-$His_2$ zinc finger proteins are one of the most common DNA-binding motifs found in eukaryotic transcription factors. These zinc fingers are compact domains containing a single amphipathic α-helix stabilized by two β-strands and zinc ligation. Amino acids on the surface of the α-helix contact bases in the major groove of DNA. Zinc finger proteins typically contain multiple fingers that make tandem contacts along the DNA. The mode of DNA recognition is principally a one-to-one interaction between amino acids from the recognition helix and DNA bases. One finger usually recognizes 3 base pairs (bp). As these fingers function as independent modules, fingers with different triplet specificities can be combined to give specific recognition of longer DNA sequences. This simple, modular structure of zinc finger domains and the wide variety of DNA sequences they can recognize make them an attractive framework for the design of novel DNA-binding proteins.

The ability to rapidly prepare proteins with predefined specificities for DNA sequences could enable a wide range of technologies that might be used for example to direct the expression of genes or to physically modify genes and genomes. In order to develop a universal system for gene regulation, much effort has been applied to the development of artificial transcription factors based on polydactyl zinc finger proteins (Blancafort, P., Segal, D. J., and Barbas, C. F., 3rd. (2004) Mol Pharmacol 66(6), 1361-1371; Beerli, R. R., and Barbas, C. F., 3rd. (2002) Nat Biotechnol 20(2), 135-141; Jantz, D., and Berg, J. M. (2004) Chem Rev. 104(2), 789-799). Such a system might have considerable impact on biology and biotechnology and offer a new approach for treatment of diseases based on directed gene regulation. It has now been shown that gene expression can be specifically altered using artificial transcription factors based on polydactyl zinc finger proteins that bind to 18 base pair (bp) target sites (Blancafort, P., Segal, D. J., and Barbas, C. F., 3rd. (2004) Mol Pharmacol 66(6), 1361-1371; Beerli, R. R., and Barbas, C. F., 3rd. (2002) Nat Biotechnol 20(2), 135-141). Targeting of sites as small as 9 bp can also provide some degree of regulatory specificity presumably through the aid of chromatin occlusion (Zhang, L., Spratt, S. K., Liu, Q., Johnstone, B., Qi, H., Raschke, E. E., Jamieson, A. C., Rebar, E. J., Wolffe, A. P., and Case, C. C. (2000) J Biol Chem 275(43), 33850-33860; Liu, P. Q., Rebar, E. J., Zhang, L., Liu, Q., Jamieson, A. C., Liang, Y., Qi, H., Li, P. X., Chen, B., Mendel, M. C., Zhong, X., Lee, Y. L., Eisenberg, S. P., Spratt, S. K., Case, C. C., and Wolffe, A. P. (2001) *J Biol Chem* 276(14), 11323-11334; Blancafort, P., Magnenat, L., and Barbas, C. F., 3rd. (2003) *Nat Biotechnol* 21(3), 269-274). In addition to transcriptional regulation, novel zinc finger DNA-binding specificities are showing tremendous promise in directing homologous recombination through their fusion with the Fok I nuclease domain (Urnov F D, M. J., Lee Y L, Beausejour C M, Rock J M, Augustus S, Jamieson A C, Porteus M H, Gregory P D, Holmes M C. (2005) *Nature* 435(7042), 646-651; Bibikova, M., Beumer, K., Trautman, J. K., and Carroll, D. (2003) *Science* 300(5620), 764).

Zinc finger domains of the type $Cys_2$-$His_2$ are a unique and promising class of proteins for the recognition of extended DNA sequences due to their modular nature. Each domain consists of approximately 30 amino acids folded into a $\beta\beta\alpha$ structure stabilized by hydrophobic interactions and chelation of a zinc ion by the conserved $Cys_2$-$His_2$ residues (Miller, J., McLachlan, A. D., and Klug, A. (1985) *EMBO J.* 4(6), 1609-1614; Lee, M. S., Gippert, G. P., Soman, K. V., Case, D. A., and Wright, P. E. (1989) *Science* (Washington, D.C., 1883-) 245(4918), 635-637). To date, the best-characterized protein of this family of zinc finger proteins is the mouse transcription factor Zif268. Each of the three zinc finger domains of Zif268 binds to a 3 bp subsite by insertion of the α-recognition helix into the major groove of the DNA double helix (Pavletich, N. P., and Pabo, C. O. (1991) *Science* (Washington, D.C., 1883-) 252(5007), 809-817; Elrod-Erickson, M., Rould, M. A., Nekludova, L., and Pabo, C. O. (1996) *Structure* 4, 1171-1180). To facilitate the rapid construction of DNA-binding proteins and to study protein-DNA interactions, domains have previously been created that bind to the 5'-GNN-3' and 5'-ANN-3' family of DNA sequences (Segal, D. J., Dreier, B., Beerli, R. R., and Barbas, C. F., 3rd. (1999) *Proc Natl Acad Sci USA* 96(6), 2758-2763; Dreier, B., Segal, D. J., and Barbas, C. F., 3rd. (2000) *J Mol Biol* 303(4), 489-502; Dreier, B., Beerli, R. R., Segal, D. J., Flippin, J. D., and Barbas, C. F., 3rd. (2001) *J Biol Chem* 276(31), 29466-29478). It was demonstrated that these domains function as modular recognition units that can be assembled into polydactyl zinc finger proteins that specifically recognize from 9 to 18 bp target sites. Significantly, an 18 bp site is long enough to potentially be unique within the human, or any other genome and transcriptional specificity of such proteins has been demonstrated in transgenic plants and human cells using array analysis (Guan, X., Stege, J., Kim, M., Dahmani, Z., Fan, N., Heifetz, P., Barbas, C. F., 3rd, and Briggs, S. P. (2002) *Proc Natl Acad Sci USA* 99(20), 13296-13301; Tan, S., Guschin, D., Davalos, A., Lee, Y. L., Snowden, A. W., Jouvenot, Y., Zhang, H. S., Howes, K., McNamara, A. R., Lai, A., Ullman, C., Reynolds, L., Moore, M., Isalan, M., Berg, L. P., Campos, B., Qi, H., Spratt, S. K., Case, C. C., Pabo, C. O., Campisi, J., and Gregory, P. D. (2003) *Proc. Nat. Acad. Sci., USA.* 100(21), 11997-12002). In addition to constitutive regulation, fusion of ligand-binding domains from nuclear hormone receptors with specific binding domains provides inducible gene regulation with this class of transcription factors (Beerli, R. R., Schopfer, U., Dreier, B., and Barbas, C. F., 3rd. (2000) *J Biol Chem* 275(42), 32617-32627). To provide for ultimate freedom in DNA targeting it is important to identify the 64 DNA-binding domains required to target each possible 3-bp subsite.

Due to the limited structural data on zinc finger/DNA interactions (Pavletich, N. P., and Pabo, C. O. (1993) *Science* (Washington, D.C., 1883-) 261(5129), 1701-1707; Kim, C. A., and Berg, J. M. (1996) *Nature Structural Biology* 3, 940-945; Fairall, L., Schwabe, J. W. R., Chapman, L., Finch, J. T., and Rhodes, D. (1993) *Nature (London)* 366(6454), 483-487; Houbaviy, H. B., Usheva, A., Shenk, T., and Burley, S. K. (1996) *Proc. Natl. Acad. Sci. U.S.A.* 93(24), 13577-13582; Wuttke, D. S., Foster, M. P., Case, D. A., Gottesfeld, J. M., and Wright, P. E. (1997) *J. Mol. Biol.* 273(1), 183-206; Nolte, R. T., Conlin, R. M., Harrison, S. C., and Brown, R. S. (1998) *Proc. Natl. Acad. Sci. U.S.A.* 95(6), 2938-2943) de novo design of zinc proteins that bind with a high degree of specificity to novel sequences has been of limited success (Havranek J J, D. C., Baker D. (2004) *J Mol Biol.* 344(1), 59-70). Crystallographic data and mutagenesis studies concerning the mode of interaction of zinc finger domains of the $Cys_2$-$His_2$ family has guided us in the construction of phage display libraries for selection of domains that recognize many DNA subsites (Dreier, B., Beerli, R. R., Segal, D. J., Flippin, J. D., and Barbas, C. F., 3rd. (2001) *J Biol Chem* 276(31), 29466-29478). The analysis of the Zif268/DNA complex suggests that DNA binding is predominantly achieved by the interaction of amino acid residues of the α-helix in positions −1, 3, and 6 with the 3', middle, and 5' nucleotides of a 3 bp DNA subsite, respectively (Pavletich, N. P., and Pabo, C. O. (1991) *Science* (Washington, D.C., 1883-) 252(5007), 809-817; Elrod-Erickson, M., Rould, M. A., Nekludova, L., and Pabo, C. O. (1996) *Structure* 4, 1171-1180). Positions 1, 2, and 5 of the α-helix make direct or water-mediated contacts with the phosphate backbone of the DNA and are important contributors to the ultimate specificity of the protein. Leucine is typically found in position 4 and packs into the hydrophobic core of the domain Position 2 of the α-helix interacts with other helix residues and, in addition, can make contact with a nucleotide outside the 3 bp subsite resulting in target site overlap (Segal, D. J., Dreier, B., Beerli, R. R., and Barbas, C. F., 3rd. (1999) *Proc Natl Acad Sci USA* 96(6), 2758-2763; Dreier, B., Beerli, R. R., Segal, D. J., Flippin, J. D., and Barbas, C. F., 3rd. (2001) *J Biol Chem* 276(31), 29466-29478; Wolfe S A, G. H., Ramm E I, Pabo C O. (1999) *J Mol Biol.* 285(5), 1917-1934; Isalan, M., Choo, Y., and Klug, A. (1997) *Proc. Natl. Acad. Sci. U.S.A.* 94(11), 5617-5621; Pabo C. O., Nekludova, L. (2000) *J Mol Biol.* 301(3), 597-624).

The most studied scaffold for building proteins of novel specificity have been the murine transcription factor Zif268 and the structurally related human transcription factor Sp1.

FIG. 1 shows the zinc finger-DNA complex of the murine transcription factor Zif268.

Figure 2:
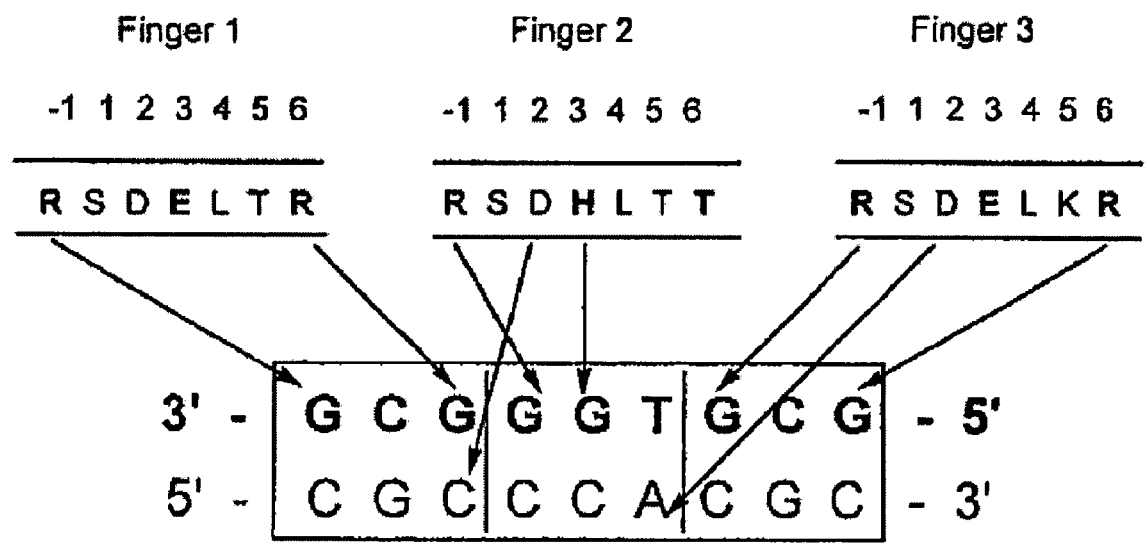
FIG. 2 is a diagram showing the protein-DNA interaction of the transcription factor Zif268 in terms of the interaction between specific bases of the DNA and specific amino acids of the three fingers of the transcription factor.

The structure and DNA-binding specificity of both proteins are well-studied (Elrod-Erickson, M., Rould, M. A., Nekludova, L., and Pabo, C. O. (1996) *Structure* 4, 1171-1180; Narayan, V. A, Kriwacki, R. W., and Caradonna, J. P. (1997), *J. Biol. Chem.* 272, 7801-7809). FIG. 2 shows the protein-DNA interaction of the transcription factor Zif268 in terms of the interaction between specific bases of the DNA and specific amino acids of the three fingers of the transcription factor. Positions −1, 3, and −6 were generally observed to contact the 3'-, middle, and 5'-nucleotides of a base triplet, respectively. Positions −2, 1, and 5 are often involved in direct or water mediated contacts to the phosphate backbone. Position 4 is typically a leucine residue that packs in the hydrophobic core of the domain. Position 2 has been shown to interact with other helix residues and/or bases depending on the helix structure. In the Zif268-DNA complex aspartate at position 2 of finger 2 and in position 2 of finger 3 contacts cytosine or adenine, respectively, on the complementary DNA strand, which is called "target site overlap." Distinguished from other zinc finger binding proteins Zif268 and Sp1 show only low inter-domain cooperative binding activity, which make them attractive frameworks for investigation of zinc finger structure-activity relationships and for the design of novel zinc finger domains.

However, the structural details of recognition are still complicated to define. The selection of zinc-finger domains which had been characterized in detail to specifically bind to DNA focused so far on the 5'-(GNN)-3' target family. Some information about amino acid-base interactions in detail from this work is provided in Table 1.

Most of the successful selections have involved sites of this form. For the majority of the remaining 48 triplets, only a few fingers with the desired specificity have been reported. It is not yet known to what extent this represents an intrinsic preference of zinc fingers for binding to 5'-(GNN)-3' targets or just the limited target sites which have been tested so far. According to the fact that "cross-strand" interactions from position 2 to the neighboring base pair on the adjacent triplet can influence the specificity of binding, the simple model that zinc fingers are essentially independent modules binding three base pairs has to be revised to a model that considers synergy between adjacent fingers. The construction of multifinger proteins remains challenging not only because of the inter-domain cooperativity but also because effects of the linker region and the β-strands of the zinc finger protein structure have to be considered. The goal of the work reported in this Example is to select zinc finger domains which bind specifically to 5'-(TNN)-3' DNA sequences. To date, recognition of the 5'-nucleotide by the amino acid in position 6 of the α-helix is not understood, except the interaction of the 5'-guanine with arginine or lysine (Table 1).

Results

To extend the number of domains, an existing phage display library was used for the selection. This library had previously generated domains for 5'-(GNN)-3' binding zinc finger domains and should be suitable for the selections of domains binding specifically to 5'-(TNN)-3' target sites as well, because the aspartate in position 2 of the finger-3 helix of these three-finger proteins allows the recognition of a 5'-guanine or thymine in the finger 2 target site (FIG. 2). The construction of the phage display library was based on the C7 protein, a variant of Zif268. Two sublibraries were constructed in the phage display vector pComb3H. The NNK library involved randomization of amino acid residues of the α-helix of finger 2 at positions −1, 1, 2, 3, 5, and 6 using a codon doping strategy that allows for all amino acid combinations, excluding stop codons, generating 32 codon possibilities. The VNS library was constructed by randomization of positions −2, −1, 1, 2, 3, 5, and 6, which excludes the aromatic amino acids Tyr, Phe, and Trp, as well as stop codons, leaving 24 possibilities for each codon. The libraries consisted of $4.4 \times 10^9$ and $3.5 \times 10^9$ members, respectively, each capable of recognizing sequences of the 5'-GCGNNNGCG-3' (SEQ ID NO: 423) type. These sublibraries were amplified and combined for the selection procedure. Within six rounds of panning the concentration of competitor DNA was increased and the target concentration decreased to increase the selection pressure (Tables 3, 8, 11). After the last round of panning, the DNA sequence of four single clones selected for each of the 5'-(TNN)-3' target sites was determined and the amino acid sequence deduced. From the first set of panning (each set consisted of 6 DNA targets which were studied in parallel, consensus sequences were found that bound selectively to 5'-(TAA)-3', 5'-(TAC)-3', 5'-(TAG)-3', 5'-(TAT)-3', and 5'-(TTG)-3' DNA target sites. No consensus sequence was found for clones selected to bind 5'-(TCG)-3'.

Figure 3:
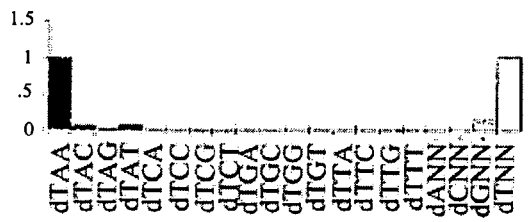
FIG. 3 is a first series of graphs showing the results of the multitarget specificity assay for a number of zinc fingers generated by the process of Example 1: ((a) QAS-N-LIS (TAA-1a-2) (SEQ ID NO: 1; binding 5'-(TAA)-3'; (b) SRG-N-LKS (TAC-2c-2) (SEQ ID NO: 2; binding 5'-(TAC)-3'; (c) ARG-N-LKS (TAC-2d-2) (SEQ ID NO: 7; binding 5'-(TAC)-3'; (d) RLD-N-LQT (TAG-3c-2) (SEQ ID NO: 3; binding 5'-(TAG)-3'; (e) RSD-N-LTT (TAG-3d-2) (SEQ ID NO: 8; binding 5'-(TAG)-3'; (f) ARG-N-LRT (TAT-4c-8) (SEQ ID NO: 4; binding 5'-(TAT)-3'); (g) VRG-N-KLS (TAT-4d-2) (SEQ ID NO: 9; binding 5'-(TAT)-3'); and (h) RKD-A-LRG (TTG-6c-2) (SEQ ID NO: 5; binding 5'-(TTG)-3')).
Figure 3:
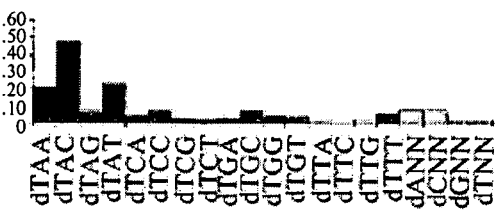
Figure 3:
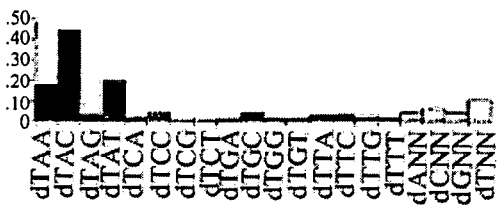
Figure 3:
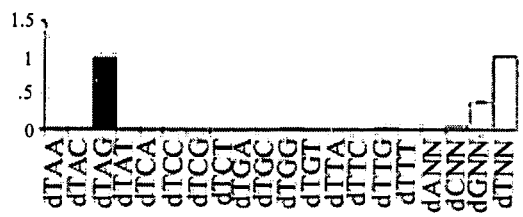
Figure 3:
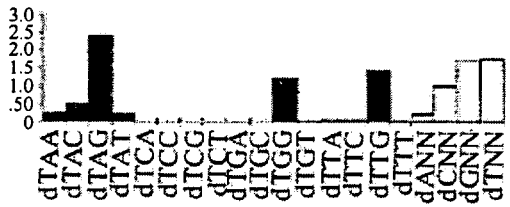
Figure 3:
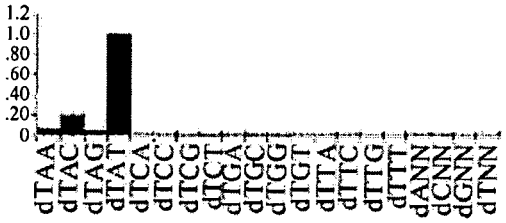
Figure 3:
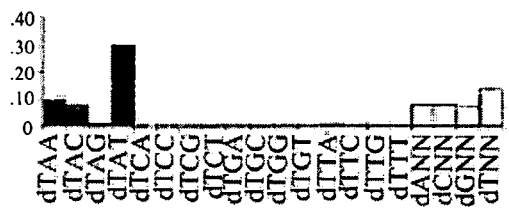
Figure 3:
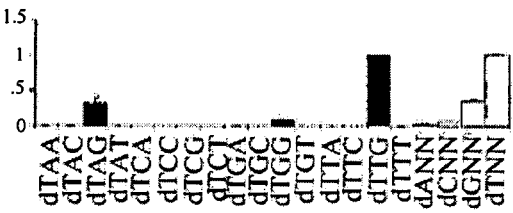

Generally, each set showed good conservation on the amino acid level. In the case of domains binding selectively to 5'-(TAA)-3', all four clones analyzed had the same amino acid sequence within the helical region of finger 2 (positions −1 to 6). Clones which had been selected to bind to 5'-(TAC)-3' DNA targets showed conservation for positions 1, 2, 3, 4, 5, and 6, while position −1 was identified as Ala or Ser. In contrast, the recognition of a 3'-cytosine by 5'-(GNN)-3'-specific domains is mediated by amino acids Asp or Glu (Table 1). Clones selected to bind 5'-(TAG)-3' sequences showed conservation in positions 1, 2, 3, 54, and 6. Position 1 can be Leu or Ser and position 5 Gln or Thr. Both positions are not involved directly in interactions with the DNA bases but often in water mediated contacts to the phosphate backbone (FIG. 2). Domains binding to 5'-(TAT)-3' were conserved in positions 1, 2, 3, 4, 5, and 6, while position −1 was found to be Ala or Val. For domains binding 5'-(GNN)-3' subsites, recognition of a 3'-thymine was achieved by Thr or Ser in position 1. Further, all clones binding to 5'-(TAN)-3' subsites isolated in the work leading to this Example showed conservation in position 3 of the α-helix, indicating that the recognition of a middle adenine is mediated by $Asn^3$. This finding is consistent with results from the 5'-(GNN)-3' study (Table 1). In addition, domains selected to bind 5'-(TTG)-3' were conserved in positions 1, 2, 3, 4, 5, and 6, while position −1 can be Arg or Glu. $Arg^{-1}$ was also strongly selected for the recognition of a 3'-guanine characterized previously for all domains binding 5'-(GNG)-3' target sites (Table 1). Interestingly, the domains selected in the work leading to Example 1 to specifically bind 5'-(TNN)-3' showed conservation in position 6 of the α-helix which usually mediates the recognition of the 5'-nucleotide within a 3-base-pair subsite. Amino acids Thr, Ser, and Gly were identified in position 6. $Thr^6$ is also present in the finger-2 domain of Zif268 (FIG. 2), but no contact had been observed in structural studies of the protein/DNA complex from that position. Surprisingly, phage display selections resulted in a few specific amino acid residues which showed preferential recognition of a 5'-thymine (FIG. 3).

The coding region for the 3-finger proteins containing the newly selected finger-2 domains were cloned into the expression vector pMal and transformed into XL-1 blue. After induction with IPTG, protein extracts were prepared. The binding specificity of these proteins to all of the 16-possible 5'-(TNN)-3' finger-2 subsites was studied by multi-target ELISA (FIG. 3). All proteins showed a high degree of binding specificity for their target DNA subsites (FIG. 3). Clones selected to bind specifically to 5'-(TAC)-3' differ only in position −1 (Ser or Ala) of finger 2, which is responsible for the 3'-nucleotide recognition. Both of the investigated clones show slight cross-reactivity with 5'-(TAA)-3' and 5'-(TAT)-3' DNA targets. Clones selected for 5'-(TAG)-3' DNA targets differ in positions 1 (Leu or Ser) and 5 (Gln or Thr) of finger 2. Since both residues are usually not involved in direct contact with the DNA bases, it was surprising that these helices showed different DNA-binding preferences. Clone TAG-3d-2 binds to 5'-(TNG)-3' target sites, without discrimination of the middle nucleotide. Clone TAG-3c-2 showed highly specific binding to its target. Both clones selected to bind to 5'-(TAT)-3' differ in the amino acid sequence of finger 2 in positions −1 (Ala or Val), 5 (Arg or Lys), and 6 (Thr or Ser); please note that these are highly conservative amino acid substitutions in all cases, and both clones show selection for similar amino acid side chains in these positions (−1 for hydrophobic, 5 for basic, and 6 for polar, uncharged residues). Interestingly, both clones prefer binding to their target site, but with relatively low affinity as estimated by the $OD_{405}$ value, and less discrimination for the 3'-nucleotide recognition when position −1 is Val (clone 4d-2). The clone which had been selected to bind to 5'-(TTG)-3' DNA target showed slight cross-reactivity to 5'-(TAG)-3', and, to a less extent, to 5'-(TGG)-3'. Similar effects have been observed for the selection of 5'-(GNG)-3' binding proteins. The second panning set contained the DNA targets 5'-(TCA)-3', 5'-(TCC)-3', 5'-(TCT)-3', 5'-(TGA)-3', 5'-(TGC)-3', and 5'-(TCG)-3' as no consensus sequence for the α-helix of finger 2 was found for these targets after the first panning procedure. After 6 rounds of selection 4 single clones from each pool were analyzed by DNA sequencing and deduction of the amino acid residues in the α-helix. None of the sets showed a consensus sequence of their selected finger-2 domains. Surprisingly, even for the selection of the positive control 5'-(TGA)-3' no consensus sequence was found. A domain binding to this DNA subsite had been characterized in a previous study, and was used here for the attempt to isolate a more specific clone. One reason for the failure to isolate any domains from the second panning set might have been the relatively high selection pressure that was chosen (Table 8). The panning procedure for these targets was therefore repeated, but with a lower concentration of competitors. Even using very mild selection pressure, no domains were isolated to specifically bind their target DNA or showed any conservation on the amino acid level (Tables 10-12).

Summary

The work reported in this Example aimed at the selection of new zinc finger domains with binding specificity for 5'-(TNN)-3' DNA targets.

By screening a phage display library which had been constructed based on the D7 protein, five new finger-2 domains were found to bind selectively to 5'-(TAA)-3', 5'-(TAC)-3', 5'-(TAG)-3', 5'-(TAT)-3', and 5'-(TTG)-3' DNA target sites. Amino acid sequences of the newly selected domains reveal strong homology with the amino acid sequences of zinc finger domains reported earlier, especially for the recognition of a 3'-adenine by Gln in position −1, a middle adenine by Asp in position 3 and a 3'-guanine by Arg in position −1 (Table 1). This homology was not known for zinc finger domains binding sequences of the form 5'-(TNN)-3'. Moreover, analysis of the new finger-2 domains lead to further insights into the possible interaction pattern of position 6 in the helical region with a 5'-thymine. Based on these results, recognition of a 5'-thymine might be achieved by Ser, Thr, or Gly.

Experimental

1. Library Amplification Selection was based on a phage display library which randomized six amino acids of finger 2 of the C7 protein (derivative of Zif268). This library was generated by cloning of DNA fragments randomized by PCR into the phage display vector pComb3H and transformation into *Escherichia coli*. The library contained $10^9$ members.

The phage library was amplified by infecting 10 ml culture (SB media) of *E. coli* (ER2537) at $OD_{600}$ ~1.0 with 10 µl of the phage library. 10 ml of SB containing 50 µg/ml of carbenicillin was added after 1 h of shaking at 37° C. 2 ml of helper phage (VCSM13; ≈$10^{13}$ cfu/ml) were added after an additional hour and the culture was transferred into 200 ml of fresh SB media containing 50 µg/ml of carbenicillin and 90 µM $ZnCl_2$. After 2 hours shaking at 37° C., kanamycin was added to 70 µg/ml. The culture was incubated at 37° C. overnight. The next morning phage were prepared by PEG/NaCl preparation, pooled and used for panning against 6 different DNA targets per set. Six rounds were performed for selection of target binding phage with increasing amounts of competitor DNA (Tables 4, 8, 11).

2. Selection Procedure For the preparation of phage the overnight cultures were centrifuged 20 minutes at 5,000 rpm in a JLA-10.5 rotor in a Beckman J2-HS centrifuge. The phage from the culture supernatants were precipitated with 4% PEG 8000 and 0.5 M NaCl for 30 minutes on ice. The mixture was centrifuged for another 30 minutes at 9,000 rpm. The supernatant was discarded and the phage pellets were air dried (10-20 min). The phage pellets were resuspended in 1% BSA/zinc buffer A (10 mM Tris, pH 7.5; 90 m M KCl, 1 mM $MgCl_2$, 90 µM $ZnCl_2$) containing 5 mM fresh DTT, and sterile filtered through an 0.2 µM CA-membrane/CF-prefilter syringe filter). Titers of these "input" phage were determined by serial dilution and inoculation of ER2537 at $OD_{600}$=1.0. The phage preparations were stored at 4° C. after adding 10 µl of 2% $NaN_3$.

100 µl of these phage preparations were used for the binding reaction to the target oligonucleotides. The binding reactions were performed in a 500-µl volume of 1% Blotto in zinc buffer A containing 5 mM fresh DTT, sheared herring sperm DNA as non-specific competitor, and different concentrations of competitor oligonucleotides (Tables 4, 8, 11). Blotto, zinc buffer A containing 5 mM fresh DTT, sheared herring sperm DNA, the competitor oligonucleotides, and the phage preparations were mixed together and incubated for 1 h at 4° C. (or 30 min at room temperature) with constant gentle mixing. Target oligonucleotide was then added and incubation was continued overnight at 4° C. (or for 3 h at room temperature). 50 µl of streptavidin-coated magnetic beads (Dynal) were washed twice with 500 µl 1% BSA in zinc buffer A and then blocked with 500 µl 5% Blotto in zinc buffer A also overnight at 4° C. (or for 3 hours at room temperature) with constant gentle mixing.

The blocking solution was discarded and replaced by the whole volume of the binding reaction mixture. The binding of the biotinylated target oligonucleotides to the streptavidin-coated magnetic beads was performed for 1 hour at 4° C. with constant gentle mixing. The beads were washed 10 times with 2% Tween in zinc buffer A containing 5 mM fresh DTT by gentle mixing. For the last washing step zinc buffer A (5 mM DTT) was used to remove the detergent. DNA-bound phage were eluted from the magnetic beads adding 25 µl of 10 mg/ml trypsin in zinc buffer A for 30 minutes at room temperature. The proteolysis was stopped by addition of 75 µl of SB media.

The 100 µl elution mixture was used to infect 5 ml of ER 2537 *E. coli* cells in SB at $OD_{600}$=1.0. After 30 min incubating at 37° C. 5 ml SB containing 50 µg/ml carbenicillin was added. At this step, 10 µl of the reaction mixture was removed and mixed with 100 µl SB medium to determine the number of "output" phages (Tables 3, 7, and 10). Cells were plated in serial dilution on LB plates containing 50 µg/ml carbenicillin. After 30 min, 1 ml of helper phage was added and the whole mixture was transferred into a centrifuge bottle with 100 ml of fresh, prewarmed SB media containing 50 µg/ml carbenicillin and 90 µM $ZnCl_2$. After 1.5 hours, kanamycin was added to 70 µg/ml. The cultures were incubated overnight at 37° C.

DNA Isolation After the last round of panning the bacterial pellet was resuspended in 10 ml of P1 buffer (QIAprep Spin Miniprep Kit 250, QIAGEN Inc.). 500 µl of this suspension was used to prepare DNA using this kit. The remaining volume was stored at 20° C. 1.5 µg of the isolated DNA was mixed with 200 ng of the Omp seq GTG primer and analyzed for the sequence.

Bacterial Extracts of pMal-Fusion Proteins for ELISA Assays The selected zinc finger proteins were cloned into the pMal vector (New England Biolabs) for expression. The constructs were transferred into the *E. coli* strain XL1-Blue by electroporation and streaked on LB plates containing 50 µg/ml carbenicillin. Four single colonies of each mutant were inoculated into 3 ml of SB media containing 50 µg/ml carbenicillin and 1% glucose. Cultures were grown overnight at 37° C. 1.2 ml of the cultures were transformed into 20 ml of fresh SB media containing 50 µg/ml carbenicillin, 0.2% glucose, 90 µg/ml $ZnCl_2$ and grown at 37° C. for another 2 hours. IPTG was added to a final concentration of 0.3 mM. Incubation was continued for 2 hours. The cultures were centrifuged at 4° C. for 5 minutes at 3500 rpm in a Beckman GPR centrifuge. Bacterial pellets were resuspended in 1.2 ml of zinc buffer A containing 5 mM fresh DTT. Protein extracts were isolated by freeze/thaw procedure using dry ice/ethanol and warm water. This procedure was repeated 6 times. Samples were centrifuged at 4° C. for 5 minutes in an Eppendorf centrifuge. The supernatant was transferred to a clean 1.5 ml centrifuge tube and used for the ELISA assays.

ELISA Assays Streptavidin at a concentration of 0.2 µg/25 µl in PBS was added to each well of a 96-well ELISA plate (Costar 3690, high binding, Corning, Inc.) then incubated for 1 hour at 37° C. (or overnight at 4° C.). The plates were washed 2 times with water, then biotinylated oligonucleotide at 0.025 µg/25 µg in PBS, or only PBS for BSA controls, was added and incubated for 1 hour at 37° C. The plates were washed 2 times with water. For blocking reaction each well was filed with 3% BSA in PBS (filtered) and incubated for 1 hour at 37° C. The BSA was removed and 25 µl of the bacterial extract or phage suspension was added to the wells. After incubation for 1 hour at 37° C. the plates were washed 10 times with water. An α-MBP antibody was added to the wells followed by addition of an α-m-alkPhos antibody (for pMal-fusion proteins; diluted 1:1000 in PBS) or α-M13 mAb conjugated to horseradish peroxidase (Pharmacia) (for phage suspensions (diluted 1:5000 in PBS) was added to the wells and incubated for 1 hour at 37° C. The plates were washed 10 times with water. 25 µl of alkaline phosphatase substrate solution (Sigma) for α-m-alkPhos Ab or 25 µl of ABTS substrate (for α-M13 mAb) was added to each well. Incubation was performed at room temperature. The $OD_{405}$ of each well was usually determined at 20 and 60 minute time points.

TABLE 3

Panning chart 5'-TNN-3' C7.Lib Set 1

|  |  | Round 1 | Round 2 | Round 3 | Round 4 | Round 5 | Round 6 |
|---|---|---|---|---|---|---|---|
| Phage in |  |  |  |  |  |  |  |
| VNS | 1.2 × E10 |  |  |  |  |  |  |
| NNK | 1.3 × E10 |  |  |  |  |  |  |
| 1-TAA |  |  | 2.0 × E11 | 5.2 × E12 | 2.7 × E12 | 2.1 × E12 | 2.3 × E12 |
| 2-TAC |  |  | 4.8 × E11 | 4.0 × E12 | 2.4 × E12 | 1.2 × E12 | 3.9 × E12 |
| 3-TAG |  |  | 5.1 × E11 | 1.0 × E13 | 1.7 × E12 | 1.4 × E12 | 5.1 × E11 |
| 4-TAT |  |  | 1.7 × E11 | 3.6 × E12 | 2.4 × E12 | 1.2 × E12 | 6.9 × E12 |
| 5-TCG |  |  | 3.4 × E11 | 4.2 × E12 | 2.8 × E12 | 7.8 × E11 | 1.0 × E12 |
| 6-TTG |  |  | 4.0 × E11 | 6.8 × E12 | 3.2 × E12 | 1.0 × E12 | 3.6 × E11 |
| Phage out |  |  |  |  |  |  |  |
| 1-TAA |  | 1.1 × E6 | 6.5 × E5 | 3.4 × E5 | 8.6 × E6 | 4.5 × E7 | 1.5 × E8 |
| 2-TAC |  | 1.2 × E6 | 8.5 × E5 | 5.3 × E5 | 5.0 × E5 | 7.9 × E5 | 2.9 × E7 |
| 3-TAG |  | 1.7 × E6 | 1.1 × E6 | 6.7 × E6 | 1.2 × E8 | 8.5 × E7 | 2.3 × E8 |
| 4-TAT |  | 1.1 × E6 | 9.0 × E5 | 4.2 × E5 | 5.2 × E5 | 3.4 × E6 | 1.1 × E8 |
| 5-TCG |  | 4.6 × E5 | 1.3 × E6 | 4.6 × E5 | 2.5 × E5 | 1.2 × E5 | 4.5 × e5 |
| 6-TTG |  | 1.3 × E6 | 8.7 × E5 | 3.5 × E5 | 1.8 × E6 | 1.9 × E7 | 1.3 × E8 |

TABLE 4

Competitor/Target concentration for panning (C7-TNN) Set 1

|  | Round 1 | Round 2 | Round 3 | Round 4 | Round 5 | Round 6 |
|---|---|---|---|---|---|---|
| target | 0.4 µg | 0.4 µg | 0.4 µg | 0.4 µg | 0.2 µg | 0.2 µg |
| herring sperm DNA | 20 µg | 20 µg | 10 µg | 10 µg | 10 µg | 10 µg |
| XNN competitors |  |  |  |  |  |  |
| ANN |  | 0.128 µg | 0.256 µg | 0.256 µg | 0.256 µg | 1.024 µg |
| CNN |  | 0.128 µg | 0.256 µg | 0.256 µg | 0.256 µg | 1.024 µg |
| GNN |  | 0.064 µg | 0.128 µg | 0.128 µg | 0.128 µg | 0.512 µg |
| TNN | / | / | / | / | / | / |
|  |  | 1:50 | 1:25 | 1:25 | 1:12.5 | 1:0.3125 |
| specific competitors |  |  |  |  |  |  |
| TNN (−target) | / | 0.32 µg | 0.64 µg 3-TAG 0.32 µg | 1.28 µg | 1.28 µg 3-TAG 0.256 µg | 1.6 µg 3-TAG 5.18 µg |
|  |  | 1:20 | 1:10 | 1:5 | 1:2.5 | 1:1.25 |
| GGG (WT) | 0.64 µg | 1.28 µg | 2.56 µg | 2.56 µg | 2.56 µg | 2.56 µg |
| TAG Competitor | / | / | / | 0.01 µg in 1, 2, 4 | 0.01 µg in 1, 2, 4 | 0.01 µg in 1 0.05 µg in 2, 4 |

TABLE 5 pComb Round 6 TNN set 1 panning

| Sequence # | Clone # | Amino Acid sequence |
|---|---|---|
| bk007 | TAA - 1a | QASNLIS |
| bk008 | TAA - 1b | QASNLIS |
| bk009 | TAA - 1c | QASNLIS |
| bk010 | TAA - 1d | QASNLIS |
| bk011 | TAC - 2a | ARGNLKS |
| bk012 | TAC - 2b | SRGNLKS |
| bk013 | TAC - 2c | SRGNLKS |
| bk014 | TAC - 2d | ARGNLKS |
| bk015 | TAC - 3a | RLDNLQT |
| bk016 | TAC - 3b | RLDNLQT |
| bk017 | TAC - 3c | RLDNLQT |
| bk018 | TAC - 3d | RSDNLTT |
| bk019 | TAT - 4a | ARGNLRT |
| bk020 | TAT - 4b | ARGNLRT |
| bk021 | TAT - 4c | ARGNLRT |
| bk022 | TAT - 4d | VRGNLRT |
| bk023 | TCG - 5a | RLRALDR |
| bk024 | TCG - 5b | bad read |
| bk025 | TCG - 5c | bad read |
| bk026 | TCG - 5d | DMGALEA |
| bk027 | TTG - 6a | RKDALRG |
| bk028 | TTG - 6b | RKDALRG |
| bk029 | TTG - 6c | EKDALRG |
| bk030 | TTG - 6d | RKDALRG |

TABLE 6 pMAL - subclones

| Sequence # | Clone # | Amino Acid sequence |
|---|---|---|
| bk031 | TAA - 1a - 2 | bad read |
| bk042 | TAC - 2c - 2 | SRGNLKS |
| bk045 | TAC - 2d - 2 | ARGNLKS |
| bk033 | TAG - 3c - 2 | RLDNLQT |
| bk034 | TAG - 3d - 2 | RSDNLTT |
| bk035 | TAT - 4d - 2 | VRGNLKS |
| bk036 | TTG - 6c - 2 | RKDALRG |
| bk037 | TTG - 6d - 2 | RKDALRG |
| bk038 | TAA - 1a - 2 | QASNLIS |
| bk039 | TAC - 2d - 7 | RSDNLTT |
| bk040 | TAT - 4c - 8 | ARGNLRT |

TABLE 7

Panning chart 5'-TNN-3' C7.Lib Set 2

| | Round 1 | Round 2 | Round 3 | Round 4 | Round 5 | Round 6 |
|---|---|---|---|---|---|---|
| Phage in | | | | | | |
| VNS | E10 | | | | | |
| NNK | E10 | | | | | |
| 1- TCA | | 1.0 × E12 | 1.4 × E12 | 1.0 × E12 | 1.3 × E12 | 2.3 × E12 |
| 2- TCC | | 1.9 × E12 | 3.5 × E12 | 7.5 × E11 | 1.7 × E12 | 3.9 × E12 |
| 3- TCG | | 2.6 × E12 | 1.9 × E12 | 1.0 × E12 | 1.0 × E12 | 5.1 × E11 |
| 4- TCT | | 6.3 × E12 | 4.3 × E11 | 1.0 × E12 | 1.3 × E12 | 6.9 × E13 |
| 5- TGA | | 1.9 × E12 | 1.2 × E13 | 6.1 × E11 | 1.9 × E12 | 1.0 × E12 |
| 6- TGC | | 7.2 × E12 | 4.3 × E12 | 1.1 × E12 | 2.5 × E12 | 3.6 × E11 |
| Phage out | | | | | | |
| 1- TCA | 1.5 × E6 | 1.4 × E6 | 2.8 × E6 | — | 8.4 × E5 | 1.5 × E8 |
| 2- TCC | 9.5 × E5 | 1.3 × E6 | 3.9 × E6 | 7.6 × E5 | 1.6 × E6 | 2.9 × E7 |
| 3- TCG | 3.3 × E6 | 1.2 × E6 | 1.5 × E6 | 1.2 × E6 | 4.3 × E5 | 2.3 × E8 |
| 4- TCT | 1.7 × E6 | 6.6 × E5 | 3.1 × E6 | 1.4 × E6 | 6.4 × E5 | 1.1 × E8 |
| 5- TGA | 7.9 × E5 | 2.3 × E6 | 8.7 × E5 | 1.5 × E6 | 1.2 × E6 | 4.5 × E5 |
| 6- TGC | 5.6 × E5 | 9.3 × E5 | 2.6 × E6 | 1.2 × E6 | 5.7 × E5 | 1.3 × E8 |

TABLE 8

Competitor/Target concentration for panning (C7 - TNN) Set 2

| | Round 1 | Round 2 | Round 3 | Round 4 | Round 5 | Round 6 |
|---|---|---|---|---|---|---|
| target | 0.4 μg | 0.4 μg | 0.4 μg | 0.4 μg | 0.2 μg | 0.2 μg |
| herring sperm DNA | 20 μg | 20 μg | 10 μg | 10 μg | 10 μg | 10 μg |
| XNN competitors | | | | | | |
| ANN | 0.128 μg | 0.256 μg | 0.521 μg | 2.520 μg | 5.120 μg | 5.120 μg |
| CNN | 0.128 μg | 0.256 μg | 0.521 μg | 2.520 μg | 5.120 μg | 5.120 μg |
| GNN | 0.064 μg | 0.128 μg | 0.256 μg | 0.521 μg | 2.560 μg | 2.560 μg |
| TNN | / | / | / | / | / | / |
| | 1:50 | 1:25 | 1:12.5 | 1:6.25 | 1:3.125 | 1:1.56 |

TABLE 8-continued

Competitor/Target concentration for panning (C7 - TNN) Set 2

|  | Round 1 | Round 2 | Round 3 | Round 4 | Round 5 | Round 6 |
|---|---|---|---|---|---|---|
| specific competitors |  |  |  |  |  |  |
| TNN (−target) | But TCG 0.16 μg | → 0.32 μg 1:20 | → 1.28 μg 1:5 | → 2.52 μg 1:1.25 | → 10.04 μg 1:0.315 | → 10.04 μg 1:0.156 |
| GGG (WT) additional competitors | 0.64 μg | 1.28 μg | 2.56 μg | 2.56 μg | 2.56 μg | 2.56 μg |
| TAG 3 | 0.01 μg | 0.05 μg | 0.1 μg | 0.4 μg | 0.8 μg | 1 μg |
| TGG 3 |  | 0.01 μg | 0.02 μg | 0.1 μg | 0.2 μg | 0.5 μg |
| TCA 3 |  |  | 0.02 μg | 0.05 μg | 0.2 μg | 0.5 μg |
| TCC 3 |  |  | 0.02 μg | 0.05 μg | 0.2 μg | 0.5 μg |
| TCG 1 |  |  |  |  |  | 0.5 μg |
| TCT 2 |  |  | 0.02 μg |  |  | 0.5 μg |
| TGA |  |  |  |  |  |  |

TABLE 9 pComb Round 6 TNN set 2 panning

| Sequence # | Clone # | Amino Acid sequence |
|---|---|---|
| bk054 | TCA - 1a | RSDHLTT |
| bk055 | TCA - 1b | RSDHLTT |
| bk056 | TCA - 1c | bad read |
| bk057 | TCA - 1d | AQQLLMW |
| bk058 | TCC - 2a | bad read |
| bk059 | TCC - 2b | RSDERKR |
| bk060 | TCC - 2c | DYQSLRQ |
| bk061 | TCC - 2d | CFSRLVR |
| bk062 | TCG - 3a | GDGGLWE |
| bk063 | TCG - 3b | bad read |
| bk064 | TCG - 3c | LQRPLRG |
| bk065 | TCG - 3d | QGLACAA |
| bk066 | TCT - 4a | no finger 2 and 3 |
| bk067 | TCT - 4b | WVGWLGS |
| bk068 | TCT - 4c | RLRDIQF |
| bk069 | TCT - 4d | GRSQLSC |
| bk070 | TGA - 5a | GWQRLLT |
| bk071 | TGA - 5b | SGRPLAS |
| bk072 | TGA - 5c | bad read |
| bk073 | TGA - 5d | APRLLGP |
| bk074 | TGC - 6a | bad read |
| bk075 | TGC - 6b | APKALGW |
| bk076 | TGC - 6c | SVHELQG |
| bk077 | TGC - 6d | AQAALSW |

TABLE 10

Panning chart 5'-TNN-3' C7.Lib Set 2/second time

|  | Round 1 | Round 2 | Round 3 | Round 4 | Round 5 | Round 6 |
|---|---|---|---|---|---|---|
| Phage in |  |  |  |  |  |  |
| VNS | E10 |  |  |  |  |  |
| NNK | E10 |  |  |  |  |  |
| 1- TCA |  | 1.5 × E12 | 1.3 × E12 | 2.5 × E12 | 3.8 × E12 | 1.4 × E12 |
| 2- TCC |  | 1.6 × E12 | 1.8 × E12 | 1.7 × E11 | 1.2 × E12 | 1.6 × E12 |
| 3- TCG |  | 7.1 × E11 | 9.8 × E11 | 1.8 × E12 | 1.3 × E12 | 2.0 × E12 |
| 4- TCT |  | 9.4 × E11 | 1.2 × E12 | 1.9 × E12 | 1.8 × E12 | 1.6 × E13 |
| 5- TGA |  | 1.5 × E12 | 1.2 × E12 | 1.5 × E12 | 8.4 × E11 | 1.7 × E12 |
| 6- TGC |  | 9.4 × E12 | 7.6 × E11 | 1.5 × E12 | 6.8 × E11 | 1.2 × E12 |
| Phage out |  |  |  |  |  |  |
| 1- TCA | 4.2 × E6 | 3.6 × E6 | 5.9 × E5 | 1.1 × E6 | 2.7 × E6 | 1.5 × E6 |
| 2- TCC | 1.4 × E6 | 5.4 × E6 | 5.2 × E5 | 8.3 × E5 | 2.5 × E6 | 1.1 × E6 |
| 3- TCG | 2.1 × E6 | 5.5 × E6 | 1.1 × E6 | 3.7 × E5 | 2.2 × E6 | 6.6 × E6 |
| 4- TCT | 7.6 × E5 | 5.1 × E6 | 8.8 × E5 | 2.2 × E6 | 1.2 × E6 | 1.5 × E6 |
| 5- TGA | 1.1 × E6 | 2.5 × E6 | 4.7 × E6 | 7.6 × E5 | 1.5 × E6 | 1.1 × E6 |
| 6- TGC | 1.2 × E6 | 1.4 × E6 | 5.4 × E5 | 7.4 × E5 | 1.3 × E6 | 1.4 × E6 |

TABLE 11

Competitor/Target concentration for panning (C7-TNN) Set 2/second time

|  | Round 1 | Round 2 | Round 3 | Round 4 | Round 5 | Round 6 |
|---|---|---|---|---|---|---|
| target | 0.4 μg | 0.4 μg | 0.4 μg | 0.2 μg | 0.2 μg | 0.2 μg |
| herring sperm DNA | 20 μg | 20 μg | 20 μg | 10 μg | 10 μg | 10 μg |
| XNN competitors |  |  |  |  |  |  |
| ANN | 0.128 μg | 0.256 μg | 0.521 μg | 0.521 μg | 1.240 μg | 2.480 μg |
| CNN | 0.128 μg | 0.256 μg | 0.521 μg | 0.521 μg | 1.240 μg | 2.480 μg |
| GNN | 0.064 μg | 0.128 μg | 0.256 μg | 0.256 μg | 0.512 μg | 1.240 μg |
| TNN | / 1:50 | / 1:25 | / 1:12.5 | / 1:6.25 | / 1:3.125 | / 1:1.56 |
| specific competitors |  |  |  |  |  |  |
| TNN (−target) | but TCG 0.16 μg / | → 0.32 μg 1:20 | → 0.64 μg 1:10 | → 0.64 μg 1:5 | → 1.92 μg 1:1 | → 9.6 μg 1:0.2 |
| GGG (WT) additional competitors | 0.64 μg | 1.28 μg | 2.56 μg | 2.56 μg | 2.56 μg | 2.56 μg |
| TTA |  |  |  |  |  | 0.02 μg |
| TTC |  |  |  |  |  | 0.02 μg |
| TAG 3 |  |  |  | 0.01 μg | 0.1 μg | 0.04 μg |
| TTG 3 |  |  |  | 0.01 μg | 0.1 μg | 0.04 μg |
| TTT 1 |  |  |  |  |  | 0.02 μg |
| TAC 2 |  |  |  |  |  | 0.02 μg |

TABLE 12 pComb Round 6 TNN set 2 panning/second time

| Sequence # | Clone # | Amino Acid sequence |
|---|---|---|
| bk078 | TCA - 1a | GANALRR |
| bk079 | TCA - 1b | QSLLLGA |
| bk080 | TCA - 1c | RSDHLTT |
| bk081 | TCA - 1d | HRGTLGG |
| bk082 | TCC - 2a | QVGLLAR |
| bk083 | TCC - 2b | GARGLRG |
| bk084 | TCC - 2c | DKHMLDT |
| bk085 | TCC - 2d | DLGGLRQ |
| bk086 | TCG - 3a | QCYRLER |
| bk087 | TCG - 3b | QCYRLER |
| bk088 | TCG - 3c | QCYRLER |
| bk089 | TCG - 3d | QCYRLER |
| bk090 | TCT - 4a | AEAELQR |
| bk091 | TCT - 4b | RSDHLTT |
| bk092 | TCT - 4c | QGGVLAA |
| bk093 | TCT - 4d | RSDERKR |
| bk094 | TGA - 5a | bad read |
| bk095 | TGA - 5b | RSDHLTT |
| bk096 | TGA - 5c | QCRCLVT |
| bk097 | TGA - 5d | HPEALDN |
| bk098 | TGC - 6a | no finger 2 |
| bk099 | TGC - 6b | GRGALQA |
| bk100 | TGC - 6c | RSDHLTT |
| bk101 | TGC - 6d | LASRLQQ |

Results of the multitarget specificity assay for a number of the zinc fingers analyzed are shown in FIG. 3. These are: (a) QAS-N-LIS (TAA-1a-2) (SEQ ID NO: 1; binding 5'-(TAA)-3'; (b) SRG-N-LKS (TAC-2c-2) (SEQ ID NO: 2; binding 5'-(TAC)-3'; (c) ARG-N-LKS (TAC-2d-2) (SEQ ID NO: 7; binding 5'-(TAC)-3'; (d) RLD-N-LQT (TAG-3c-2) (SEQ ID NO: 3; binding 5'-(TAG)-3'; (e) RSD-N-LTT (TAG-3d-2) (SEQ ID NO: 8; binding 5'-(TAG)-3'; (f) ARG-N-LRT (TAT-4c-8) (SEQ ID NO: 4; binding 5'-(TAT)-3'); (g) VRG-N-KLS (TAT-4d-2) (SEQ ID NO: 9; binding 5'-(TAT)-3'); and (h) RKD-A-LRG (TTG-6c-2) (SEQ ID NO: 5; binding 5'-(TTG)-3').

Figure 4:
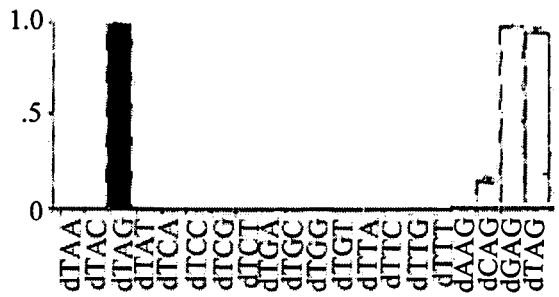
FIG. 4 is a second series of graphs showing the results of the multitarget specificity assay for a number of additional zinc fingers analyzed: ((a) RLD-N-LQT (SEQ ID NO: 3; binding 5'-(TAG)-3'; (b) ARG-N-LRT (SEQ ID NO: 4; binding 5'-(TAT)-3'; (c) SRG-N-LKS (SEQ ID NO: 2; binding 5'-(TAT)-3t; (d) QAS-N-LIS (SEQ ID NO: 1; binding 5'-(TAA)-3'; (e) RED-N-LHT (SEQ ID NO: 6; binding 5'-(TAG)-3'; and (f) ARG-N-LKS (SEQ ID NO: 7; binding 5'-(TAT)-3')).
Figure 4:
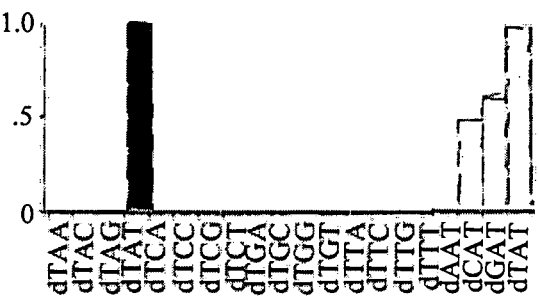
Figure 4:
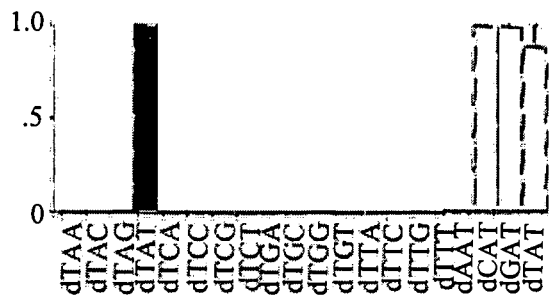
Figure 4:
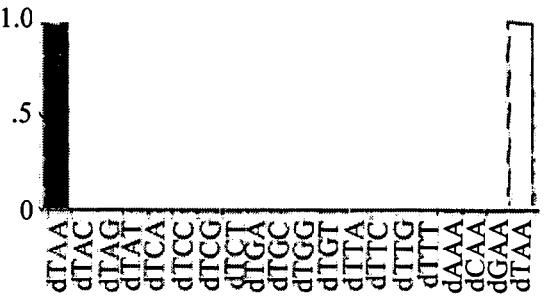
Figure 4:
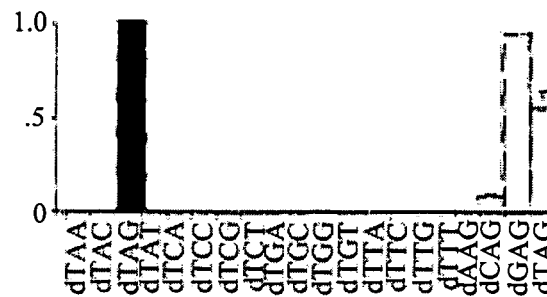
Figure 4:
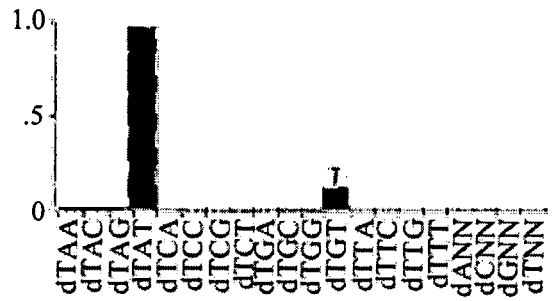
Figure 5:
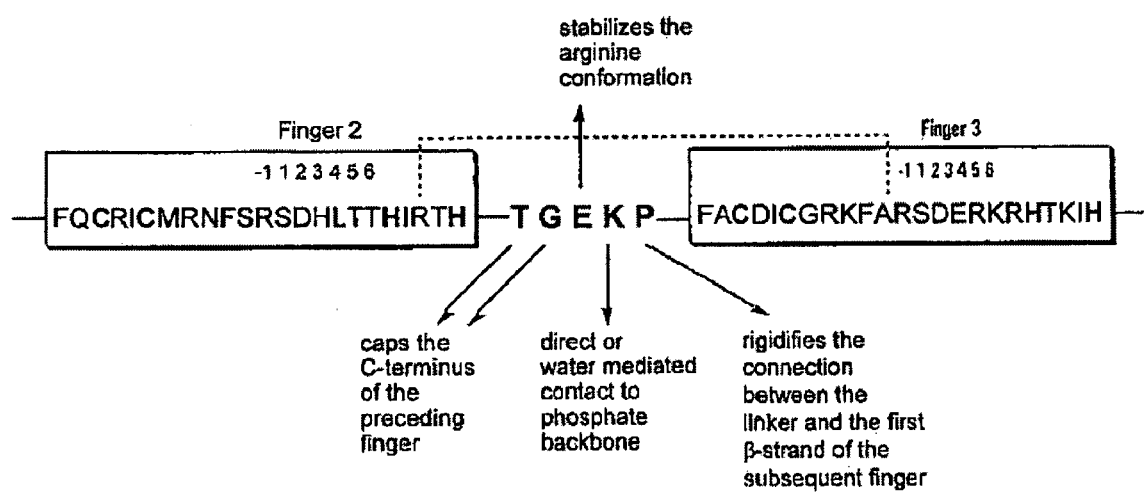
FIG. 5 is a diagram showing the structure and function of the linker region of the zinc finger protein Zif268.

FIG. 4 shows a second set of multitarget specificity results on different fingers generated: (a) RLD-N-LQT (SEQ ID NO: 3; binding 5'-(TAG)-3'; (b) ARG-N-LRT (SEQ ID NO: 4; binding 5'-(TAT)-3'; (c) SRG-N-LKS (SEQ ID NO: 2; binding 5'-(TAT)-3'; (d) QAS-N-LIS (SEQ ID NO: 1; binding 5'-(TAA)-3'; (e) RED-N-LHT (SEQ ID NO: 6; binding 5'-(TAG)-3'; and (f) ARG-N-LKS (SEQ ID NO: 7; binding 5'-(TAT)-3').

EXAMPLE 2

Design of New Randomized Zinc Finger Libraries with Changed Linker Regions

Introduction

The linker region that connects neighboring zinc fingers is an important structural element that helps control the spacing of the fingers along the DNA site. The most common linker arrangement has five residues between the final histidine of one finger and the first conserved aromatic amino acid of the next finger. Roughly half of the linkers of zinc fingers found in the Transcription Factor Database conform to the consensus sequence TGEKP (SEQ ID NO: 412). The structural role of each of the linker residues has already been examined (FIG. 4). The docking of adjacent fingers is further stabilized by contact between the side chain of position 9 of the preceding finger's helix and the backbone carbonyl or side chain at position −2 of the subsequent finger This contact can be correlated with the TGEKP (SEQ ID NO: 412) linker. Whenever it occurs between zinc fingers there are almost always three residues between the two histidines of the preceding finger, and in 80% of these proteins there is a basic amino acid (arginine or lysine) at position 9. When arginine occurs in this position, it makes an interfinger contact with the backbone carbonyl at position −2. In some structures, the conformation of this arginine has been found to be stabilized by an interaction with glutamate from the linker.

Mutagenesis studies have demonstrated that the linker sequence is important for high-affinity DNA binding. Some point mutations result in 10-100 fold decrease of DNA binding affinity and can lead to a loss of function in vivo. NMR studies indicate that the TGEKP (SEQ ID NO: 412) linker is flexible in the free protein, but becomes more rigid upon binding to DNA.

$Cys_2$-$His_2$ zinc finger proteins often bind their target sites with high affinity and specificity. Several groups have noted that as the number of TGEKP (SEQ ID NO: 412)-linked fingers increases from one to two to three, there is an accompanying increase in DNA-binding affinity. Proteins containing three fingers, such as Zif268 and SP1, bind their preferred sequences with dissociation constants typically between $10^{-8}$ M and $10^{-11}$ M. Unexpectedly the attachment of additional fingers using the TGEKP (SEQ ID NO: 412) linker leads only to modest additional increase of binding affinity to DNA. The reasons for that are not entirely clear and further studies are needed to understand the basis of this effect. The structural and energetic problems arising from the presence of four or more fingers in a multifinger protein may arise from the distortion of the DNA molecule that is caused by zinc fingers upon binding to DNA. Zinc fingers connected by TGEKP (SEQ ID NO: 412) linkers adopt a helical arrangement when bound to DNA that does not perfectly match the helical pitch of the DNA, so that as more fingers are attached, more steric hindrance accumulates The negative energetic consequences of steric hindrance therefore weaken the binding affinity from what it would be in the absence of steric hindrance. Studies of supercoiling levels have shows that zinc finger binding unwinds the DNA by approximately 18° per finger. In the resulting complex, DNA assumes a variant B-form conformation with about 11 base pairs per turn and an enlarged major groove.

There were two approaches which have been used so far to generate polydactyl zinc finger proteins that bind specifically and with high affinity to their DNA targets. One of them is the insertion of a longer, flexible linker between two sets of canonically linked fingers, which would be a covalent arrangement. A six-finger construct consisting of two three-finger proteins derived from Zif268 and NRE connected by a longer, flexible linker showed a femtomolar dissociation constant. Another possibility is the attachment of a dimerization domain onto a canonical set of zinc fingers. The dimerization domain induces the assembly of zinc fingers to a larger complex and thereby the recognition of a longer DNA target site. This approach is fully modular as the stability of the dimer can be influenced which allows, e.g., a tuning of the on and off states.

Design Concept

Design strategies for polydactyl zinc finger proteins, which all used canonical linkers to connect the additional fingers, gave relatively modest increased in DNA-binding affinity. Structural and biochemical analysis show that DNA is often slightly unwound when bound to zinc finger peptides. Modeling studies showed that the canonical linker is a bit too short to allow favorable docking, e.g., of Zif268 on ideal B-DNA. The reason for this is that the helical periodicity of the zinc fingers does not quite match the helical periodicity of B-DNA and the strain of unwinding becomes a more serious problem when more fingers are used; this has the effect of reducing the binding affinity because binding becomes energetically relatively less favorable.

It was decided to study the influence of the structure of the linker region on the DNA-binding affinity of polydactyl zinc finger proteins using phage display. Therefore, two different polydactyl zinc finger proteins were chosen, B3C2 and Vegf 5'16; both are six-finger proteins with a DNA binding affinity of about 1 nm.

Figure 6:
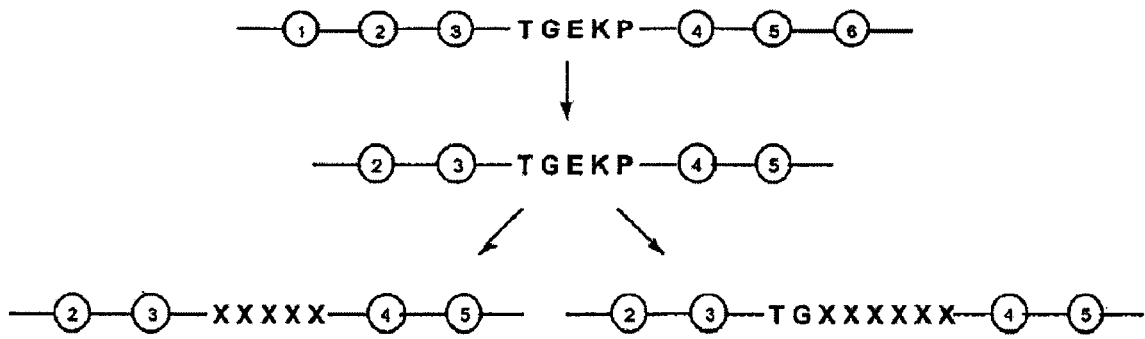
FIG. 6 is a diagram showing a design concept for the construction of improved linkers (Example 2).

Two different kinds of libraries for each of the peptides were constructed. The first one randomized the five positions of the canonical linker TGEKP (SEQ ID NO: 412) to select variants with changed amino acid sequence that might be less constrained and might be able to bind tighter to DNA. A longer, more flexible linker was also desired. The second set of libraries kept the T and G in the canonical linker TGEKP (SEQ ID NO: 412), randomized the third, fourth, and fifth positions and added three additional amino acids (FIG. 6). Four-finger proteins (containing fingers 2-5) were constructed from the six-finger proteins to make the library construction easier. These four-finger proteins were taken as templates for the PCR to construct the randomized libraries.

EXAMPLE 3

Gel Mobility Shift Analysis

Prospective Example

Gelshift analysis is performed with purified protein (Protein Fusion and Purification System, New England Biolabs) essentially as described In general, fusion proteins are purified to >90% homogeneity using the Protein Fusion and Purification System (New England Biolabs), except that ZBA/5 mM DTT is used as the column buffer. Protein purity and concentration are determined from Coomassie blue-stained 15% SDS-PAGE gels by comparison to BSA standards. Target oligonucleotides are labeled at their 5' or 3' ends with [$^{32}$P] and gel purified. Eleven 3-fold serial dilutions of protein are incubated in 20 μl binding reactions (1×Binding Buffer/10% glycerol/≈1 pM target oligonucleotide) for three hours at room temperature, then resolved on a 5% polyacrlyamide gel in 0.5×TBE buffer. Quantitation of dried gels is performed using a PhosphorImager and ImageQuant software (Molecular Dynamics), and the $K_D$ is determined by Scatchard analysis.

EXAMPLE 4

General Methods

Prospective Example

Transfection and Luciferase Assays

HeLa cells are used at a confluency of 40-60%. Cells are transfected with 160 ng reporter plasmid (pGL3-promoter constructs) and 40 ng of effector plasmid (zinc finger-effector domain fusions in pcDNA3) in 24 well plates. Cell extracts are prepared 48 hrs after transfection and measured with luciferase assay reagent (Promega) in a MicroLumat LB96P luminometer (EG & Berthold, Gaithersburg, Md.).

Retroviral Gene Targeting and Flow Cytometric Analysis

These assays are performed as described [Beerli et al., (2000) Proc Natl Acad Sci USA 97(4), 1495-1500; Beerli et al., (2000) J. Biol. Chem. 275(42), 32617-32627]. As primary antibody an ErbB-1-specific mAb EGFR (Santa Cruz), ErbB- 2-specific mAb FSP77 (gift from Nancy E. Hynes; Harwerth et al., 1992) and an ErbB-3-specific mAb SGP1 (Oncogene Research Products) are used. Fluorescently labeled donkey F(ab')$_2$ anti-mouse IgG is used as secondary antibody (Jackson Immuno-Research).

EXAMPLE 5

Construction of Zinc Finger-Effector Domain Fusion Proteins

Prospective Example

For the construction of zinc finger-effector domain fusion proteins, DNAs encoding amino acids 473 to 530 of the ets repressor factor (ERF) repressor domain (ERD) (Sgouras, D. N., Athanasiou, M. A., Beal, G. J., Jr., Fisher, R. J., Blair, D. G. & Mavrothalassitis, G. J. (1995) EMBO J. 14, 4781-4793), amino acids 1 to 97 of the KRAB domain of KOX1 (Margolin, J. F., Friedman, J. R., Meyer, W., K.-H., Vissing, H., Thiesen, H.-J. & Rauscher III, F. J. (1994) Proc Natl. Acad. Sci. USA 91, 4509-4513), or amino acids 1 to 36 of the Mad mSIN3 interaction domain (SID) (Ayer, D. E., Laherty, C. D., Lawrence, Q. A., Armstrong, A. P. & Eisenman, R. N. (1996) Mol. Cell. Biol. 16, 5772-5781) are assembled from overlapping oligonucleotides using Taq DNA polymerase. The coding region for amino acids 413 to 489 of the VP16 transcriptional activation domain (Sadowski, I., Ma, J., Triezenberg, S. & Ptashne, M. (1988) Nature 335, 563-564) is PCR amplified from pcDNA3/C$_7$-C$_7$-VP16 (10). The VP64 DNA, encoding a tetrameric repeat of VP16's minimal activation domain, comprising amino acids 437 to 447 (Seipel, K., Georgiev, O. & Schaffner, W. (1992) EMBO J. 11, 4961-4968), is generated from two pairs of complementary oligonucleotides. The resulting fragments are fused to zinc finger coding regions by standard cloning procedures, such that each resulting construct contained an internal SV40 nuclear localization signal, as well as a C-terminal HA decapeptide tag. Fusion constructs are cloned in the eukaryotic expression vector pcDNA3 (Invitrogen).

EXAMPLE 6

Construction of Luciferase Reporter Plasmids

Prospective Example

An erbB-2 promoter fragment comprising nucleotides −758 to −1, relative to the ATG initiation codon, is PCR amplified from human bone marrow genomic DNA with the TaqExpand DNA polymerase mix (Boehringer Mannheim) and cloned into pGL3basic (Promega), upstream of the firefly luciferase gene. A human erbB-2 promoter fragment encompassing nucleotides −1571 to −24, is excised from pSVOALD5'/erbB-2(N—N) (Hudson, L. G., Ertl, A. P. & Gill, G. N. (1990) J. Biol. Chem. 265, 4389-4393) by Hind3 digestion and subcloned into pGL3basic, upstream of the firefly luciferase gene.

EXAMPLE 7

Luciferase Assays

Prospective Example

For all transfections, HeLa cells are used at a confluency of 40-60%. Typically, cells are transfected with 400 ng reporter plasmid (pGL3-promoter constructs or, as negative control, pGL3basic), 50 ng effector plasmid (zinc finger constructs in pcDNA3 or, as negative control, empty pcDNA3), and 200 ng internal standard plasmid (phrAct-bGal) in a well of a 6 well dish using the lipofectamine reagent (Gibco BRL). Cell extracts are prepared approximately 48 hours after transfection. Luciferase activity is measured with luciferase assay reagent (Promega), βGal activity with Galacto-Light (Tropix), in a MicroLumat LB 96P luminometer (EG&G Berthold). Luciferase activity is normalized on βGal activity.

EXAMPLE 8

Regulation of the erbB-2 Gene in Hela Cells

Prospective Example

The erbB-2 gene is targeted for imposed regulation. To regulate the native erbB-2 gene, a synthetic repressor protein and a transactivator protein are utilized (R. R. Beerli, D. J. Segal, B. Dreier, C. F. Barbas, III, Proc. Natl. Acad. Sci. USA 95, 14628 (1998)). This DNA-binding protein is constructed from 6 pre-defined and modular zinc finger domains (D. J. Segal, B. Dreier, R. R. Beerli, C. F. Barbas, III, Proc. Natl. Acad. Sci. USA 96, 2758 (1999)). The repressor protein contains the Kox-1 KRAB domain (J. F. Margolin et al., Proc. Natl. Acad. Sci. USA 91, 4509 (1994)), whereas the transactivator VP64 contains a tetrameric repeat of the minimal activation domain (K. Seipel, O. Georgiev, W. Schaffner, EMBO J. 11, 4961 (1992)) derived from the herpes simplex virus protein VP16.

A derivative of the human cervical carcinoma cell line HeLa, HeLa/tet-off, is utilized (M. Gossen and H. Bujard, Proc. Natl. Acad. Sci. USA 89, 5547 (1992)). Since HeLa cells are of epithelial origin they express ErbB-2 and are well suited for studies of erbB-2 gene targeting. HeLa/tet-off cells produce the tetracycline-controlled transactivator, allowing induction of a gene of interest under the control of a tetracycline response element (TRE) by removal of tetracycline or its derivative doxycycline (Dox) from the growth medium. This system is used to place the transcription factors under chemical control Thus, repressor and activator plasmids are constructed and subcloned into pRevTRE (Clontech) using BamHI and ClaI restriction sites, and into PMX-IRES-GFP [X. Liu et al., Proc. Natl. Acad. Sci. USA 94, 10669 (1997)] using BamHI and NotI restriction sites. Fidelity of the PCR amplification are confirmed by sequencing, transfected into HeLa/tet-off cells, and 20 stable clones each are isolated and analyzed for Dox-dependent target gene regulation. The constructs are transfected into the HeLa/tet-off cell line (M. Gossen and H. Bujard, Proc. Natl. Acad. Sci. USA 89, 5547 (1992)) using Lipofectamine Plus reagent (Gibco BRL). After two weeks of selection in hygromycin-containing medium, in the presence of 2 mg/ml Dox, stable clones are isolated and analyzed for Dox-dependent regulation of ErbB-2 expression. Western blots, immunoprecipitations, Northern blots, and flow cytometric analyses are carried out essentially as described [D. Graus-Porta, R. R. Beerli, N. E. Hynes, Mol. Cell. Biol. 15, 1182 (1995)]. As a read-out of erbB-2 promoter activity, ErbB-2 protein levels are initially analyzed by Western blotting. A significant fraction of these clones will show regulation of ErbB-2 expression upon removal of Dox for 4 days, i.e., downregulation of ErbB-2 in repressor clones and upregulation in activator clones. ErbB-2 protein levels are correlated with altered levels of their specific mRNA, indicating that regulation of ErbB-2 expression is a result of repression or activation of transcription.

EXAMPLE 9

Introduction of the Coding Regions of the E2S-KRAB. E2S-VP64. E3F-KRAB and E3F-VP64 Proteins into the Retroviral Vector pM-IRES-GFP Prospective Example In order to express the E2S-KRAB, E2S-VP64, E3F-KRAB and E3F-VP64 proteins in several cell lines, their coding regions are introduced into the retroviral vector pMX-IRES-GFP.

The sequences of these constructs are selected to bind to specific regions of the ErbB-2 or ErbB-3 promoters. The coding regions are PCR amplified from pcDNA3-based expression plasmids (R. R. Beerli, D. J. Segal, B. Dreier, C. F. Barbas, III, Proc. Natl. Acad. Sci. USA 95, 14628 (1998)) and are subcloned into pRevTRE (Clontech) using BamHI and ClaI restriction sites, and into pMX-IRES-GFP [X. Liu et al., Proc. Natl. Acad. Sci. USA 94, 10669 (1997)] using BamHI and NotI restriction sites. Fidelity of the PCR amplification is confirmed by sequencing. This vector expresses a single bicistronic message for the translation of the zinc finger protein and, from an internal ribosome-entry site (IRES), the green fluorescent protein (GFP). Since both coding regions share the same mRNA, their expression is physically linked to one another and GFP expression is an indicator of zinc finger expression. Virus prepared from these plasmids is then used to infect the human carcinoma cell line A431.

EXAMPLE 10

Regulation of ErbB-2 and ErbB-3 Gene Expression

Prospective Example

Plasmids from Example 9 are transiently transfected into the amphotropic packaging cell line Phoenix Ampho using Lipofectamine Plus (Gibco BRL) and, two days later, culture supernatants are used for infection of target cells in the presence of 8 mg/ml polybrene. Three days after infection, cells are harvested for analysis. Three days after infection, ErbB-2 and ErbB-3 expression was measured by flow cytometry. The results are expected to show that E2S-KRAB and E2S-VP64 compositions inhibited and enhanced ErbB-2 gene expression, respectively. The data are expected to show that E3F-KRAB and E3F-VP64 compositions inhibited and enhanced ErbB-2 gene expression, respectively.

The human erbB-2 and erbB-3 genes were chosen as model targets for the development of zinc finger-based transcriptional switches. Members of the ErbB receptor family play important roles in the development of human malignancies. In particular, erbB-2 is overexpressed as a result of gene amplification and/or transcriptional deregulation in a high percentage of human adenocarcinomas arising at numerous sites, including breast, ovary, lung, stomach, and salivary gland (Hynes, N. E. & Stern, D. F. (1994) Biochim. Biophys. Acta 1198, 165-184). Increased expression of ErbB-2 leads to constitutive activation of its intrinsic tyrosine kinase, and has been shown to cause the transformation of cultured cells. Numerous clinical studies have shown that patients bearing tumors with elevated ErbB-2 expression levels have a poorer prognosis (Hynes, N. E. & Stern, D. F. (1994) Biochim. Biophys. Acta 1198, 165-184). In addition to its involvement in human cancer, erbB-2 plays important biological roles, both in the adult and during embryonic development of mammals (Hynes, N. E. & Stern, D. F. (1994) Biochim. Biophys. Acta 1198, 165-184, Altiok, N., Bessereau, J.-L. & Changeux, J.-P. (1995) EMBO J. 14, 4258-4266, Lee, K.-F., Simon, H., Chen, H., Bates, B., Hung, M.-C. & Hauser, C. (1995) Nature 378, 394-398).

The erbB-2 promoter therefore represents an interesting test case for the development of artificial transcriptional regulators. This promoter has been characterized in detail and has been shown to be relatively complex, containing both a TATA-dependent and a TATA-independent transcriptional initiation site (Ishii, S., Imamoto, F., Yamanashi, Y., Toyoshima, K. & Yamamoto, T. (1987) Proc. Natl. Acad. Sci. USA 84, 43744378). Whereas early studies showed that polydactyl proteins could act as transcriptional regulators that specifically activate or repress transcription, these proteins bound upstream of an artificial promoter to six tandem repeats of the proteins binding site (Liu, Q., Segal, D. J., Ghiara, J. B. & Barbas, C. F. (1997) Proc. Natl. Acad. Sci. USA 94, 5525-5530). Furthermore, this study utilized polydactyl proteins that were not modified in their binding specificity. Herein, we are testing the efficacy of polydactyl proteins assembled from predefined building blocks to bind a single site in the native erbB-2 and erbB-3 promoter.

For generating polydactyl proteins with desired DNA-binding specificity, the present studies have focused on the assembly of predefined zinc finger domains, which contrasts the sequential selection strategy proposed by Greisman and Pabo (Greisman, H. A. & Pabo, C. O. (1997) Science 275, 657-661). Such a strategy would require the sequential generation and selection of six zinc finger libraries for each required protein, making this experimental approach inaccessible to most laboratories and extremely time-consuming to all. Further, since it is difficult to apply specific negative selection against binding alternative sequences in this strategy, proteins may result that are relatively unspecific as was recently reported (Kim, J.-S. & Pabo, C. O. (1997) J. Biol. Chem. 272, 29795-29800).

The general utility of two different strategies for generating three-finger proteins recognizing 18 bp of DNA sequence is investigated. Each strategy was based on the modular nature of the zinc finger domain, and takes advantage of a family of zinc finger domains recognizing triplets of the 5'-(NNN)-3'. Three six-finger proteins recognizing half-sites of erbB-2 or erbB-3 target sites are generated in the first strategy by fusing the pre-defined finger 2 (F2) domain variants together using a PCR assembly strategy.

The affinity of each of the proteins for its target is determined by electrophoretic mobility-shift assays. These studies are expected to demonstrate that the zinc finger peptides have affinities comparable to Zif268 and other natural transcription factors.

The affinity of each protein for the DNA target site is determined by gel-shift analysis.

EXAMPLE 11

Computer Modeling

Prospective Example

Computer models are generated using Insight II (Molecular Simulations, Inc.). Models are based on the coordinates of the co-crystal structures of Zif268-DNA (PDB accession 1AAY). The structures are not energy minimized and are presented only to suggest possible interactions Hydrogen bonds are considered plausible when the distance between the heavy atoms was 3 (±0.3) Å and the angle formed by the heavy atoms and hydrogen is 120° or greater.

EXAMPLE 12

Construction of Artificial Transcription Factors Incorporating Zinc Finger Nucleotide Binding Domains Specifically Binding TNN Sequences and Targeting the Highly Conserved Primer-Binding Site of HIV-1

AIDS is a viral immune system disorder that has reached pandemic proportions in the last several decades. The virus responsible for the disease, human immunodeficiency virus (HIV), infects CD4 T cells and establishes a latent pool of infected cells. Current treatment for AIDS involves the use of a multidrug cocktail referred to as highly active antiretroviral therapy (HAART). While HAART has proven to be a potent treatment for the disease, there are significant drawbacks to this approach, including toxicity, numerous side effects, and more importantly, mutation of the virus to escape the effects of the cocktail (21). Furthermore, despite initial decreases in viral load immediately following HAART, a reservoir of latently infected cells remain in the patient's blood and virus is rapidly reactivated following drug withdrawal (48). Thus, new methods need to be developed to counteract the ability of HIV to escape therapy by mutation and also to prevent latently infected cells from replenishing viral titers in the patient. While HIV-1 does have a high mutation rate, certain sequences in the viral genome must be conserved for proper replication of the virus, and targeting these sequences for the development of new therapies is the goal of many researchers.

The virus life cycle consists of a number of steps that require both virus and host factors. Interruption of any one of these steps would provide a viable means for inhibiting virus production. One particularly well-studied step of the HIV-1 life cycle is transcription of RNA from the integrated viral genome. The HIV-1 5' long terminal repeat (LTR) contains binding sites for a number of host transcription factors, including Sp1, NF-κB, and Lef-1 (43). Binding of these factors mediates initiation of transcription by RNA polymerase II, and binding of the HIV-1 Tat protein to the trans-activating response element on the nascent transcript stimulates elongation by recruitment of a host protein, positive transcription elongation factor b (37). A number of strategies have been employed to target HIV-1 transcription including ribozymes (19, 59), antisense oligonucleotides (2), and more recently, RNA interference (RNAi) (8, 25, 26). One drawback of these approaches is that they are designed to target mRNA; thus, multiple copies of the target must be inactivated. Highly expressed mRNAs may be difficult to completely repress, as most viral transcripts are. Therefore, a more efficient strategy is to target transcription at the DNA level, as only one DNA provirus must be bound to inhibit virus production.

The $C_2H_2$ zinc finger (ZF) motif is the most ubiquitous DNA-binding motif in metazoans. A single zinc finger consists of a simple ββα fold coordinated by a zinc ion; residues in the α-helix make specific contacts with three nucleotides. Previous work has led to the identification of domains that recognize the 5'-(G/A/C)NN-3' subsets of the 64-member triplet alphabet (16, 17, 49). In addition, many domains recognizing the 5'-TNN-3' family of sequences are disclosed in this application. The modularity of the zinc finger motif allows the construction of polydactyl transcription factors that potentially bind to unique sites in a genome. Appending a transcriptional activator, such as the VP16 transactivation domain (47), or a repressor, such as the Kruppel-associated box (KRAB) domain (38), allows potent up- or down-regulation of a gene of interest (3-5, 34). Such artificial transcription factors have been shown to regulate numerous endogenous genes in many different animal and plant cells (3, 22, 23, 28, 53, 61).

We have previously used artificial zinc finger transcription factors to regulate the HIV-1 5' LTR (50). One of the proteins tested, designated HLTR3, effectively inhibits HIV-1 transcription after transient transfection and inhibits viral replication in cell lines and in peripheral blood mononuclear cells (PBMCs) that stably express the transcription factor. HLTR3 binds to a site in the HIV-1 LTR that overlaps two Sp1-binding sites. Other studies have also targeted this region with ZF transcription factors (30, 45). This sequence is well conserved in the B lade, but this region shows significant sequence variation in some other B clades (27). Thus, we sought to target a sequence in the LTR that is well conserved across all clades. The tRNA primer-binding site (PBS) is the most highly conserved site in the HIV-1 genome. Human $tRNA^{Lys}_3$ binds to the PBS and is used as a primer for reverse transcription (36, 39). The PBS is completely conserved across clades (14), and mutations to the PBS negatively affect virus production and infectivity (42, 46). Sequences flanking the PBS are also highly conserved. Furthermore, the PBS is located at the 3' end of the LTR in a nucleosome-free sequence that is accessible to DNase I and micrococcal nuclease digestion (54); therefore, a ZF protein targeted to this site should bind and regulate transcription.

In this study, several ZF proteins were designed to bind to sequences within the HIV-1 PBS and flanking sequences and were fused to the KRAB repression domain. These transcription factors were tested for their ability to repress transcription of the LTR in reporter assays and to inhibit virus production after infection of PBMCs. Finally, an escape assay was performed to determine if long-term exposure to the ZF would induce mutation of the virus that could reduce the effectiveness of the repressor. Our results suggest transcriptional repressors that target the HIV-1 PBS are potential new therapeutics for HIV-1 disease.

Materials and Methods

Construction of custom DNA-binding proteins. DNA-binding proteins containing six zinc finger domains were assembled onto an Sp1C zinc finger scaffold using methods and domains described previously (4, 16, 18, 49). Briefly, overlapping PCR primers were designed to encode zinc finger domains that had been previously determined to bind unique 3-bp sites. Three-finger proteins were assembled by overlap PCR then assembled into six-finger proteins by AgeI/XmaI ligation. Recently, we released a web-based program called Zinc Finger Tools that allows zinc finger proteins to be automatically designed (http://www.scripps.edu/mbTharbas/zfdesign/zfdesignhome.php). For in vitro characterization, the constructs were cloned into the prokaryotic expression vector pMAL-c2 (New England Biolabs). Fusions with the maltose-binding protein were expressed and purified with the Protein Fusion and Purification system (New England Biolabs). Electrophoretic mobility shift assays were performed as described previously (4, 49).

Effector and reporter plasmids. The PBS1, PBS1a, PBS2, and PBS3 six-finger proteins were cloned into a pcDNA-based effector plasmid containing the KRAB repression domain as described previously (4). The four six-finger proteins were also cloned into the pMX retroviral and pSIN lentiviral vectors by digesting pMX KRAB-HLTR3 and pSIN-KRAB-HLTR3 (50) with Sf1 and then ligating each of the four six-finger proteins digested with Sf1 from the pMal-c2 vectors with the pMX retroviral and pSIN lentiviral vectors. The HIV-1 LTR reporter, LTR658-luc, was constructed by amplifying the HIV LTR by PCR from the plasmid pII-Ienv3-1 (National Institutes of Health AIDS Research and Reference Reagent Program [NARRRP]) (52) using the forward primer 5'-GATACGACAGCTAGCTG-GAAGGGCTAATTCACTCCC-3' (SEQ ID NO: 426) and the reverse primer 5'-AACGTCTGGCTCGAGTTCAG-GTCCCTGTTCGGGCGCCACTGCTAGAGATTTTC C-3' (SEQ ID NO: 427). The PCR product was digested with NheI and XhoI and was ligated into the pGL3 control vector (Promega) previously digested with NheI and XhoI. The pGL3 promoter vector (Promega), driven by the simian virus 40 (5V40) promoter, was used as a negative control. Cell culture and transient transfection assays. HeLa cells (American Type Culture Collection), TZM-bl cells (NARRRP) (15, 44, 60), and Gag-Pol 293 cells (Clontech) were maintained at 37° C. and 5% CO2 in Dulbecco's modified Eagle's medium (Gibco) supplemented with 10% fetal calf serum and 1% penicillin-streptomycin-antimycotic (Gibco). For transient transfection assays, approximately $5\times10^4$ cells were seeded into 24-well plates to 40 to 60% confluence. HeLa cells were transfected with 10 ng of reporter plasmid, 75 ng of the Tat-expressing plasmid pSV2tat72 (NARRRP) (20), 100 ng of effector plasmid, and 100 ng of CMV-lacZ plasmid using Lipofectamine transfection reagent (Invitrogen). TZM-bl cells were transfected similarly, except that no reporter plasmid was used and 50 ng of the Renilla luciferase plasmid pRL-CMV (Promega) was transfected in place of CMV-lacZ. Cell extracts were prepared ~48 h after transfection. Luciferase and 3-galactosidase activities were measured using assay reagent kits from Promega and Tropix, respectively, in a MicroLumat LB96P luminometer (EG&G Berthold, Gaithersburg, Md.). Luciferase activity was normalized to 3-galactosidase activity in HeLa cells and to Renilla luciferase activity in TZM-bl cells. Determination of ZF protein expression and inhibition of transiently transfected, plasmid-based HIV expression were performed as described previously (50).

Retroviral delivery of ZF proteins and chromatin immunoprecipitation (ChIP). Retroviral transductions of the KRAB-PBS proteins into TZM-bl cells were performed using the Moloney murine leukemia virus-based pMX vector, essentially as described previously (35). Transduction efficiency was monitored by flow cytometric analysis of green fluorescent protein expressed via an internal ribosome entry site within the zinc finger expression cassette (data not shown). Approximately $10^7$ infected cells were cross-linked with 1% formaldehyde, and chromatin was prepared as described previously (7). Chromatin was immunoprecipitated with 1 µg RNA polymerase II antibody (Santa Cruz Biotechnology), 10 µl ZF antibody (35), or no antibody. Immunoprecipitated chromatin was washed extensively and DNA was purified as described previously. Immunoprecipitated DNA, as well as a 1:100 dilution of 20% of the total input DNA taken from the no-antibody samples, was amplified by 30 to 35 cycles of PCR using the HIV-1 LTR primers 5'-CCGCTGGG-GACTTTCCAGGGA-3' (SEQ ID NO: 428) and 5'-CACT-GCTAGAGATTTTCCACACTG-3' (SEQ ID NO: 429)

Northern blot analysis of tRNA expression. HeLa cells were plated at a density of $2\times10^6$ cells on a 10-cm dish, and cells were transfected with 4 µg of plasmid expressing the indicated KRAB-ZF or empty plasmid as a negative control. After 48 h, total RNA was isolated using TRIzol Reagent (Invitrogen). A total of 60 µg of RNA was separated on a 15% Tris-borate-EDTA-urea polyacrylamide gel and transferred to a GeneScreen Plus membrane (Perkin-Elmer) with an XCell II Blot Module (Invitrogen) according to the manufacturer's instructions. Prehybridization of the membrane was done in 5 ml of Rapid-hyb buffer (Amersham Biosciences) at 42° C. for 15 min. The membrane was then hybridized with $10^6$ to $10^7$ cpm of a $^{32}$P-end-labeled tRNA probe for 1 to 2 h at 42° C. The blot was washed twice for 15 mm at 42° C. in 0.1% SDS-0.1×SSC (15 mM NaCl and 1.5 mM sodium citrate) and then exposed 24 to 48 h on a phosphor screen, which was developed with a Molecular Dynamics phosphorimager. The sequence of the $tRNA^{Lys}_3$ probe is 5'-CGCCCGM-CAGGGAC-3' (SEQ ID NO: 430) and the $tRNA^{Phe}$ probe is 5'-TGCCGAAACCCGGGA-3' (SEQ ID NO: 431).

Lentiviral production and delivery and HIV-1 infection of PMBC. Lentiviral production, titration, transduction into PBMCs, and subsequent challenge with HIV-1 were performed with a self-inactivating lentiviral vector system as described previously (50). The in vitro selection of HIV-1 clones resistant to PBS zinc fingers was performed as described by Keulen et al. (29). Briefly, selection was initiated by infection of SupT1 cells with wild-type NL4-3 (multiplicity of infection [MOI] of 0.02). After 1 h at 37° C., the culture was split, and cells were transduced with each zinc finger repressor at an MOI of 1 or 10. An assay of nontransduced cells was used to determine the levels of viral replication and cell growth in the absence of inhibitory zinc finger. Cells were transduced a second time at day 5. At day 5, after the second transduction, half of the cultures were used for titration in a 96-well plate, by limiting dilution as described by Keulen et al. (29). After 1 week, samples from individual wells were transferred to 24-well plates to optimize cell growth and viral replication. Cell-free supernatant and cells were harvested from individual wells when large syncytia were observed. Genotypic analysis of cells was performed with primers overlapping the PBS region. PCR products were cloned into a TA cloning vector (pGEM-Teasy; Promega), and individual clones were sequenced. After 2 to 3 weeks of culture, 20 wells were considered positive by comparison with viral replication in non-expressing zinc finger cells. No positive wells were obtained after titration of cells transduced with an MOI of 10. It is possible that wild-type virus was able to replicate in some of the wells with transduction at an MOI of 1. Therefore, the in vitro-selected viruses were passaged onto fresh SupT1 cells previously transduced with SIN-PBSB at an MOI of 1. Ten samples were able to replicate optimally at an MOI of 1. Sequence analysis of these 10 viruses revealed the presence of a G-to-A mutation in the PBS site.

Results

Figure 7:
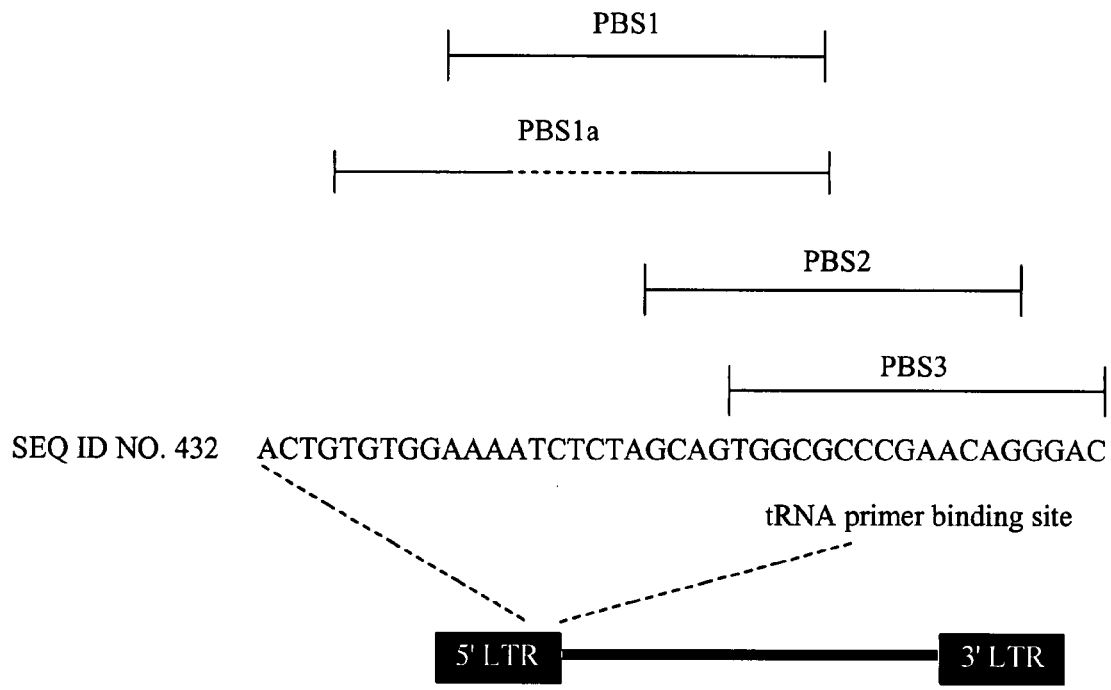
FIG. 7 is a diagram showing binding sites of PBS zinc finger proteins on the HIV-1 LTR. The sequence shown is from an HXB2 reference strain (Example 12).
Figure 8:
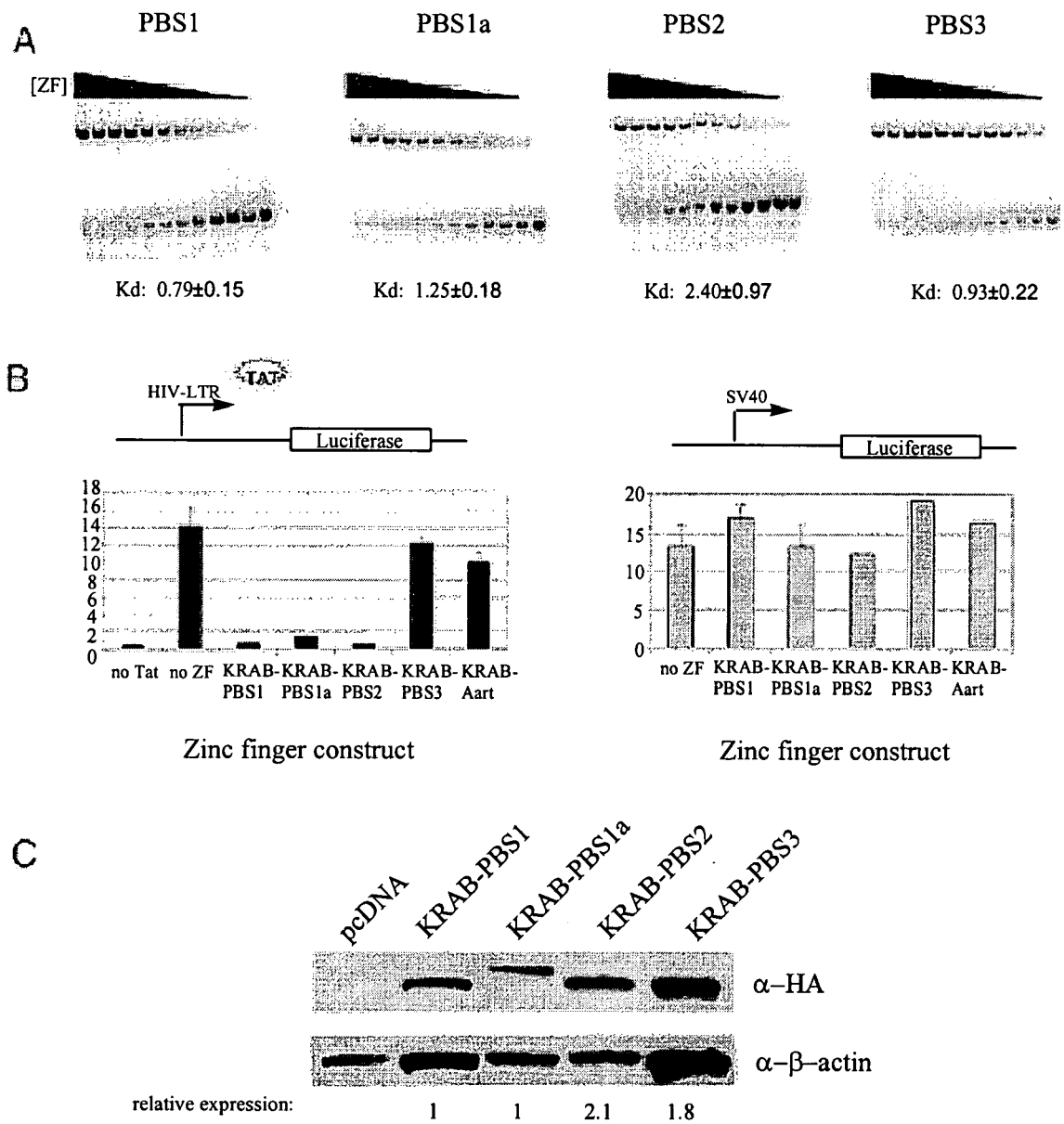
FIG. 8 shows PBS zinc finger-binding constants and inhibition of HIV-1 LTR in a transient transfection assay. (A) Gel shifts of the PBS zinc fingers. A $^{32}$P-labeled DNA hairpin oligonucleotide containing the PBS sequence was incubated with decreasing amounts of protein. The density of free and bound DNA was quantitated using ImageQuant software, and the $K_D$ for each protein was calculated. (B) Transient reporter assays comparing repression of the PBS proteins fused to the KRAB repression domains. The graph on the left shows results from transfection of KRAB-zinc finger proteins with an HIV-1 LTR-driven luciferase reporter and a plasmid expressing the Tat protein. The graph on the right shows control transfection of KRAB-zinc finger proteins with an SV40 promoter-driven luciferase reporter. (C) Protein expression levels of PBS zinc finger proteins. Cells were transiently transfected with zinc finger proteins as in panel (B), and cell extracts were prepared. Proteins were separated by sodium dodecyl sulfate-polyacrylamide gel electrophoresis and transferred to polyvinylidene difluoride membranes. Blots were probed with an antibody recognizing the HA tag on the zinc finger proteins or a β-actin antibody. Relative protein expression was calculated by normalizing zinc finger expression to β-actin expression in each sample.

Design, expression, and analysis of primer-binding site zinc finger proteins. Four zinc finger proteins were constructed to bind to the HIV-1 PBS (FIG. 7; Table 13) FIG. 7 is a diagram showing binding sites of PBS zinc finger proteins on the HIV-1 LTR. The sequence shown is from an HXB2 reference strain. Three of the proteins were designed to bind to 18 nucleotide sequences just upstream or within the PBS. One of the proteins, PBS1a, was designed to bind to two nonadjacent 9-bp sites separated by 7 bp. It consisted of two three-finger domains separated by a long linker (GGGSGGGGEKP) (SEQ ID NO: 422). As an initial assessment of their ability to regulate H1V-1 transcription, the binding constant of each of the ZFs to the PBS was determined. Proteins were expressed and purified as maltose-binding protein fusion proteins and then tested for the ability to bind an oligonucleotide hairpin containing the PBS sequence in multitarget enzyme-linked immunosorbent assays and electrophoretic mobility shift assays (EMSAS) as described previously (50). The equilibrium dissociation constant ($K_D$) values of the proteins PBS1, PBS1a, PBS2, and PBS3 for their targets were 0.79, 1.25, 2.4, and 0.93 nM, respectively, as determined by EMSA (FIG. 8A). FIG. 8 shows PBS zinc finger-binding constants and inhibition of HIV-1 LTR in a transient transfection assay. (A) Gel shifts of the PBS zinc fingers. A $^{32}$P-labeled DNA hairpin oligonucleotide containing the PBS sequence was incubated with decreasing amounts of protein. The density of free and bound DNA was quantitated using ImageQuant software, and the $K_D$ for each protein was calculated. (B) Transient reporter assays comparing repression of the PBS proteins fused to the KRAB repression domains. The graph on the left shows results from transfection of KRAB-zinc finger proteins with an HIV-1 LTR-driven luciferase reporter and a plasmid expressing the Tat protein. The graph on the right shows control transfection of KRAB-zinc finger proteins with an SV40 promoter-driven luciferase reporter. (C) Protein expression levels of PBS zinc finger proteins. Cells were transiently transfected with zinc finger proteins as in panel (B), and cell extracts were prepared. Proteins were separated by sodium dodecyl sulfate-polyacrylamide gel electrophoresis and transferred to polyvinylidene difluoride membranes. Blots were probed with an antibody recognizing the HA tag on the zinc finger proteins or a β-actin antibody. Relative protein expression was calculated by normalizing zinc finger expression to β-actin expression in each sample.

reporter. In addition, none of the PBS zinc fingers expressed with the addition of the repression domain altered expression of a luciferase reporter driven by the SV40 promoter (FIG. 8B). Finally, to ensure that these observations were not due to differences in protein expression, Western blot analysis was performed. KRAB-PBS2 and KRAB-PBS3 were expressed at ~2-fold-higher levels than KRAB-PBS1 and KRAB-PBS1a (FIG. 8C).

Figure 9:
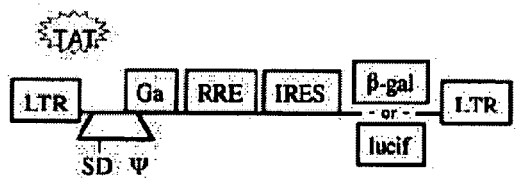
FIG. 9 shows repression and in vivo binding of PBS zinc finger proteins on a chromosomally integrated HIV-1 LTR reporter. (A) KRAB-PBS zinc finger proteins and Tat were transiently expressed in the TZM-bl cell line, a HeLa cell line containing chromosomally integrated HIV constructs that drive expression of luciferase and lacZ genes. (B) Chromatin immunoprecipitation of zinc finger protein-bound HIV-1 LTR. Zinc finger proteins were expressed by retroviral transduction in TZM-bl cells. Cells were cross-linked with formaldehyde, and nuclear extract was prepared. The extract was incubated with RNA polymerase II (pol II) or an antibody recognizing an Sp1 consensus zinc finger (Sp1C) and precipitated with Staph A cells. Immunoprecipitated DNA was purified and analyzed by PCR for the presence of the HIV-1 LTR using primers specific for the LTR. (C) Northern blot of tRNA$^{Lys}{}_3$. HeLa cells were transfected with the indicated KRAB-ZF proteins, and total RNA was extracted. RNA was separated by denaturing polyacrylamide gels and transferred to a membrane, which was probed with radiolabeled oligonucleotides for tRNA$^{Lys}{}_3$ and tRNA$^{Phe}$. The numbers below each lane represent the relative expression of tRNA$^{Lys}{}_3$ after normalization to tRNA$^{Phe}$.
Figure 9:
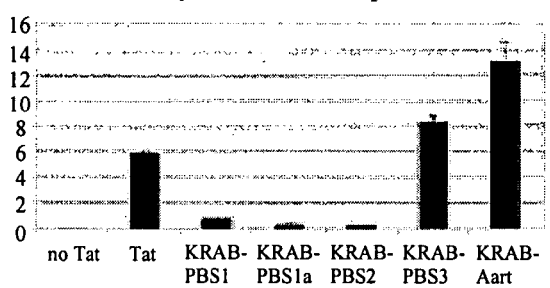
Figure 9:
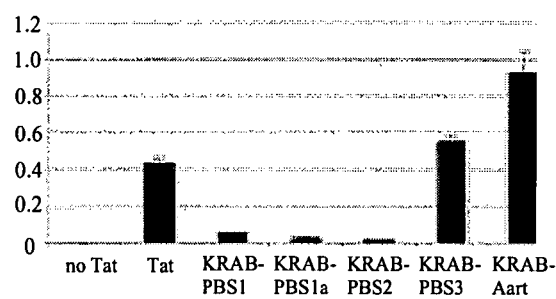
Figure 9:
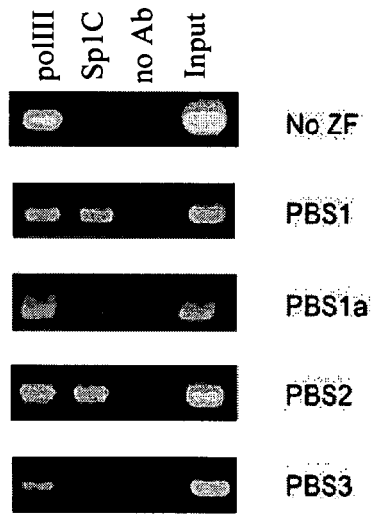
Figure 9:
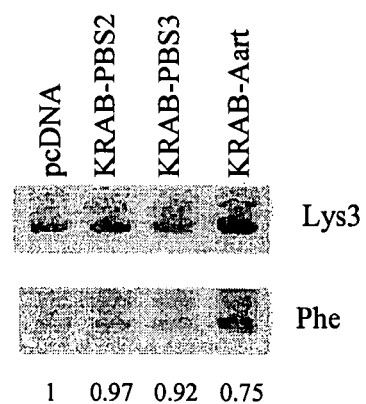

Repression of HIV-1 LTR expression in chromatin by PBS ZF's. In a transient transfection, a reporter plasmid is not packaged into chromatin in the same manner as a chromosomal gene, and so regulation seen in a transient assay may not be observed with a genomic target. It is a more relevant assay to test the ability of the PBS-binding ZF proteins to repress a reporter integrated into a mammalian genome. Thus, the transient transfection of the PBS ZFs and Tat was repeated in the TZM-bl cell line, a HeLa derivative that contains integrated copies of a lentivirus-based luciferase reporter and a β-galactosidase reporter (FIG. 9A, top). FIG. 9 shows repression and in vivo binding of PBS zinc finger proteins on a chromosomally integrated HIV-1 LTR reporter. (A) KRAB-PBS zinc finger proteins and Tat were transiently expressed in the TZM-bl cell line, a HeLa cell line containing chromosomally integrated HIV constructs that drive expression of

TABLE 13

ZF Sequences Assembled to Regulate the HIV-1 LTR sE

| | ZF helix | | | | | | Predicted target site[c] |
|---|---|---|---|---|---|---|---|
| TF$_{SZF}$ | F6 | F5 | F4 | F3 | F2 | F1 | Half site 1-half site 2 |
| PBS1[a] | QRANLRA | RGGWLQA | QRHSLTE | QSGDLRR | RSDVLVR | RSDDLVR | 5'-AAA TCT CTA-GCA GTG GCG-3' |
| PBS1a[b] | RSDVLVR | RSDHLTT | QRANLRA | QSGDLRR | RSDVLVR | RSDDLVR | 5'-GTG TGG AAA atctcta GCA GTG GCG-3' |
| PBS2 | QSGDLRR | RSDVLVR | RSDDLVR | HTGHLLE | QSSNLVR | RADNLTE | 5'-GCA GTG GCG-CCC GAA CAG-3' |
| PBS3 | RSDHLTT | HTGHLLE | RNDTLTE | DSGNLRV | RSDHLTN | DPGNLVR | 5'-TGG CGC CCG-AAC AGG GAC-3' |

[a]ZF helices are positioned in the antiparallel orientation (COOH-F6 to F1-NH2) relative to the DNA target sequence. Amino acid positions −1 to +6 of each DNA recognition sequence are shown. Web-based software is available for automated zinc finger protein design (http://www.scripps.edu/mb/barbas/zfdesign/zfdesignhome.php).
[b]PBS1a is composed of two three-finger ZFs separated by a long flexible linker (Gly$_3$SerGly$_4$). F3 to F1 bind to the second half site, GCA GTG GCG, and F6 to F4 bind to the first half site, GTG TGG AAA. The intervening nonbound DNA sequence is indicated by lowercase letters.
[c]Predicted target DNA sequences are presented in the 5' to 3' orientation.

SEQ ID NOs: for the ZF helices are, from F1 to F6: For PBS1: SEQ ID NO: 453, 452, 451, 450, 46, and 449; for PBS1a: SEQ ID NOs: 453, 452, 451, 449, 14, and 452; for PBS2: SEQ ID NOs: 456, 455, 454, 453, 452, and 451; and for PBS3: SEQ ID NOs: 460, 459, 458, 457, 454, and 14. SEQ ID NOs for the target sites are: SEQ ID NO: 433, 434, 435, and 436 for PBS1, PBs1a, PBS2, and PBS3, respectively.

To enable repression of transcription, the ZF proteins were fused to the KRAB domain. The proteins were then expressed in HeLa cells, along with LTR658-luc, a luciferase reporter driven by the HIV-1 LTR, and a construct expressing the Tat protein. As a negative control, a six-finger protein that does not bind the HIV-1 LTR but is functional in regulating reporters containing its target sequence, KRAB-Aart, was also tested. KRAB-PBS1, KRAB-PBS1a, and KRAB-PBS2 repressed expression of the reporter by 20, 9.5, and 28 fold, respectively. No significant repression was observed for KRAB-PBS3; as expected, KRAB-Aart did not repress the luciferase and lacZ genes. (B) Chromatin immunoprecipitation of zinc finger protein-bound HIV-1 LTR. Zinc finger proteins were expressed by retroviral transduction in TZM-bl cells. Cells were cross-linked with formaldehyde, and nuclear extract was prepared. The extract was incubated with RNA polymerase II (pol II) or an antibody recognizing an Sp1 consensus zinc finger (Sp1C) and precipitated with Staph A cells. Immunoprecipitated DNA was purified and analyzed by PCR for the presence of the HIV-1 LTR using primers specific for the LTR. (C) Northern blot of tRNA$^{Lys}_3$. HeLa cells were transfected with the indicated KRAB-ZF proteins, and total RNA was extracted. RNA was separated by denaturing polyacrylamide gels and transferred to a membrane, which was probed with radiolabeled oligonucleotides for tRNA$^{Lys}_3$ and tRNA$^{Phe}$. The numbers below each lane represent the relative expression of tRNA$^{Lys}_3$ after normalization to tRNA$^{Phe}$. Repression of the HIV-1 LTR was observed in the presence of KRAB-PBS1, KRAB-PBS1a, and KRAB- PBS2, while KRAB-PBS3 and KRAB-Aart showed no repression, as was observed when the reporter was transiently transfected (FIG. 9A). The ZFs repressed the chromosomally integrated reporters at levels similar to those observed in the transient assay. The luciferase reporter was repressed 7 fold by KRAB-PBS1, 15 fold by KRAB-PBS1a, and 20 fold by KRABPBS2. Similar levels of repression were also observed for the 3-galactosidase reporter.

To ensure that the PBS ZFs bound to the HIV-1 LTR, the ChIP assay was performed with TZM-bl cells. The PBS ZFs were expressed in TZM-bl cells by retroviral infection. The cells were cross-linked with formaldehyde, and chromatin was sonicated and isolated from the nuclei. ZFs bound to DNA were immunoprecipitated with an antibody that recognizes the zinc finger backbone, and immunoprecipitated DNA was analyzed by PCR using primers specific for the HIV-1 LTR. Chromatin was immunoprecipitated with a RNA polymerase II antibody as a positive control. In agreement with the reporter assays, we found that KRAB-PBS1, KRAB-PBS1a, and KRAB-PBS2 were bound to the HIV-1 LTR, whereas KRAB-PBS3 did not bind to the LTR in vivo (FIG. 9B). Because the primer-binding site is complementary to tRNA$^{Lys}_3$, it is possible that KRAB-PBS3 could bind to the tRNA$^{Lys}_3$ gene and to the HIV LTR and repress expression of the tRNA, since the KRAB domain has been shown to affect RNA polymerase III transcription (41, 51). To test this possibility, a Northern blot was performed to measure the levels of tRNA$^{Lys}_3$ in the presence of KRAB-PBS2, KRAB-PBS3, or KRAB-Aart. After normalization to tRNA$^{Phe}$ was performed, we found no significant effect on tRNA$^{Lys}_3$ levels from any of the ZF proteins (FIG. 9C).

Figure 10:
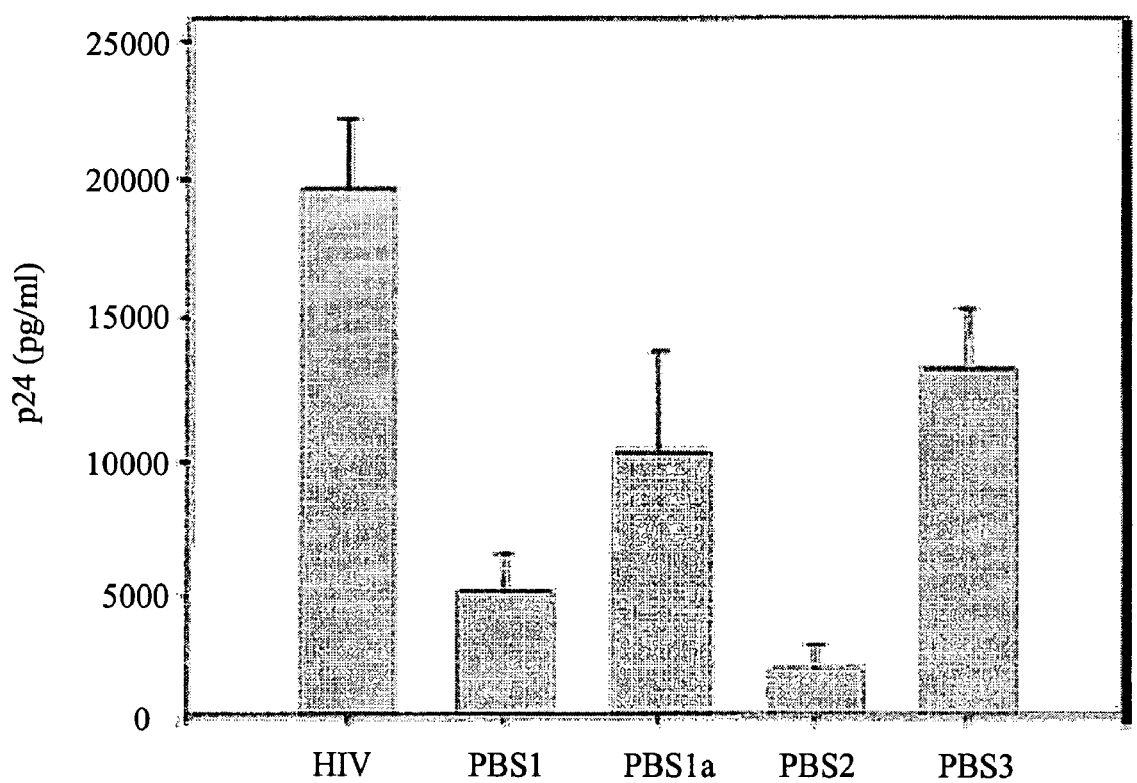
FIG. 10 is a graph showing transient inhibition of virus production of PBS zinc finger proteins. Plasmids expressing the indicated KRAB-PBS zinc finger and the genome of the NL4-3 strain of HIV-1 were cotransfected into 293T cells. Virus production was monitored by a p24 ELISA.

Inhibition of HIV-1 virus production by PBS ZF's. As a preliminary test of the ability of the PBS ZFs to inhibit HIV-1 virus production under conditions of an infection, each of the KRAB-PBS expression plasmids was cotransfected with a plasmid encoding the HIV-1 strain NL4-3 genome. After 48 h, significant inhibition of virus production was seen in cells expressing KRAB-PBS1 (75%) and KRAB-PBS2 (~90%), whereas KRAB-PBS1a and KRAB-PBS3 inhibited virus production by <50% (FIG. 10). FIG. 10 is a graph showing transient inhibition of virus production of PBS zinc finger proteins. Plasmids expressing the indicated KRAB-PBS zinc finger and the genome of the NL4-3 strain of HIV-1 were cotransfected into 293T cells. Virus production was monitored by a p24 ELISA.

Figure 11:
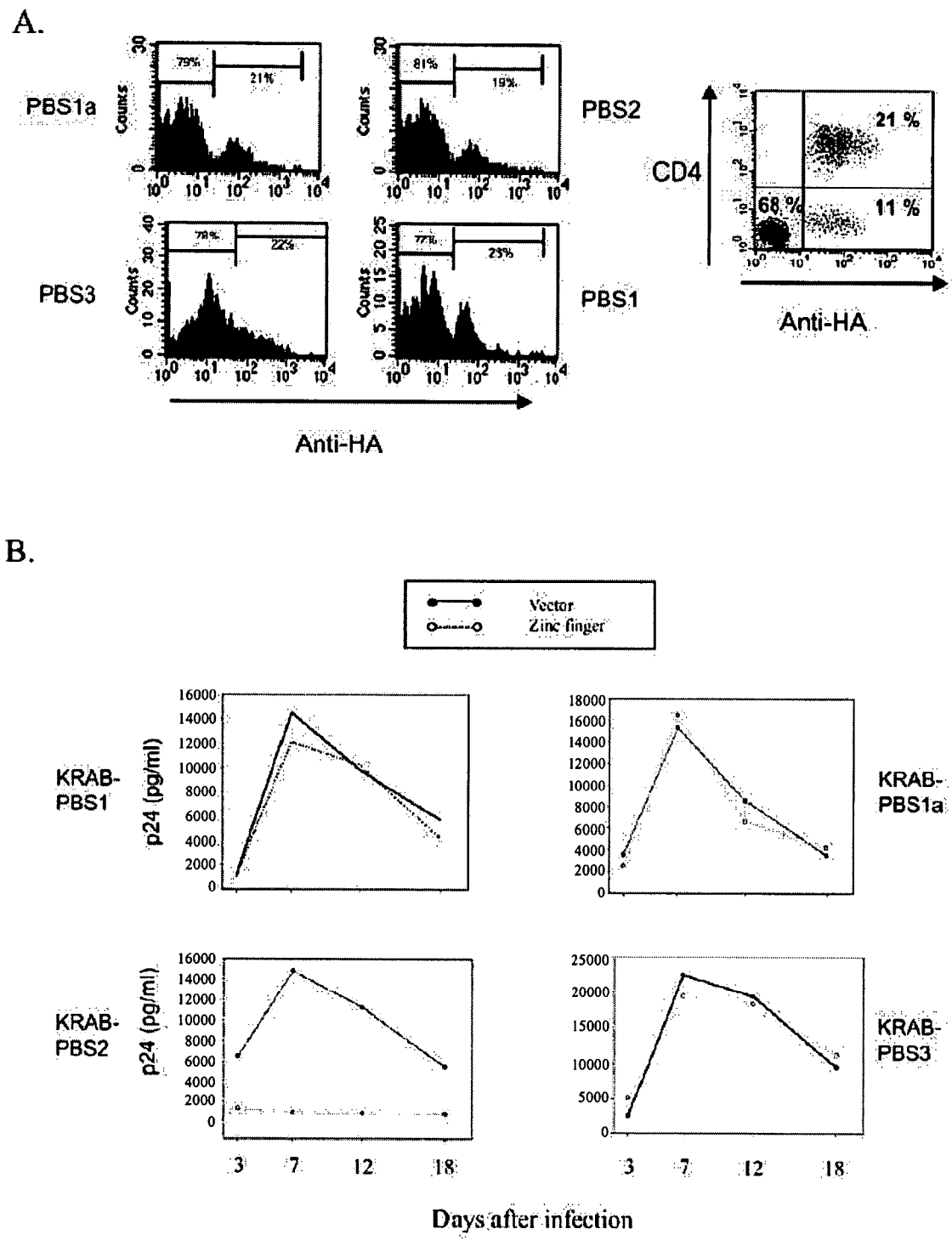
FIG. 11 shows the inhibition of HIV virus production by PBS zinc fingers in primary cells. (A) Flow cytometry analysis of zinc finger expression in PBMCs. PMBCs were transduced with lentiviral vectors that express KRAB-PBS zinc finger proteins. Cells were fixed and stained with an antibody that recognizes the C-terminal HA tag of the ZFs and analyzed by flow cytometry for zinc finger expression. The right panel shows flow cytometry analyses of KRAB-PBS2-transduced cells stained for CD4 and HA antibodies. (B) PBMCs were transduced with the indicated KRAB-PBS lentiviral vector and then challenged with infection by the HIV-1 strain NL4-3 at an MOI of 0.1. p24 levels were monitored at 3, 7, 12, and 18 days after infection.
Figure 12:
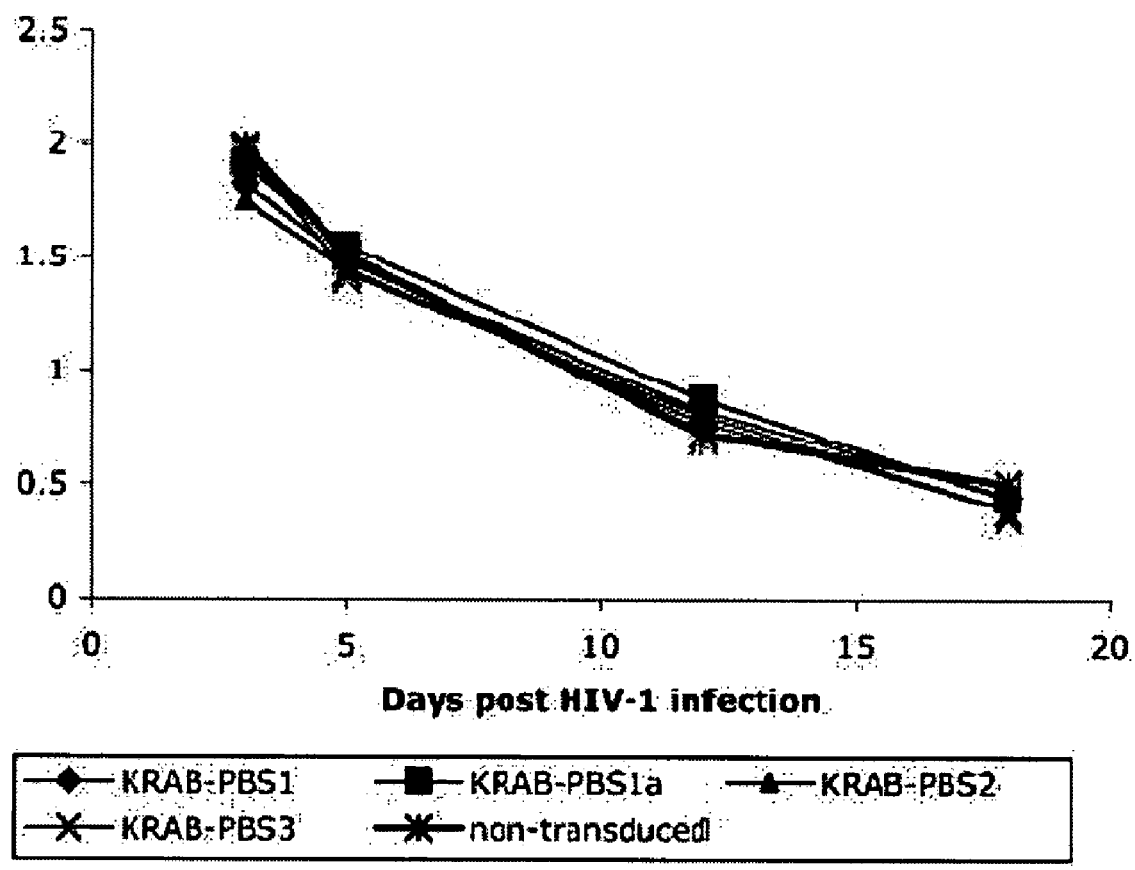
FIG. 12 is a graph showing that transduction of PBMCs with zinc finger (ZF) proteins did not affect cell viability. PBMCs transduced with the indicated ZF transcription factor or nontransduced cells were challenged with HIV-1. At the indicated time points, cell viability was determined by the WST-1 assay.

We next explored whether the transcription factors could inhibit virus production in a more physiological setting. Therefore, we analyzed the effect of the PBS ZFs on viral replication in primary T cells infected with HIV-1. PBMCs were transduced with lentiviral vectors that expressed the KRAB-PBS transcription factors. Flow cytometry analysis using an antibody that recognizes the C-terminal hemagglutinin (HA) tag of the ZFs was performed to determine the efficiency of transduction; approximately 20 to 30% of the PBMCs expressed the ZFs (FIG. 11A). FIG. 11 shows the inhibition of HIV virus production by PBS zinc fingers in primary cells. (A) Flow cytometry analysis of zinc finger expression in PBMCs. PMBCs were transduced with lentiviral vectors that express KRAB-PBS zinc finger proteins. Cells were fixed and stained with an antibody that recognizes the C-terminal HA tag of the ZFs and analyzed by flow cytometry for zinc finger expression. The right panel shows flow cytometry analyses of KRAB-PBS2-transduced cells stained for CD4 and HA antibodies. (B) PBMCs were transduced with the indicated KRAB-PBS lentiviral vector and then challenged with infection by the HIV-1 strain NL4-3 at an MOI of 0.1. p24 levels were monitored at 3, 7, 12, and 18 days after infection. We also performed a flow cytometry analysis in which KRAB-PBS2-transduced cells were stained with a CD4 antibody in addition to the HA antibody, which showed that approximately two-thirds of the transduced cells were CD4-expressing and therefore HIV-1-permissive cells (FIG. 11A). These results agree with our previous results in transducing peripheral blood mononuclear cells (50). Transduced cells were challenged with HIV-1, and virus production was monitored by p24 quantitation. Of the four PBS-binding transcription factors, only KRAB-PBS2 was able to inhibit virus production. In cells transduced with KRAB-PBS2, a >90% reduction of virus production was observed, compared to that for nontransduced cells (FIG. 11B). To ensure that the reduced virus production was not due to cytotoxicity due to overexpression of KRAB-PBS2, cell viability was measured at various time points after HIV-1 infection. All samples were found to have similar viability at all time points measured (FIG. 12). FIG. 12 is a graph showing that transduction of PBMCs with zinc finger (ZF) proteins did not affect cell viability. PBMCs transduced with the indicated ZF transcription factor or nontransduced cells were challenged with HIV-1. At the indicated time points, cell viability was determined by the WST-1 assay.

Figure 13:
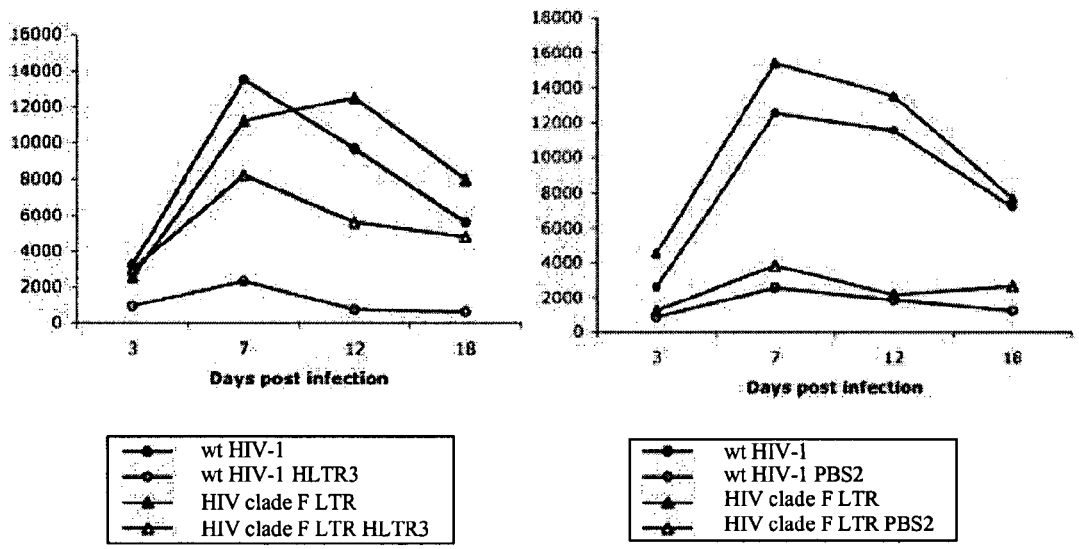
FIG. 13 is a graph showing reduced effectiveness of KRAB-HLT1 on the F-subtype LTR. (A) Sequence comparisons of the HLTR3 and PBS2 ZF-binding sites in different HIV-1 M-group subtypes. Dashes indicate sequence identity, and dots indicate deletions. (B) PBMCs transduced with either KRAB-HLTR3 (left) or KRAB-PBS2 (right) were challenged with B-subtype viruses containing either wild-type or F-subtype LTR. Virus replication was monitored by measuring p24 production.

We previously found that KRAB-HLTR3, a protein designed to bind at a Sp1 site in the HIV-1 LTR, effectively inhibited viral replication. The HLTR3 ZF protein was designed to bind to the LTR of the B subtype of HIV-1, the predominant strain of the virus in the United States and Europe and the virus used in most studies. However, the sequence of this region of the LTR varies among subtypes. Examination of the sequences from De Baar et al. (14) of the HLTR3-binding sites for a number of subtypes shows that there are few differences in the HLTR3-binding sequences, suggesting that KRAB-HLTR3 may be able to inhibit replication of these viruses (FIG. 13A). FIG. 13 is a graph showing reduced effectiveness of KRAB-HLT1 on the F-subtype LTR. (A) Sequence comparisons of the HLTR3 and PBS2 ZF-binding sites in different HIV-1 M-group subtypes. Dashes indicate sequence identity, and dots indicate deletions. (B) PBMCs transduced with either KRAB-HLTR3 (left) or KRAB-PBS2 (right) were challenged with B-subtype viruses containing either wild-type or F-subtype LTR. Virus replication was monitored by measuring p24 production. However, the F-subtype HLTR3 sequence differs greatly from the B subtype, and 9 nucleotides out of 18 differ from the B-subtype HLTR3 target sequence. In contrast, the sequence of the target site for KRAB-PBS2 is identical for the subtypes analyzed. To test the ability of KRAB-HLTR3 to regulate the F-subtype LTR, a B-subtype virus with the U3 region of the LTR replaced by the U3 sequence of an F-subtype virus was used. PBMCs were transduced with KRAI3-HLTR3 and then challenged with the chimeric virus. As expected, the ability of KRAB-HLTR3 to inhibit production of the F-subtype LTR virus was severely reduced compared to the wild-type virus (FIG. 13B). KRAB-PBS2 inhibited replication of the chimeric virus and the B-subtype virus to the same degree, as expected, since both of the viruses tested contain the PBS from the B subtype. However, the KRAB-PBS2-binding site sequences are identical in the F subtype and the B subtype, so it would be expected that KRAB-PBS2 would be able to inhibit F-subtype viruses. Thus, while there are limitations in the potential use of KRAB-HLTR3 as an anti-HIV-1 therapeutic agent, KRAB-PBS2 could potentially be used to treat any known HIV-1 strain.

Figure 14:
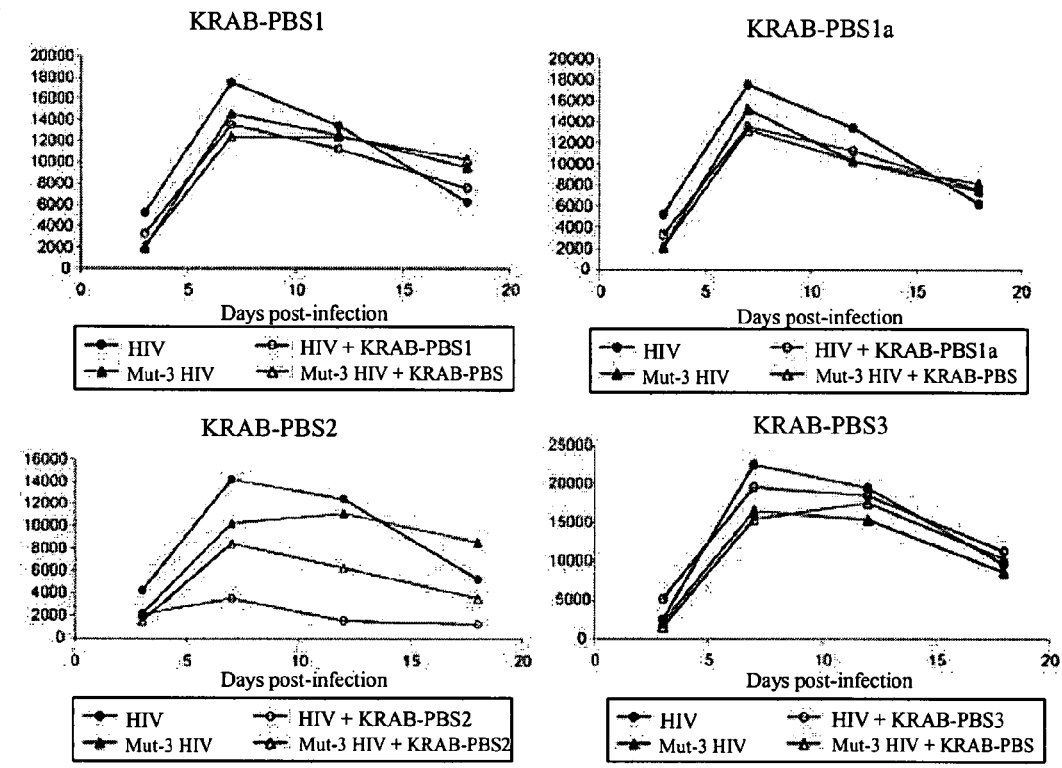
FIG. 14 shows mutation of the primer-binding site in response to zinc finger repression. (A) PBMCs were transduced with KRAB-PBS2 and infected with HIV-1. Virus was collected from the supernatant and used to reinfect a new population of transduced cells. After several rounds, output virus was cloned, and the primer-binding site regions from 20 clones were sequenced. The sites of mutation are indicated by underlining. (B) Infection of KRAB-PBS-transduced PMBCs by wild-type and Mut-3 HIV. (C) Gel shift of PBS2 with wild-type and Mut-3 hairpin oligonucleotides.
Figure 14:
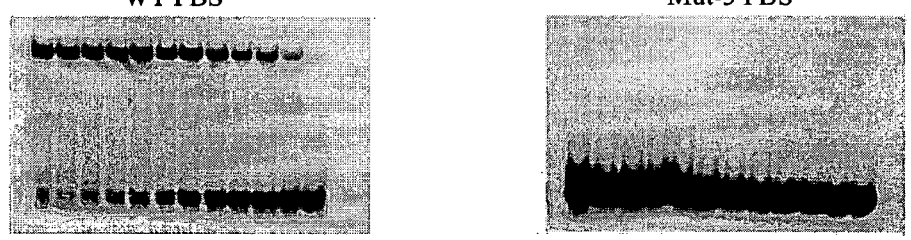

A major difficulty in AIDS treatment is the ability of HIV to mutate rapidly and develop resistance to therapeutic agents. We chose the primer-binding site as the target site for our transcription factors because it is conserved in all known subtypes of HIV-1, suggesting that this sequence is immutable for viral replication. Indeed, many studies have shown that mutations to the PBS cause reduced rates of virus production. Of the four ZF transcription factors we designed to bind to the PBS, KRAB-PBS2 most effectively repressed viral transcription and replication. We wished to determine whether repeated exposure of HIV-1 to KRAB-PBS2 would result in mutations that would allow the virus to escape regulation. PBMCs transduced with KRAB-PBS2 were infected by the NL4-3 strain of HIV-1, and the virus produced was collected and was used to infect a new population of KRAB-PBS2-transduced PBMCs. After several rounds of infection, the resulting viruses were cloned and the primer-binding site regions of 20 clones were sequenced. Of the 20 clones, only 2 contained the wild-type PBS sequence; the remaining 18 consisted of three different sequences with one or two mutations in the PBS (FIG. 14A). FIG. 14 shows mutation of the primer-binding site in response to zinc finger repression. (A) PBMCs were transduced with KRAB-PBS2 and infected with HIV-1. Virus was collected from the supernatant and used to reinfect a new population of transduced cells. After several rounds, output virus was cloned, and the primer-binding site regions from 20 clones were sequenced. The sites of mutation are indicated by underlining. (B) Infection of KRAB-PBS-transduced PMBCs by wild-type and Mut-3 HIV. (C) Gel shift of PBS2 with wild-type and Mut-3 hairpin oligonucleotides. The viral clone with the mutation that occurred in half of clones sequenced, designated Mut-3, was packaged into virus and used to infect PBMCs that had been transduced with the PBS ZFs to determine if this virus was resistant to regulation by the designed transcription factors. As with the wild-type virus, KRAB-PBS1, KRAB-PBS1a, and KRABPBS3 had no effect on Mut-3 virus replication. KRAB-PBS2 was able to repress Mut-3 virus replication, but much less effectively than repression of wild-type virus (FIG. 14B). In addition, the mutated virus produced much lower levels of virus than the wild-type HIV-1. These results suggest that the mutations to the PBS decrease the affinity of KRAB-PBS2 for its target sequence. To test this, an EMSA was performed to determine if the PBS2 ZF could bind to the Mut-3 sequence. We found that the PBS2 ZF bound so weakly to this sequence that the binding constant for this interaction could not be calculated (FIG. 14C). Thus, it appears that the PBS region can tolerate mutation to escape regulation by the ZF, but at the cost of efficiency of viral production.

Discussion

The PBS sequence is identical in all HIV-1 subtypes identified, and all natural strains of HIV-1 use tRNA$^{Lys}_3$ for initiation of reverse transcription (31). Studies examining the effects of mutation have found that altering the sequence of the PBS results in decreased viral replication and that mutant viruses rapidly revert to the native tRNA$^{Lys}_3$ priming site (42, 46). These key features make therapies that take advantage of conserved nature of this region promising. In this study, we designed, expressed, and characterized artificial zinc finger transcription factors that regulate HIV-1 transcription through binding to the highly conserved primer-binding site. Of the four ZF transcription factors that we tested, only one, KRABPBS2, was able to inhibit REV-i viral production. Curiously, two other proteins, KRAB-PBS1 and KRAB-PBS1a, bound to the PBS sequence, as demonstrated by the ChIP assay, and inhibited the HIV-1 LTR in transient reporter assays, but they did not inhibit viral replication in PBMCs. One possible explanation is that in the assays with both the transient and stable reporters, KRAB-PBS2 was a slightly better repressor than the other two proteins. Thus, it may be that there is some threshold level of transcriptional repression that is necessary for effective inhibition of viral replication; of the ZFs tested, only KRAB-PBS2 reached this level.

KRAB-PBS3 was unable to regulate the HIV-1 LTR in any of our assays and was unable to bind to the LTR in the nucleus, as shown by the ChIP assay, despite having a $K_D$ value for the double-stranded DNA-binding site comparable to those of the other ZFs that were tested by the gel shift assay. One possibility is that KRAB-PBS3 binds to the tRNA$^{Lys}_3$ gene, which contains the same sequence as the HIV-1 PBS. Since there are multiple copies of tRNA genes in the nucleus, it could conceivably outcompete the single integrated copy of the HIV genome for the binding of KRAB-PBS3. However, in the transient transfection of the reporter, thousands of copies of the HIV LTR were present in the nucleus, yet KRAB-PBS3 still failed to repress transcription from the LTR (FIG. 8). Also, while direct binding of KRAB-PBS3 to the tRNA$^{Lys}_3$ gene was not examined, no repression of tRNA$^{Lys}_3$ was seen by Northern blot (FIG. 9). Thus, it is possible that in a cellular environment, the LTR has a conformation that does not allow binding of KRAB-PBS3. This phenomenon was observed for other ZF transcription factors designed to bind to the HIV-1 LTR. In studies by Reynolds et al. and Kim et al. (30, 45), multiple polydactyl transcription factors were constructed that targeted the Sp1-binding sites of the LTR; in both studies, the majority of the proteins showed no regulation when tested by reporter assays These findings demonstrate the need to use multiple assays to determine the effectiveness of designed transcription factors. Hopefully, as more ZF transcription factors are constructed and tested, the parameters for target site selection will become clearer. Recently released web-based software now allows for the automatic design of artificial zinc finger transcription factors (http://www.scripps.edu/mb/barbas/zfdesign/zfdesignhome.php).

To determine whether long-term exposure of HIV-I to KRAB-PBS2 would induce mutations in the PBS that reduced the effectiveness of the repressor, we selected for escape variants of virus by passaging virus in multiple rounds using cells transduced with KRAB-PBS2. We did indeed find that the resulting virus contained mutations in the PBS and was more resistant to regulation by KRAB-PBS2; however, this virus also had delayed replication kinetics compared to the wild type. The viral mutant we tested had a CC-to-GA mutation in the sixth and seventh nucleotides of the PBS (FIG. 14A). Mutational analyses of the PBS suggest that the first six nucleotides of the HIV-1 PBS are necessary for initiation of minus-strand synthesis, whereas the last five nucleotides are important for efficient template transfer during plus-strand synthesis (9, 46, 57). A subsequent study, using a replication competent virus with a PBS complementary to tRNA$^{Lys}_3$ in nucleotides 1 to 6 and complementary to tRNA$^{Phe}$ in nucleotides 7 to 18, along with a five-nucleotide insertion downstream of the PBS, tested viruses with point mutations in each of the first six nucleotides for their ability to replicate. Of two viruses with mutations at the sixth nucleotide, the mutant with a C-to-A mutation was not infectious. The mutant with a C-to-U mutation was infectious, although the appearance of virus was delayed relative to the wild type (56). Consistent with our observations here, some mutations at the sixth nucleotide of the PBS are tolerated, as was the C-to-G mutation we observed at the sixth nucleotide.

The fact that the mutated virus appears to be viable suggests that the virus may be using an alternative tRNA to prime reverse transcription. However, a search of the database found no tRNAs that match the sequence of this new PBS. Thus, it is likely that tRNA$^{Lys}_3$ is the primer and that these mutations arise during reverse transcription and are continuously selected by the pressure to escape regulation by KRAB-PBS2 instead of being repaired. In most studies of mutation of the PBS, viruses with a mutated PBS that are cultured with no selective pressure typically revert back to the wild-type PBS sequence (11, 33, 58). However, there have been instances where mutations designed to enable HIV to use different tRNAs have resulted in stable clones. In particular, viruses have been isolated that can use $tRNA^{Lys}_{1,2}$, $tRNA^{His}$, and $tRNA^{Met}$ (1 12, 40, 55). Importantly, these isolates have come about through laboratory manipulation of HTV-1, and there is no evidence suggesting that these mutations could occur in nature. The only natural primer variation concerns the infrequent use of $tRNA^{Lys}_{5}$, which causes a single-nucleotide polymorphism in about 5% of the HTV-simian immunodeficiency virus isolates (12, 13). These results suggest that the best strategy for using KRAB-PBS2 as a therapy for AIDS would be to discontinue treatment at intervals to allow any viruses that have mutated to revert and then resume treatment with KRAB-PBS2. During the "resting" period, alternative therapies may be used, including but not limited to ZF proteins that target other sites in the HTV-1 LTR, such as KRAB-HLTR3. However, further studies need to be performed to determine if the mutant viruses we have isolated would indeed revert to the wild-type PBS sequence in the absence of KRAB-PBS2.

RNAi has recently emerged as a potential treatment for a number of diseases. In particular, several studies have been performed with short interfering RNA (siRNA) molecules targeting HIV-1 and have shown potent down-regulation of viral gene expression (8, 25, 26). Unfortunately, long-term studies have shown that prolonged exposure to siRNAs results in mutations of the virus that allow it to escape regulation (6, 10). Recently, a study showed that an siRNA targeting the PBS was able to inhibit HIV-1 infection (24). Although no mutation in the PBS was seen up to 14 days after exposure to the siRNA, our studies suggest that HIV can mutate the PBS region to escape targeting by RNAi. This could be a significant drawback in the use of siRNA strategies, as it has been shown that a single point mutation can be sufficient for HIV to escape regulation by siRNAs (6). However, the strategy suggested above for allowing the PBS sequence to revert may also be applied to any therapy involving RNA interference. In fact, the use of both RNA interference and transcription factors in the treatment of HIV-1 could prove to be a potent therapeutic mixture, since they act at two different levels. This approach has already been demonstrated in the regulation of the vegf-a gene, in which the use of artificial transcription factors and siRNA was shown to have a greater repression together than individually (32).

In conclusion, the results of this study have identified KRAB-PBS2 as a transcription factor with the potential for use in anti-HIV therapy. Like KRAB-HLTR3, KRAB-PBS2 can inhibit virus production in primary lymphocytes for extended periods with no apparent toxicity. Significantly, KRAB-PBS2 can inhibit replication of viruses that escape regulation of KRAB-HLTR3. As KRAB-PBS2 targets a sequence that is highly conserved in all known subtypes of HIV-1, it has the potential to be used as therapy in any region of the globe. As established by small-molecule approaches to HIV-1, gene-based approaches should also incorporate a cocktail of effectors to limit HIV-1 escape.

REFERENCES

The following references are cited by their numerical references in Example 12. Please note that these numerical references apply only to Example 12.

1. Abbink, T. E., N. Beerens, and B. Berkhout. 2004. Forced selection of a human immunodeficiency virus type 1 variant that uses a non-self tRNA primer for reverse transcription: involvement of viral RNA sequences and the reverse transcriptase enzyme. J. Virol. 78:10706-10714.
2. Barnor, J. S., N. Miyano-Kurosaki, K. Yamaguchi, A. Sakamoto, K. Ishikawa, Y. Inagaki, N. Yamamoto, M. Osei-Kwasi, B. Ofori-Adjei, and H. Takaku. 2004. Intracellular expression of antisense RNA transcripts complementary to the human immunodeficiency virus type-1 vif gene inhibits viral replication in infected T-lymphoblastoid cells. Biochem. Biophys. Res. Commun. 320:544-550.
3. Beerli, R. R., B. Dreier, and C. F. Barbas IIL 2000. Positive and negative regulation of endogenous genes by designed transcription factors. Proc. Natl. Acad. Sci. USA 97:1495-1500.
4. Beerli, R. R., D. J. Segal, B. Dreier, and C. F. Barbas IIL 1998. Toward controlling gene expression at will: specific regulation of the erbB-2/HER-2 promoter by using polydactyl zinc finger proteins constructed from modular building blocks. Proc. Natl. Acad. Sci. USA 95:14628-14633.
5. Blancafort, P., D. J. Segal, and C. F. Barbas III. 2004. Designing transcription factor architectures for drug discovery. Mol. Pharmacol. 66:1361-1371.
6. Boden, D., O. Pusch, F. Lee, L. Tucker, and B. Ramratnam. 2003. Human immunodeficiency virus type 1 escape from RNA interference. J. Virol. 77:11531-11535.
7. Boyd, K. E., J. Wells, J. Gutman, S. M. Bartley, and P. J. Farnham. 1998. c-Myc target gene specificity is determined by a post-DNA binding mechanism. Proc. Natl. Acad. Sci. USA 95:13887-13892.
8. Coburn, G. A., and B. R. Cullen. 2002. Potent and specific inhibition of human immunodeficiency virus type 1 replication by RNA interference. J. Virol. 76:9225-9231.
9. Das, A. T., and B. Berkhout. 1995. Efficient extension of a misaligned tRNA-primer during replication of the HIV-1 retrovirus. Nucleic Acids Res. 23: 1319-1326.
10. Das, A. T., T. R. Brummelkamp, E. M. Westerhout, M. Vink, M. Madiredjo, R. Bernards, and B. Berkhout. 2004. Human immunodeficiency virus type 1 escapes from RNA interference-mediated inhibition. J. Virol. 78:2601-2605.
11. Das, A. T., B. Kiaver, and B. Berkhout. 1995. Reduced replication of human immunodeficiency virus type 1 mutants that use reverse transcription primers other than the natural tRNA. J. Virol. 69:3090-3097.
12. Das, A. T., B. Kiaver, and B. Berkhout. 1997. Sequence variation of the human immunodeficiency virus primer-binding site suggests the use of an alternative tRNA(Lys) molecule in reverse transcription. J. Gen Virol. 78: 837-840.
13. Das, A. T., M. Vink, and B. Berkhout. 2005. Alternative tRNA priming of human immunodeficiency virus type I reverse transcription explains sequence variation in the primer-binding site that has been attributed to APOBEC3G activity. J. Virol. 79:3179-3181.
14. Be Baar, M. P., A. De Ronde, B. Berkhout, M. Cornelissen, K. H. Van Der Horn, A. M. Van Der Schoot, F. De Wolf, V. V. Lukashov, and J. Goudsmit. 2000. Subtype-specific sequence variation of the HIV type 1 long terminal repeat and primer-binding site. AIDS Res. Hum. Retrovir. 16:499-504.

15. Derdeyn, C. A., J. M. Decker, J. N. Sfakianos, X. Wu, W. A. O'Brien, L. Ratner, J. C. Kappes, G. M. Shaw, and E. Hunter. 2000. Sensitivity of human immunodeficiency virus type 1 to the fusion inhibitor T-20 is modulated by coreceptor specificity defined by the V3 loop of gp120. J. Virol. 74:8358-8367.

16. Dreier, B., R. R. Beerli, D. J. Segal, J. D. Flippin, and C. F. Barbas III. 2001. Development of zinc finger domains for recognition of the 5'-ANN-3' family of DNA sequences and their use in the construction of artificial transcription factors. J. Biol. Chem. 276:29466-29478.

17. Dreier, B., R. P. Fuller, D. J. Segal, C. V. Lund, P. Blancafort, A. Huber, B. Koksch, and C. F. Barbas III. 2005. Development of zinc finger domains for recognition of the 5'-CNN-3' family DNA sequences and their use in the construction of artificial transcription factors. I. Biol. Chem. 280:35588-35597.

18. Dreier, B., D. J. Segal, and C. F. Barbas III. 2000. Insights into the molecular recognition of the 5'-GNN-3' family of DNA sequences by zinc finger domains. 1. Mol. Biol. 303:489-502.

19. Feng, Y., M. Leavitt, R. Tritz, E. Duarte, D. Kang, M. Mamounas, P. Gilles, F. Wong-Staal, S. Kennedy, J. Merson, M. Yu, and J. R. Barber. 2000. Inhibition of CCR5-dependent HIV-1 infection by hairpin ribozyme gene therapy against CC-chemokine receptor 5. Virology 276:271-278.

20. Frankel, A. D., and C. O. Pabo. 1988. Cellular uptake of the tat protein from human immunodeficiency virus. Cell 55:1189-1193.

21. Gea-Banacloche, J. C., and H. Clifford Lane. 1999. Immune reconstitution in HIV infection. AIDS 13:525-538.

22. Graslund, T., X. Li, L. Magnenat, M. Popkov, and C. F. Barbas III. 2005. Exploring strategies for the design of artificial transcription factors: targeting sites proximal to known regulatory regions for the induction of gamma-globin expression and the treatment of sickle cell disease. J. Biol. Chem. 280:3707-3714.

23. Guan, X., J. Stege, M. Kim, Z. Dahmani, N. Fan, P. Heifetz, C. F. Barbas III, and S. P. Briggs. 2002. Heritable endogenous gene regulation in plants with designed polydactyl zinc finger transcription factors. Proc. Natl. Acad. Sci. USA 99:13296-13301.

24. Han, W., M. Wind-Rotolo, R. L. Kirkman, and C. D. Morrow. 2004. Inhibition of human immunodeficiency virus type 1 replication by siRNA targeted to the highly conserved primer binding site. Virology 330:221-232.

25. Hu, W. V., C. P. Myers, J. M. Kilzer, S. L. Pfaff, and F. D. Bushman. 2002. Inhibition of retroviral pathogenesis by RNA interference. Curr. Biol. 12: 1301-1311.

26. Jacque, J. M., K. Triques, and M. Stevenson. 2002. Modulation of HIV-1 replication by RNA interference. Nature 418:435-438.

27. Jeeninga, R. E., M. Hoogenkamp, M. Armand-Ugon, M. de Baar, K. Verhoeft and B. Berkhout. 2000. Functional differences between the long terminal repeat transcriptional promoters of human immunodeficiency virus type 1 subtypes A through G. J. Virol. 74:3740-3751.

28. Jouvenot, Y., V. Ginjala, L. Zhang, P. Q. Liu, M. Oshimura, A. P. Feinberg, A. P. Wolffe, R. Ohisson, and P. D. Gregory. 2003. Targeted regulation of imprinted genes by synthetic zinc-finger transcription factors. Gene Ther. 10:513-522.

29. Keuien, W., N. K. Back, A. van Wijk, C. A. Boucher, and B. Berkhout. 1997. Initial appearance of the 184Ile variant in lamivudine-treated patients is caused by the mutational bias of human immunodeficiency virus type 1 reverse transcriptase. J. Virol. 71:3346-3350.

30. Kim, Y. S., J. M. Kim, D. L. Jung, J. E. Kang, S. Lee, J. S. Kim, W. Seol, H. C. Shin, H. S. Kwon, C. Van Lint, N. Hernandez, and M. W. Hur. 2005. Artificial zinc finger fusions targeting Sp1-binding sites and the trans-activator-responsive element potently repress transcription and replication of HIV-1. J. Biol. Chem. 280:21545-21552.

31. Kleiman, L. 2002. tRNA(Lys3): the primer tRNA for reverse transcription in HIV-1. IUBMB Life 53:107-114.

32. Kwon, H. S., H. C. Shin, and J. S. Kim. 2005. Suppression of vascular endothelial growth factor expression at the transcriptional and post-transcriptional levels. Nucleic Acids Res. 33:e74.

33. Li, X., J. Mak, E. J. Arts, Z. Gu, L. Kleiman, M. A. Wainberg, and M. A. Parniak. 1994. Effects of alterations of primer-binding site sequences on human immunodeficiency virus type 1 replication. I. Virol. 68:6198-6206.

34. Liu, Q., B. J. Segal, J. B. Ghiara, and C. F. Barbas III. 1997. Design of polydactyl zinc-finger proteins for unique addressing within complex genomes. Proc. Natl. Acad. Sci. USA 94:5525-5530.

35. Magnenat, L., P. Blancafort, and C. F. Barbas III. 2004. In vivo selection of combinatorial libraries and designed affinity maturation of polydactyl zinc finger transcription factors for ICAM-1 provides new insights into gene regulation. J. Mol. Biol. 341:635-649.

36. Mak, J., and L. Kleiman. 1997. Primer tRNAs for reverse transcription. J. Virol. 71:8087-8095.

37. Marcello, A., M. Lusic, G. Pegoraro, V. Pellegrini, F. Beltram, and M. Giacca. 2004. Nuclear organization and the control of HIV-1 transcription. Gene 326:1-11.

38. Margolin, J. F., J. R. Friedman, W. K. Meyer, H. Vissing, H. J. Thiesen, and F. J. Rauscher III. 1994. Kruppel-associated boxes are potent transcriptional repression domains. Proc. Natl. Acad. Sci. USA 91:4509-4513.

39. Marquet, I L, C. Isel, C. Ehresmann, and B. Ehresmann. 1995. tRNAs as primer of reverse transcriptases. Biochimie 77:113-124.

40. Moore-Rigdon, K. L., B. R. Kosloff, R. L. Kirkman, and C. B. Morrow. 2005. Preferences for the selection of unique tRNA primers revealed from analysis of HIV-1 replication in peripheral blood mononuclear cells. Retrovirology 2:21.

41. Moosmann, P., O. Georgiev, H. J. Thiesen, M. Hagmann, and W. Schaffner. 1997. Silencing of RNA polymerases II and III-dependent transcription by the KRAB protein domain of KOX1, a Kruppel-type zinc finger factor. Biol. Chem. 378:669-677.

42. Nagashunmugam, T., A. Velpandi, C. S. Goldsmith, S. R. Zaki, V. S. Kalyanaraman, and A. Srinivasan. 1992. Mutation in the primer binding site of the type 1 human immunodeficiency virus genome affects virus production and infectivity. Proc. Natl. Acad. Sci. USA 89:4114-4118.

43. Pereira, L. A., K. Bentley, A. Peeters, M. J. Churchill, and N. J. Deacon. 2000. A compilation of cellular transcription factor interactions with the HIV-1 LTR promoter. Nucleic Acids Res. 28:663-668.

44. Platt, E. J., K. Wehrly, S. E. Kuhmann, B. Chesebro, and D. Kabat. 1998. Effects of CCR5 and CD4 cell surface concentrations on infections by macrophagetropic isolates of human immunodeficiency virus type 1. J. Virol. 72:2855-2864.

45. Reynolds, L., C. Uliman, M. Moore, M. Isalan, M. J West, P. Clapham, A. Mug, and Y. Choo. 2003. Repression of the HIV-1 5' LTR promoter and inhibition of HIV-1 replication by using engineered zinc-finger transcription factors. Proc. Natl. Acad. Sci. USA 100:1615-1620.
46. Rhim, H., J. Park, and C. D. Morrow. 1991. Deletions in the tRNA$^{Lys}$ primer-binding site of human immunodeficiency virus type 1 identify essential regions for reverse transcription. J. Virol. 65:4555-4564.
47. Sadowski, I., J. Ma, S. Triezenberg, and M. Ptashne. 1988. GAL4-VP16 is an unusually potent transcriptional activator. Nature 335:563-564.
48. Schrager, L. K., and M. P. D'Souza. 1998. Cellular and anatomical reservoirs of HIV-1 in patients receiving potent antiretroviral combination therapy. JAMA 280:67-71.
49. Segal, D. J., B. Dreier, R. R. Beerli, and C. F. Barbas III. 1999. Toward controlling gene expression at will: selection and design of zinc finger domains recognizing each of the 5'-GNN-3' DNA target sequences. Proc. Natl. Acad. Sci. USA 96:2758-2763.
50. Segal, D. J., J. Goncalves, S. Eberhardy, C. H. Swan, B. F. Torbett, X. Li, and C. F. Barbas III. 2004. Attenuation of HIV-1 replication in primary human cells with a designed zinc finger transcription factor. J. Biol. Chem. 279: 14509-14519.
51. Senatore, B., A. Cafieri, L Di Marino, M. Rosati, P. P. Di Nocera, and G. Grimaldi. 1999. A variety of RNA polymerases II and III-dependent promoter classes is repressed by factors containing the Kruppel-associated/finger preceding box of zinc finger proteins. Gene 234:381-394.
52. Sodroski, J., W. C. Goh, C. Rosen, K. Campbell, and W. A. Haseltine. 1986. Role of the HTLV-III/LAV envelope in syncytium formation and cytopathicity. Nature 322:470-474.
53. Stege, J. T., X. Guan, T. Ho, R. N. Beachy, and C. F. Barbas III 2002. Controlling gene expression in plants using synthetic zinc finger transcription factors. Plant J. 32:1077-1086.
54. Verdin, E., P. Paras, Jr., and C. Van Lint. 1993. Chromatin disruption in the promoter of human immunodeficiency virus type 1 during transcriptional activation. EMBO J. 12:3249-3259.
55. Wakefield, J. K., S. M. Kang, and C. D. Morrow. 1996. Construction of a type 1 human immunodeficiency virus that maintains a primer binding site complementary to tRNA$^{His}$. J. Virol. 70:966-975.
56. Wakefield, J. K., and C. D. Morrow. 1996. Mutations within the primer binding site of the human immunodeficiency virus type 1 define sequence requirements essential for reverse transcription. Virology 220:290-298.
57. Wakefield, J. K., H. Rhim, and C. D. Morrow. 1994. Minimal sequence requirements of a functional human immunodeficiency virus type 1 primer binding site. J. Virol. 68:1605-1614.
58. Wakefield, J. K., A. G. Wolf, and C. D. Morrow. 1995. Human immunodeficiency virus type 1 can use different tRNAs as primers for reverse transcription but selectively maintains a primer binding site complementary to tRNA$^{Lys}_3$. 1. Virol. 69:6021-6029.
59. Waninger, S., K. Kuhen, X. Hu, J. E. Chatterton, F. Wong-Staal, and H. Tang. 2004. Identification of cellular cofactors for human immunodeficiency virus replication via a ribozyme-based genomics approach. J. Virol. 78:12829-12837.
60. Wei, X., J. M., Decker, H. Liu, Z. Zhang, R. B. Arani, J. M. Kilby, M. S. Saag, X. Wu, G. M. Shaw, and J. C. Kappes. 2002. Emergence of resistant human immunodeficiency virus type 1 in patients receiving fusion inhibitor (T-20) monotherapy. Antimicrob. Agents Chemother. 46:1896-1905.
61. Zhang, L., S. K. Spratt, Q. Liu, B. Johnstone, H. Qi, E. E. Raschke, A. C. Jamieson, E. J. Rebar, A. P. Wolfe, and C. C. Case. 2000. Synthetic zinc finger transcription factor action at an endogenous chromosomal site. Activation of the human erythropoietin gene. J. Biol. Chem. 275:33850-33860.

TABLE 14

Summary of Protein and Nucleic Acid Sequences Recited

| Heptapeptide | SEQ ID NO |
|---|---|
| Heptapeptide Zinc Finger Moieties | |
| QAS-N-LIS | 1 |
| SRG-N-LKS | 2 |
| RLD-N-LQT | 3 |
| ARG-N-LRT | 4 |
| RKD-A-LRG | 5 |
| RED-N-LHT | 6 |
| ARG-N-LKS | 7 |
| RSD-N-LTT | 8 |
| VRG-N-LKS | 9 |
| VRG-N-LRT | 10 |
| RLR-A-LDR | 11 |
| DMG-A-LEA | 12 |
| EKD-A-LRG | 13 |
| RSD-H-LTT | 14 |
| AQQ-L-LMW | 15 |
| RSD-E-RKR | 16 |
| DYQ-S-LRQ | 17 |
| CFS-R-LVR | 18 |
| GDG-G-LWE | 19 |
| LQR-P-LRG | 20 |
| QGL-A-CAA | 21 |
| WVG-W-LGS | 22 |
| RLR-D-IQF | 23 |
| GRS-Q-LSG | 24 |
| GWQ-R-LLT | 25 |
| SGR-P-LAS | 26 |
| APR-L-LGP | 27 |
| APK-A-LGW | 28 |
| SVH-E-LQG | 29 |
| AQA-A-LSW | 30 |
| GAN-A-LRR | 31 |
| QSL-L-LGA | 32 |
| HRG-T-LGG | 33 |
| QVG-L-LAR | 34 |
| GAR-G-LRG | 35 |
| DKH-M-LDT | 36 |
| DLG-G-LRQ | 37 |
| QCY-R-LER | 38 |
| AEA-E-LQR | 39 |
| QGG-V-LAA | 40 |
| QGR-C-LVT | 41 |
| HPE-A-LDN | 42 |
| GRG-A-LQA | 43 |
| LAS-R-LQQ | 44 |
| RED-N-LIS | 45 |
| RGG-W-LOA | 46 |
| LAS-N-LIS | 47 |
| EAS-N-LIS | 48 |
| RAS-N-LIS | 49 |
| TAS-N-LIS | 50 |
| SAS-N-LIS | 51 |
| QAS-T-LIS | 52 |
| QAS-D-LIS | 53 |
| QAS-E-LIS | 54 |
| QAS-H-LIS | 55 |
| QAS-K-LIS | 56 |
| QAS-S-LIS | 57 |
| QAS-A-LIS | 58 |
| DAS-T-LIS | 59 |
| DAS-D-LIS | 60 |

TABLE 14-continued

Summary of Protein and Nucleic Acid Sequences Recited

| Heptapeptide | SEQ ID NO |
|---|---|
| DAS-E-LIS | 61 |
| DAS-H-LIS | 62 |
| DAS-K-LIS | 63 |
| DAS-S-LIS | 64 |
| DAS-A-LIS | 65 |
| EAS-T-LIS | 66 |
| EAS-D-LIS | 67 |
| EAS-E-LIS | 68 |
| EAS-H-LIS | 69 |
| EAS-K-LIS | 70 |
| EAS-S-LIS | 71 |
| EAS-A-LIS | 72 |
| RAS-T-LIS | 73 |
| RAS-D-LIS | 74 |
| RAS-E-LIS | 75 |
| RAS-H-LIS | 76 |
| RAS-K-LIS | 77 |
| RAS-S-LIS | 78 |
| RAS-A-LIS | 79 |
| TAS-T-LIS | 80 |
| TAS-D-LIS | 81 |
| TAS-E-LIS | 82 |
| TAS-H-LIS | 83 |
| TAS-K-LIS | 84 |
| TAS-S-LIS | 85 |
| TAS-A-LIS | 86 |
| SAS-T-LIS | 87 |
| SAS-D-LIS | 88 |
| SAS-E-LIS | 89 |
| SAS-H-LIS | 90 |
| SAS-K-LIS | 91 |
| SAS-S-LIS | 92 |
| SAS-A-LIS | 93 |
| QLD-N-LQT | 94 |
| DLD-N-LQT | 95 |
| ELD-N-LQT | 96 |
| TLD-N-LQT | 97 |
| SLD-N-LQT | 98 |
| RLD-T-LQT | 99 |
| RLD-D-LQT | 100 |
| RLD-E-LQT | 101 |
| RLD-H-LQT | 102 |
| RLD-K-LQT | 103 |
| RLD-S-LQT | 104 |
| RLD-A-LQT | 105 |
| QLD-T-LQT | 106 |
| QLD-D-LQT | 107 |
| QLD-E-LQT | 108 |
| QLD-H-LQT | 109 |
| QLD-K-LQT | 110 |
| QLD-S-LQT | 111 |
| QLD-A-LQT | 112 |
| DLD-T-LQT | 113 |
| DLD-D-LQT | 114 |
| DLD-E-LQT | 115 |
| DLD-H-LQT | 116 |
| DLD-K-LQT | 117 |
| DLD-S-LQT | 118 |
| DLD-A-LQT | 119 |
| ELD-T-LQT | 120 |
| ELD-D-LQT | 121 |
| ELD-E-LQT | 122 |
| ELD-H-LQT | 123 |
| ELD-K-LQT | 124 |
| ELD-S-LQT | 125 |
| ELD-A-LQT | 126 |
| TLD-T-LQT | 127 |
| TLD-D-LQT | 128 |
| TLD-E-LQT | 129 |
| TLD-H-LQT | 130 |
| TLD-K-LQT | 131 |
| TLD-S-LQT | 132 |
| TLD-A-LQT | 133 |
| SLD-T-LQT | 134 |

TABLE 14-continued

Summary of Protein and Nucleic Acid Sequences Recited

| Heptapeptide | SEQ ID NO |
|---|---|
| SLD-D-LQT | 135 |
| SLD-E-LQT | 136 |
| SLD-H-LQT | 137 |
| SLD-K-LQT | 138 |
| SLD-S-LQT | 139 |
| SLD-A-LQT | 140 |
| ARG-T-LRT | 141 |
| ARG-D-LRT | 142 |
| ARG-E-LRT | 143 |
| ARG-H-LRT | 144 |
| ARG-K-LRT | 145 |
| ARG-S-LRT | 146 |
| ARG-A-LRT | 147 |
| SRG-T-LRT | 148 |
| SRG-D-LRT | 149 |
| SRG-E-LRT | 150 |
| SRG-H-LRT | 151 |
| SRG-K-LRT | 152 |
| SRG-S-LRT | 153 |
| SRG-A-LRT | 154 |
| QKD-A-LRG | 155 |
| DKD-A-LRG | 156 |
| EKD-A-LRG | 157 |
| TKD-A-LRG | 158 |
| SKD-A-LRG | 159 |
| RKD-N-LRG | 160 |
| RKD-T-LRG | 161 |
| RKD-D-LRG | 162 |
| RKD-E-LRG | 163 |
| RKD-H-LRG | 164 |
| RKD-K-LRG | 165 |
| RKD-S-LRG | 166 |
| QKD-N-LRG | 167 |
| QKD-T-LRG | 168 |
| QKD-D-LRG | 169 |
| QKD-E-LRG | 170 |
| QKD-H-LRG | 171 |
| QKD-K-LRG | 172 |
| QKD-S-LRG | 173 |
| DKD-N-LRG | 174 |
| DKD-T-LRG | 175 |
| DKD-D-LRG | 176 |
| DKD-E-LRG | 177 |
| DKD-H-LRG | 178 |
| DKD-K-LRG | 179 |
| DKD-S-LRG | 180 |
| EKD-N-LRG | 181 |
| EKD-T-LRG | 182 |
| EKD-D-LRG | 183 |
| EKD-E-LRG | 184 |
| EKD-H-LRG | 185 |
| EKD-K-LRG | 186 |
| EKD-S-LRG | 187 |
| TKD-N-LRG | 188 |
| TKD-T-LRG | 189 |
| TKD-D-LRG | 190 |
| TKD-E-LRG | 191 |
| TKD-H-LRG | 192 |
| TKD-K-LRG | 193 |
| TKD-S-LRG | 194 |
| SKD-N-LRG | 195 |
| SKD-T-LRG | 196 |
| SKD-D-LRG | 197 |
| SKD-E-LRG | 198 |
| SKD-H-LRG | 199 |
| SKD-K-LRG | 200 |
| SKD-S-LRG | 201 |
| VRG-T-LRT | 202 |
| VRG-D-LRT | 203 |
| VRG-E-LRT | 204 |
| VRG-H-LRT | 205 |
| VRG-K-LRT | 206 |
| VRG-S-LRT | 207 |
| VRG-T-LRT | 208 |

TABLE 14-continued

Summary of Protein and Nucleic Acid Sequences Recited

| Heptapeptide | SEQ ID NO |
|---|---|
| QLR-A-LDR | 209 |
| DLR-A-LDR | 210 |
| ELR-A-LDR | 211 |
| TLR-A-LDR | 212 |
| SLR-A-LDR | 213 |
| RSD-N-RKR | 214 |
| RSD-T-RKR | 215 |
| RSD-D-RKR | 216 |
| RSD-H-RKR | 217 |
| RSD-K-RKR | 218 |
| RSD-S-RKR | 219 |
| RSD-A-RKR | 220 |
| QYQ-S-LRQ | 221 |
| EYQ-S-LRQ | 222 |
| RYQ-S-LRQ | 223 |
| TYQ-S-LRQ | 224 |
| SYQ-S-LRQ | 225 |
| RLR-N-IQF | 226 |
| RLR-T-IQF | 227 |
| RLR-E-IQF | 228 |
| RLR-H-IQF | 229 |
| RLR-K-IQF | 230 |
| RLR-S-IQF | 231 |
| RLR-A-IQF | 232 |
| DSL-L-LGA | 233 |
| ESL-L-LGA | 234 |
| RSL-L-LGA | 235 |
| TSL-L-LGA | 236 |
| SSL-L-LGA | 237 |
| HRG-N-LGG | 238 |
| HRG-D-LGG | 239 |
| HRG-E-LGG | 240 |
| HRG-H-LGG | 241 |
| HRG-K-LGG | 242 |
| HRG-S-LGG | 243 |
| HRG-A-LGG | 244 |
| QKH-M-LDT | 245 |
| EKH-M-LDT | 246 |
| RKH-M-LDT | 247 |
| TKH-M-LDT | 248 |
| SKH-M-LDT | 249 |
| QLG-G-LRQ | 250 |
| ELG-G-LRQ | 251 |
| RLG-G-LRQ | 252 |
| TLG-G-LRQ | 253 |
| SLG-G-LRQ | 254 |
| AEA-N-LQR | 255 |
| AEA-T-LQR | 256 |
| AEA-D-LQR | 257 |
| AEA-H-LQR | 258 |
| AEA-K-LQR | 259 |
| AEA-S-LQR | 260 |
| AEA-A-LQR | 261 |
| DGR-C-LVT | 262 |
| EGR-C-LVT | 263 |
| RGR-C-LVT | 264 |
| TGR-C-LVT | 265 |
| SGR-C-LVT | 266 |
| QED-N-LHT | 267 |
| DED-N-LHT | 268 |
| EED-N-LHT | 269 |
| SED-N-LHT | 270 |
| RED-T-LHT | 271 |
| RED-D-LHT | 272 |
| RED-E-LHT | 273 |
| RED-H-LHT | 274 |
| RED-K-LHT | 275 |
| RED-S-LHT | 276 |
| RED-A-LHT | 277 |
| QED-T-LHT | 278 |
| QED-D-LHT | 279 |
| QED-E-LHT | 280 |
| QED-H-LHT | 281 |
| QED-K-LHT | 282 |
| QED-S-LHT | 283 |
| QED-A-LHT | 284 |
| DED-T-LHT | 285 |
| DED-D-LHT | 286 |
| DED-E-LHT | 287 |
| DED-H-LHT | 288 |
| DED-K-LHT | 289 |
| DED-S-LHT | 290 |
| DED-A-LHT | 291 |
| EED-T-LHT | 292 |
| EED-D-LHT | 293 |
| EED-E-LHT | 294 |
| EED-H-LHT | 295 |
| EED-K-LHT | 296 |
| EED-S-LHT | 297 |
| EED-A-LHT | 298 |
| TED-T-LHT | 299 |
| TED-D-LHT | 300 |
| TED-E-LHT | 301 |
| TED-H-LHT | 302 |
| TED-K-LHT | 303 |
| TED-S-LHT | 304 |
| TED-A-LHT | 305 |
| SED-T-LHT | 306 |
| SED-D-LHT | 307 |
| SED-E-LHT | 308 |
| SED-H-LHT | 309 |
| SED-K-LHT | 310 |
| SED-S-LHT | 311 |
| SED-A-LHT | 312 |
| QED-N-LIS | 313 |
| DED-N-LIS | 314 |
| EED-N-LIS | 315 |
| SED-N-LIS | 316 |
| RED-T-LIS | 317 |
| RED-D-LIS | 318 |
| RED-E-LIS | 319 |
| RED-H-LIS | 320 |
| RED-K-LIS | 321 |
| RED-S-LIS | 322 |
| RED-A-LIS | 323 |
| QED-T-LIS | 324 |
| QED-D-LIS | 325 |
| QED-E-LIS | 326 |
| QED-H-LIS | 327 |
| QED-K-LIS | 328 |
| QED-S-LIS | 329 |
| QED-A-LIS | 330 |
| DED-T-LIS | 331 |
| DED-D-LIS | 332 |
| DED-E-LIS | 333 |
| DED-H-LIS | 334 |
| DED-K-LIS | 335 |
| DED-S-LIS | 336 |
| DED-A-LIS | 337 |
| EED-T-LIS | 338 |
| EED-D-LIS | 339 |
| EED-E-LIS | 340 |
| EED-H-LIS | 341 |
| EED-K-LIS | 342 |
| EED-S-LIS | 343 |
| EED-A-LIS | 344 |
| TED-T-LIS | 345 |
| TED-D-LIS | 346 |
| TED-E-LIS | 347 |
| TED-H-LlS | 348 |
| TED-K-LIS | 349 |
| TED-S-LIS | 350 |
| TED-A-LIS | 351 |
| SED-T-LIS | 352 |
| SED-D-LIS | 353 |
| SED-E-LIS | 354 |
| SED-H-LIS | 355 |
| SED-K-LIS | 356 |

TABLE 14-continued

Summary of Protein and Nucleic Acid Sequences Recited

| Heptapeptide | SEQ ID NO |
|---|---|
| SED-S-LIS | 357 |
| SED-A-LIS | 358 |
| TGG-W-LQA | 359 |
| SGG-W-LQA | 360 |
| DGG-W-LQA | 361 |
| TGG-W-LQA | 362 |
| QGG-W-LQA | 363 |
| RGG-T-LQA | 364 |
| RGG-D-LQA | 365 |
| RGG-E-LQA | 366 |
| RGG-N-LQA | 367 |
| RGG-H-LQA | 368 |
| RGG-K-LQA | 369 |
| RGG-S-LQA | 370 |
| RGG-A-LQA | 371 |
| TGG-T-LQA | 372 |
| TGG-D-LQA | 373 |
| TGG-E-LQA | 374 |
| TGG-N-LQA | 375 |
| TGG-H-LQA | 376 |
| TGG-K-LQA | 377 |
| TGG-S-LQA | 378 |
| TGG-A-LQA | 379 |
| SGG-T-LQA | 380 |
| SGG-D-LQA | 381 |
| SGG-E-LQA | 382 |
| SGG-N-LQA | 383 |
| SGG-H-LQA | 384 |
| SGG-K-LQA | 385 |
| SGG-S-LQA | 386 |
| SGG-A-LQA | 387 |
| DGG-T-LQA | 388 |
| DGG-D-LQA | 389 |
| DGG-E-LQA | 390 |
| DGG-N-LQA | 391 |
| DGG-H-LQA | 392 |
| DGG-K-LQA | 393 |
| DGG-S-LQA | 394 |
| DGG-A-LQA | 395 |
| EGG-T-LQA | 396 |
| EGG-D-LQA | 397 |
| EGG-E-LQA | 398 |
| EGG-N-LQA | 399 |
| EGG-H-LQA | 400 |
| EGG-K-LQA | 401 |
| EGG-S-LQA | 402 |
| EGG-A-LQA | 403 |
| QGG-T-LQA | 404 |
| QGG-D-LQA | 405 |
| QGG-E-LQA | 406 |
| QGG-N-LQA | 407 |
| QGG-H-LQA | 408 |
| QGG-K-LQA | 409 |
| QGG-S-LQA | 410 |
| QGG-A-LQA | 411 |
| Other Protein Sequences | |
| TGEKP (Linker) | 412 |
| RSD-E-LKR (Zinc finger domain) | 413 |
| TGGGGSGGGGTGEKP (Linker) | 414 |
| DALDDFDLDML (Activation domain) | 415 |
| LRQKDGGGSERP (Linker) | 416 |
| LRQKDGERP (Linker) | 417 |
| GGRGRGRGRQ (Linker) | 418 |
| QNKKGGSGDGKKKQHI (Linker) | 419 |
| TGGERP (Linker) | 420 |
| ATGEKP (Linker) | 421 |
| GGGSGGGGEGP (Linker) | 422 |
| QRA-N-LRA | 449 |
| QRH-S-LTE | 450 |
| QSG-D-LRR | 451 |
| RSD-V-LVR | 452 |
| RSD-D-LVR | 453 |

TABLE 14-continued

Summary of Protein and Nucleic Acid Sequences Recited

| Heptapeptide | SEQ ID NO |
|---|---|
| HTG-H-LLE | 454 |
| QSS-N-LVR | 455 |
| RAD-N-LTE | 456 |
| RND-T-LTE | 457 |
| DSG-N-LRV | 458 |
| RSD-H-LTN | 459 |
| DPG-N-LVR | 460 |
| Nucleotide Sequences | |
| GCGNNNGCG | 423 |
| GATCNNGGG | 424 |
| AAATCTCTAGCAGTGGGG | 425 |
| GATACGACAGCTAGCTGGAAGGGCTAATTGACTCCC | 426 |
| AACGTCTGGCTCGAGTTGAGGTCCCTGTTGGGGGGCCACT-GGTAGAGATTTTCC | 427 |
| CCGGTGGGGACTTTCCAGGGA | 428 |
| CACTGCTAGAGATTTTCCACAGTG | 429 |
| CGCCCGAACAGGGAG | 430 |
| TGCCGAAACCCGGGA | 431 |
| ACTGTGTGGAAAATCTCTAGCAGTGGGGCCCGAACAGGGAC | 432 |
| AAATCTCTAGGAGTGGGG | 433 |
| GTCTGGAAAATCTCTAGCAGTGGCG | 434 |
| GCAGTGGCGCGGGAAGAG | 435 |
| TGGCGGGCGAACAGCGAG | 436 |
| GGAGGGGTGGCCTGGGCG | 437 |
| GGAGGTGTGGTTTGGGCG | 438 |
| GGAGGCGTGACCTGGGGG | 439 |
| GGAGGCGTGACCTGGGCG | 440 |
| GGAGGTGTGGCCGGGGCG | 441 |
| AGGGCGGTCCAGAGGGCG | 442 |
| GGAGGGTCGGGTGGGCG | 443 |
| GGAGTGGCGGGGGAACAG | 444 |
| CAGTGTGGAAAATCTCTAGGAGTGGGGCCGGAAGAGGGACCTGAAAGCGAA | 445 |
| GAGTGTGGAAAATCTCTAGCACTGGCGCCCGAACAGGGACGTGAAAGCGAA | 446 |
| CAGTGTGGAAAATGTCTAGCAGTGAGGGGCGAACAGGGAGCTGAAAGCGAA | 447 |
| CAGTGTGGAAAATCTGTAGCAGTGGGGGAGGAAGAGGGAGCTGAAAGGGAA | 448 |

ADVANTAGES OF THE INVENTION

The present invention provides versatile binding proteins for nucleic acid sequences, particularly DNA sequences. These binding proteins can be coupled with transcription modulators and can therefore be utilized for the upregulation or downregulation of particular genes in a specific manner. These binding proteins can, therefore, be used in gene therapy or protein therapy for the treatment of cancer, autoimmune diseases, metabolic disorders, developmental disorders, and other diseases or conditions associated with the dysregulation of gene expression.

The polypeptides, polypeptide compositions, isolated heptapeptides, pharmaceutical compositions, and methods according to the present invention possess industrial applicability for the preparation of medicaments that can treat diseases and conditions treatable by the control or modulation of gene expression, including HIV-1 infection.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

We claim:

1. A polynucleotide encoding a non-naturally occurring polypeptide which is a zinc finger nucleotide binding polypeptide having a region with plurality of linked nucleotide binding regions, wherein the polypeptide is non-naturally occurring at least as a result of the selection and linkage of the plurality of nucleotide binding regions, wherein the nucleotide binding regions are from 7 to 10 amino acid residues, wherein at least one of the nucleotide binding regions binds preferentially to a target nucleotide of the formula TNN, where N is A, C, G or T and includes SEQ ID NO:5 or SEQ ID NO:13.

2. The polynucleotide of claim 1 wherein the binding region of the polypeptide encoded by the polynucleotide includes SEQ ID NO:5.

3. The polynucleotide of claim 1 wherein the binding region of the polypeptide encoded by the polynucleotide includes SEQ ID NO:13.

4. The polynucleotide of claim 1 wherein the nucleotide binding region of the polypeptide encoded by the polynucleotide is 7 residues and has α-helical structure.

5. The polynucleotide of claim 1, wherein the nucleotide binding region of the polypeptide encoded by the polynucleotide further comprises a 7-amino acid zinc finger domain in which the seven amino acids of the domain are numbered from −1 to 6, and wherein the domain is selected from the group consisting of:

(a) a zinc finger nucleotide binding domain specifically binding the nucleotide sequence 5'-(TAA)-3', wherein the amino acid residue of the domain numbered −1 is selected from the group consisting of N and S;

(b) a zinc finger nucleotide binding domain specifically binding the nucleotide sequence 5'-(TCA)-3', wherein the amino acid residue of the domain numbered −1 is S;

(c) a zinc finger nucleotide binding domain specifically binding the nucleotide sequence 5'-(TNG)-3', wherein N is any of A, C, G, or T, wherein the amino acid residue of the domain numbered −1 is selected from the group consisting of N, Q, H, S, T, and I;

(d) a zinc finger nucleotide binding domain specifically binding the nucleotide sequence 5'-(TCG)-3' or 5'-(TGG)-3', wherein the amino acid residue numbered 2 of the domain is D;

(e) a zinc finger nucleotide binding domain specifically binding the nucleotide sequence 5'-(TNT)-3', wherein N is any of A, C, G, or T, wherein the amino acid residue of the domain numbered −1 is selected from the group consisting of R, N, Q, H, S, T, and C;

(f) a zinc finger nucleotide binding domain specifically binding the nucleotide sequence 5'-(TNC)-3', wherein N is any of A, C, G, or T, wherein the amino acid residue of the domain numbered −1 is selected from the group consisting of Q, N, S, G, H, and D;

(g) a zinc finger nucleotide binding domain specifically binding the nucleotide sequence 5'-(TAN)-3', wherein N is any of A, C, G, or T, wherein the amino acid residue of the domain numbered 3 is selected from the group consisting of H, G, V, P, I, and K;

(h) a zinc finger nucleotide binding domain specifically binding the nucleotide sequence 5'-(TCN)-3', wherein N is any of A, C, G, or T, wherein the amino acid residue of the domain numbered 3 is selected from the group consisting of T, D, H, K, R, and N;

(i) a zinc finger nucleotide binding domain specifically binding the nucleotide sequence 5'-(TCC)-3', wherein the amino acid residue of the domain numbered 3 is selected from the group consisting of N, H, S, D, T, Q, and G;

(j) a zinc finger nucleotide binding domain specifically binding the nucleotide sequence 5'-(TCG)-3', wherein the amino acid residue of the domain numbered 3 is selected from the group consisting of T, H, S, D, N, Q, and G;

(k) a zinc finger nucleotide binding domain specifically binding the nucleotide sequence 5'-(TGC)-3' or 5'-(TGT)-3', wherein the amino acid residue of the domain numbered 3 is H;

(l) a zinc finger nucleotide binding domain specifically binding a nucleotide sequence selected from the group consisting of 5'-(TGG)-3' and 5'-(TGT)-3', wherein the amino acid residue of the domain numbered 3 is selected from the group consisting of S, D, T, N, Q, and G;

(m) a zinc finger nucleotide binding domain specifically binding the nucleotide sequence 5'-(TGC)-3', wherein the amino acid residue of the domain numbered 3 is selected from the group consisting of W, T, and H;

(n) a zinc finger nucleotide binding domain specifically binding a nucleotide sequence selected from the group consisting of 5'-(TTA)-3' and 5'-(TTG)-3', wherein the amino acid residue of the domain numbered 3 is selected from the group consisting of S and A;

(o) a zinc finger nucleotide binding domain specifically binding a nucleotide sequence selected from the group consisting of 5'-(TTC)-3' and 5'-(TTT)-3', wherein the amino acid residue of the domain numbered 3 is H;

(p) a zinc finger nucleotide binding domain specifically binding the nucleotide sequence 5'-(TNA)-3', wherein N is any of A, C, G, or T, wherein the amino acid residue of the domain numbered −1 is R; and (q) a zinc finger nucleotide binding domain specifically binding the nucleotide sequence 5'-(TNT)-3', wherein N is any of A, C, G, or T, wherein the amino acid residue of the domain numbered −1 is selected from the group consisting of S, T, and H.

6. The polynucleotide of claim 1 operatively linked to at least one other polynucleotide encoding a zinc finger nucleotide binding polypeptide binding preferentially to a target nucleotide of the formula ANN, CNN, or GNN, where N is A, C, G, or T.

7. The polynucleotide of claim 6 operatively linked to a polynucleotide encoding one or more transcription regulating factors.

8. The polynucleotide of claim 1 wherein the polypeptide encoded by the polynucleotide is operatively linked to one or more transcription regulating factors.

9. The polynucleotide of claim 8 wherein the transcription regulating factor operatively linked to the polypeptide encoded by the polynucleotide is a repressor of transcription.

10. The polynucleotide of claim 8 wherein the transcription regulating factor operatively linked to the polypeptide encoded by the polynucleotide is an activator of transcription.

11. The polynucleotide of claim 8 wherein the transcription regulating factor operatively linked to the polypeptide encoded by the polynucleotide is selected from the group consisting of histone deacetylase and a modulator of histone deacetylase expression.

12. The polynucleotide of claim 8 wherein the polypeptide encoded by the polynucleotide is an artificial transcription factor that binds at least a portion of the HIV-1 tRNA primer-binding site.

13. The polynucleotide of claim 12 wherein the artificial transcription factor encoded by the polynucleotide has six zinc finger DNA-binding domains and has one zinc finger DNA binding domain that binds preferentially to a target nucleotide of the formula TNN, where N is A, C, G or T.

14. The polynucleotide of claim 12 wherein the artificial transcription factor encoded by the polynucleotide includes at least one KRAB repression domain.

15. A vector comprising the isolated and purified polynucleotide of claim 1.

16. A host cell transformed or transfected with the vector of claim 15.

17. A host cell transformed or transfected with the polynucleotide of claim 1.

18. An isolated and purified polynucleotide encoding a polypeptide composition wherein the polypeptide composition comprises a plurality of the polypeptides encoded by the polynucleotides of claim 1, wherein the polypeptides are operatively linked to each other.

19. The polynucleotide of claim 18 wherein the polypeptides encoded by the polynucleotide are operatively linked via a flexible peptide linker of from 5 to 15 amino acid residues encoded by the polynucleotide.

20. The polynucleotide of claim 19 wherein the linker encoded by the polynucleotide has a sequence selected from the group consisting of SEQ ID NO: 412, SEQ ID NO: 414, SEQ ID NO: 416, SEQ ID NO: 417, SEQ ID NO: 418, SEQ ID NO: 419, SEQ ID NO: 420, SEQ ID NO: 421, and SEQ ID NO: 422.

21. The polynucleotide of claim 18 wherein the composition encoded by the polynucleotide comprises from 2 to 18 polypeptides.

22. The polynucleotide of claim 21 wherein the composition encoded by the polynucleotide comprises from 2 to 12 polypeptides.

23. The polynucleotide of claim 22 wherein the composition encoded by the polynucleotide binds to a nucleotide sequence that contains a sequence of the formula 5'-(TNN)$_n$-3', where N is A, C, G or T and n is 2 to 12.

24. The polynucleotide of claim 22 wherein the composition encoded by the polynucleotide comprises from 2 to 6 polypeptides.

25. The polynucleotide of claim 24 wherein the composition encoded by the polynucleotide binds to a nucleotide sequence that contains a sequence of the formula 5'-(TNN)$_n$-3', where N is A, C, G or T and n is 2 to 6.

26. The polynucleotide of claim 18 wherein the composition encoded by the polynucleotide further comprises at least one polypeptide with a binding region that binds a nucleotide subsite of the sequence 5'-(ANN)-3', 5'-(CNN)-3', or 5'-(GNN)-3'.

27. The polynucleotide of claim 18 wherein the binding region of each polypeptide encoded by the polynucleotide has the amino acid sequence of SEQ ID NO:5.

28. The polynucleotide of claim 18 wherein the binding region of each polypeptide encoded by the polynucleotide has the amino acid sequence of SEQ ID NO:5 or SEQ ID NO:13.

29. The polynucleotide of claim 18 wherein the nucleotide binding region of each polypeptide encoded by the polynucleotide is 7 residues and has α-helical structure.

30. The polynucleotide of claim 18, wherein the nucleotide binding region of each polypeptide encoded by the polynucleotide further comprises a 7-amino acid zinc finger domain in which the seven amino acids of the domain are numbered from −1 to 6, and wherein the domain is selected from the group consisting of:

(a) a zinc finger nucleotide binding domain specifically binding the nucleotide sequence 5'-(TAA)-3', wherein the amino acid residue of the domain numbered −1 is selected from the group consisting of N and S;

(b) a zinc finger nucleotide binding domain specifically binding the nucleotide sequence 5'-(TCA)-3', wherein the amino acid residue of the domain numbered −1 is S;

(c) a zinc finger nucleotide binding domain specifically binding the nucleotide sequence 5'-(TNG)-3', wherein N is any of A, C, G, or T, wherein the amino acid residue of the domain numbered −1 is selected from the group consisting of N, Q, H, S, T, and I;

(d) a zinc finger nucleotide binding domain specifically binding the nucleotide sequence 5'-(TCG)-3' or 5'-(TGG)-3', wherein the amino acid residue numbered 2 of the domain is D;

(e) a zinc finger nucleotide binding domain specifically binding the nucleotide sequence 5'-(TNT)-3', wherein N is any of A, C, G, or T, wherein the amino acid residue of the domain numbered −1 is selected from the group consisting of R, N, Q, H, S, T, and C;

(f) a zinc finger nucleotide binding domain specifically binding the nucleotide sequence 5'-(TNC)-3', wherein N is any of A, C, G, or T, wherein the amino acid residue of the domain numbered −1 is selected from the group consisting of Q, N, S, G, H, and D;

(g) a zinc finger nucleotide binding domain specifically binding the nucleotide sequence 5'-(TAN)-3', wherein N is any of A, C, G, or T, wherein the amino acid residue of the domain numbered 3 is selected from the group consisting of H, G, V, P, I, and K;

(h) a zinc finger nucleotide binding domain specifically binding the nucleotide sequence 5'-(TCN)-3', wherein N is any of A, C, G, or T, wherein the amino acid residue of the domain numbered 3 is selected from the group consisting of T, D, H, K, R, and N;

(i) a zinc finger nucleotide binding domain specifically binding the nucleotide sequence 5'-(TCC)-3', wherein the amino acid residue of the domain numbered 3 is selected from the group consisting of N, H, S, D, T, Q, and G;

(j) a zinc finger nucleotide binding domain specifically binding the nucleotide sequence 5'-(TCG)-3', wherein the amino acid residue of the domain numbered 3 is selected from the group consisting of T, H, S, D, N, Q, and G;

(k) a zinc finger nucleotide binding domain specifically binding the nucleotide sequence 5'-(TGC)-3' or 5'-(TGT)-3', wherein the amino acid residue of the domain numbered 3 is H;

(l) a zinc finger nucleotide binding domain specifically binding a nucleotide sequence selected from the group consisting of 5'-(TGG)-3' and 5'-(TGT)-3', wherein the amino acid residue of the domain numbered 3 is selected from the group consisting of S, D, T, N, Q, and G;

(m) a zinc finger nucleotide binding domain specifically binding the nucleotide sequence 5'-(TGC)-3', wherein the amino acid residue of the domain numbered 3 is selected from the group consisting of W, T, and H;

(n) a zinc finger nucleotide binding domain specifically binding a nucleotide sequence selected from the group consisting of 5'-(TTA)-3' and 5'-(TTG)-3', wherein the amino acid residue of the domain numbered 3 is selected from the group consisting of S and A;

(o) a zinc finger nucleotide binding domain specifically binding a nucleotide sequence selected from the group consisting of 5'-(TTC)-3' and 5'-(TTT)-3', wherein the amino acid residue of the domain numbered 3 is H;

(p) a zinc finger nucleotide binding domain specifically binding the nucleotide sequence 5'-(TNA)-3', wherein N is any of A, C, G, or T, wherein the amino acid residue of the domain numbered −1 is R; and (q) a zinc finger nucleotide binding domain specifically binding the nucleotide sequence 5'-(TNT)-3', wherein N is any of A, C, G, or T, wherein the amino acid residue of the domain numbered −1 is selected from the group consisting of S, T, and H.

31. The polynucleotide of claim 18 wherein the polypeptide composition encoded by the polynucleotide comprises a bispecific zinc finger protein comprising two halves, each half comprising six zinc finger nucleotide binding domains, where at least one of the halves includes at least one domain binding a target nucleotide sequence of the form 5'-(TNN)-3', such that the two halves of the bispecific zinc fingers can operate independently.

32. The polynucleotide of claim 31 wherein the two halves of the bispecific zinc finger protein encoded by the polynucleotide are joined by a linker.

33. The polynucleotide of claim 32 wherein the linker of the bispecific zinc finger protein encoded by the polynucleotide has the amino acid residue sequence TGGGGSGGGGTGEKP (SEQ ID NO: 414).

34. The polynucleotide of claim 18 wherein the polypeptide composition encoded by the polynucleotide further comprises the nuclease catalytic domain of FokI such that the polypeptide composition directs site-specific cleavage at a chosen genomic target.

35. The polynucleotide of claim 18 wherein the polypeptide composition encoded by the polynucleotide is operatively linked to at least one other zinc finger nucleotide binding polypeptide binding preferentially to a target nucleotide of the formula ANN, CNN, or GNN, where N is A, C, G or T.

36. The polynucleotide of claim 18 wherein the polypeptide composition encoded by the polynucleotide is operatively linked to one or more transcription regulating factors.

37. The polynucleotide of claim 36 wherein the transcription regulating factor operatively linked to the polypeptide encoded by the polynucleotide is a repressor of transcription.

38. The polynucleotide of claim 36 wherein the transcription regulating factor operatively linked to the polypeptide encoded by the polynucleotide is an activator of transcription.

39. The polynucleotide of claim 36 wherein the transcription regulating factor operatively linked to the polypeptide encoded by the polynucleotide is selected from the group consisting of histone deacetylase and a modulator of histone deacetylase expression.

40. A vector comprising the isolated and purified polynucleotide of claim 18.

41. A host cell transformed or transfected with the vector of claim 40.

42. A host cell transformed or transfected with the polynucleotide of claim 18.

43. A polynucleotide encoding a non-naturally occurring polypeptide having a region with plurality of linked nucleotide binding regions, wherein the polypeptide is non-naturally occurring at least as a result of the selection and linkage of the plurality of nucleotide binding regions, wherein at least one of the binding regions of the polypeptide encoded by the polynucleotide has an amino acid sequence selected from the group consisting of:

(a) the binding region of the amino acid sequence of SEQ ID NO:5 or SEQ ID NO:13; and (b) a binding region differing from the amino acid sequence of SEQ ID NO:5 or SEQ ID NO:13 by no more than two conservative amino acid substitutions, wherein the dissociation constant is no greater than 125% of that of the polypeptide before the substitutions are made, and wherein a conservative amino acid substitution is one of the following substitutions: Ala/Gly or Ser; Arg/Lys; Asp/Glu; Gly/Asp; Gly/Ala or Pro; Ile/Leu or Val; Leu/Ile or Val; Lys/Arg or Gln or Glu; Met/Leu or Tyr or Ile; Phe/Met or Leu or Tyr; Val/Ile or Leu.

44. A polynucleotide encoding a polypeptide composition comprising a plurality of polypeptides, wherein at least one polypeptide is non-naturally occurring and includes an amino acid sequence selected from the group consisting of:

(a) the binding region of the amino acid sequence of SEQ ID NO:5 or SEQ ID NO:13; and (b) a binding region differing from the amino acid sequence of SEQ ID NO:5 or SEQ ID NO:13 by no more than two conservative amino acid substitutions, wherein the dissociation constant is no greater than 125% of that of the polypeptide before the substitutions are made, and wherein a conservative amino acid substitution is one of the following substitutions: Ala/Gly or Ser; Arg/Lys; Asp/Glu; Gly/Asp; Gly/Ala or Pro; Ile/Leu or Val; Leu/Ile or Val; Lys/Arg or Gln or Glu; Met/Leu or Tyr or Ile; Phe/Met or Leu or Tyr; Val/Ile or Leu.

* * * * *

```
                         SEQUENCE LISTING

<160> NUMBER OF SEQ ID NOS: 460

<210> SEQ ID NO 1
<211> LENGTH: 7
<212> TYPE: PRT
<213> ORGANISM: Artificial
<220> FEATURE:
<223> OTHER INFORMATION: Synthetically Generated Peptide

<400> SEQUENCE: 1

Gln Ala Ser Asn Leu Ile Ser
1               5

<210> SEQ ID NO 2
<211> LENGTH: 7
<212> TYPE: PRT
<213> ORGANISM: Artificial
<220> FEATURE:
<223> OTHER INFORMATION: Synthetically Generated Peptide

<400> SEQUENCE: 2

Ser Arg Gly Asn Leu Lys Ser
1               5

<210> SEQ ID NO 3
```

```
<211> LENGTH: 7
<212> TYPE: PRT
<213> ORGANISM: Artificial
<220> FEATURE:
<223> OTHER INFORMATION: Synthetically Generated Peptide

<400> SEQUENCE: 3

Arg Leu Asp Asn Leu Gln Thr
1               5

<210> SEQ ID NO 4
<211> LENGTH: 7
<212> TYPE: PRT
<213> ORGANISM: Artificial
<220> FEATURE:
<223> OTHER INFORMATION: Synthetically Generated Peptide

<400> SEQUENCE: 4

Ala Arg Gly Asn Leu Arg Thr
1               5

<210> SEQ ID NO 5
<211> LENGTH: 7
<212> TYPE: PRT
<213> ORGANISM: Artificial
<220> FEATURE:
<223> OTHER INFORMATION: Synthetically Generated Peptide

<400> SEQUENCE: 5

Arg Lys Asp Ala Leu Arg Gly
1               5

<210> SEQ ID NO 6
<211> LENGTH: 7
<212> TYPE: PRT
<213> ORGANISM: Artificial
<220> FEATURE:
<223> OTHER INFORMATION: Synthetically Generated Peptide

<400> SEQUENCE: 6

Arg Glu Asp Asn Leu His Thr
1               5

<210> SEQ ID NO 7
<211> LENGTH: 7
<212> TYPE: PRT
<213> ORGANISM: Artificial
<220> FEATURE:
<223> OTHER INFORMATION: Synthetically Generated Peptide

<400> SEQUENCE: 7

Ala Arg Gly Asn Leu Lys Ser
1               5

<210> SEQ ID NO 8
<211> LENGTH: 7
<212> TYPE: PRT
<213> ORGANISM: Artificial
<220> FEATURE:
<223> OTHER INFORMATION: Synthetically Generated Peptide

<400> SEQUENCE: 8

Arg Ser Asp Asn Leu Thr Thr
1               5

<210> SEQ ID NO 9
<211> LENGTH: 7
```

```
<212> TYPE: PRT
<213> ORGANISM: Artificial
<220> FEATURE:
<223> OTHER INFORMATION: Synthetically Generated Peptide

<400> SEQUENCE: 9

Val Arg Gly Asn Leu Lys Ser
1               5

<210> SEQ ID NO 10
<211> LENGTH: 7
<212> TYPE: PRT
<213> ORGANISM: Artificial
<220> FEATURE:
<223> OTHER INFORMATION: Synthetically Generated Peptide

<400> SEQUENCE: 10

Val Arg Gly Asn Leu Arg Thr
1               5

<210> SEQ ID NO 11
<211> LENGTH: 7
<212> TYPE: PRT
<213> ORGANISM: Artificial
<220> FEATURE:
<223> OTHER INFORMATION: Synthetically Generated Peptide

<400> SEQUENCE: 11

Arg Leu Arg Ala Leu Asp Arg
1               5

<210> SEQ ID NO 12
<211> LENGTH: 7
<212> TYPE: PRT
<213> ORGANISM: Artificial
<220> FEATURE:
<223> OTHER INFORMATION: Synthetically Generated Peptide

<400> SEQUENCE: 12

Asp Met Gly Ala Leu Glu Ala
1               5

<210> SEQ ID NO 13
<211> LENGTH: 7
<212> TYPE: PRT
<213> ORGANISM: Artificial
<220> FEATURE:
<223> OTHER INFORMATION: Synthetically Generated Peptide

<400> SEQUENCE: 13

Glu Lys Asp Ala Leu Arg Gly
1               5

<210> SEQ ID NO 14
<211> LENGTH: 7
<212> TYPE: PRT
<213> ORGANISM: Artificial
<220> FEATURE:
<223> OTHER INFORMATION: Synthetically Generated Peptide

<400> SEQUENCE: 14

Arg Ser Asp His Leu Thr Thr
1               5

<210> SEQ ID NO 15
<211> LENGTH: 7
<212> TYPE: PRT
```

```
-continued

<213> ORGANISM: Artificial
<220> FEATURE:
<223> OTHER INFORMATION: Synthetically Generated Peptide

<400> SEQUENCE: 15

Ala Gln Gln Leu Leu Met Trp
1               5

<210> SEQ ID NO 16
<211> LENGTH: 7
<212> TYPE: PRT
<213> ORGANISM: Artificial
<220> FEATURE:
<223> OTHER INFORMATION: Synthetically Generated Peptide

<400> SEQUENCE: 16

Arg Ser Asp Glu Arg Lys Arg
1               5

<210> SEQ ID NO 17
<211> LENGTH: 7
<212> TYPE: PRT
<213> ORGANISM: Artificial
<220> FEATURE:
<223> OTHER INFORMATION: Synthetically Generated Peptide

<400> SEQUENCE: 17

Asp Tyr Gln Ser Leu Arg Gln
1               5

<210> SEQ ID NO 18
<211> LENGTH: 7
<212> TYPE: PRT
<213> ORGANISM: Artificial
<220> FEATURE:
<223> OTHER INFORMATION: Synthetically Generated Peptide

<400> SEQUENCE: 18

Cys Phe Ser Arg Leu Val Arg
1               5

<210> SEQ ID NO 19
<211> LENGTH: 7
<212> TYPE: PRT
<213> ORGANISM: Artificial
<220> FEATURE:
<223> OTHER INFORMATION: Synthetically Generated Peptide

<400> SEQUENCE: 19

Gly Asp Gly Gly Leu Trp Glu
1               5

<210> SEQ ID NO 20
<211> LENGTH: 7
<212> TYPE: PRT
<213> ORGANISM: Artificial
<220> FEATURE:
<223> OTHER INFORMATION: Synthetically Generated Peptide

<400> SEQUENCE: 20

Leu Gln Arg Pro Leu Arg Gly
1               5

<210> SEQ ID NO 21
<211> LENGTH: 7
<212> TYPE: PRT
<213> ORGANISM: Artificial
```

```
<220> FEATURE:
<223> OTHER INFORMATION: Synthetically Generated Peptide

<400> SEQUENCE: 21

Gln Gly Leu Ala Cys Ala Ala
1               5

<210> SEQ ID NO 22
<211> LENGTH: 7
<212> TYPE: PRT
<213> ORGANISM: Artificial
<220> FEATURE:
<223> OTHER INFORMATION: Synthetically Generated Peptide

<400> SEQUENCE: 22

Trp Val Gly Trp Leu Gly Ser
1               5

<210> SEQ ID NO 23
<211> LENGTH: 7
<212> TYPE: PRT
<213> ORGANISM: Artificial
<220> FEATURE:
<223> OTHER INFORMATION: Synthetically Generated Peptide

<400> SEQUENCE: 23

Arg Leu Arg Asp Ile Gln Phe
1               5

<210> SEQ ID NO 24
<211> LENGTH: 7
<212> TYPE: PRT
<213> ORGANISM: Artificial
<220> FEATURE:
<223> OTHER INFORMATION: Synthetically Generated Peptide

<400> SEQUENCE: 24

Gly Arg Ser Gln Leu Ser Cys
1               5

<210> SEQ ID NO 25
<211> LENGTH: 7
<212> TYPE: PRT
<213> ORGANISM: Artificial
<220> FEATURE:
<223> OTHER INFORMATION: Synthetically Generated Peptide

<400> SEQUENCE: 25

Gly Trp Gln Arg Leu Leu Thr
1               5

<210> SEQ ID NO 26
<211> LENGTH: 7
<212> TYPE: PRT
<213> ORGANISM: Artificial
<220> FEATURE:
<223> OTHER INFORMATION: Synthetically Generated Peptide

<400> SEQUENCE: 26

Ser Gly Arg Pro Leu Ala Ser
1               5

<210> SEQ ID NO 27
<211> LENGTH: 7
<212> TYPE: PRT
<213> ORGANISM: Artificial
<220> FEATURE:
```

<223> OTHER INFORMATION: Synthetically Generated Peptide

<400> SEQUENCE: 27

Ala Pro Arg Leu Leu Gly Pro
1               5

<210> SEQ ID NO 28
<211> LENGTH: 7
<212> TYPE: PRT
<213> ORGANISM: Artificial
<220> FEATURE:
<223> OTHER INFORMATION: Synthetically Generated Peptide

<400> SEQUENCE: 28

Ala Pro Lys Ala Leu Gly Trp
1               5

<210> SEQ ID NO 29
<211> LENGTH: 7
<212> TYPE: PRT
<213> ORGANISM: Artificial
<220> FEATURE:
<223> OTHER INFORMATION: Synthetically Generated Peptide

<400> SEQUENCE: 29

Ser Val His Glu Leu Gln Gly
1               5

<210> SEQ ID NO 30
<211> LENGTH: 7
<212> TYPE: PRT
<213> ORGANISM: Artificial
<220> FEATURE:
<223> OTHER INFORMATION: Synthetically Generated Peptide

<400> SEQUENCE: 30

Ala Gln Ala Ala Leu Ser Trp
1               5

<210> SEQ ID NO 31
<211> LENGTH: 7
<212> TYPE: PRT
<213> ORGANISM: Artificial
<220> FEATURE:
<223> OTHER INFORMATION: Synthetically Generated Peptide

<400> SEQUENCE: 31

Gly Ala Asn Ala Leu Arg Arg
1               5

<210> SEQ ID NO 32
<211> LENGTH: 7
<212> TYPE: PRT
<213> ORGANISM: Artificial
<220> FEATURE:
<223> OTHER INFORMATION: Synthetically Generated Peptide

<400> SEQUENCE: 32

Gln Ser Leu Leu Leu Gly Ala
1               5

<210> SEQ ID NO 33
<211> LENGTH: 7
<212> TYPE: PRT
<213> ORGANISM: Artificial
<220> FEATURE:
<223> OTHER INFORMATION: Synthetically Generated Peptide

```
<400> SEQUENCE: 33

His Arg Gly Thr Leu Gly Gly
1               5

<210> SEQ ID NO 34
<211> LENGTH: 7
<212> TYPE: PRT
<213> ORGANISM: Artificial
<220> FEATURE:
<223> OTHER INFORMATION: Synthetically Generated Peptide

<400> SEQUENCE: 34

Gln Val Gly Leu Leu Ala Arg
1               5

<210> SEQ ID NO 35
<211> LENGTH: 7
<212> TYPE: PRT
<213> ORGANISM: Artificial
<220> FEATURE:
<223> OTHER INFORMATION: Synthetically Generated Peptide

<400> SEQUENCE: 35

Gly Ala Arg Gly Leu Arg Gly
1               5

<210> SEQ ID NO 36
<211> LENGTH: 7
<212> TYPE: PRT
<213> ORGANISM: Artificial
<220> FEATURE:
<223> OTHER INFORMATION: Synthetically Generated Peptide

<400> SEQUENCE: 36

Asp Lys His Met Leu Asp Thr
1               5

<210> SEQ ID NO 37
<211> LENGTH: 7
<212> TYPE: PRT
<213> ORGANISM: Artificial
<220> FEATURE:
<223> OTHER INFORMATION: Synthetically Generated Peptide

<400> SEQUENCE: 37

Asp Leu Gly Gly Leu Arg Gln
1               5

<210> SEQ ID NO 38
<211> LENGTH: 7
<212> TYPE: PRT
<213> ORGANISM: Artificial
<220> FEATURE:
<223> OTHER INFORMATION: Synthetically Generated Peptide

<400> SEQUENCE: 38

Gln Cys Tyr Arg Leu Glu Arg
1               5

<210> SEQ ID NO 39
<211> LENGTH: 7
<212> TYPE: PRT
<213> ORGANISM: Artificial
<220> FEATURE:
<223> OTHER INFORMATION: Synthetically Generated Peptide
```

```
<400> SEQUENCE: 39

Ala Glu Ala Glu Leu Gln Arg
1               5

<210> SEQ ID NO 40
<211> LENGTH: 7
<212> TYPE: PRT
<213> ORGANISM: Artificial
<220> FEATURE:
<223> OTHER INFORMATION: Synthetically Generated Peptide

<400> SEQUENCE: 40

Gln Gly Gly Val Leu Ala Ala
1               5

<210> SEQ ID NO 41
<211> LENGTH: 7
<212> TYPE: PRT
<213> ORGANISM: Artificial
<220> FEATURE:
<223> OTHER INFORMATION: Synthetically Generated Peptide

<400> SEQUENCE: 41

Gln Gly Arg Cys Leu Val Thr
1               5

<210> SEQ ID NO 42
<211> LENGTH: 7
<212> TYPE: PRT
<213> ORGANISM: Artificial
<220> FEATURE:
<223> OTHER INFORMATION: Synthetically Generated Peptide

<400> SEQUENCE: 42

His Pro Glu Ala Leu Asp Asn
1               5

<210> SEQ ID NO 43
<211> LENGTH: 7
<212> TYPE: PRT
<213> ORGANISM: Artificial
<220> FEATURE:
<223> OTHER INFORMATION: Synthetically Generated Peptide

<400> SEQUENCE: 43

Gly Arg Gly Ala Leu Gln Ala
1               5

<210> SEQ ID NO 44
<211> LENGTH: 7
<212> TYPE: PRT
<213> ORGANISM: Artificial
<220> FEATURE:
<223> OTHER INFORMATION: Synthetically Generated Peptide

<400> SEQUENCE: 44

Leu Ala Ser Arg Leu Gln Gln
1               5

<210> SEQ ID NO 45
<211> LENGTH: 7
<212> TYPE: PRT
<213> ORGANISM: Artificial
<220> FEATURE:
<223> OTHER INFORMATION: Synthetically Generated Peptide

<400> SEQUENCE: 45
```

```
Arg Glu Asp Asn Leu Ile Ser
1               5

<210> SEQ ID NO 46
<211> LENGTH: 7
<212> TYPE: PRT
<213> ORGANISM: Artificial
<220> FEATURE:
<223> OTHER INFORMATION: Synthetically Generated Peptide

<400> SEQUENCE: 46

Arg Gly Gly Trp Leu Gln Ala
1               5

<210> SEQ ID NO 47
<211> LENGTH: 7
<212> TYPE: PRT
<213> ORGANISM: Artificial
<220> FEATURE:
<223> OTHER INFORMATION: Synthetically Generated Peptide

<400> SEQUENCE: 47

Asp Ala Ser Asn Leu Ile Ser
1               5

<210> SEQ ID NO 48
<211> LENGTH: 7
<212> TYPE: PRT
<213> ORGANISM: Artificial
<220> FEATURE:
<223> OTHER INFORMATION: Synthetically Generated Peptide

<400> SEQUENCE: 48

Glu Ala Ser Asn Leu Ile Ser
1               5

<210> SEQ ID NO 49
<211> LENGTH: 7
<212> TYPE: PRT
<213> ORGANISM: Artificial
<220> FEATURE:
<223> OTHER INFORMATION: Synthetically Generated Peptide

<400> SEQUENCE: 49

Arg Ala Ser Asn Leu Ile Ser
1               5

<210> SEQ ID NO 50
<211> LENGTH: 7
<212> TYPE: PRT
<213> ORGANISM: Artificial
<220> FEATURE:
<223> OTHER INFORMATION: Synthetically Generated Peptide

<400> SEQUENCE: 50

Thr Ala Ser Asn Leu Ile Ser
1               5

<210> SEQ ID NO 51
<211> LENGTH: 7
<212> TYPE: PRT
<213> ORGANISM: Artificial
<220> FEATURE:
<223> OTHER INFORMATION: Synthetically Generated Peptide

<400> SEQUENCE: 51
```

```
Ser Ala Ser Asn Leu Ile Ser
1               5

<210> SEQ ID NO 52
<211> LENGTH: 7
<212> TYPE: PRT
<213> ORGANISM: Artificial
<220> FEATURE:
<223> OTHER INFORMATION: Synthetically Generated Peptide

<400> SEQUENCE: 52

Gln Ala Ser Thr Leu Ile Ser
1               5

<210> SEQ ID NO 53
<211> LENGTH: 7
<212> TYPE: PRT
<213> ORGANISM: Artificial
<220> FEATURE:
<223> OTHER INFORMATION: Synthetically Generated Peptide

<400> SEQUENCE: 53

Gln Ala Ser Asp Leu Ile Ser
1               5

<210> SEQ ID NO 54
<211> LENGTH: 7
<212> TYPE: PRT
<213> ORGANISM: Artificial
<220> FEATURE:
<223> OTHER INFORMATION: Synthetically Generated Peptide

<400> SEQUENCE: 54

Gln Ala Ser Glu Leu Ile Ser
1               5

<210> SEQ ID NO 55
<211> LENGTH: 7
<212> TYPE: PRT
<213> ORGANISM: Artificial
<220> FEATURE:
<223> OTHER INFORMATION: Synthetically Generated Peptide

<400> SEQUENCE: 55

Gln Ala Ser His Leu Ile Ser
1               5

<210> SEQ ID NO 56
<211> LENGTH: 7
<212> TYPE: PRT
<213> ORGANISM: Artificial
<220> FEATURE:
<223> OTHER INFORMATION: Synthetically Generated Peptide

<400> SEQUENCE: 56

Gln Ala Ser Lys Leu Ile Ser
1               5

<210> SEQ ID NO 57
<211> LENGTH: 7
<212> TYPE: PRT
<213> ORGANISM: Artificial
<220> FEATURE:
<223> OTHER INFORMATION: Synthetically Generated Peptide

<400> SEQUENCE: 57

Gln Ala Ser Ser Leu Ile Ser
```

<210> SEQ ID NO 58
<211> LENGTH: 7
<212> TYPE: PRT
<213> ORGANISM: Artificial
<220> FEATURE:
<223> OTHER INFORMATION: Synthetically Generated Peptide

<400> SEQUENCE: 58

Gln Ala Ser Ala Leu Ile Ser
1               5

<210> SEQ ID NO 59
<211> LENGTH: 7
<212> TYPE: PRT
<213> ORGANISM: Artificial
<220> FEATURE:
<223> OTHER INFORMATION: Synthetically Generated Peptide

<400> SEQUENCE: 59

Asp Ala Ser Thr Leu Ile Ser
1               5

<210> SEQ ID NO 60
<211> LENGTH: 7
<212> TYPE: PRT
<213> ORGANISM: Artificial
<220> FEATURE:
<223> OTHER INFORMATION: Synthetically Generated Peptide

<400> SEQUENCE: 60

Asp Ala Ser Asp Leu Ile Ser
1               5

<210> SEQ ID NO 61
<211> LENGTH: 7
<212> TYPE: PRT
<213> ORGANISM: Artificial
<220> FEATURE:
<223> OTHER INFORMATION: Synthetically Generated Peptide

<400> SEQUENCE: 61

Asp Ala Ser Glu Leu Ile Ser
1               5

<210> SEQ ID NO 62
<211> LENGTH: 7
<212> TYPE: PRT
<213> ORGANISM: Artificial
<220> FEATURE:
<223> OTHER INFORMATION: Synthetically Generated Peptide

<400> SEQUENCE: 62

Asp Ala Ser His Leu Ile Ser
1               5

<210> SEQ ID NO 63
<211> LENGTH: 7
<212> TYPE: PRT
<213> ORGANISM: Artificial
<220> FEATURE:
<223> OTHER INFORMATION: Synthetically Generated Peptide

<400> SEQUENCE: 63

Asp Ala Ser Lys Leu Ile Ser
1               5

<210> SEQ ID NO 64
<211> LENGTH: 7
<212> TYPE: PRT
<213> ORGANISM: Artificial
<220> FEATURE:
<223> OTHER INFORMATION: Synthetically Generated Peptide

<400> SEQUENCE: 64

Asp Ala Ser Ser Leu Ile Ser
1               5

<210> SEQ ID NO 65
<211> LENGTH: 7
<212> TYPE: PRT
<213> ORGANISM: Artificial
<220> FEATURE:
<223> OTHER INFORMATION: Synthetically Generated Peptide

<400> SEQUENCE: 65

Asp Ala Ser Ala Leu Ile Ser
1               5

<210> SEQ ID NO 66
<211> LENGTH: 7
<212> TYPE: PRT
<213> ORGANISM: Artificial
<220> FEATURE:
<223> OTHER INFORMATION: Synthetically Generated Peptide

<400> SEQUENCE: 66

Glu Ala Ser Thr Leu Ile Ser
1               5

<210> SEQ ID NO 67
<211> LENGTH: 7
<212> TYPE: PRT
<213> ORGANISM: Artificial
<220> FEATURE:
<223> OTHER INFORMATION: Synthetically Generated Peptide

<400> SEQUENCE: 67

Glu Ala Ser Asp Leu Ile Ser
1               5

<210> SEQ ID NO 68
<211> LENGTH: 7
<212> TYPE: PRT
<213> ORGANISM: Artificial
<220> FEATURE:
<223> OTHER INFORMATION: Synthetically Generated Peptide

<400> SEQUENCE: 68

Glu Ala Ser Glu Leu Ile Ser
1               5

<210> SEQ ID NO 69
<211> LENGTH: 7
<212> TYPE: PRT
<213> ORGANISM: Artificial
<220> FEATURE:
<223> OTHER INFORMATION: Synthetically Generated Peptide

<400> SEQUENCE: 69

Glu Ala Ser His Leu Ile Ser
1               5

```
<210> SEQ ID NO 70
<211> LENGTH: 7
<212> TYPE: PRT
<213> ORGANISM: Artificial
<220> FEATURE:
<223> OTHER INFORMATION: Synthetically Generated Peptide

<400> SEQUENCE: 70

Glu Ala Ser Lys Leu Ile Ser
1               5

<210> SEQ ID NO 71
<211> LENGTH: 7
<212> TYPE: PRT
<213> ORGANISM: Artificial
<220> FEATURE:
<223> OTHER INFORMATION: Synthetically Generated Peptide

<400> SEQUENCE: 71

Glu Ala Ser Ser Leu Ile Ser
1               5

<210> SEQ ID NO 72
<211> LENGTH: 7
<212> TYPE: PRT
<213> ORGANISM: Artificial
<220> FEATURE:
<223> OTHER INFORMATION: Synthetically Generated Peptide

<400> SEQUENCE: 72

Glu Ala Ser Ala Leu Ile Ser
1               5

<210> SEQ ID NO 73
<211> LENGTH: 7
<212> TYPE: PRT
<213> ORGANISM: Artificial
<220> FEATURE:
<223> OTHER INFORMATION: Synthetically Generated Peptide

<400> SEQUENCE: 73

Arg Ala Ser Thr Leu Ile Ser
1               5

<210> SEQ ID NO 74
<211> LENGTH: 7
<212> TYPE: PRT
<213> ORGANISM: Artificial
<220> FEATURE:
<223> OTHER INFORMATION: Synthetically Generated Peptide

<400> SEQUENCE: 74

Arg Ala Ser Asp Leu Ile Ser
1               5

<210> SEQ ID NO 75
<211> LENGTH: 7
<212> TYPE: PRT
<213> ORGANISM: Artificial
<220> FEATURE:
<223> OTHER INFORMATION: Synthetically Generated Peptide

<400> SEQUENCE: 75

Arg Ala Ser Glu Leu Ile Ser
1               5
```

```
<210> SEQ ID NO 76
<211> LENGTH: 7
<212> TYPE: PRT
<213> ORGANISM: Artificial
<220> FEATURE:
<223> OTHER INFORMATION: Synthetically Generated Peptide

<400> SEQUENCE: 76

Arg Ala Ser His Leu Ile Ser
1               5

<210> SEQ ID NO 77
<211> LENGTH: 7
<212> TYPE: PRT
<213> ORGANISM: Artificial
<220> FEATURE:
<223> OTHER INFORMATION: Synthetically Generated Peptide

<400> SEQUENCE: 77

Arg Ala Ser Lys Leu Ile Ser
1               5

<210> SEQ ID NO 78
<211> LENGTH: 7
<212> TYPE: PRT
<213> ORGANISM: Artificial
<220> FEATURE:
<223> OTHER INFORMATION: Synthetically Generated Peptide

<400> SEQUENCE: 78

Arg Ala Ser Ser Leu Ile Ser
1               5

<210> SEQ ID NO 79
<211> LENGTH: 7
<212> TYPE: PRT
<213> ORGANISM: Artificial
<220> FEATURE:
<223> OTHER INFORMATION: Synthetically Generated Peptide

<400> SEQUENCE: 79

Arg Ala Ser Ala Leu Ile Ser
1               5

<210> SEQ ID NO 80
<211> LENGTH: 7
<212> TYPE: PRT
<213> ORGANISM: Artificial
<220> FEATURE:
<223> OTHER INFORMATION: Synthetically Generated Peptide

<400> SEQUENCE: 80

Thr Ala Ser Thr Leu Ile Ser
1               5

<210> SEQ ID NO 81
<211> LENGTH: 7
<212> TYPE: PRT
<213> ORGANISM: Artificial
<220> FEATURE:
<223> OTHER INFORMATION: Synthetically Generated Peptide

<400> SEQUENCE: 81

Thr Ala Ser Asp Leu Ile Ser
1               5

<210> SEQ ID NO 82
```

```
<211> LENGTH: 7
<212> TYPE: PRT
<213> ORGANISM: Artificial
<220> FEATURE:
<223> OTHER INFORMATION: Synthetically Generated Peptide

<400> SEQUENCE: 82

Thr Ala Ser Glu Leu Ile Ser
1               5

<210> SEQ ID NO 83
<211> LENGTH: 7
<212> TYPE: PRT
<213> ORGANISM: Artificial
<220> FEATURE:
<223> OTHER INFORMATION: Synthetically Generated Peptide

<400> SEQUENCE: 83

Thr Ala Ser His Leu Ile Ser
1               5

<210> SEQ ID NO 84
<211> LENGTH: 7
<212> TYPE: PRT
<213> ORGANISM: Artificial
<220> FEATURE:
<223> OTHER INFORMATION: Synthetically Generated Peptide

<400> SEQUENCE: 84

Thr Ala Ser Lys Leu Ile Ser
1               5

<210> SEQ ID NO 85
<211> LENGTH: 7
<212> TYPE: PRT
<213> ORGANISM: Artificial
<220> FEATURE:
<223> OTHER INFORMATION: Synthetically Generated Peptide

<400> SEQUENCE: 85

Thr Ala Ser Ser Leu Ile Ser
1               5

<210> SEQ ID NO 86
<211> LENGTH: 7
<212> TYPE: PRT
<213> ORGANISM: Artificial
<220> FEATURE:
<223> OTHER INFORMATION: Synthetically Generated Peptide

<400> SEQUENCE: 86

Thr Ala Ser Ala Leu Ile Ser
1               5

<210> SEQ ID NO 87
<211> LENGTH: 7
<212> TYPE: PRT
<213> ORGANISM: Artificial
<220> FEATURE:
<223> OTHER INFORMATION: Synthetically Generated Peptide

<400> SEQUENCE: 87

Ser Ala Ser Thr Leu Ile Ser
1               5

<210> SEQ ID NO 88
<211> LENGTH: 7
```

```
<212> TYPE: PRT
<213> ORGANISM: Artificial
<220> FEATURE:
<223> OTHER INFORMATION: Synthetically Generated Peptide

<400> SEQUENCE: 88

Ser Ala Ser Asp Leu Ile Ser
1               5

<210> SEQ ID NO 89
<211> LENGTH: 7
<212> TYPE: PRT
<213> ORGANISM: Artificial
<220> FEATURE:
<223> OTHER INFORMATION: Synthetically Generated Peptide

<400> SEQUENCE: 89

Ser Ala Ser Glu Leu Ile Ser
1               5

<210> SEQ ID NO 90
<211> LENGTH: 7
<212> TYPE: PRT
<213> ORGANISM: Artificial
<220> FEATURE:
<223> OTHER INFORMATION: Synthetically Generated Peptide

<400> SEQUENCE: 90

Ser Ala Ser His Leu Ile Ser
1               5

<210> SEQ ID NO 91
<211> LENGTH: 7
<212> TYPE: PRT
<213> ORGANISM: Artificial
<220> FEATURE:
<223> OTHER INFORMATION: Synthetically Generated Peptide

<400> SEQUENCE: 91

Ser Ala Ser Lys Leu Ile Ser
1               5

<210> SEQ ID NO 92
<211> LENGTH: 7
<212> TYPE: PRT
<213> ORGANISM: Artificial
<220> FEATURE:
<223> OTHER INFORMATION: Synthetically Generated Peptide

<400> SEQUENCE: 92

Ser Ala Ser Ser Leu Ile Ser
1               5

<210> SEQ ID NO 93
<211> LENGTH: 7
<212> TYPE: PRT
<213> ORGANISM: Artificial
<220> FEATURE:
<223> OTHER INFORMATION: Synthetically Generated Peptide

<400> SEQUENCE: 93

Ser Ala Ser Ala Leu Ile Ser
1               5

<210> SEQ ID NO 94
<211> LENGTH: 7
<212> TYPE: PRT
```

```
<213> ORGANISM: Artificial
<220> FEATURE:
<223> OTHER INFORMATION: Synthetically Generated Peptide

<400> SEQUENCE: 94

Gln Leu Asp Asn Leu Gln Thr
1               5

<210> SEQ ID NO 95
<211> LENGTH: 7
<212> TYPE: PRT
<213> ORGANISM: Artificial
<220> FEATURE:
<223> OTHER INFORMATION: Synthetically Generated Peptide

<400> SEQUENCE: 95

Asp Leu Asp Asn Leu Gln Thr
1               5

<210> SEQ ID NO 96
<211> LENGTH: 7
<212> TYPE: PRT
<213> ORGANISM: Artificial
<220> FEATURE:
<223> OTHER INFORMATION: Synthetically Generated Peptide

<400> SEQUENCE: 96

Glu Leu Asp Asn Leu Gln Thr
1               5

<210> SEQ ID NO 97
<211> LENGTH: 7
<212> TYPE: PRT
<213> ORGANISM: Artificial
<220> FEATURE:
<223> OTHER INFORMATION: Synthetically Generated Peptide

<400> SEQUENCE: 97

Thr Leu Asp Asn Leu Gln Thr
1               5

<210> SEQ ID NO 98
<211> LENGTH: 7
<212> TYPE: PRT
<213> ORGANISM: Artificial
<220> FEATURE:
<223> OTHER INFORMATION: Synthetically Generated Peptide

<400> SEQUENCE: 98

Ser Leu Asp Asn Leu Gln Thr
1               5

<210> SEQ ID NO 99
<211> LENGTH: 7
<212> TYPE: PRT
<213> ORGANISM: Artificial
<220> FEATURE:
<223> OTHER INFORMATION: Synthetically Generated Peptide

<400> SEQUENCE: 99

Arg Leu Asp Thr Leu Gln Thr
1               5

<210> SEQ ID NO 100
<211> LENGTH: 7
<212> TYPE: PRT
<213> ORGANISM: Artificial
```

```
<220> FEATURE:
<223> OTHER INFORMATION: Synthetically Generated Peptide

<400> SEQUENCE: 100

Arg Leu Asp Asp Leu Gln Thr
1               5

<210> SEQ ID NO 101
<211> LENGTH: 7
<212> TYPE: PRT
<213> ORGANISM: Artificial
<220> FEATURE:
<223> OTHER INFORMATION: Synthetically Generated Peptide

<400> SEQUENCE: 101

Arg Leu Asp Glu Leu Gln Thr
1               5

<210> SEQ ID NO 102
<211> LENGTH: 7
<212> TYPE: PRT
<213> ORGANISM: Artificial
<220> FEATURE:
<223> OTHER INFORMATION: Synthetically Generated Peptide

<400> SEQUENCE: 102

Arg Leu Asp His Leu Gln Thr
1               5

<210> SEQ ID NO 103
<211> LENGTH: 7
<212> TYPE: PRT
<213> ORGANISM: Artificial
<220> FEATURE:
<223> OTHER INFORMATION: Synthetically Generated Peptide

<400> SEQUENCE: 103

Arg Leu Asp Lys Leu Gln Thr
1               5

<210> SEQ ID NO 104
<211> LENGTH: 7
<212> TYPE: PRT
<213> ORGANISM: Artificial
<220> FEATURE:
<223> OTHER INFORMATION: Synthetically Generated Peptide

<400> SEQUENCE: 104

Arg Leu Asp Ser Leu Gln Thr
1               5

<210> SEQ ID NO 105
<211> LENGTH: 7
<212> TYPE: PRT
<213> ORGANISM: Artificial
<220> FEATURE:
<223> OTHER INFORMATION: Synthetically Generated Peptide

<400> SEQUENCE: 105

Arg Leu Asp Ala Leu Gln Thr
1               5

<210> SEQ ID NO 106
<211> LENGTH: 7
<212> TYPE: PRT
<213> ORGANISM: Artificial
<220> FEATURE:
```

<223> OTHER INFORMATION: Synthetically Generated Peptide

<400> SEQUENCE: 106

Gln Leu Asp Thr Leu Gln Thr
1               5

<210> SEQ ID NO 107
<211> LENGTH: 7
<212> TYPE: PRT
<213> ORGANISM: Artificial
<220> FEATURE:
<223> OTHER INFORMATION: Synthetically Generated Peptide

<400> SEQUENCE: 107

Gln Leu Asp Asp Leu Gln Thr
1               5

<210> SEQ ID NO 108
<211> LENGTH: 7
<212> TYPE: PRT
<213> ORGANISM: Artificial
<220> FEATURE:
<223> OTHER INFORMATION: Synthetically Generated Peptide

<400> SEQUENCE: 108

Gln Leu Asp Glu Leu Gln Thr
1               5

<210> SEQ ID NO 109
<211> LENGTH: 7
<212> TYPE: PRT
<213> ORGANISM: Artificial
<220> FEATURE:
<223> OTHER INFORMATION: Synthetically Generated Peptide

<400> SEQUENCE: 109

Gln Leu Asp His Leu Gln Thr
1               5

<210> SEQ ID NO 110
<211> LENGTH: 7
<212> TYPE: PRT
<213> ORGANISM: Artificial
<220> FEATURE:
<223> OTHER INFORMATION: Synthetically Generated Peptide

<400> SEQUENCE: 110

Gln Leu Asp Lys Leu Gln Thr
1               5

<210> SEQ ID NO 111
<211> LENGTH: 7
<212> TYPE: PRT
<213> ORGANISM: Artificial
<220> FEATURE:
<223> OTHER INFORMATION: Synthetically Generated Peptide

<400> SEQUENCE: 111

Gln Leu Asp Ser Leu Gln Thr
1               5

<210> SEQ ID NO 112
<211> LENGTH: 7
<212> TYPE: PRT
<213> ORGANISM: Artificial
<220> FEATURE:
<223> OTHER INFORMATION: Synthetically Generated Peptide

```
<400> SEQUENCE: 112

Gln Leu Asp Ala Leu Gln Thr
1               5

<210> SEQ ID NO 113
<211> LENGTH: 7
<212> TYPE: PRT
<213> ORGANISM: Artificial
<220> FEATURE:
<223> OTHER INFORMATION: Synthetically Generated Peptide

<400> SEQUENCE: 113

Asp Leu Asp Thr Leu Gln Thr
1               5

<210> SEQ ID NO 114
<211> LENGTH: 7
<212> TYPE: PRT
<213> ORGANISM: Artificial
<220> FEATURE:
<223> OTHER INFORMATION: Synthetically Generated Peptide

<400> SEQUENCE: 114

Asp Leu Asp Asp Leu Gln Thr
1               5

<210> SEQ ID NO 115
<211> LENGTH: 7
<212> TYPE: PRT
<213> ORGANISM: Artificial
<220> FEATURE:
<223> OTHER INFORMATION: Synthetically Generated Peptide

<400> SEQUENCE: 115

Asp Leu Asp Glu Leu Gln Thr
1               5

<210> SEQ ID NO 116
<211> LENGTH: 7
<212> TYPE: PRT
<213> ORGANISM: Artificial
<220> FEATURE:
<223> OTHER INFORMATION: Synthetically Generated Peptide

<400> SEQUENCE: 116

Asp Leu Asp His Leu Gln Thr
1               5

<210> SEQ ID NO 117
<211> LENGTH: 7
<212> TYPE: PRT
<213> ORGANISM: Artificial
<220> FEATURE:
<223> OTHER INFORMATION: Synthetically Generated Peptide

<400> SEQUENCE: 117

Asp Leu Asp Lys Leu Gln Thr
1               5

<210> SEQ ID NO 118
<211> LENGTH: 7
<212> TYPE: PRT
<213> ORGANISM: Artificial
<220> FEATURE:
<223> OTHER INFORMATION: Synthetically Generated Peptide
```

```
<400> SEQUENCE: 118

Asp Leu Asp Ser Leu Gln Thr
1               5

<210> SEQ ID NO 119
<211> LENGTH: 7
<212> TYPE: PRT
<213> ORGANISM: Artificial
<220> FEATURE:
<223> OTHER INFORMATION: Synthetically Generated Peptide

<400> SEQUENCE: 119

Asp Leu Asp Ala Leu Gln Thr
1               5

<210> SEQ ID NO 120
<211> LENGTH: 7
<212> TYPE: PRT
<213> ORGANISM: Artificial
<220> FEATURE:
<223> OTHER INFORMATION: Synthetically Generated Peptide

<400> SEQUENCE: 120

Glu Leu Asp Thr Leu Gln Thr
1               5

<210> SEQ ID NO 121
<211> LENGTH: 7
<212> TYPE: PRT
<213> ORGANISM: Artificial
<220> FEATURE:
<223> OTHER INFORMATION: Synthetically Generated Peptide

<400> SEQUENCE: 121

Glu Leu Asp Asp Leu Gln Thr
1               5

<210> SEQ ID NO 122
<211> LENGTH: 7
<212> TYPE: PRT
<213> ORGANISM: Artificial
<220> FEATURE:
<223> OTHER INFORMATION: Synthetically Generated Peptide

<400> SEQUENCE: 122

Glu Leu Asp Glu Leu Gln Thr
1               5

<210> SEQ ID NO 123
<211> LENGTH: 7
<212> TYPE: PRT
<213> ORGANISM: Artificial
<220> FEATURE:
<223> OTHER INFORMATION: Synthetically Generated Peptide

<400> SEQUENCE: 123

Glu Leu Asp His Leu Gln Thr
1               5

<210> SEQ ID NO 124
<211> LENGTH: 7
<212> TYPE: PRT
<213> ORGANISM: Artificial
<220> FEATURE:
<223> OTHER INFORMATION: Synthetically Generated Peptide

<400> SEQUENCE: 124
```

```
Glu Leu Asp Lys Leu Gln Thr
1               5

<210> SEQ ID NO 125
<211> LENGTH: 7
<212> TYPE: PRT
<213> ORGANISM: Artificial
<220> FEATURE:
<223> OTHER INFORMATION: Synthetically Generated Peptide

<400> SEQUENCE: 125

Glu Leu Asp Ser Leu Gln Thr
1               5

<210> SEQ ID NO 126
<211> LENGTH: 7
<212> TYPE: PRT
<213> ORGANISM: Artificial
<220> FEATURE:
<223> OTHER INFORMATION: Synthetically Generated Peptide

<400> SEQUENCE: 126

Glu Leu Asp Ala Leu Gln Thr
1               5

<210> SEQ ID NO 127
<211> LENGTH: 7
<212> TYPE: PRT
<213> ORGANISM: Artificial
<220> FEATURE:
<223> OTHER INFORMATION: Synthetically Generated Peptide

<400> SEQUENCE: 127

Thr Leu Asp Thr Leu Gln Thr
1               5

<210> SEQ ID NO 128
<211> LENGTH: 7
<212> TYPE: PRT
<213> ORGANISM: Artificial
<220> FEATURE:
<223> OTHER INFORMATION: Synthetically Generated Peptide

<400> SEQUENCE: 128

Thr Leu Asp Asp Leu Gln Thr
1               5

<210> SEQ ID NO 129
<211> LENGTH: 7
<212> TYPE: PRT
<213> ORGANISM: Artificial
<220> FEATURE:
<223> OTHER INFORMATION: Synthetically Generated Peptide

<400> SEQUENCE: 129

Thr Leu Asp Glu Leu Gln Thr
1               5

<210> SEQ ID NO 130
<211> LENGTH: 7
<212> TYPE: PRT
<213> ORGANISM: Artificial
<220> FEATURE:
<223> OTHER INFORMATION: Synthetically Generated Peptide

<400> SEQUENCE: 130
```

```
Thr Leu Asp His Leu Gln Thr
1               5

<210> SEQ ID NO 131
<211> LENGTH: 7
<212> TYPE: PRT
<213> ORGANISM: Artificial
<220> FEATURE:
<223> OTHER INFORMATION: Synthetically Generated Peptide

<400> SEQUENCE: 131

Thr Leu Asp Lys Leu Gln Thr
1               5

<210> SEQ ID NO 132
<211> LENGTH: 7
<212> TYPE: PRT
<213> ORGANISM: Artificial
<220> FEATURE:
<223> OTHER INFORMATION: Synthetically Generated Peptide

<400> SEQUENCE: 132

Thr Leu Asp Ser Leu Gln Thr
1               5

<210> SEQ ID NO 133
<211> LENGTH: 7
<212> TYPE: PRT
<213> ORGANISM: Artificial
<220> FEATURE:
<223> OTHER INFORMATION: Synthetically Generated Peptide

<400> SEQUENCE: 133

Thr Leu Asp Ala Leu Gln Thr
1               5

<210> SEQ ID NO 134
<211> LENGTH: 7
<212> TYPE: PRT
<213> ORGANISM: Artificial
<220> FEATURE:
<223> OTHER INFORMATION: Synthetically Generated Peptide

<400> SEQUENCE: 134

Ser Leu Asp Thr Leu Gln Thr
1               5

<210> SEQ ID NO 135
<211> LENGTH: 7
<212> TYPE: PRT
<213> ORGANISM: Artificial
<220> FEATURE:
<223> OTHER INFORMATION: Synthetically Generated Peptide

<400> SEQUENCE: 135

Ser Leu Asp Asp Leu Gln Thr
1               5

<210> SEQ ID NO 136
<211> LENGTH: 7
<212> TYPE: PRT
<213> ORGANISM: Artificial
<220> FEATURE:
<223> OTHER INFORMATION: Synthetically Generated Peptide

<400> SEQUENCE: 136

Ser Leu Asp Glu Leu Gln Thr
```

```
1               5

<210> SEQ ID NO 137
<211> LENGTH: 7
<212> TYPE: PRT
<213> ORGANISM: Artificial
<220> FEATURE:
<223> OTHER INFORMATION: Synthetically Generated Peptide

<400> SEQUENCE: 137

Ser Leu Asp His Leu Gln Thr
1               5

<210> SEQ ID NO 138
<211> LENGTH: 7
<212> TYPE: PRT
<213> ORGANISM: Artificial
<220> FEATURE:
<223> OTHER INFORMATION: Synthetically Generated Peptide

<400> SEQUENCE: 138

Ser Leu Asp Lys Leu Gln Thr
1               5

<210> SEQ ID NO 139
<211> LENGTH: 7
<212> TYPE: PRT
<213> ORGANISM: Artificial
<220> FEATURE:
<223> OTHER INFORMATION: Synthetically Generated Peptide

<400> SEQUENCE: 139

Ser Leu Asp Ser Leu Gln Thr
1               5

<210> SEQ ID NO 140
<211> LENGTH: 7
<212> TYPE: PRT
<213> ORGANISM: Artificial
<220> FEATURE:
<223> OTHER INFORMATION: Synthetically Generated Peptide

<400> SEQUENCE: 140

Ser Leu Asp Ala Leu Gln Thr
1               5

<210> SEQ ID NO 141
<211> LENGTH: 7
<212> TYPE: PRT
<213> ORGANISM: Artificial
<220> FEATURE:
<223> OTHER INFORMATION: Synthetically Generated Peptide

<400> SEQUENCE: 141

Ala Arg Gly Thr Leu Arg Thr
1               5

<210> SEQ ID NO 142
<211> LENGTH: 7
<212> TYPE: PRT
<213> ORGANISM: Artificial
<220> FEATURE:
<223> OTHER INFORMATION: Synthetically Generated Peptide

<400> SEQUENCE: 142

Ala Arg Gly Asp Leu Arg Thr
1               5
```

```
<210> SEQ ID NO 143
<211> LENGTH: 7
<212> TYPE: PRT
<213> ORGANISM: Artificial
<220> FEATURE:
<223> OTHER INFORMATION: Synthetically Generated Peptide

<400> SEQUENCE: 143

Ala Arg Gly Glu Leu Arg Thr
1               5

<210> SEQ ID NO 144
<211> LENGTH: 7
<212> TYPE: PRT
<213> ORGANISM: Artificial
<220> FEATURE:
<223> OTHER INFORMATION: Synthetically Generated Peptide

<400> SEQUENCE: 144

Ala Arg Gly His Leu Arg Thr
1               5

<210> SEQ ID NO 145
<211> LENGTH: 7
<212> TYPE: PRT
<213> ORGANISM: Artificial
<220> FEATURE:
<223> OTHER INFORMATION: Synthetically Generated Peptide

<400> SEQUENCE: 145

Ala Arg Gly Lys Leu Arg Thr
1               5

<210> SEQ ID NO 146
<211> LENGTH: 7
<212> TYPE: PRT
<213> ORGANISM: Artificial
<220> FEATURE:
<223> OTHER INFORMATION: Synthetically Generated Peptide

<400> SEQUENCE: 146

Ala Arg Gly Ser Leu Arg Thr
1               5

<210> SEQ ID NO 147
<211> LENGTH: 7
<212> TYPE: PRT
<213> ORGANISM: Artificial
<220> FEATURE:
<223> OTHER INFORMATION: Synthetically Generated Peptide

<400> SEQUENCE: 147

Ala Arg Gly Ala Leu Arg Thr
1               5

<210> SEQ ID NO 148
<211> LENGTH: 7
<212> TYPE: PRT
<213> ORGANISM: Artificial
<220> FEATURE:
<223> OTHER INFORMATION: Synthetically Generated Peptide

<400> SEQUENCE: 148

Ser Arg Gly Thr Leu Arg Thr
1               5
```

```
<210> SEQ ID NO 149
<211> LENGTH: 7
<212> TYPE: PRT
<213> ORGANISM: Artificial
<220> FEATURE:
<223> OTHER INFORMATION: Synthetically Generated Peptide

<400> SEQUENCE: 149

Ser Arg Gly Asp Leu Arg Thr
1               5

<210> SEQ ID NO 150
<211> LENGTH: 7
<212> TYPE: PRT
<213> ORGANISM: Artificial
<220> FEATURE:
<223> OTHER INFORMATION: Synthetically Generated Peptide

<400> SEQUENCE: 150

Ser Arg Gly Glu Leu Arg Thr
1               5

<210> SEQ ID NO 151
<211> LENGTH: 7
<212> TYPE: PRT
<213> ORGANISM: Artificial
<220> FEATURE:
<223> OTHER INFORMATION: Synthetically Generated Peptide

<400> SEQUENCE: 151

Ser Arg Gly His Leu Arg Thr
1               5

<210> SEQ ID NO 152
<211> LENGTH: 7
<212> TYPE: PRT
<213> ORGANISM: Artificial
<220> FEATURE:
<223> OTHER INFORMATION: Synthetically Generated Peptide

<400> SEQUENCE: 152

Ser Arg Gly Lys Leu Arg Thr
1               5

<210> SEQ ID NO 153
<211> LENGTH: 7
<212> TYPE: PRT
<213> ORGANISM: Artificial
<220> FEATURE:
<223> OTHER INFORMATION: Synthetically Generated Peptide

<400> SEQUENCE: 153

Ser Arg Gly Ser Leu Arg Thr
1               5

<210> SEQ ID NO 154
<211> LENGTH: 7
<212> TYPE: PRT
<213> ORGANISM: Artificial
<220> FEATURE:
<223> OTHER INFORMATION: Synthetically Generated Peptide

<400> SEQUENCE: 154

Ser Arg Gly Ala Leu Arg Thr
1               5
```

<210> SEQ ID NO 155
<211> LENGTH: 7
<212> TYPE: PRT
<213> ORGANISM: Artificial
<220> FEATURE:
<223> OTHER INFORMATION: Synthetically Generated Peptide

<400> SEQUENCE: 155

Gln Lys Asp Ala Leu Arg Gly
1               5

<210> SEQ ID NO 156
<211> LENGTH: 7
<212> TYPE: PRT
<213> ORGANISM: Artificial
<220> FEATURE:
<223> OTHER INFORMATION: Synthetically Generated Peptide

<400> SEQUENCE: 156

Asp Lys Asp Ala Leu Arg Gly
1               5

<210> SEQ ID NO 157
<211> LENGTH: 7
<212> TYPE: PRT
<213> ORGANISM: Artificial
<220> FEATURE:
<223> OTHER INFORMATION: Synthetically Generated Peptide

<400> SEQUENCE: 157

Glu Lys Asp Ala Leu Arg Gly
1               5

<210> SEQ ID NO 158
<211> LENGTH: 7
<212> TYPE: PRT
<213> ORGANISM: Artificial
<220> FEATURE:
<223> OTHER INFORMATION: Synthetically Generated Peptide

<400> SEQUENCE: 158

Thr Lys Asp Ala Leu Arg Gly
1               5

<210> SEQ ID NO 159
<211> LENGTH: 7
<212> TYPE: PRT
<213> ORGANISM: Artificial
<220> FEATURE:
<223> OTHER INFORMATION: Synthetically Generated Peptide

<400> SEQUENCE: 159

Ser Lys Asp Ala Leu Arg Gly
1               5

<210> SEQ ID NO 160
<211> LENGTH: 7
<212> TYPE: PRT
<213> ORGANISM: Artificial
<220> FEATURE:
<223> OTHER INFORMATION: Synthetically Generated Peptide

<400> SEQUENCE: 160

Arg Lys Asp Asn Leu Arg Gly
1               5

<210> SEQ ID NO 161

```
<211> LENGTH: 7
<212> TYPE: PRT
<213> ORGANISM: Artificial
<220> FEATURE:
<223> OTHER INFORMATION: Synthetically Generated Peptide

<400> SEQUENCE: 161

Arg Lys Asp Thr Leu Arg Gly
1               5

<210> SEQ ID NO 162
<211> LENGTH: 7
<212> TYPE: PRT
<213> ORGANISM: Artificial
<220> FEATURE:
<223> OTHER INFORMATION: Synthetically Generated Peptide

<400> SEQUENCE: 162

Arg Lys Asp Asp Leu Arg Gly
1               5

<210> SEQ ID NO 163
<211> LENGTH: 7
<212> TYPE: PRT
<213> ORGANISM: Artificial
<220> FEATURE:
<223> OTHER INFORMATION: Synthetically Generated Peptide

<400> SEQUENCE: 163

Arg Lys Asp Glu Leu Arg Gly
1               5

<210> SEQ ID NO 164
<211> LENGTH: 7
<212> TYPE: PRT
<213> ORGANISM: Artificial
<220> FEATURE:
<223> OTHER INFORMATION: Synthetically Generated Peptide

<400> SEQUENCE: 164

Arg Lys Asp His Leu Arg Gly
1               5

<210> SEQ ID NO 165
<211> LENGTH: 7
<212> TYPE: PRT
<213> ORGANISM: Artificial
<220> FEATURE:
<223> OTHER INFORMATION: Synthetically Generated Peptide

<400> SEQUENCE: 165

Arg Lys Asp Lys Leu Arg Gly
1               5

<210> SEQ ID NO 166
<211> LENGTH: 7
<212> TYPE: PRT
<213> ORGANISM: Artificial
<220> FEATURE:
<223> OTHER INFORMATION: Synthetically Generated Peptide

<400> SEQUENCE: 166

Arg Lys Asp Ser Leu Arg Gly
1               5

<210> SEQ ID NO 167
<211> LENGTH: 7
```

```
<212> TYPE: PRT
<213> ORGANISM: Artificial
<220> FEATURE:
<223> OTHER INFORMATION: Synthetically Generated Peptide

<400> SEQUENCE: 167

Gln Lys Asp Asn Leu Arg Gly
1               5

<210> SEQ ID NO 168
<211> LENGTH: 7
<212> TYPE: PRT
<213> ORGANISM: Artificial
<220> FEATURE:
<223> OTHER INFORMATION: Synthetically Generated Peptide

<400> SEQUENCE: 168

Gln Lys Asp Thr Leu Arg Gly
1               5

<210> SEQ ID NO 169
<211> LENGTH: 7
<212> TYPE: PRT
<213> ORGANISM: Artificial
<220> FEATURE:
<223> OTHER INFORMATION: Synthetically Generated Peptide

<400> SEQUENCE: 169

Gln Lys Asp Asp Leu Arg Gly
1               5

<210> SEQ ID NO 170
<211> LENGTH: 7
<212> TYPE: PRT
<213> ORGANISM: Artificial
<220> FEATURE:
<223> OTHER INFORMATION: Synthetically Generated Peptide

<400> SEQUENCE: 170

Gln Lys Asp Glu Leu Arg Gly
1               5

<210> SEQ ID NO 171
<211> LENGTH: 7
<212> TYPE: PRT
<213> ORGANISM: Artificial
<220> FEATURE:
<223> OTHER INFORMATION: Synthetically Generated Peptide

<400> SEQUENCE: 171

Gln Lys Asp His Leu Arg Gly
1               5

<210> SEQ ID NO 172
<211> LENGTH: 7
<212> TYPE: PRT
<213> ORGANISM: Artificial
<220> FEATURE:
<223> OTHER INFORMATION: Synthetically Generated Peptide

<400> SEQUENCE: 172

Gln Lys Asp Lys Leu Arg Gly
1               5

<210> SEQ ID NO 173
<211> LENGTH: 7
<212> TYPE: PRT
```

```
-continued

<213> ORGANISM: Artificial
<220> FEATURE:
<223> OTHER INFORMATION: Synthetically Generated Peptide

<400> SEQUENCE: 173

Gln Lys Asp Ser Leu Arg Gly
1               5

<210> SEQ ID NO 174
<211> LENGTH: 7
<212> TYPE: PRT
<213> ORGANISM: Artificial
<220> FEATURE:
<223> OTHER INFORMATION: Synthetically Generated Peptide

<400> SEQUENCE: 174

Asp Lys Asp Asn Leu Arg Gly
1               5

<210> SEQ ID NO 175
<211> LENGTH: 7
<212> TYPE: PRT
<213> ORGANISM: Artificial
<220> FEATURE:
<223> OTHER INFORMATION: Synthetically Generated Peptide

<400> SEQUENCE: 175

Asp Lys Asp Thr Leu Arg Gly
1               5

<210> SEQ ID NO 176
<211> LENGTH: 7
<212> TYPE: PRT
<213> ORGANISM: Artificial
<220> FEATURE:
<223> OTHER INFORMATION: Synthetically Generated Peptide

<400> SEQUENCE: 176

Asp Lys Asp Asp Leu Arg Gly
1               5

<210> SEQ ID NO 177
<211> LENGTH: 7
<212> TYPE: PRT
<213> ORGANISM: Artificial
<220> FEATURE:
<223> OTHER INFORMATION: Synthetically Generated Peptide

<400> SEQUENCE: 177

Asp Lys Asp Glu Leu Arg Gly
1               5

<210> SEQ ID NO 178
<211> LENGTH: 7
<212> TYPE: PRT
<213> ORGANISM: Artificial
<220> FEATURE:
<223> OTHER INFORMATION: Synthetically Generated Peptide

<400> SEQUENCE: 178

Asp Lys Asp His Leu Arg Gly
1               5

<210> SEQ ID NO 179
<211> LENGTH: 7
<212> TYPE: PRT
<213> ORGANISM: Artificial
```

```
<220> FEATURE:
<223> OTHER INFORMATION: Synthetically Generated Peptide

<400> SEQUENCE: 179

Asp Lys Asp Lys Leu Arg Gly
1               5

<210> SEQ ID NO 180
<211> LENGTH: 7
<212> TYPE: PRT
<213> ORGANISM: Artificial
<220> FEATURE:
<223> OTHER INFORMATION: Synthetically Generated Peptide

<400> SEQUENCE: 180

Asp Lys Asp Ser Leu Arg Gly
1               5

<210> SEQ ID NO 181
<211> LENGTH: 7
<212> TYPE: PRT
<213> ORGANISM: Artificial
<220> FEATURE:
<223> OTHER INFORMATION: Synthetically Generated Peptide

<400> SEQUENCE: 181

Glu Lys Asp Asn Leu Arg Gly
1               5

<210> SEQ ID NO 182
<211> LENGTH: 7
<212> TYPE: PRT
<213> ORGANISM: Artificial
<220> FEATURE:
<223> OTHER INFORMATION: Synthetically Generated Peptide

<400> SEQUENCE: 182

Glu Lys Asp Thr Leu Arg Gly
1               5

<210> SEQ ID NO 183
<211> LENGTH: 7
<212> TYPE: PRT
<213> ORGANISM: Artificial
<220> FEATURE:
<223> OTHER INFORMATION: Synthetically Generated Peptide

<400> SEQUENCE: 183

Glu Lys Asp Asp Leu Arg Gly
1               5

<210> SEQ ID NO 184
<211> LENGTH: 7
<212> TYPE: PRT
<213> ORGANISM: Artificial
<220> FEATURE:
<223> OTHER INFORMATION: Synthetically Generated Peptide

<400> SEQUENCE: 184

Glu Lys Asp Glu Leu Arg Gly
1               5

<210> SEQ ID NO 185
<211> LENGTH: 7
<212> TYPE: PRT
<213> ORGANISM: Artificial
<220> FEATURE:
```

<223> OTHER INFORMATION: Synthetically Generated Peptide

<400> SEQUENCE: 185

Glu Lys Asp His Leu Arg Gly
1               5

<210> SEQ ID NO 186
<211> LENGTH: 7
<212> TYPE: PRT
<213> ORGANISM: Artificial
<220> FEATURE:
<223> OTHER INFORMATION: Synthetically Generated Peptide

<400> SEQUENCE: 186

Glu Lys Asp Lys Leu Arg Gly
1               5

<210> SEQ ID NO 187
<211> LENGTH: 7
<212> TYPE: PRT
<213> ORGANISM: Artificial
<220> FEATURE:
<223> OTHER INFORMATION: Synthetically Generated Peptide

<400> SEQUENCE: 187

Glu Lys Asp Ser Leu Arg Gly
1               5

<210> SEQ ID NO 188
<211> LENGTH: 7
<212> TYPE: PRT
<213> ORGANISM: Artificial
<220> FEATURE:
<223> OTHER INFORMATION: Synthetically Generated Peptide

<400> SEQUENCE: 188

Thr Lys Asp Asn Leu Arg Gly
1               5

<210> SEQ ID NO 189
<211> LENGTH: 7
<212> TYPE: PRT
<213> ORGANISM: Artificial
<220> FEATURE:
<223> OTHER INFORMATION: Synthetically Generated Peptide

<400> SEQUENCE: 189

Thr Lys Asp Thr Leu Arg Gly
1               5

<210> SEQ ID NO 190
<211> LENGTH: 7
<212> TYPE: PRT
<213> ORGANISM: Artificial
<220> FEATURE:
<223> OTHER INFORMATION: Synthetically Generated Peptide

<400> SEQUENCE: 190

Thr Lys Asp Asp Leu Arg Gly
1               5

<210> SEQ ID NO 191
<211> LENGTH: 7
<212> TYPE: PRT
<213> ORGANISM: Artificial
<220> FEATURE:
<223> OTHER INFORMATION: Synthetically Generated Peptide

```
<400> SEQUENCE: 191

Thr Lys Asp Glu Leu Arg Gly
1               5

<210> SEQ ID NO 192
<211> LENGTH: 7
<212> TYPE: PRT
<213> ORGANISM: Artificial
<220> FEATURE:
<223> OTHER INFORMATION: Synthetically Generated Peptide

<400> SEQUENCE: 192

Thr Lys Asp His Leu Arg Gly
1               5

<210> SEQ ID NO 193
<211> LENGTH: 7
<212> TYPE: PRT
<213> ORGANISM: Artificial
<220> FEATURE:
<223> OTHER INFORMATION: Synthetically Generated Peptide

<400> SEQUENCE: 193

Thr Lys Asp Lys Leu Arg Gly
1               5

<210> SEQ ID NO 194
<211> LENGTH: 7
<212> TYPE: PRT
<213> ORGANISM: Artificial
<220> FEATURE:
<223> OTHER INFORMATION: Synthetically Generated Peptide

<400> SEQUENCE: 194

Thr Lys Asp Ser Leu Arg Gly
1               5

<210> SEQ ID NO 195
<211> LENGTH: 7
<212> TYPE: PRT
<213> ORGANISM: Artificial
<220> FEATURE:
<223> OTHER INFORMATION: Synthetically Generated Peptide

<400> SEQUENCE: 195

Ser Lys Asp Asn Leu Arg Gly
1               5

<210> SEQ ID NO 196
<211> LENGTH: 7
<212> TYPE: PRT
<213> ORGANISM: Artificial
<220> FEATURE:
<223> OTHER INFORMATION: Synthetically Generated Peptide

<400> SEQUENCE: 196

Ser Lys Asp Thr Leu Arg Gly
1               5

<210> SEQ ID NO 197
<211> LENGTH: 7
<212> TYPE: PRT
<213> ORGANISM: Artificial
<220> FEATURE:
<223> OTHER INFORMATION: Synthetically Generated Peptide
```

-continued

```
<400> SEQUENCE: 197

Ser Lys Asp Asp Leu Arg Gly
1               5

<210> SEQ ID NO 198
<211> LENGTH: 7
<212> TYPE: PRT
<213> ORGANISM: Artificial
<220> FEATURE:
<223> OTHER INFORMATION: Synthetically Generated Peptide

<400> SEQUENCE: 198

Ser Lys Asp Glu Leu Arg Gly
1               5

<210> SEQ ID NO 199
<211> LENGTH: 7
<212> TYPE: PRT
<213> ORGANISM: Artificial
<220> FEATURE:
<223> OTHER INFORMATION: Synthetically Generated Peptide

<400> SEQUENCE: 199

Ser Lys Asp His Leu Arg Gly
1               5

<210> SEQ ID NO 200
<211> LENGTH: 7
<212> TYPE: PRT
<213> ORGANISM: Artificial
<220> FEATURE:
<223> OTHER INFORMATION: Synthetically Generated Peptide

<400> SEQUENCE: 200

Ser Lys Asp Lys Leu Arg Gly
1               5

<210> SEQ ID NO 201
<211> LENGTH: 7
<212> TYPE: PRT
<213> ORGANISM: Artificial
<220> FEATURE:
<223> OTHER INFORMATION: Synthetically Generated Peptide

<400> SEQUENCE: 201

Ser Lys Asp Ser Leu Arg Gly
1               5

<210> SEQ ID NO 202
<211> LENGTH: 7
<212> TYPE: PRT
<213> ORGANISM: Artificial
<220> FEATURE:
<223> OTHER INFORMATION: Synthetically Generated Peptide

<400> SEQUENCE: 202

Val Arg Gly Thr Leu Arg Thr
1               5

<210> SEQ ID NO 203
<211> LENGTH: 7
<212> TYPE: PRT
<213> ORGANISM: Artificial
<220> FEATURE:
<223> OTHER INFORMATION: Synthetically Generated Peptide

<400> SEQUENCE: 203
```

```
Val Arg Gly Asp Leu Arg Thr
1               5

<210> SEQ ID NO 204
<211> LENGTH: 7
<212> TYPE: PRT
<213> ORGANISM: Artificial
<220> FEATURE:
<223> OTHER INFORMATION: Synthetically Generated Peptide

<400> SEQUENCE: 204

Val Arg Gly Glu Leu Arg Thr
1               5

<210> SEQ ID NO 205
<211> LENGTH: 7
<212> TYPE: PRT
<213> ORGANISM: Artificial
<220> FEATURE:
<223> OTHER INFORMATION: Synthetically Generated Peptide

<400> SEQUENCE: 205

Val Arg Gly His Leu Arg Thr
1               5

<210> SEQ ID NO 206
<211> LENGTH: 7
<212> TYPE: PRT
<213> ORGANISM: Artificial
<220> FEATURE:
<223> OTHER INFORMATION: Synthetically Generated Peptide

<400> SEQUENCE: 206

Val Arg Gly Lys Leu Arg Thr
1               5

<210> SEQ ID NO 207
<211> LENGTH: 7
<212> TYPE: PRT
<213> ORGANISM: Artificial
<220> FEATURE:
<223> OTHER INFORMATION: Synthetically Generated Peptide

<400> SEQUENCE: 207

Val Arg Gly Ser Leu Arg Thr
1               5

<210> SEQ ID NO 208
<211> LENGTH: 7
<212> TYPE: PRT
<213> ORGANISM: Artificial
<220> FEATURE:
<223> OTHER INFORMATION: Synthetically Generated Peptide

<400> SEQUENCE: 208

Val Arg Gly Thr Leu Arg Thr
1               5

<210> SEQ ID NO 209
<211> LENGTH: 7
<212> TYPE: PRT
<213> ORGANISM: Artificial
<220> FEATURE:
<223> OTHER INFORMATION: Synthetically Generated Peptide

<400> SEQUENCE: 209
```

```
Gln Leu Arg Ala Leu Asp Arg
1               5

<210> SEQ ID NO 210
<211> LENGTH: 7
<212> TYPE: PRT
<213> ORGANISM: Artificial
<220> FEATURE:
<223> OTHER INFORMATION: Synthetically Generated Peptide

<400> SEQUENCE: 210

Asp Leu Arg Ala Leu Asp Arg
1               5

<210> SEQ ID NO 211
<211> LENGTH: 7
<212> TYPE: PRT
<213> ORGANISM: Artificial
<220> FEATURE:
<223> OTHER INFORMATION: Synthetically Generated Peptide

<400> SEQUENCE: 211

Glu Leu Arg Ala Leu Asp Arg
1               5

<210> SEQ ID NO 212
<211> LENGTH: 7
<212> TYPE: PRT
<213> ORGANISM: Artificial
<220> FEATURE:
<223> OTHER INFORMATION: Synthetically Generated Peptide

<400> SEQUENCE: 212

Thr Leu Arg Ala Leu Asp Arg
1               5

<210> SEQ ID NO 213
<211> LENGTH: 7
<212> TYPE: PRT
<213> ORGANISM: Artificial
<220> FEATURE:
<223> OTHER INFORMATION: Synthetically Generated Peptide

<400> SEQUENCE: 213

Ser Leu Arg Ala Leu Asp Arg
1               5

<210> SEQ ID NO 214
<211> LENGTH: 7
<212> TYPE: PRT
<213> ORGANISM: Artificial
<220> FEATURE:
<223> OTHER INFORMATION: Synthetically Generated Peptide

<400> SEQUENCE: 214

Arg Ser Asp Asn Arg Lys Arg
1               5

<210> SEQ ID NO 215
<211> LENGTH: 7
<212> TYPE: PRT
<213> ORGANISM: Artificial
<220> FEATURE:
<223> OTHER INFORMATION: Synthetically Generated Peptide

<400> SEQUENCE: 215

Arg Ser Asp Thr Arg Lys Arg
```

-continued

```
1               5

<210> SEQ ID NO 216
<211> LENGTH: 7
<212> TYPE: PRT
<213> ORGANISM: Artificial
<220> FEATURE:
<223> OTHER INFORMATION: Synthetically Generated Peptide

<400> SEQUENCE: 216

Arg Ser Asp Asp Arg Lys Arg
1               5

<210> SEQ ID NO 217
<211> LENGTH: 7
<212> TYPE: PRT
<213> ORGANISM: Artificial
<220> FEATURE:
<223> OTHER INFORMATION: Synthetically Generated Peptide

<400> SEQUENCE: 217

Arg Ser Asp His Arg Lys Arg
1               5

<210> SEQ ID NO 218
<211> LENGTH: 7
<212> TYPE: PRT
<213> ORGANISM: Artificial
<220> FEATURE:
<223> OTHER INFORMATION: Synthetically Generated Peptide

<400> SEQUENCE: 218

Arg Ser Asp Lys Arg Lys Arg
1               5

<210> SEQ ID NO 219
<211> LENGTH: 7
<212> TYPE: PRT
<213> ORGANISM: Artificial
<220> FEATURE:
<223> OTHER INFORMATION: Synthetically Generated Peptide

<400> SEQUENCE: 219

Arg Ser Asp Ser Arg Lys Arg
1               5

<210> SEQ ID NO 220
<211> LENGTH: 7
<212> TYPE: PRT
<213> ORGANISM: Artificial
<220> FEATURE:
<223> OTHER INFORMATION: Synthetically Generated Peptide

<400> SEQUENCE: 220

Arg Ser Asp Ala Arg Lys Arg
1               5

<210> SEQ ID NO 221
<211> LENGTH: 7
<212> TYPE: PRT
<213> ORGANISM: Artificial
<220> FEATURE:
<223> OTHER INFORMATION: Synthetically Generated Peptide

<400> SEQUENCE: 221

Gln Tyr Gln Ser Leu Arg Gln
1               5
```

<210> SEQ ID NO 222
<211> LENGTH: 7
<212> TYPE: PRT
<213> ORGANISM: Artificial
<220> FEATURE:
<223> OTHER INFORMATION: Synthetically Generated Peptide

<400> SEQUENCE: 222

Glu Tyr Gln Ser Leu Arg Gln
1               5

<210> SEQ ID NO 223
<211> LENGTH: 7
<212> TYPE: PRT
<213> ORGANISM: Artificial
<220> FEATURE:
<223> OTHER INFORMATION: Synthetically Generated Peptide

<400> SEQUENCE: 223

Arg Tyr Gln Ser Leu Arg Gln
1               5

<210> SEQ ID NO 224
<211> LENGTH: 7
<212> TYPE: PRT
<213> ORGANISM: Artificial
<220> FEATURE:
<223> OTHER INFORMATION: Synthetically Generated Peptide

<400> SEQUENCE: 224

Thr Tyr Gln Ser Leu Arg Gln
1               5

<210> SEQ ID NO 225
<211> LENGTH: 7
<212> TYPE: PRT
<213> ORGANISM: Artificial
<220> FEATURE:
<223> OTHER INFORMATION: Synthetically Generated Peptide

<400> SEQUENCE: 225

Ser Tyr Gln Ser Leu Arg Gln
1               5

<210> SEQ ID NO 226
<211> LENGTH: 7
<212> TYPE: PRT
<213> ORGANISM: Artificial
<220> FEATURE:
<223> OTHER INFORMATION: Synthetically Generated Peptide

<400> SEQUENCE: 226

Arg Leu Arg Asn Ile Gln Phe
1               5

<210> SEQ ID NO 227
<211> LENGTH: 7
<212> TYPE: PRT
<213> ORGANISM: Artificial
<220> FEATURE:
<223> OTHER INFORMATION: Synthetically Generated Peptide

<400> SEQUENCE: 227

Arg Leu Arg Thr Ile Gln Phe
1               5

```
<210> SEQ ID NO 228
<211> LENGTH: 7
<212> TYPE: PRT
<213> ORGANISM: Artificial
<220> FEATURE:
<223> OTHER INFORMATION: Synthetically Generated Peptide

<400> SEQUENCE: 228

Arg Leu Arg Glu Ile Gln Phe
1               5

<210> SEQ ID NO 229
<211> LENGTH: 7
<212> TYPE: PRT
<213> ORGANISM: Artificial
<220> FEATURE:
<223> OTHER INFORMATION: Synthetically Generated Peptide

<400> SEQUENCE: 229

Arg Leu Arg His Ile Gln Phe
1               5

<210> SEQ ID NO 230
<211> LENGTH: 7
<212> TYPE: PRT
<213> ORGANISM: Artificial
<220> FEATURE:
<223> OTHER INFORMATION: Synthetically Generated Peptide

<400> SEQUENCE: 230

Arg Leu Arg Lys Ile Gln Phe
1               5

<210> SEQ ID NO 231
<211> LENGTH: 7
<212> TYPE: PRT
<213> ORGANISM: Artificial
<220> FEATURE:
<223> OTHER INFORMATION: Synthetically Generated Peptide

<400> SEQUENCE: 231

Arg Leu Arg Ser Ile Gln Phe
1               5

<210> SEQ ID NO 232
<211> LENGTH: 7
<212> TYPE: PRT
<213> ORGANISM: Artificial
<220> FEATURE:
<223> OTHER INFORMATION: Synthetically Generated Peptide

<400> SEQUENCE: 232

Arg Leu Arg Ala Ile Gln Phe
1               5

<210> SEQ ID NO 233
<211> LENGTH: 7
<212> TYPE: PRT
<213> ORGANISM: Artificial
<220> FEATURE:
<223> OTHER INFORMATION: Synthetically Generated Peptide

<400> SEQUENCE: 233

Asp Ser Leu Leu Leu Gly Ala
1               5
```

```
<210> SEQ ID NO 234
<211> LENGTH: 7
<212> TYPE: PRT
<213> ORGANISM: Artificial
<220> FEATURE:
<223> OTHER INFORMATION: Synthetically Generated Peptide

<400> SEQUENCE: 234

Glu Ser Leu Leu Leu Gly Ala
1               5

<210> SEQ ID NO 235
<211> LENGTH: 7
<212> TYPE: PRT
<213> ORGANISM: Artificial
<220> FEATURE:
<223> OTHER INFORMATION: Synthetically Generated Peptide

<400> SEQUENCE: 235

Arg Ser Leu Leu Leu Gly Ala
1               5

<210> SEQ ID NO 236
<211> LENGTH: 7
<212> TYPE: PRT
<213> ORGANISM: Artificial
<220> FEATURE:
<223> OTHER INFORMATION: Synthetically Generated Peptide

<400> SEQUENCE: 236

Thr Ser Leu Leu Leu Gly Ala
1               5

<210> SEQ ID NO 237
<211> LENGTH: 7
<212> TYPE: PRT
<213> ORGANISM: Artificial
<220> FEATURE:
<223> OTHER INFORMATION: Synthetically Generated Peptide

<400> SEQUENCE: 237

Ser Ser Leu Leu Leu Gly Ala
1               5

<210> SEQ ID NO 238
<211> LENGTH: 7
<212> TYPE: PRT
<213> ORGANISM: Artificial
<220> FEATURE:
<223> OTHER INFORMATION: Synthetically Generated Peptide

<400> SEQUENCE: 238

His Arg Gly Asn Leu Gly Gly
1               5

<210> SEQ ID NO 239
<211> LENGTH: 7
<212> TYPE: PRT
<213> ORGANISM: Artificial
<220> FEATURE:
<223> OTHER INFORMATION: Synthetically Generated Peptide

<400> SEQUENCE: 239

His Arg Gly Asp Leu Gly Gly
1               5

<210> SEQ ID NO 240
```

```
<211> LENGTH: 7
<212> TYPE: PRT
<213> ORGANISM: Artificial
<220> FEATURE:
<223> OTHER INFORMATION: Synthetically Generated Peptide

<400> SEQUENCE: 240

His Arg Gly Glu Leu Gly Gly
1               5

<210> SEQ ID NO 241
<211> LENGTH: 7
<212> TYPE: PRT
<213> ORGANISM: Artificial
<220> FEATURE:
<223> OTHER INFORMATION: Synthetically Generated Peptide

<400> SEQUENCE: 241

His Arg Gly His Leu Gly Gly
1               5

<210> SEQ ID NO 242
<211> LENGTH: 7
<212> TYPE: PRT
<213> ORGANISM: Artificial
<220> FEATURE:
<223> OTHER INFORMATION: Synthetically Generated Peptide

<400> SEQUENCE: 242

His Arg Gly Lys Leu Gly Gly
1               5

<210> SEQ ID NO 243
<211> LENGTH: 7
<212> TYPE: PRT
<213> ORGANISM: Artificial
<220> FEATURE:
<223> OTHER INFORMATION: Synthetically Generated Peptide

<400> SEQUENCE: 243

His Arg Gly Ser Leu Gly Gly
1               5

<210> SEQ ID NO 244
<211> LENGTH: 7
<212> TYPE: PRT
<213> ORGANISM: Artificial
<220> FEATURE:
<223> OTHER INFORMATION: Synthetically Generated Peptide

<400> SEQUENCE: 244

His Arg Gly Ala Leu Gly Gly
1               5

<210> SEQ ID NO 245
<211> LENGTH: 7
<212> TYPE: PRT
<213> ORGANISM: Artificial
<220> FEATURE:
<223> OTHER INFORMATION: Synthetically Generated Peptide

<400> SEQUENCE: 245

Gln Lys His Met Leu Asp Thr
1               5

<210> SEQ ID NO 246
<211> LENGTH: 7
```

```
<212> TYPE: PRT
<213> ORGANISM: Artificial
<220> FEATURE:
<223> OTHER INFORMATION: Synthetically Generated Peptide

<400> SEQUENCE: 246

Glu Lys His Met Leu Asp Thr
1               5

<210> SEQ ID NO 247
<211> LENGTH: 7
<212> TYPE: PRT
<213> ORGANISM: Artificial
<220> FEATURE:
<223> OTHER INFORMATION: Synthetically Generated Peptide

<400> SEQUENCE: 247

Arg Lys His Met Leu Asp Thr
1               5

<210> SEQ ID NO 248
<211> LENGTH: 7
<212> TYPE: PRT
<213> ORGANISM: Artificial
<220> FEATURE:
<223> OTHER INFORMATION: Synthetically Generated Peptide

<400> SEQUENCE: 248

Thr Lys His Met Leu Asp Thr
1               5

<210> SEQ ID NO 249
<211> LENGTH: 7
<212> TYPE: PRT
<213> ORGANISM: Artificial
<220> FEATURE:
<223> OTHER INFORMATION: Synthetically Generated Peptide

<400> SEQUENCE: 249

Ser Lys His Met Leu Asp Thr
1               5

<210> SEQ ID NO 250
<211> LENGTH: 7
<212> TYPE: PRT
<213> ORGANISM: Artificial
<220> FEATURE:
<223> OTHER INFORMATION: Synthetically Generated Peptide

<400> SEQUENCE: 250

Gln Leu Gly Gly Leu Arg Gln
1               5

<210> SEQ ID NO 251
<211> LENGTH: 7
<212> TYPE: PRT
<213> ORGANISM: Artificial
<220> FEATURE:
<223> OTHER INFORMATION: Synthetically Generated Peptide

<400> SEQUENCE: 251

Glu Leu Gly Gly Leu Arg Gln
1               5

<210> SEQ ID NO 252
<211> LENGTH: 7
<212> TYPE: PRT
```

```
<213> ORGANISM: Artificial
<220> FEATURE:
<223> OTHER INFORMATION: Synthetically Generated Peptide

<400> SEQUENCE: 252

Arg Leu Gly Gly Leu Arg Gln
1               5

<210> SEQ ID NO 253
<211> LENGTH: 7
<212> TYPE: PRT
<213> ORGANISM: Artificial
<220> FEATURE:
<223> OTHER INFORMATION: Synthetically Generated Peptide

<400> SEQUENCE: 253

Thr Leu Gly Gly Leu Arg Gln
1               5

<210> SEQ ID NO 254
<211> LENGTH: 7
<212> TYPE: PRT
<213> ORGANISM: Artificial
<220> FEATURE:
<223> OTHER INFORMATION: Synthetically Generated Peptide

<400> SEQUENCE: 254

Ser Leu Gly Gly Leu Arg Gln
1               5

<210> SEQ ID NO 255
<211> LENGTH: 7
<212> TYPE: PRT
<213> ORGANISM: Artificial
<220> FEATURE:
<223> OTHER INFORMATION: Synthetically Generated Peptide

<400> SEQUENCE: 255

Ala Glu Ala Asn Leu Gln Arg
1               5

<210> SEQ ID NO 256
<211> LENGTH: 7
<212> TYPE: PRT
<213> ORGANISM: Artificial
<220> FEATURE:
<223> OTHER INFORMATION: Synthetically Generated Peptide

<400> SEQUENCE: 256

Ala Glu Ala Thr Leu Gln Arg
1               5

<210> SEQ ID NO 257
<211> LENGTH: 7
<212> TYPE: PRT
<213> ORGANISM: Artificial
<220> FEATURE:
<223> OTHER INFORMATION: Synthetically Generated Peptide

<400> SEQUENCE: 257

Ala Glu Ala Asp Leu Gln Arg
1               5

<210> SEQ ID NO 258
<211> LENGTH: 7
<212> TYPE: PRT
<213> ORGANISM: Artificial
```

```
<220> FEATURE:
<223> OTHER INFORMATION: Synthetically Generated Peptide

<400> SEQUENCE: 258

Ala Glu Ala His Leu Gln Arg
1               5

<210> SEQ ID NO 259
<211> LENGTH: 7
<212> TYPE: PRT
<213> ORGANISM: Artificial
<220> FEATURE:
<223> OTHER INFORMATION: Synthetically Generated Peptide

<400> SEQUENCE: 259

Ala Glu Ala Lys Leu Gln Arg
1               5

<210> SEQ ID NO 260
<211> LENGTH: 7
<212> TYPE: PRT
<213> ORGANISM: Artificial
<220> FEATURE:
<223> OTHER INFORMATION: Synthetically Generated Peptide

<400> SEQUENCE: 260

Ala Glu Ala Ser Leu Gln Arg
1               5

<210> SEQ ID NO 261
<211> LENGTH: 7
<212> TYPE: PRT
<213> ORGANISM: Artificial
<220> FEATURE:
<223> OTHER INFORMATION: Synthetically Generated Peptide

<400> SEQUENCE: 261

Ala Glu Ala Ala Leu Gln Arg
1               5

<210> SEQ ID NO 262
<211> LENGTH: 7
<212> TYPE: PRT
<213> ORGANISM: Artificial
<220> FEATURE:
<223> OTHER INFORMATION: Synthetically Generated Peptide

<400> SEQUENCE: 262

Asp Gly Arg Cys Leu Val Thr
1               5

<210> SEQ ID NO 263
<211> LENGTH: 7
<212> TYPE: PRT
<213> ORGANISM: Artificial
<220> FEATURE:
<223> OTHER INFORMATION: Synthetically Generated Peptide

<400> SEQUENCE: 263

Glu Gly Arg Cys Leu Val Thr
1               5

<210> SEQ ID NO 264
<211> LENGTH: 7
<212> TYPE: PRT
<213> ORGANISM: Artificial
<220> FEATURE:
```

<223> OTHER INFORMATION: Synthetically Generated Peptide

<400> SEQUENCE: 264

Arg Gly Arg Cys Leu Val Thr
1               5

<210> SEQ ID NO 265
<211> LENGTH: 7
<212> TYPE: PRT
<213> ORGANISM: Artificial
<220> FEATURE:
<223> OTHER INFORMATION: Synthetically Generated Peptide

<400> SEQUENCE: 265

Thr Gly Arg Cys Leu Val Thr
1               5

<210> SEQ ID NO 266
<211> LENGTH: 7
<212> TYPE: PRT
<213> ORGANISM: Artificial
<220> FEATURE:
<223> OTHER INFORMATION: Synthetically Generated Peptide

<400> SEQUENCE: 266

Ser Gly Arg Cys Leu Val Thr
1               5

<210> SEQ ID NO 267
<211> LENGTH: 7
<212> TYPE: PRT
<213> ORGANISM: Artificial
<220> FEATURE:
<223> OTHER INFORMATION: Synthetically Generated Peptide

<400> SEQUENCE: 267

Gln Glu Asp Asn Leu His Thr
1               5

<210> SEQ ID NO 268
<211> LENGTH: 7
<212> TYPE: PRT
<213> ORGANISM: Artificial
<220> FEATURE:
<223> OTHER INFORMATION: Synthetically Generated Peptide

<400> SEQUENCE: 268

Asp Glu Asp Asn Leu His Thr
1               5

<210> SEQ ID NO 269
<211> LENGTH: 7
<212> TYPE: PRT
<213> ORGANISM: Artificial
<220> FEATURE:
<223> OTHER INFORMATION: Synthetically Generated Peptide

<400> SEQUENCE: 269

Glu Glu Asp Asn Leu His Thr
1               5

<210> SEQ ID NO 270
<211> LENGTH: 7
<212> TYPE: PRT
<213> ORGANISM: Artificial
<220> FEATURE:
<223> OTHER INFORMATION: Synthetically Generated Peptide

```
<400> SEQUENCE: 270

Ser Glu Asp Asn Leu His Thr
1               5

<210> SEQ ID NO 271
<211> LENGTH: 7
<212> TYPE: PRT
<213> ORGANISM: Artificial
<220> FEATURE:
<223> OTHER INFORMATION: Synthetically Generated Peptide

<400> SEQUENCE: 271

Arg Glu Asp Thr Leu His Thr
1               5

<210> SEQ ID NO 272
<211> LENGTH: 7
<212> TYPE: PRT
<213> ORGANISM: Artificial
<220> FEATURE:
<223> OTHER INFORMATION: Synthetically Generated Peptide

<400> SEQUENCE: 272

Arg Glu Asp Asp Leu His Thr
1               5

<210> SEQ ID NO 273
<211> LENGTH: 7
<212> TYPE: PRT
<213> ORGANISM: Artificial
<220> FEATURE:
<223> OTHER INFORMATION: Synthetically Generated Peptide

<400> SEQUENCE: 273

Arg Glu Asp Glu Leu His Thr
1               5

<210> SEQ ID NO 274
<211> LENGTH: 7
<212> TYPE: PRT
<213> ORGANISM: Artificial
<220> FEATURE:
<223> OTHER INFORMATION: Synthetically Generated Peptide

<400> SEQUENCE: 274

Arg Glu Asp His Leu His Thr
1               5

<210> SEQ ID NO 275
<211> LENGTH: 7
<212> TYPE: PRT
<213> ORGANISM: Artificial
<220> FEATURE:
<223> OTHER INFORMATION: Synthetically Generated Peptide

<400> SEQUENCE: 275

Arg Glu Asp Lys Leu His Thr
1               5

<210> SEQ ID NO 276
<211> LENGTH: 7
<212> TYPE: PRT
<213> ORGANISM: Artificial
<220> FEATURE:
<223> OTHER INFORMATION: Synthetically Generated Peptide
```

```
<400> SEQUENCE: 276

Arg Glu Asp Ser Leu His Thr
1               5

<210> SEQ ID NO 277
<211> LENGTH: 7
<212> TYPE: PRT
<213> ORGANISM: Artificial
<220> FEATURE:
<223> OTHER INFORMATION: Synthetically Generated Peptide

<400> SEQUENCE: 277

Arg Glu Asp Ala Leu His Thr
1               5

<210> SEQ ID NO 278
<211> LENGTH: 7
<212> TYPE: PRT
<213> ORGANISM: Artificial
<220> FEATURE:
<223> OTHER INFORMATION: Synthetically Generated Peptide

<400> SEQUENCE: 278

Gln Glu Asp Thr Leu His Thr
1               5

<210> SEQ ID NO 279
<211> LENGTH: 7
<212> TYPE: PRT
<213> ORGANISM: Artificial
<220> FEATURE:
<223> OTHER INFORMATION: Synthetically Generated Peptide

<400> SEQUENCE: 279

Gln Glu Asp Asp Leu His Thr
1               5

<210> SEQ ID NO 280
<211> LENGTH: 7
<212> TYPE: PRT
<213> ORGANISM: Artificial
<220> FEATURE:
<223> OTHER INFORMATION: Synthetically Generated Peptide

<400> SEQUENCE: 280

Gln Glu Asp Glu Leu His Thr
1               5

<210> SEQ ID NO 281
<211> LENGTH: 7
<212> TYPE: PRT
<213> ORGANISM: Artificial
<220> FEATURE:
<223> OTHER INFORMATION: Synthetically Generated Peptide

<400> SEQUENCE: 281

Gln Glu Asp His Leu His Thr
1               5

<210> SEQ ID NO 282
<211> LENGTH: 7
<212> TYPE: PRT
<213> ORGANISM: Artificial
<220> FEATURE:
<223> OTHER INFORMATION: Synthetically Generated Peptide

<400> SEQUENCE: 282
```

```
Gln Glu Asp Lys Leu His Thr
1               5
```

<210> SEQ ID NO 283
<211> LENGTH: 7
<212> TYPE: PRT
<213> ORGANISM: Artificial
<220> FEATURE:
<223> OTHER INFORMATION: Synthetically Generated Peptide

<400> SEQUENCE: 283

```
Gln Glu Asp Ser Leu His Thr
1               5
```

<210> SEQ ID NO 284
<211> LENGTH: 7
<212> TYPE: PRT
<213> ORGANISM: Artificial
<220> FEATURE:
<223> OTHER INFORMATION: Synthetically Generated Peptide

<400> SEQUENCE: 284

```
Gln Glu Asp Ala Leu His Thr
1               5
```

<210> SEQ ID NO 285
<211> LENGTH: 7
<212> TYPE: PRT
<213> ORGANISM: Artificial
<220> FEATURE:
<223> OTHER INFORMATION: Synthetically Generated Peptide

<400> SEQUENCE: 285

```
Asp Glu Asp Thr Leu His Thr
1               5
```

<210> SEQ ID NO 286
<211> LENGTH: 7
<212> TYPE: PRT
<213> ORGANISM: Artificial
<220> FEATURE:
<223> OTHER INFORMATION: Synthetically Generated Peptide

<400> SEQUENCE: 286

```
Asp Glu Asp Asp Leu His Thr
1               5
```

<210> SEQ ID NO 287
<211> LENGTH: 7
<212> TYPE: PRT
<213> ORGANISM: Artificial
<220> FEATURE:
<223> OTHER INFORMATION: Synthetically Generated Peptide

<400> SEQUENCE: 287

```
Asp Glu Asp Glu Leu His Thr
1               5
```

<210> SEQ ID NO 288
<211> LENGTH: 7
<212> TYPE: PRT
<213> ORGANISM: Artificial
<220> FEATURE:
<223> OTHER INFORMATION: Synthetically Generated Peptide

<400> SEQUENCE: 288

```
Asp Glu Asp His Leu His Thr
1               5
```

<210> SEQ ID NO 289
<211> LENGTH: 7
<212> TYPE: PRT
<213> ORGANISM: Artificial
<220> FEATURE:
<223> OTHER INFORMATION: Synthetically Generated Peptide

<400> SEQUENCE: 289

```
Asp Glu Asp Lys Leu His Thr
1               5
```

<210> SEQ ID NO 290
<211> LENGTH: 7
<212> TYPE: PRT
<213> ORGANISM: Artificial
<220> FEATURE:
<223> OTHER INFORMATION: Synthetically Generated Peptide

<400> SEQUENCE: 290

```
Asp Glu Asp Ser Leu His Thr
1               5
```

<210> SEQ ID NO 291
<211> LENGTH: 7
<212> TYPE: PRT
<213> ORGANISM: Artificial
<220> FEATURE:
<223> OTHER INFORMATION: Synthetically Generated Peptide

<400> SEQUENCE: 291

```
Asp Glu Asp Ala Leu His Thr
1               5
```

<210> SEQ ID NO 292
<211> LENGTH: 7
<212> TYPE: PRT
<213> ORGANISM: Artificial
<220> FEATURE:
<223> OTHER INFORMATION: Synthetically Generated Peptide

<400> SEQUENCE: 292

```
Glu Glu Asp Thr Leu His Thr
1               5
```

<210> SEQ ID NO 293
<211> LENGTH: 7
<212> TYPE: PRT
<213> ORGANISM: Artificial
<220> FEATURE:
<223> OTHER INFORMATION: Synthetically Generated Peptide

<400> SEQUENCE: 293

```
Glu Glu Asp Asp Leu His Thr
1               5
```

<210> SEQ ID NO 294
<211> LENGTH: 7
<212> TYPE: PRT
<213> ORGANISM: Artificial
<220> FEATURE:
<223> OTHER INFORMATION: Synthetically Generated Peptide

<400> SEQUENCE: 294

```
Glu Glu Asp Glu Leu His Thr
```

-continued

```
1               5

<210> SEQ ID NO 295
<211> LENGTH: 7
<212> TYPE: PRT
<213> ORGANISM: Artificial
<220> FEATURE:
<223> OTHER INFORMATION: Synthetically Generated Peptide

<400> SEQUENCE: 295

Glu Glu Asp His Leu His Thr
1               5

<210> SEQ ID NO 296
<211> LENGTH: 7
<212> TYPE: PRT
<213> ORGANISM: Artificial
<220> FEATURE:
<223> OTHER INFORMATION: Synthetically Generated Peptide

<400> SEQUENCE: 296

Glu Glu Asp Lys Leu His Thr
1               5

<210> SEQ ID NO 297
<211> LENGTH: 7
<212> TYPE: PRT
<213> ORGANISM: Artificial
<220> FEATURE:
<223> OTHER INFORMATION: Synthetically Generated Peptide

<400> SEQUENCE: 297

Glu Glu Asp Ser Leu His Thr
1               5

<210> SEQ ID NO 298
<211> LENGTH: 7
<212> TYPE: PRT
<213> ORGANISM: Artificial
<220> FEATURE:
<223> OTHER INFORMATION: Synthetically Generated Peptide

<400> SEQUENCE: 298

Glu Glu Asp Ala Leu His Thr
1               5

<210> SEQ ID NO 299
<211> LENGTH: 7
<212> TYPE: PRT
<213> ORGANISM: Artificial
<220> FEATURE:
<223> OTHER INFORMATION: Synthetically Generated Peptide

<400> SEQUENCE: 299

Thr Glu Asp Thr Leu His Thr
1               5

<210> SEQ ID NO 300
<211> LENGTH: 7
<212> TYPE: PRT
<213> ORGANISM: Artificial
<220> FEATURE:
<223> OTHER INFORMATION: Synthetically Generated Peptide

<400> SEQUENCE: 300

Thr Glu Asp Asp Leu His Thr
1               5
```

```
<210> SEQ ID NO 301
<211> LENGTH: 7
<212> TYPE: PRT
<213> ORGANISM: Artificial
<220> FEATURE:
<223> OTHER INFORMATION: Synthetically Generated Peptide

<400> SEQUENCE: 301

Thr Glu Asp Glu Leu His Thr
1               5

<210> SEQ ID NO 302
<211> LENGTH: 7
<212> TYPE: PRT
<213> ORGANISM: Artificial
<220> FEATURE:
<223> OTHER INFORMATION: Synthetically Generated Peptide

<400> SEQUENCE: 302

Thr Glu Asp His Leu His Thr
1               5

<210> SEQ ID NO 303
<211> LENGTH: 7
<212> TYPE: PRT
<213> ORGANISM: Artificial
<220> FEATURE:
<223> OTHER INFORMATION: Synthetically Generated Peptide

<400> SEQUENCE: 303

Thr Glu Asp Lys Leu His Thr
1               5

<210> SEQ ID NO 304
<211> LENGTH: 7
<212> TYPE: PRT
<213> ORGANISM: Artificial
<220> FEATURE:
<223> OTHER INFORMATION: Synthetically Generated Peptide

<400> SEQUENCE: 304

Thr Glu Asp Ser Leu His Thr
1               5

<210> SEQ ID NO 305
<211> LENGTH: 7
<212> TYPE: PRT
<213> ORGANISM: Artificial
<220> FEATURE:
<223> OTHER INFORMATION: Synthetically Generated Peptide

<400> SEQUENCE: 305

Thr Glu Asp Ala Leu His Thr
1               5

<210> SEQ ID NO 306
<211> LENGTH: 7
<212> TYPE: PRT
<213> ORGANISM: Artificial
<220> FEATURE:
<223> OTHER INFORMATION: Synthetically Generated Peptide

<400> SEQUENCE: 306

Ser Glu Asp Thr Leu His Thr
1               5
```

```
<210> SEQ ID NO 307
<211> LENGTH: 7
<212> TYPE: PRT
<213> ORGANISM: Artificial
<220> FEATURE:
<223> OTHER INFORMATION: Synthetically Generated Peptide

<400> SEQUENCE: 307

Ser Glu Asp Asp Leu His Thr
1               5

<210> SEQ ID NO 308
<211> LENGTH: 7
<212> TYPE: PRT
<213> ORGANISM: Artificial
<220> FEATURE:
<223> OTHER INFORMATION: Synthetically Generated Peptide

<400> SEQUENCE: 308

Ser Glu Asp Glu Leu His Thr
1               5

<210> SEQ ID NO 309
<211> LENGTH: 7
<212> TYPE: PRT
<213> ORGANISM: Artificial
<220> FEATURE:
<223> OTHER INFORMATION: Synthetically Generated Peptide

<400> SEQUENCE: 309

Ser Glu Asp His Leu His Thr
1               5

<210> SEQ ID NO 310
<211> LENGTH: 7
<212> TYPE: PRT
<213> ORGANISM: Artificial
<220> FEATURE:
<223> OTHER INFORMATION: Synthetically Generated Peptide

<400> SEQUENCE: 310

Ser Glu Asp Lys Leu His Thr
1               5

<210> SEQ ID NO 311
<211> LENGTH: 7
<212> TYPE: PRT
<213> ORGANISM: Artificial
<220> FEATURE:
<223> OTHER INFORMATION: Synthetically Generated Peptide

<400> SEQUENCE: 311

Ser Glu Asp Ser Leu His Thr
1               5

<210> SEQ ID NO 312
<211> LENGTH: 7
<212> TYPE: PRT
<213> ORGANISM: Artificial
<220> FEATURE:
<223> OTHER INFORMATION: Synthetically Generated Peptide

<400> SEQUENCE: 312

Ser Glu Asp Ala Leu His Thr
1               5
```

```
<210> SEQ ID NO 313
<211> LENGTH: 7
<212> TYPE: PRT
<213> ORGANISM: Artificial
<220> FEATURE:
<223> OTHER INFORMATION: Synthetically Generated Peptide

<400> SEQUENCE: 313

Gln Glu Asp Asn Leu Ile Ser
1               5

<210> SEQ ID NO 314
<211> LENGTH: 7
<212> TYPE: PRT
<213> ORGANISM: Artificial
<220> FEATURE:
<223> OTHER INFORMATION: Synthetically Generated Peptide

<400> SEQUENCE: 314

Asp Glu Asp Asn Leu Ile Ser
1               5

<210> SEQ ID NO 315
<211> LENGTH: 7
<212> TYPE: PRT
<213> ORGANISM: Artificial
<220> FEATURE:
<223> OTHER INFORMATION: Synthetically Generated Peptide

<400> SEQUENCE: 315

Glu Glu Asp Asn Leu Ile Ser
1               5

<210> SEQ ID NO 316
<211> LENGTH: 7
<212> TYPE: PRT
<213> ORGANISM: Artificial
<220> FEATURE:
<223> OTHER INFORMATION: Synthetically Generated Peptide

<400> SEQUENCE: 316

Ser Glu Asp Asn Leu Ile Ser
1               5

<210> SEQ ID NO 317
<211> LENGTH: 7
<212> TYPE: PRT
<213> ORGANISM: Artificial
<220> FEATURE:
<223> OTHER INFORMATION: Synthetically Generated Peptide

<400> SEQUENCE: 317

Arg Glu Asp Thr Leu Ile Ser
1               5

<210> SEQ ID NO 318
<211> LENGTH: 7
<212> TYPE: PRT
<213> ORGANISM: Artificial
<220> FEATURE:
<223> OTHER INFORMATION: Synthetically Generated Peptide

<400> SEQUENCE: 318

Arg Glu Asp Asp Leu Ile Ser
1               5

<210> SEQ ID NO 319
```

```
<211> LENGTH: 7
<212> TYPE: PRT
<213> ORGANISM: Artificial
<220> FEATURE:
<223> OTHER INFORMATION: Synthetically Generated Peptide

<400> SEQUENCE: 319

Arg Glu Asp Glu Leu Ile Ser
1               5

<210> SEQ ID NO 320
<211> LENGTH: 7
<212> TYPE: PRT
<213> ORGANISM: Artificial
<220> FEATURE:
<223> OTHER INFORMATION: Synthetically Generated Peptide

<400> SEQUENCE: 320

Arg Glu Asp His Leu Ile Ser
1               5

<210> SEQ ID NO 321
<211> LENGTH: 7
<212> TYPE: PRT
<213> ORGANISM: Artificial
<220> FEATURE:
<223> OTHER INFORMATION: Synthetically Generated Peptide

<400> SEQUENCE: 321

Arg Glu Asp Lys Leu Ile Ser
1               5

<210> SEQ ID NO 322
<211> LENGTH: 7
<212> TYPE: PRT
<213> ORGANISM: Artificial
<220> FEATURE:
<223> OTHER INFORMATION: Synthetically Generated Peptide

<400> SEQUENCE: 322

Arg Glu Asp Ser Leu Ile Ser
1               5

<210> SEQ ID NO 323
<211> LENGTH: 7
<212> TYPE: PRT
<213> ORGANISM: Artificial
<220> FEATURE:
<223> OTHER INFORMATION: Synthetically Generated Peptide

<400> SEQUENCE: 323

Arg Glu Asp Ala Leu Ile Ser
1               5

<210> SEQ ID NO 324
<211> LENGTH: 7
<212> TYPE: PRT
<213> ORGANISM: Artificial
<220> FEATURE:
<223> OTHER INFORMATION: Synthetically Generated Peptide

<400> SEQUENCE: 324

Gln Glu Asp Thr Leu Ile Ser
1               5

<210> SEQ ID NO 325
<211> LENGTH: 7
```

```
<212> TYPE: PRT
<213> ORGANISM: Artificial
<220> FEATURE:
<223> OTHER INFORMATION: Synthetically Generated Peptide

<400> SEQUENCE: 325

Gln Glu Asp Asp Leu Ile Ser
1               5

<210> SEQ ID NO 326
<211> LENGTH: 7
<212> TYPE: PRT
<213> ORGANISM: Artificial
<220> FEATURE:
<223> OTHER INFORMATION: Synthetically Generated Peptide

<400> SEQUENCE: 326

Gln Glu Asp Glu Leu Ile Ser
1               5

<210> SEQ ID NO 327
<211> LENGTH: 7
<212> TYPE: PRT
<213> ORGANISM: Artificial
<220> FEATURE:
<223> OTHER INFORMATION: Synthetically Generated Peptide

<400> SEQUENCE: 327

Gln Glu Asp His Leu Ile Ser
1               5

<210> SEQ ID NO 328
<211> LENGTH: 7
<212> TYPE: PRT
<213> ORGANISM: Artificial
<220> FEATURE:
<223> OTHER INFORMATION: Synthetically Generated Peptide

<400> SEQUENCE: 328

Gln Glu Asp Lys Leu Ile Ser
1               5

<210> SEQ ID NO 329
<211> LENGTH: 7
<212> TYPE: PRT
<213> ORGANISM: Artificial
<220> FEATURE:
<223> OTHER INFORMATION: Synthetically Generated Peptide

<400> SEQUENCE: 329

Gln Glu Asp Ser Leu Ile Ser
1               5

<210> SEQ ID NO 330
<211> LENGTH: 7
<212> TYPE: PRT
<213> ORGANISM: Artificial
<220> FEATURE:
<223> OTHER INFORMATION: Synthetically Generated Peptide

<400> SEQUENCE: 330

Gln Glu Asp Ala Leu Ile Ser
1               5

<210> SEQ ID NO 331
<211> LENGTH: 7
<212> TYPE: PRT
```

```
<213> ORGANISM: Artificial
<220> FEATURE:
<223> OTHER INFORMATION: Synthetically Generated Peptide

<400> SEQUENCE: 331

Asp Glu Asp Thr Leu Ile Ser
1               5

<210> SEQ ID NO 332
<211> LENGTH: 7
<212> TYPE: PRT
<213> ORGANISM: Artificial
<220> FEATURE:
<223> OTHER INFORMATION: Synthetically Generated Peptide

<400> SEQUENCE: 332

Asp Glu Asp Asp Leu Ile Ser
1               5

<210> SEQ ID NO 333
<211> LENGTH: 7
<212> TYPE: PRT
<213> ORGANISM: Artificial
<220> FEATURE:
<223> OTHER INFORMATION: Synthetically Generated Peptide

<400> SEQUENCE: 333

Asp Glu Asp Glu Leu Ile Ser
1               5

<210> SEQ ID NO 334
<211> LENGTH: 7
<212> TYPE: PRT
<213> ORGANISM: Artificial
<220> FEATURE:
<223> OTHER INFORMATION: Synthetically Generated Peptide

<400> SEQUENCE: 334

Asp Glu Asp His Leu Ile Ser
1               5

<210> SEQ ID NO 335
<211> LENGTH: 7
<212> TYPE: PRT
<213> ORGANISM: Artificial
<220> FEATURE:
<223> OTHER INFORMATION: Synthetically Generated Peptide

<400> SEQUENCE: 335

Asp Glu Asp Lys Leu Ile Ser
1               5

<210> SEQ ID NO 336
<211> LENGTH: 7
<212> TYPE: PRT
<213> ORGANISM: Artificial
<220> FEATURE:
<223> OTHER INFORMATION: Synthetically Generated Peptide

<400> SEQUENCE: 336

Asp Glu Asp Ser Leu Ile Ser
1               5

<210> SEQ ID NO 337
<211> LENGTH: 7
<212> TYPE: PRT
<213> ORGANISM: Artificial
```

```
<220> FEATURE:
<223> OTHER INFORMATION: Synthetically Generated Peptide

<400> SEQUENCE: 337

Asp Glu Asp Ala Leu Ile Ser
1               5

<210> SEQ ID NO 338
<211> LENGTH: 7
<212> TYPE: PRT
<213> ORGANISM: Artificial
<220> FEATURE:
<223> OTHER INFORMATION: Synthetically Generated Peptide

<400> SEQUENCE: 338

Glu Glu Asp Thr Leu Ile Ser
1               5

<210> SEQ ID NO 339
<211> LENGTH: 7
<212> TYPE: PRT
<213> ORGANISM: Artificial
<220> FEATURE:
<223> OTHER INFORMATION: Synthetically Generated Peptide

<400> SEQUENCE: 339

Glu Glu Asp Asp Leu Ile Ser
1               5

<210> SEQ ID NO 340
<211> LENGTH: 7
<212> TYPE: PRT
<213> ORGANISM: Artificial
<220> FEATURE:
<223> OTHER INFORMATION: Synthetically Generated Peptide

<400> SEQUENCE: 340

Glu Glu Asp Glu Leu Ile Ser
1               5

<210> SEQ ID NO 341
<211> LENGTH: 7
<212> TYPE: PRT
<213> ORGANISM: Artificial
<220> FEATURE:
<223> OTHER INFORMATION: Synthetically Generated Peptide

<400> SEQUENCE: 341

Glu Glu Asp His Leu Ile Ser
1               5

<210> SEQ ID NO 342
<211> LENGTH: 7
<212> TYPE: PRT
<213> ORGANISM: Artificial
<220> FEATURE:
<223> OTHER INFORMATION: Synthetically Generated Peptide

<400> SEQUENCE: 342

Glu Glu Asp Lys Leu Ile Ser
1               5

<210> SEQ ID NO 343
<211> LENGTH: 7
<212> TYPE: PRT
<213> ORGANISM: Artificial
<220> FEATURE:
```

```
<223> OTHER INFORMATION: Synthetically Generated Peptide

<400> SEQUENCE: 343

Glu Glu Asp Ser Leu Ile Ser
1               5

<210> SEQ ID NO 344
<211> LENGTH: 7
<212> TYPE: PRT
<213> ORGANISM: Artificial
<220> FEATURE:
<223> OTHER INFORMATION: Synthetically Generated Peptide

<400> SEQUENCE: 344

Glu Glu Asp Ala Leu Ile Ser
1               5

<210> SEQ ID NO 345
<211> LENGTH: 7
<212> TYPE: PRT
<213> ORGANISM: Artificial
<220> FEATURE:
<223> OTHER INFORMATION: Synthetically Generated Peptide

<400> SEQUENCE: 345

Thr Glu Asp Thr Leu Ile Ser
1               5

<210> SEQ ID NO 346
<211> LENGTH: 7
<212> TYPE: PRT
<213> ORGANISM: Artificial
<220> FEATURE:
<223> OTHER INFORMATION: Synthetically Generated Peptide

<400> SEQUENCE: 346

Thr Glu Asp Asp Leu Ile Ser
1               5

<210> SEQ ID NO 347
<211> LENGTH: 7
<212> TYPE: PRT
<213> ORGANISM: Artificial
<220> FEATURE:
<223> OTHER INFORMATION: Synthetically Generated Peptide

<400> SEQUENCE: 347

Thr Glu Asp Glu Leu Ile Ser
1               5

<210> SEQ ID NO 348
<211> LENGTH: 7
<212> TYPE: PRT
<213> ORGANISM: Artificial
<220> FEATURE:
<223> OTHER INFORMATION: Synthetically Generated Peptide

<400> SEQUENCE: 348

Thr Glu Asp His Leu Ile Ser
1               5

<210> SEQ ID NO 349
<211> LENGTH: 7
<212> TYPE: PRT
<213> ORGANISM: Artificial
<220> FEATURE:
<223> OTHER INFORMATION: Synthetically Generated Peptide
```

```
<400> SEQUENCE: 349

Thr Glu Asp Lys Leu Ile Ser
1               5

<210> SEQ ID NO 350
<211> LENGTH: 7
<212> TYPE: PRT
<213> ORGANISM: Artificial
<220> FEATURE:
<223> OTHER INFORMATION: Synthetically Generated Peptide

<400> SEQUENCE: 350

Thr Glu Asp Ser Leu Ile Ser
1               5

<210> SEQ ID NO 351
<211> LENGTH: 7
<212> TYPE: PRT
<213> ORGANISM: Artificial
<220> FEATURE:
<223> OTHER INFORMATION: Synthetically Generated Peptide

<400> SEQUENCE: 351

Thr Glu Asp Ala Leu Ile Ser
1               5

<210> SEQ ID NO 352
<211> LENGTH: 7
<212> TYPE: PRT
<213> ORGANISM: Artificial
<220> FEATURE:
<223> OTHER INFORMATION: Synthetically Generated Peptide

<400> SEQUENCE: 352

Ser Glu Asp Thr Leu Ile Ser
1               5

<210> SEQ ID NO 353
<211> LENGTH: 7
<212> TYPE: PRT
<213> ORGANISM: Artificial
<220> FEATURE:
<223> OTHER INFORMATION: Synthetically Generated Peptide

<400> SEQUENCE: 353

Ser Glu Asp Asp Leu Ile Ser
1               5

<210> SEQ ID NO 354
<211> LENGTH: 7
<212> TYPE: PRT
<213> ORGANISM: Artificial
<220> FEATURE:
<223> OTHER INFORMATION: Synthetically Generated Peptide

<400> SEQUENCE: 354

Ser Glu Asp Glu Leu Ile Ser
1               5

<210> SEQ ID NO 355
<211> LENGTH: 7
<212> TYPE: PRT
<213> ORGANISM: Artificial
<220> FEATURE:
<223> OTHER INFORMATION: Synthetically Generated Peptide
```

-continued

```
<400> SEQUENCE: 355

Ser Glu Asp His Leu Ile Ser
1               5

<210> SEQ ID NO 356
<211> LENGTH: 7
<212> TYPE: PRT
<213> ORGANISM: Artificial
<220> FEATURE:
<223> OTHER INFORMATION: Synthetically Generated Peptide

<400> SEQUENCE: 356

Ser Glu Asp Lys Leu Ile Ser
1               5

<210> SEQ ID NO 357
<211> LENGTH: 7
<212> TYPE: PRT
<213> ORGANISM: Artificial
<220> FEATURE:
<223> OTHER INFORMATION: Synthetically Generated Peptide

<400> SEQUENCE: 357

Ser Glu Asp Ser Leu Ile Ser
1               5

<210> SEQ ID NO 358
<211> LENGTH: 7
<212> TYPE: PRT
<213> ORGANISM: Artificial
<220> FEATURE:
<223> OTHER INFORMATION: Synthetically Generated Peptide

<400> SEQUENCE: 358

Ser Glu Asp Ala Leu Ile Ser
1               5

<210> SEQ ID NO 359
<211> LENGTH: 7
<212> TYPE: PRT
<213> ORGANISM: Artificial
<220> FEATURE:
<223> OTHER INFORMATION: Synthetically Generated Peptide

<400> SEQUENCE: 359

Thr Gly Gly Trp Leu Gln Ala
1               5

<210> SEQ ID NO 360
<211> LENGTH: 7
<212> TYPE: PRT
<213> ORGANISM: Artificial
<220> FEATURE:
<223> OTHER INFORMATION: Synthetically Generated Peptide

<400> SEQUENCE: 360

Ser Gly Gly Trp Leu Gln Ala
1               5

<210> SEQ ID NO 361
<211> LENGTH: 7
<212> TYPE: PRT
<213> ORGANISM: Artificial
<220> FEATURE:
<223> OTHER INFORMATION: Synthetically Generated Peptide

<400> SEQUENCE: 361
```

```
Asp Gly Gly Trp Leu Gln Ala
1               5

<210> SEQ ID NO 362
<211> LENGTH: 7
<212> TYPE: PRT
<213> ORGANISM: Artificial
<220> FEATURE:
<223> OTHER INFORMATION: Synthetically Generated Peptide

<400> SEQUENCE: 362

Glu Gly Gly Trp Leu Gln Ala
1               5

<210> SEQ ID NO 363
<211> LENGTH: 7
<212> TYPE: PRT
<213> ORGANISM: Artificial
<220> FEATURE:
<223> OTHER INFORMATION: Synthetically Generated Peptide

<400> SEQUENCE: 363

Gln Gly Gly Trp Leu Gln Ala
1               5

<210> SEQ ID NO 364
<211> LENGTH: 7
<212> TYPE: PRT
<213> ORGANISM: Artificial
<220> FEATURE:
<223> OTHER INFORMATION: Synthetically Generated Peptide

<400> SEQUENCE: 364

Arg Gly Gly Thr Leu Gln Ala
1               5

<210> SEQ ID NO 365
<211> LENGTH: 7
<212> TYPE: PRT
<213> ORGANISM: Artificial
<220> FEATURE:
<223> OTHER INFORMATION: Synthetically Generated Peptide

<400> SEQUENCE: 365

Arg Gly Gly Asp Leu Gln Ala
1               5

<210> SEQ ID NO 366
<211> LENGTH: 7
<212> TYPE: PRT
<213> ORGANISM: Artificial
<220> FEATURE:
<223> OTHER INFORMATION: Synthetically Generated Peptide

<400> SEQUENCE: 366

Arg Gly Gly Glu Leu Gln Ala
1               5

<210> SEQ ID NO 367
<211> LENGTH: 7
<212> TYPE: PRT
<213> ORGANISM: Artificial
<220> FEATURE:
<223> OTHER INFORMATION: Synthetically Generated Peptide

<400> SEQUENCE: 367
```

```
Arg Gly Gly Asn Leu Gln Ala
1               5

<210> SEQ ID NO 368
<211> LENGTH: 7
<212> TYPE: PRT
<213> ORGANISM: Artificial
<220> FEATURE:
<223> OTHER INFORMATION: Synthetically Generated Peptide

<400> SEQUENCE: 368

Arg Gly Gly His Leu Gln Ala
1               5

<210> SEQ ID NO 369
<211> LENGTH: 7
<212> TYPE: PRT
<213> ORGANISM: Artificial
<220> FEATURE:
<223> OTHER INFORMATION: Synthetically Generated Peptide

<400> SEQUENCE: 369

Arg Gly Gly Lys Leu Gln Ala
1               5

<210> SEQ ID NO 370
<211> LENGTH: 7
<212> TYPE: PRT
<213> ORGANISM: Artificial
<220> FEATURE:
<223> OTHER INFORMATION: Synthetically Generated Peptide

<400> SEQUENCE: 370

Arg Gly Gly Ser Leu Gln Ala
1               5

<210> SEQ ID NO 371
<211> LENGTH: 7
<212> TYPE: PRT
<213> ORGANISM: Artificial
<220> FEATURE:
<223> OTHER INFORMATION: Synthetically Generated Peptide

<400> SEQUENCE: 371

Arg Gly Gly Ala Leu Gln Ala
1               5

<210> SEQ ID NO 372
<211> LENGTH: 7
<212> TYPE: PRT
<213> ORGANISM: Artificial
<220> FEATURE:
<223> OTHER INFORMATION: Synthetically Generated Peptide

<400> SEQUENCE: 372

Thr Gly Gly Thr Leu Gln Ala
1               5

<210> SEQ ID NO 373
<211> LENGTH: 7
<212> TYPE: PRT
<213> ORGANISM: Artificial
<220> FEATURE:
<223> OTHER INFORMATION: Synthetically Generated Peptide

<400> SEQUENCE: 373

Thr Gly Gly Asp Leu Gln Ala
```

-continued 1               5

<210> SEQ ID NO 374
<211> LENGTH: 7
<212> TYPE: PRT
<213> ORGANISM: Artificial
<220> FEATURE:
<223> OTHER INFORMATION: Synthetically Generated Peptide

<400> SEQUENCE: 374

Thr Gly Gly Glu Leu Gln Ala
1               5

<210> SEQ ID NO 375
<211> LENGTH: 7
<212> TYPE: PRT
<213> ORGANISM: Artificial
<220> FEATURE:
<223> OTHER INFORMATION: Synthetically Generated Peptide

<400> SEQUENCE: 375

Thr Gly Gly Asn Leu Gln Ala
1               5

<210> SEQ ID NO 376
<211> LENGTH: 7
<212> TYPE: PRT
<213> ORGANISM: Artificial
<220> FEATURE:
<223> OTHER INFORMATION: Synthetically Generated Peptide

<400> SEQUENCE: 376

Thr Gly Gly His Leu Gln Ala
1               5

<210> SEQ ID NO 377
<211> LENGTH: 7
<212> TYPE: PRT
<213> ORGANISM: Artificial
<220> FEATURE:
<223> OTHER INFORMATION: Synthetically Generated Peptide

<400> SEQUENCE: 377

Thr Gly Gly Lys Leu Gln Ala
1               5

<210> SEQ ID NO 378
<211> LENGTH: 7
<212> TYPE: PRT
<213> ORGANISM: Artificial
<220> FEATURE:
<223> OTHER INFORMATION: Synthetically Generated Peptide

<400> SEQUENCE: 378

Thr Gly Gly Ser Leu Gln Ala
1               5

<210> SEQ ID NO 379
<211> LENGTH: 7
<212> TYPE: PRT
<213> ORGANISM: Artificial
<220> FEATURE:
<223> OTHER INFORMATION: Synthetically Generated Peptide

<400> SEQUENCE: 379

Thr Gly Gly Ala Leu Gln Ala
1               5

```
<210> SEQ ID NO 380
<211> LENGTH: 7
<212> TYPE: PRT
<213> ORGANISM: Artificial
<220> FEATURE:
<223> OTHER INFORMATION: Synthetically Generated Peptide

<400> SEQUENCE: 380

Ser Gly Gly Thr Leu Gln Ala
1               5

<210> SEQ ID NO 381
<211> LENGTH: 7
<212> TYPE: PRT
<213> ORGANISM: Artificial
<220> FEATURE:
<223> OTHER INFORMATION: Synthetically Generated Peptide

<400> SEQUENCE: 381

Ser Gly Gly Asp Leu Gln Ala
1               5

<210> SEQ ID NO 382
<211> LENGTH: 7
<212> TYPE: PRT
<213> ORGANISM: Artificial
<220> FEATURE:
<223> OTHER INFORMATION: Synthetically Generated Peptide

<400> SEQUENCE: 382

Ser Gly Gly Glu Leu Gln Ala
1               5

<210> SEQ ID NO 383
<211> LENGTH: 7
<212> TYPE: PRT
<213> ORGANISM: Artificial
<220> FEATURE:
<223> OTHER INFORMATION: Synthetically Generated Peptide

<400> SEQUENCE: 383

Ser Gly Gly Asn Leu Gln Ala
1               5

<210> SEQ ID NO 384
<211> LENGTH: 7
<212> TYPE: PRT
<213> ORGANISM: Artificial
<220> FEATURE:
<223> OTHER INFORMATION: Synthetically Generated Peptide

<400> SEQUENCE: 384

Ser Gly Gly His Leu Gln Ala
1               5

<210> SEQ ID NO 385
<211> LENGTH: 7
<212> TYPE: PRT
<213> ORGANISM: Artificial
<220> FEATURE:
<223> OTHER INFORMATION: Synthetically Generated Peptide

<400> SEQUENCE: 385

Ser Gly Gly Lys Leu Gln Ala
1               5
```

```
<210> SEQ ID NO 386
<211> LENGTH: 7
<212> TYPE: PRT
<213> ORGANISM: Artificial
<220> FEATURE:
<223> OTHER INFORMATION: Synthetically Generated Peptide

<400> SEQUENCE: 386

Ser Gly Gly Ser Leu Gln Ala
1               5

<210> SEQ ID NO 387
<211> LENGTH: 7
<212> TYPE: PRT
<213> ORGANISM: Artificial
<220> FEATURE:
<223> OTHER INFORMATION: Synthetically Generated Peptide

<400> SEQUENCE: 387

Ser Gly Gly Ala Leu Gln Ala
1               5

<210> SEQ ID NO 388
<211> LENGTH: 7
<212> TYPE: PRT
<213> ORGANISM: Artificial
<220> FEATURE:
<223> OTHER INFORMATION: Synthetically Generated Peptide

<400> SEQUENCE: 388

Asp Gly Gly Thr Leu Gln Ala
1               5

<210> SEQ ID NO 389
<211> LENGTH: 7
<212> TYPE: PRT
<213> ORGANISM: Artificial
<220> FEATURE:
<223> OTHER INFORMATION: Synthetically Generated Peptide

<400> SEQUENCE: 389

Asp Gly Gly Asp Leu Gln Ala
1               5

<210> SEQ ID NO 390
<211> LENGTH: 7
<212> TYPE: PRT
<213> ORGANISM: Artificial
<220> FEATURE:
<223> OTHER INFORMATION: Synthetically Generated Peptide

<400> SEQUENCE: 390

Asp Gly Gly Glu Leu Gln Ala
1               5

<210> SEQ ID NO 391
<211> LENGTH: 7
<212> TYPE: PRT
<213> ORGANISM: Artificial
<220> FEATURE:
<223> OTHER INFORMATION: Synthetically Generated Peptide

<400> SEQUENCE: 391

Asp Gly Gly Asn Leu Gln Ala
1               5
```

```
<210> SEQ ID NO 392
<211> LENGTH: 7
<212> TYPE: PRT
<213> ORGANISM: Artificial
<220> FEATURE:
<223> OTHER INFORMATION: Synthetically Generated Peptide

<400> SEQUENCE: 392

Asp Gly Gly His Leu Gln Ala
1               5

<210> SEQ ID NO 393
<211> LENGTH: 7
<212> TYPE: PRT
<213> ORGANISM: Artificial
<220> FEATURE:
<223> OTHER INFORMATION: Synthetically Generated Peptide

<400> SEQUENCE: 393

Asp Gly Gly Lys Leu Gln Ala
1               5

<210> SEQ ID NO 394
<211> LENGTH: 7
<212> TYPE: PRT
<213> ORGANISM: Artificial
<220> FEATURE:
<223> OTHER INFORMATION: Synthetically Generated Peptide

<400> SEQUENCE: 394

Asp Gly Gly Ser Leu Gln Ala
1               5

<210> SEQ ID NO 395
<211> LENGTH: 7
<212> TYPE: PRT
<213> ORGANISM: Artificial
<220> FEATURE:
<223> OTHER INFORMATION: Synthetically Generated Peptide

<400> SEQUENCE: 395

Asp Gly Gly Ala Leu Gln Ala
1               5

<210> SEQ ID NO 396
<211> LENGTH: 7
<212> TYPE: PRT
<213> ORGANISM: Artificial
<220> FEATURE:
<223> OTHER INFORMATION: Synthetically Generated Peptide

<400> SEQUENCE: 396

Glu Gly Gly Thr Leu Gln Ala
1               5

<210> SEQ ID NO 397
<211> LENGTH: 7
<212> TYPE: PRT
<213> ORGANISM: Artificial
<220> FEATURE:
<223> OTHER INFORMATION: Synthetically Generated Peptide

<400> SEQUENCE: 397

Glu Gly Gly Asp Leu Gln Ala
1               5

<210> SEQ ID NO 398
```

```
<211> LENGTH: 7
<212> TYPE: PRT
<213> ORGANISM: Artificial
<220> FEATURE:
<223> OTHER INFORMATION: Synthetically Generated Peptide

<400> SEQUENCE: 398

Glu Gly Gly Glu Leu Gln Ala
1               5

<210> SEQ ID NO 399
<211> LENGTH: 7
<212> TYPE: PRT
<213> ORGANISM: Artificial
<220> FEATURE:
<223> OTHER INFORMATION: Synthetically Generated Peptide

<400> SEQUENCE: 399

Glu Gly Gly Asn Leu Gln Ala
1               5

<210> SEQ ID NO 400
<211> LENGTH: 7
<212> TYPE: PRT
<213> ORGANISM: Artificial
<220> FEATURE:
<223> OTHER INFORMATION: Synthetically Generated Peptide

<400> SEQUENCE: 400

Glu Gly Gly His Leu Gln Ala
1               5

<210> SEQ ID NO 401
<211> LENGTH: 7
<212> TYPE: PRT
<213> ORGANISM: Artificial
<220> FEATURE:
<223> OTHER INFORMATION: Synthetically Generated Peptide

<400> SEQUENCE: 401

Glu Gly Gly Lys Leu Gln Ala
1               5

<210> SEQ ID NO 402
<211> LENGTH: 7
<212> TYPE: PRT
<213> ORGANISM: Artificial
<220> FEATURE:
<223> OTHER INFORMATION: Synthetically Generated Peptide

<400> SEQUENCE: 402

Glu Gly Gly Ser Leu Gln Ala
1               5

<210> SEQ ID NO 403
<211> LENGTH: 7
<212> TYPE: PRT
<213> ORGANISM: Artificial
<220> FEATURE:
<223> OTHER INFORMATION: Synthetically Generated Peptide

<400> SEQUENCE: 403

Glu Gly Gly Ala Leu Gln Ala
1               5

<210> SEQ ID NO 404
<211> LENGTH: 7
```

```
<212> TYPE: PRT
<213> ORGANISM: Artificial
<220> FEATURE:
<223> OTHER INFORMATION: Synthetically Generated Peptide

<400> SEQUENCE: 404

Gln Gly Gly Thr Leu Gln Ala
1               5

<210> SEQ ID NO 405
<211> LENGTH: 7
<212> TYPE: PRT
<213> ORGANISM: Artificial
<220> FEATURE:
<223> OTHER INFORMATION: Synthetically Generated Peptide

<400> SEQUENCE: 405

Gln Gly Gly Asp Leu Gln Ala
1               5

<210> SEQ ID NO 406
<211> LENGTH: 7
<212> TYPE: PRT
<213> ORGANISM: Artificial
<220> FEATURE:
<223> OTHER INFORMATION: Synthetically Generated Peptide

<400> SEQUENCE: 406

Gln Gly Gly Glu Leu Gln Ala
1               5

<210> SEQ ID NO 407
<211> LENGTH: 7
<212> TYPE: PRT
<213> ORGANISM: Artificial
<220> FEATURE:
<223> OTHER INFORMATION: Synthetically Generated Peptide

<400> SEQUENCE: 407

Gln Gly Gly Asn Leu Gln Ala
1               5

<210> SEQ ID NO 408
<211> LENGTH: 7
<212> TYPE: PRT
<213> ORGANISM: Artificial
<220> FEATURE:
<223> OTHER INFORMATION: Synthetically Generated Peptide

<400> SEQUENCE: 408

Gln Gly Gly His Leu Gln Ala
1               5

<210> SEQ ID NO 409
<211> LENGTH: 7
<212> TYPE: PRT
<213> ORGANISM: Artificial
<220> FEATURE:
<223> OTHER INFORMATION: Synthetically Generated Peptide

<400> SEQUENCE: 409

Gln Gly Gly Lys Leu Gln Ala
1               5

<210> SEQ ID NO 410
<211> LENGTH: 7
<212> TYPE: PRT
```

```
<213> ORGANISM: Artificial
<220> FEATURE:
<223> OTHER INFORMATION: Synthetically Generated Peptide

<400> SEQUENCE: 410

Gln Gly Gly Ser Leu Gln Ala
1               5

<210> SEQ ID NO 411
<211> LENGTH: 7
<212> TYPE: PRT
<213> ORGANISM: Artificial
<220> FEATURE:
<223> OTHER INFORMATION: Synthetically Generated Peptide

<400> SEQUENCE: 411

Gln Gly Gly Ala Leu Gln Ala
1               5

<210> SEQ ID NO 412
<211> LENGTH: 5
<212> TYPE: PRT
<213> ORGANISM: Artificial
<220> FEATURE:
<223> OTHER INFORMATION: Synthetically Generated Peptide

<400> SEQUENCE: 412

Thr Gly Glu Lys Pro
1               5

<210> SEQ ID NO 413
<211> LENGTH: 7
<212> TYPE: PRT
<213> ORGANISM: Artificial
<220> FEATURE:
<223> OTHER INFORMATION: Synthetically Generated Peptide

<400> SEQUENCE: 413

Arg Ser Asp Glu Leu Lys Arg
1               5

<210> SEQ ID NO 414
<211> LENGTH: 15
<212> TYPE: PRT
<213> ORGANISM: Artificial
<220> FEATURE:
<223> OTHER INFORMATION: Synthetically Generated Peptide

<400> SEQUENCE: 414

Thr Gly Gly Gly Gly Ser Gly Gly Gly Gly Thr Gly Glu Lys Pro
1               5                   10                  15

<210> SEQ ID NO 415
<211> LENGTH: 11
<212> TYPE: PRT
<213> ORGANISM: Artificial
<220> FEATURE:
<223> OTHER INFORMATION: Synthetically Generated Peptide

<400> SEQUENCE: 415

Asp Ala Leu Asp Asp Phe Asp Leu Asp Met Leu
1               5                   10

<210> SEQ ID NO 416
<211> LENGTH: 12
<212> TYPE: PRT
<213> ORGANISM: Artificial
```

```
<220> FEATURE:
<223> OTHER INFORMATION: Synthetically Generated Peptide

<400> SEQUENCE: 416

Leu Arg Gln Lys Asp Gly Gly Gly Ser Glu Arg Pro
1               5                   10

<210> SEQ ID NO 417
<211> LENGTH: 9
<212> TYPE: PRT
<213> ORGANISM: Artificial
<220> FEATURE:
<223> OTHER INFORMATION: Synthetically Generated Peptide

<400> SEQUENCE: 417

Leu Arg Gln Lys Asp Gly Glu Arg Pro
1               5

<210> SEQ ID NO 418
<211> LENGTH: 10
<212> TYPE: PRT
<213> ORGANISM: Artificial
<220> FEATURE:
<223> OTHER INFORMATION: Synthetically Generated Peptide

<400> SEQUENCE: 418

Gly Gly Arg Gly Arg Gly Arg Gly Arg Gln
1               5                   10

<210> SEQ ID NO 419
<211> LENGTH: 16
<212> TYPE: PRT
<213> ORGANISM: Artificial
<220> FEATURE:
<223> OTHER INFORMATION: Synthetically Generated Peptide

<400> SEQUENCE: 419

Gln Asn Lys Lys Gly Gly Ser Gly Asp Gly Lys Lys Lys Gln His Ile
1               5                   10                  15

<210> SEQ ID NO 420
<211> LENGTH: 6
<212> TYPE: PRT
<213> ORGANISM: Artificial
<220> FEATURE:
<223> OTHER INFORMATION: Synthetically Generated Peptide

<400> SEQUENCE: 420

Thr Gly Gly Glu Arg Pro
1               5

<210> SEQ ID NO 421
<211> LENGTH: 6
<212> TYPE: PRT
<213> ORGANISM: Artificial
<220> FEATURE:
<223> OTHER INFORMATION: Synthetically Generated Peptide

<400> SEQUENCE: 421

Ala Thr Gly Glu Lys Pro
1               5

<210> SEQ ID NO 422
<211> LENGTH: 11
<212> TYPE: PRT
<213> ORGANISM: Artificial
<220> FEATURE:
```

<223> OTHER INFORMATION: Synthetically Generated Peptide

<400> SEQUENCE: 422

Gly Gly Gly Ser Gly Gly Gly Gly Glu Gly Pro
1               5                   10

<210> SEQ ID NO 423
<211> LENGTH: 9
<212> TYPE: DNA
<213> ORGANISM: Artificial
<220> FEATURE:
<223> OTHER INFORMATION: Synthetically Generated Oligonucleotide
<220> FEATURE:
<221> NAME/KEY: misc_feature
<222> LOCATION: (4)..(6)
<223> OTHER INFORMATION: n is a, c, g, or t

<400> SEQUENCE: 423 gcgnnngcg                                                                  9

<210> SEQ ID NO 424
<211> LENGTH: 9
<212> TYPE: DNA
<213> ORGANISM: Artificial
<220> FEATURE:
<223> OTHER INFORMATION: Synthetically Generated Oligonucleotide
<220> FEATURE:
<221> NAME/KEY: misc_feature
<222> LOCATION: (5)..(6)
<223> OTHER INFORMATION: n is a, c, g, or t

<400> SEQUENCE: 424 gatcnngcg                                                                  9

<210> SEQ ID NO 425
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 425
aaatctctag cagtggcg                                                       18

<210> SEQ ID NO 426
<211> LENGTH: 36
<212> TYPE: DNA
<213> ORGANISM: Artificial
<220> FEATURE:
<223> OTHER INFORMATION: Synthetically Generated Oligonucleotide

<400> SEQUENCE: 426
gatacgacag ctagctggaa gggctaattc actccc                                   36

<210> SEQ ID NO 427
<211> LENGTH: 54
<212> TYPE: DNA
<213> ORGANISM: Artificial
<220> FEATURE:
<223> OTHER INFORMATION: Synthetically Generated Oligonucleotide

<400> SEQUENCE: 427
aacgtctggc tcgagttcag gtccctgttc gggcgccact gctagagatt ttcc               54

<210> SEQ ID NO 428
<211> LENGTH: 21
<212> TYPE: DNA

```
<213> ORGANISM: Artificial
<220> FEATURE:
<223> OTHER INFORMATION: Synthetically Generated Oligonucleotide

<400> SEQUENCE: 428
ccgctgggga ctttccaggg a                                            21

<210> SEQ ID NO 429
<211> LENGTH: 24
<212> TYPE: DNA
<213> ORGANISM: Artificial
<220> FEATURE:
<223> OTHER INFORMATION: Synthetically Generated Oligonucleotide

<400> SEQUENCE: 429
cactgctaga gattttccac actg                                         24

<210> SEQ ID NO 430
<211> LENGTH: 15
<212> TYPE: DNA
<213> ORGANISM: Artificial
<220> FEATURE:
<223> OTHER INFORMATION: Synthetically Generated Oligonucleotide

<400> SEQUENCE: 430
cgcccgaaca gggac                                                   15

<210> SEQ ID NO 431
<211> LENGTH: 15
<212> TYPE: DNA
<213> ORGANISM: Artificial
<220> FEATURE:
<223> OTHER INFORMATION: Synthetically Generated Oligonucleotide

<400> SEQUENCE: 431
tgccgaaacc cggga                                                   15

<210> SEQ ID NO 432
<211> LENGTH: 41
<212> TYPE: DNA
<213> ORGANISM: Artificial
<220> FEATURE:
<223> OTHER INFORMATION: Synthetically Generated Oligonucleotide

<400> SEQUENCE: 432
actgtgtgga aaatctctag cagtggcgcc cgaacaggga c                      41

<210> SEQ ID NO 433
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 433
aaatctctag cagtggcg                                                18

<210> SEQ ID NO 434
<211> LENGTH: 25
<212> TYPE: DNA
<213> ORGANISM: Artificial
<220> FEATURE:
<223> OTHER INFORMATION: Synthetically Generated Oligonucleotide

<400> SEQUENCE: 434
gtctggaaaa tctctagcag tggcg                                        25
```

<210> SEQ ID NO 435
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 435
gcagtggcgc ccgaacag                                                 18

<210> SEQ ID NO 436
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 436
tggcgcccga acagggac                                                 18

<210> SEQ ID NO 437
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 437
ggaggcgtgg cctgggcg                                                 18

<210> SEQ ID NO 438
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 438
ggaggtgtgg tttgggcg                                                 18

<210> SEQ ID NO 439
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 439
ggaggcgtga cctgggcg                                                 18

<210> SEQ ID NO 440
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 440
ggaggcgtga cctgggcg                                                 18

<210> SEQ ID NO 441
<211> LENGTH: 18
<212> TYPE: DNA
<213> ORGANISM: Artificial
<220> FEATURE:

```
<223> OTHER INFORMATION: Synthetically Generated Oligonucleotide

<400> SEQUENCE: 441
ggaggtgtgg ccggggcg                                            18

<210> SEQ ID NO 442
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 442
agggcggtcc agagggcg                                            18

<210> SEQ ID NO 443
<211> LENGTH: 17
<212> TYPE: DNA
<213> ORGANISM: Artificial
<220> FEATURE:
<223> OTHER INFORMATION: Synthetically Generated Oligonucleotide

<400> SEQUENCE: 443
ggagggtcgc ctgggcg                                             17

<210> SEQ ID NO 444
<211> LENGTH: 18
<212> TYPE: DNA
<213> ORGANISM: Artificial
<220> FEATURE:
<223> OTHER INFORMATION: Synthetically Generated Oligonucleotide

<400> SEQUENCE: 444
gcagtggcgc ccgaacag                                            18

<210> SEQ ID NO 445
<211> LENGTH: 51
<212> TYPE: DNA
<213> ORGANISM: Artificial
<220> FEATURE:
<223> OTHER INFORMATION: Synthetically Generated Oligonucleotide

<400> SEQUENCE: 445
cagtgtggaa aatctctagc agtggcgccc gaacagggac ctgaaagcga a         51

<210> SEQ ID NO 446
<211> LENGTH: 51
<212> TYPE: DNA
<213> ORGANISM: Artificial
<220> FEATURE:
<223> OTHER INFORMATION: Synthetically Generated Oligonucleotide

<400> SEQUENCE: 446
cagtgtggaa aatctctagc actggcgccc gaacagggac ctgaaagcga a         51

<210> SEQ ID NO 447
<211> LENGTH: 51
<212> TYPE: DNA
<213> ORGANISM: Artificial
<220> FEATURE:
<223> OTHER INFORMATION: Synthetically Generated Oligonucleotide

<400> SEQUENCE: 447
cagtgtggaa aatctctagc agtgacgccc gaacagggac ctgaaagcga a         51
```

```
<210> SEQ ID NO 448
<211> LENGTH: 51
<212> TYPE: DNA
<213> ORGANISM: Artificial
<220> FEATURE:
<223> OTHER INFORMATION: Synthetically Generated Oligonucleotide

<400> SEQUENCE: 448
cagtgtggaa aatctctagc agtggcggac gaacagggac ctgaaagcga a          51

<210> SEQ ID NO 449
<211> LENGTH: 7
<212> TYPE: PRT
<213> ORGANISM: Artificial
<220> FEATURE:
<223> OTHER INFORMATION: Synthetically Generated Peptide

<400> SEQUENCE: 449

Gln Arg Ala Asn Leu Arg Ala
1               5

<210> SEQ ID NO 450
<211> LENGTH: 7
<212> TYPE: PRT
<213> ORGANISM: Artificial
<220> FEATURE:
<223> OTHER INFORMATION: Synthetically Generated Peptide

<400> SEQUENCE: 450

Gln Arg His Ser Leu Thr Glu
1               5

<210> SEQ ID NO 451
<211> LENGTH: 7
<212> TYPE: PRT
<213> ORGANISM: Artificial
<220> FEATURE:
<223> OTHER INFORMATION: Synthetically Generated Peptide

<400> SEQUENCE: 451

Gln Ser Gly Asp Leu Arg Arg
1               5

<210> SEQ ID NO 452
<211> LENGTH: 7
<212> TYPE: PRT
<213> ORGANISM: Artificial
<220> FEATURE:
<223> OTHER INFORMATION: Synthetically Generated Peptide

<400> SEQUENCE: 452

Arg Ser Asp Val Leu Val Arg
1               5

<210> SEQ ID NO 453
<211> LENGTH: 7
<212> TYPE: PRT
<213> ORGANISM: Artificial
<220> FEATURE:
<223> OTHER INFORMATION: Synthetically Generated Peptide

<400> SEQUENCE: 453

Arg Ser Asp Asp Leu Val Arg
1               5

<210> SEQ ID NO 454
<211> LENGTH: 7
```

```
<212> TYPE: PRT
<213> ORGANISM: Artificial
<220> FEATURE:
<223> OTHER INFORMATION: Synthetically Generated Peptide

<400> SEQUENCE: 454

His Thr Gly His Leu Leu Glu
1               5

<210> SEQ ID NO 455
<211> LENGTH: 7
<212> TYPE: PRT
<213> ORGANISM: Artificial
<220> FEATURE:
<223> OTHER INFORMATION: Synthetically Generated Peptide

<400> SEQUENCE: 455

Gln Ser Ser Asn Leu Val Arg
1               5

<210> SEQ ID NO 456
<211> LENGTH: 7
<212> TYPE: PRT
<213> ORGANISM: Artificial
<220> FEATURE:
<223> OTHER INFORMATION: Synthetically Generated Peptide

<400> SEQUENCE: 456

Arg Ala Asp Asn Leu Thr Glu
1               5

<210> SEQ ID NO 457
<211> LENGTH: 7
<212> TYPE: PRT
<213> ORGANISM: Artificial
<220> FEATURE:
<223> OTHER INFORMATION: Synthetically Generated Peptide

<400> SEQUENCE: 457

Arg Asn Asp Thr Leu Thr Glu
1               5

<210> SEQ ID NO 458
<211> LENGTH: 7
<212> TYPE: PRT
<213> ORGANISM: Artificial
<220> FEATURE:
<223> OTHER INFORMATION: Synthetically Generated Peptide

<400> SEQUENCE: 458

Asp Ser Gly Asn Leu Arg Val
1               5

<210> SEQ ID NO 459
<211> LENGTH: 7
<212> TYPE: PRT
<213> ORGANISM: Artificial
<220> FEATURE:
<223> OTHER INFORMATION: Synthetically Generated Peptide

<400> SEQUENCE: 459
```

```
Arg Ser Asp His Leu Thr Asn
1               5

<210> SEQ ID NO 460
<211> LENGTH: 7
<212> TYPE: PRT
<213> ORGANISM: Artificial
<220> FEATURE:
<223> OTHER INFORMATION: Synthetically Generated Peptide

<400> SEQUENCE: 460

Asp Pro Gly Asn Leu Val Arg
1               5
```